United States Patent
Nagalla et al.

(10) Patent No.: US 8,476,008 B2
(45) Date of Patent: Jul. 2, 2013

(54) METHODS FOR DETECTING PRE-DIABETES AND DIABETES

(75) Inventors: Srinivasa R. Nagalla, Hillsboro, OR (US); Charles T. Roberts, Portland, OR (US); Vishnupriya Rao Paturi, Hyderabad (IN)

(73) Assignee: DiabetOmics, LLC, Beaverton, OR (US)

( * ) Notice: Subject to any disclaimer, the term of this patent is extended or adjusted under 35 U.S.C. 154(b) by 45 days.

(21) Appl. No.: 13/055,605

(22) PCT Filed: Jul. 23, 2009

(86) PCT No.: PCT/US2009/051578
§ 371 (c)(1),
(2), (4) Date: Jan. 24, 2011

(87) PCT Pub. No.: WO2010/011860
PCT Pub. Date: Jan. 28, 2010

(65) Prior Publication Data
US 2011/0124022 A1 May 26, 2011

Related U.S. Application Data

(60) Provisional application No. 61/083,096, filed on Jul. 23, 2008.

(51) Int. Cl.
*C12Q 1/00* (2006.01)

(52) U.S. Cl.
USPC .......................................................... 435/4

(58) Field of Classification Search
USPC .......................................................... 435/4
See application file for complete search history.

(56) References Cited

U.S. PATENT DOCUMENTS

| | | | |
|---|---|---|---|
| 3,960,949 A | 6/1976 | Ahrens et al. |
| 4,017,539 A | 4/1977 | Bosies et al. |
| 4,168,146 A | 9/1979 | Grubb et al. |
| 4,246,339 A | 1/1981 | Cole et al. |
| 4,277,560 A | 7/1981 | Gray et al. |
| 4,313,734 A | 2/1982 | Leuvering |
| 4,366,241 A | 12/1982 | Tom et al. |
| 4,435,504 A | 3/1984 | Zuk et al. |
| 4,496,654 A | 1/1985 | Katz et al. |
| 4,632,901 A | 12/1986 | Valkirs et al. |
| 4,703,017 A | 10/1987 | Campbell et al. |
| 4,740,468 A | 4/1988 | Weng et al. |
| 4,743,560 A | 5/1988 | Campbell et al. |
| 4,770,853 A | 9/1988 | Bernstein |
| 4,775,636 A | 10/1988 | Moeremans et al. |
| 4,806,311 A | 2/1989 | Greenquist |
| 4,806,312 A | 2/1989 | Greenquist |
| 4,812,293 A | 3/1989 | McLaurin et al. |
| 4,855,240 A | 8/1989 | Rosenstein et al. |
| 4,857,453 A | 8/1989 | Ullman et al. |
| 4,861,711 A | 8/1989 | Friesen et al. |
| 4,920,046 A | 4/1990 | McFarland et al. |
| 4,943,522 A | 7/1990 | Eisinger et al. |
| 4,945,042 A | 7/1990 | Geiger et al. |
| 5,001,049 A | 3/1991 | Klein et al. |
| 5,073,484 A | 12/1991 | Swanson et al. |
| 5,075,078 A | 12/1991 | Osikowicz et al. |
| 5,120,643 A | 6/1992 | Ching et al. |
| 5,126,241 A | 6/1992 | Schenk |
| 5,229,073 A | 7/1993 | Luo et al. |
| 5,279,935 A | 1/1994 | Nycz |
| 5,284,750 A | 2/1994 | Silvestrini et al. |
| 5,424,193 A | 6/1995 | Pronovost et al. |
| 5,451,504 A | 9/1995 | Fitzpatrick et al. |
| 5,451,507 A | 9/1995 | Skold et al. |
| 5,591,645 A | 1/1997 | Rosenstein |
| 5,665,539 A | 9/1997 | Sano et al. |
| 5,712,172 A | 1/1998 | Huang et al. |
| 5,798,273 A | 8/1998 | Shuler et al. |
| 6,011,049 A | 1/2000 | Whitcomb |
| 6,258,548 B1 | 7/2001 | Buck |
| 6,283,761 B1 | 9/2001 | Joao |
| 6,368,876 B1 | 4/2002 | Huang et al. |
| 6,406,921 B1 | 6/2002 | Wagner et al. |
| 6,555,390 B2 | 4/2003 | Chandler |
| 6,656,744 B2 | 12/2003 | Pronovost et al. |
| 6,699,722 B2 | 3/2004 | Bauer et al. |
| 7,517,699 B2 | 4/2009 | Bauer et al. |
| 2003/0049857 A1 | 3/2003 | Chan |
| 2004/0029175 A1 | 2/2004 | Comper |

(Continued)

FOREIGN PATENT DOCUMENTS

| | | |
|---|---|---|
| EP | 0296724 A2 | 12/1988 |
| EP | 0299428 A2 | 1/1989 |

(Continued)

OTHER PUBLICATIONS

Vitorino R. et al. Identification of Human Whole Saliva Protein Components Using Proteomics. Proteomics 4:1109-1115, 2004.*
Baldini C. et al. Proteomic Analysis of the Saliva. Autoimmunity Reviews 7:185-191, 208.*
Huang C. Comparative Proteomic Analysis of Human Whole Saliva. Archives of Oral Biology 49:951-962, 2004.*
Wilmarth P. et al. Two Dimensional LC Study of the Human Whole Saliva Proteome. J of Proteome Research 3(5)1017-1023, 2004.*
Hu, S. et al. Large Scale Identification of Proteins in Human Salivary Proteome by LC/MS and 2D Gel Electrophoresis/MS. Proteomics 5:1714-1728, 2005.*
Hu S. Human Saliva Proteome Analysis and Disease Biomarker Discovery Expert Review of Proteomis 4(4)531-8, Aug. 2007.*
Huang, C.M. "Comparative Prteomic Analysis of Human Whole Salive," Archives of Oral Biology, Pergamon Press, Dec 1, 2004, vol. 49, No. 12, pp. 951-962.
Rao, Paturi V. et al., "Proteomic Identification of Salivary Biomarkers of Type-2 Diabetes," Journal of Proteome Research, 2009, vol. 8, No. 1 pp. 239-245.
Cassiday, Laura, "Nothing to Spit At: The Salivary Proteome of Type 2 Diabetes," Journal of Proteome Research, 2009, vol. 8, No. 1, p. 3.

*Primary Examiner* — Ralph Gitomer
(74) *Attorney, Agent, or Firm* — Schwabe, Williamson & Wyatt

(57) ABSTRACT

Non-invasive methods are provided herein for the diagnosis of pre-diabetes and diabetes using biomarkers identified in a biological fluid, such as saliva. These biomarkers can be identified using proteomic methods, including but not limited to antibody based methods, such as an enzyme-linked immunosorbant assay (ELISA), a radioimmunoassay (RIA), or a lateral flow immunoassay.

16 Claims, 5 Drawing Sheets

U.S. PATENT DOCUMENTS

| | | |
|---|---|---|
| 2004/0241876 A1 | 12/2004 | Fannes |
| 2005/0239108 A1 | 10/2005 | Barletta et al. |
| 2007/0087387 A1 | 4/2007 | Devarajan |
| 2007/0161125 A1 | 7/2007 | Rosenfeld et al. |
| 2008/0280772 A1* | 11/2008 | Wong et al. ............... 506/9 |
| 2008/0300798 A1* | 12/2008 | McDevitt et al. ............ 702/19 |
| 2010/0093100 A1* | 4/2010 | Chaires et al. ............. 436/71 |

FOREIGN PATENT DOCUMENTS

| | | |
|---|---|---|
| EP | 0810436 A1 | 12/1997 |
| WO | 8808534 A1 | 11/1988 |
| WO | 9212428 A1 | 7/1992 |
| WO | 9401775 A1 | 1/1994 |
| WO | 9516207 A1 | 6/1995 |
| WO | 9706439 A1 | 2/1997 |
| WO | 9836278 A1 | 8/1998 |
| WO | 02094864 A2 | 11/2002 |
| WO | 2004088324 A2 | 10/2004 |
| WO | 2005003351 A1 | 1/2005 |
| WO | 2005024429 A1 | 3/2005 |
| WO | 2005114190 A2 | 12/2005 |
| WO | 2005117937 A2 | 12/2005 |
| WO | 2006063009 A2 | 6/2006 |
| WO | 2007146385 A2 | 12/2007 |
| WO | 2008030273 A2 | 3/2008 |
| WO | 2008030546 A2 | 3/2008 |
| WO | 2008033890 A2 | 3/2008 |
| WO | 2008089072 A2 | 7/2008 |
| WO | 2008092214 A1 | 8/2008 |
| WO | WO 2008/092214 * | 8/2008 |
| WO | 2008141285 A9 | 11/2008 |

* cited by examiner

A2MG

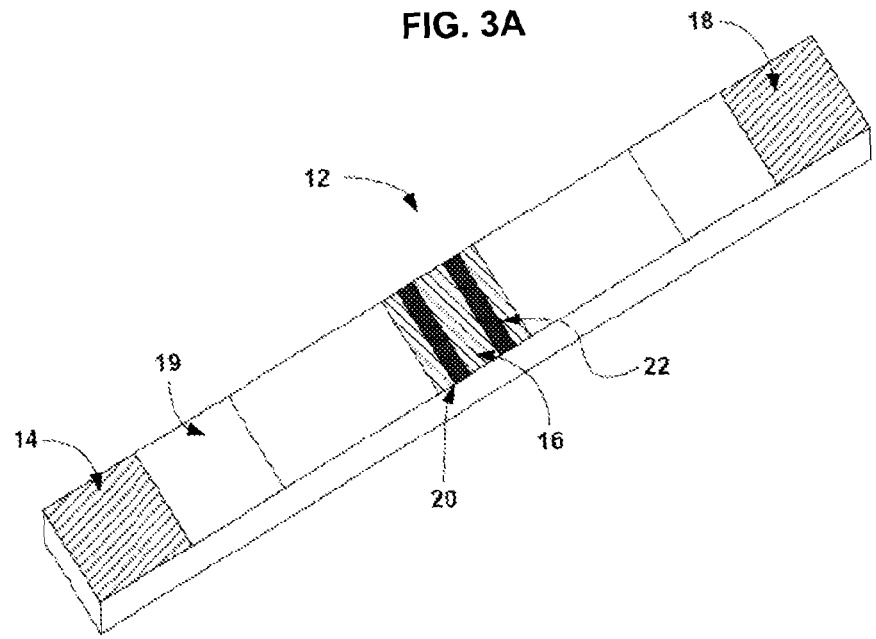
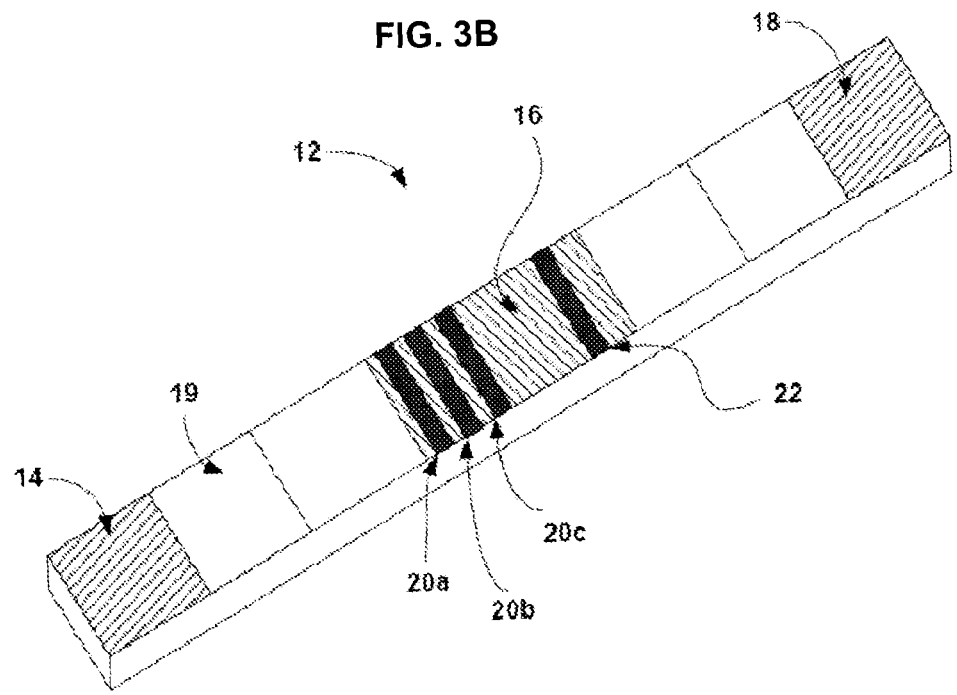

SEQUENCE LISTING

```
<160> NUMBER OF SEQ ID NOS: 67

<210> SEQ ID NO 1
<211> LENGTH: 256
<212> TYPE: PRT
<213> ORGANISM: Homo sapiens

<400> SEQUENCE: 1

Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
    130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
```

245 250 255

<210> SEQ ID NO 2
<211> LENGTH: 156
<212> TYPE: PRT
<213> ORGANISM: Homo sapiens

<400> SEQUENCE: 2

Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
            20                  25                  30

Ala Lys Lys Phe Gln Arg Gln His Met Asp Ser Asp Ser Ser Pro Ser
        35                  40                  45

Ser Ser Ser Thr Tyr Cys Asn Gln Met Met Arg Arg Arg Asn Met Thr
    50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155

<210> SEQ ID NO 3
<211> LENGTH: 911
<212> TYPE: PRT
<213> ORGANISM: Homo sapiens

<400> SEQUENCE: 3

Met Asp Gly Ala Met Gly Pro Arg Gly Leu Leu Leu Cys Met Tyr Leu
1               5                   10                  15

Val Ser Leu Leu Ile Leu Gln Ala Met Pro Ala Leu Gly Ser Ala Thr
            20                  25                  30

Gly Arg Ser Lys Ser Ser Glu Lys Arg Gln Ala Val Asp Thr Ala Val
        35                  40                  45

Asp Gly Val Phe Ile Arg Ser Leu Lys Val Asn Cys Lys Val Thr Ser
    50                  55                  60

Arg Phe Ala His Tyr Val Val Thr Ser Gln Val Val Asn Thr Ala Asn
65                  70                  75                  80

Glu Ala Arg Glu Val Ala Phe Asp Leu Glu Ile Pro Lys Thr Ala Phe
                85                  90                  95

Ile Ser Asp Phe Ala Val Thr Ala Asp Gly Asn Ala Phe Ile Gly Asp
            100                 105                 110

Ile Lys Asp Lys Val Thr Ala Trp Lys Gln Tyr Arg Lys Ala Ala Ile
        115                 120                 125

Ser Gly Glu Asn Ala Gly Leu Val Arg Ala Ser Gly Arg Thr Met Glu
    130                 135                 140

Gln Phe Thr Ile His Leu Thr Val Asn Pro Gln Ser Lys Val Thr Phe
145                 150                 155                 160

Gln Leu Thr Tyr Glu Glu Val Leu Lys Arg Asn His Met Gln Tyr Glu
                165                 170                 175

```
Ile Val Ile Lys Val Lys Pro Lys Gln Leu Val His His Phe Glu Ile
            180                 185                 190

Asp Val Asp Ile Phe Glu Pro Gln Gly Ile Ser Lys Leu Asp Ala Gln
            195                 200                 205

Ala Ser Phe Leu Pro Lys Glu Leu Ala Ala Gln Thr Ile Lys Lys Ser
210                 215                 220

Phe Ser Gly Lys Lys Gly His Val Leu Phe Arg Pro Thr Val Ser Gln
225                 230                 235                 240

Gln Gln Ser Cys Pro Thr Cys Ser Thr Ser Leu Leu Asn Gly His Phe
                245                 250                 255

Lys Val Thr Tyr Asp Val Ser Arg Asp Lys Ile Cys Asp Leu Leu Val
            260                 265                 270

Ala Asn Asn His Phe Ala His Phe Phe Ala Pro Gln Asn Leu Thr Asn
            275                 280                 285

Met Asn Lys Asn Val Val Phe Val Ile Asp Ile Ser Gly Ser Met Arg
            290                 295                 300

Gly Gln Lys Val Lys Gln Thr Lys Glu Ala Leu Leu Lys Ile Leu Gly
305                 310                 315                 320

Asp Met Gln Pro Gly Asp Tyr Phe Asp Leu Val Leu Phe Gly Thr Arg
                325                 330                 335

Val Gln Ser Trp Lys Gly Ser Leu Val Gln Ala Ser Glu Ala Asn Leu
            340                 345                 350

Gln Ala Ala Gln Asp Phe Val Arg Gly Phe Ser Leu Asp Glu Ala Thr
            355                 360                 365

Asn Leu Asn Gly Gly Leu Leu Arg Gly Ile Glu Ile Leu Asn Gln Val
            370                 375                 380

Gln Glu Ser Leu Pro Glu Leu Ser Asn His Ala Ser Ile Leu Ile Met
385                 390                 395                 400

Leu Thr Asp Gly Asp Pro Thr Glu Gly Val Thr Asp Arg Ser Gln Ile
                405                 410                 415

Leu Lys Asn Val Arg Asn Ala Ile Arg Gly Arg Phe Pro Leu Tyr Asn
            420                 425                 430

Leu Gly Phe Gly His Asn Val Asp Phe Asn Phe Leu Glu Val Met Ser
            435                 440                 445

Met Glu Asn Asn Gly Arg Ala Gln Arg Ile Tyr Glu Asp His Asp Ala
450                 455                 460

Thr Gln Gln Leu Gln Gly Phe Tyr Ser Gln Val Ala Lys Pro Leu Leu
465                 470                 475                 480

Val Asp Val Asp Leu Gln Tyr Pro Gln Asp Ala Val Leu Ala Leu Thr
                485                 490                 495

Gln Asn His His Lys Gln Tyr Tyr Glu Gly Ser Glu Ile Val Val Ala
            500                 505                 510

Gly Arg Ile Ala Asp Asn Lys Gln Ser Ser Phe Lys Ala Asp Val Gln
            515                 520                 525

Ala His Gly Glu Gly Gln Glu Phe Ser Ile Thr Cys Leu Val Asp Glu
            530                 535                 540

Glu Glu Met Lys Lys Leu Leu Arg Glu Arg Gly His Met Leu Glu Asn
545                 550                 555                 560

His Val Glu Arg Leu Trp Ala Tyr Leu Thr Ile Gln Glu Leu Leu Ala
                565                 570                 575

Lys Arg Met Lys Val Asp Arg Glu Glu Arg Ala Asn Leu Ser Ser Gln
            580                 585                 590

Ala Leu Gln Met Ser Leu Asp Tyr Gly Phe Val Thr Pro Leu Thr Ser
```

Met Ser Ile Arg Gly Met Ala Asp Gln Asp Gly Leu Lys Pro Thr Ile
            610                 615                 620

Asp Lys Pro Ser Glu Asp Ser Pro Leu Glu Met Leu Gly Pro Arg
625                 630                 635                 640

Arg Thr Phe Val Leu Ser Ala Leu Gln Pro Ser Pro Thr His Ser Ser
                645                 650                 655

Ser Asn Thr Gln Arg Leu Pro Asp Arg Val Thr Gly Val Asp Thr Asp
            660                 665                 670

Pro His Phe Ile Ile His Val Pro Gln Lys Glu Asp Thr Leu Cys Phe
            675                 680                 685

Asn Ile Asn Glu Glu Pro Gly Val Ile Leu Ser Leu Val Gln Asp Pro
690                 695                 700

Asn Thr Gly Phe Ser Val Asn Gly Gln Leu Ile Gly Asn Lys Ala Arg
705                 710                 715                 720

Ser Pro Gly Gln His Asp Gly Thr Tyr Phe Gly Arg Leu Gly Ile Ala
                725                 730                 735

Asn Pro Ala Thr Asp Phe Gln Leu Glu Val Thr Pro Gln Asn Ile Thr
            740                 745                 750

Leu Asn Pro Gly Phe Gly Gly Pro Val Phe Ser Trp Arg Asp Gln Ala
            755                 760                 765

Val Leu Arg Gln Asp Gly Val Val Thr Ile Asn Lys Lys Arg Asn
770                 775                 780

Leu Val Val Ser Val Asp Asp Gly Gly Thr Phe Glu Val Val Leu His
785                 790                 795                 800

Arg Val Trp Lys Gly Ser Ser Val His Gln Asp Phe Leu Gly Phe Tyr
                805                 810                 815

Val Leu Asp Ser His Arg Met Ser Ala Arg Thr His Gly Leu Leu Gly
            820                 825                 830

Gln Phe Phe His Pro Ile Gly Phe Glu Val Ser Asp Ile His Pro Gly
            835                 840                 845

Ser Asp Pro Thr Lys Pro Asp Ala Thr Met Val Val Arg Asn Arg Arg
850                 855                 860

Leu Thr Val Thr Arg Gly Leu Gln Lys Asp Tyr Ser Lys Asp Pro Trp
865                 870                 875                 880

His Gly Ala Glu Val Ser Cys Trp Phe Ile His Asn Asn Gly Ala Gly
                885                 890                 895

Leu Ile Asp Gly Ala Tyr Thr Asp Tyr Ile Val Pro Asp Ile Phe
            900                 905                 910

<210> SEQ ID NO 4
<211> LENGTH: 930
<212> TYPE: PRT
<213> ORGANISM: Homo sapiens

<400> SEQUENCE: 4

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
            20                  25                  30

Ile Asp Ile Tyr Ser Leu Thr Val Asp Ser Arg Val Ser Ser Arg Phe
            35                  40                  45

Ala His Thr Val Val Thr Ser Arg Val Val Asn Arg Ala Asn Thr Val
        50                  55                  60

Gln Glu Ala Thr Phe Gln Met Glu Leu Pro Lys Lys Ala Phe Ile Thr

```
                65                  70                  75                  80
Asn Phe Ser Met Asn Ile Asp Gly Met Thr Tyr Pro Gly Ile Ile Lys
                    85                  90                  95
Glu Lys Ala Glu Ala Gln Ala Gln Tyr Ser Ala Val Ala Lys Gly
            100                 105                 110
Lys Ser Ala Gly Leu Val Lys Ala Thr Gly Arg Asn Met Glu Gln Phe
        115                 120                 125
Gln Val Ser Val Ser Val Ala Pro Asn Ala Lys Ile Thr Phe Glu Leu
    130                 135                 140
Val Tyr Glu Glu Leu Leu Lys Arg Arg Leu Gly Val Tyr Glu Leu Leu
145                 150                 155                 160
Leu Lys Val Arg Pro Gln Gln Leu Val Lys His Leu Gln Met Asp Ile
                165                 170                 175
His Ile Phe Glu Pro Gln Gly Ile Ser Phe Leu Glu Thr Glu Ser Thr
            180                 185                 190
Phe Met Thr Asn Gln Leu Val Asp Ala Leu Thr Thr Trp Gln Asn Lys
        195                 200                 205
Thr Lys Ala His Ile Arg Phe Lys Pro Thr Leu Ser Gln Gln Gln Lys
    210                 215                 220
Ser Pro Glu Gln Gln Glu Thr Val Leu Asp Gly Asn Leu Ile Ile Arg
225                 230                 235                 240
Tyr Asp Val Asp Arg Ala Ile Ser Gly Gly Ser Ile Gln Ile Glu Asn
                245                 250                 255
Gly Tyr Phe Val His Tyr Phe Ala Pro Glu Gly Leu Thr Thr Met Pro
            260                 265                 270
Lys Asn Val Val Phe Val Ile Asp Lys Ser Gly Ser Met Ser Gly Arg
        275                 280                 285
Lys Ile Gln Gln Thr Arg Glu Ala Leu Ile Lys Ile Leu Asp Asp Leu
    290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
                325                 330                 335
Ala Arg Ser Phe Ala Ala Gly Ile Gln Ala Leu Gly Gly Thr Asn Ile
            340                 345                 350
Asn Asp Ala Met Leu Met Ala Val Gln Leu Leu Asp Ser Ser Asn Gln
        355                 360                 365
Glu Glu Arg Leu Pro Gly Gly Ser Val Ser Leu Ile Ile Leu Leu Thr
    370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
                405                 410                 415
Phe Gly Phe Asp Val Ser Tyr Ala Phe Leu Glu Lys Leu Ala Leu Asp
            420                 425                 430
Asn Gly Gly Leu Ala Arg Arg Ile His Glu Asp Ser Asp Ser Ala Leu
        435                 440                 445
Gln Leu Gln Asp Phe Tyr Gln Glu Val Ala Asn Pro Leu Leu Thr Ala
    450                 455                 460
Val Thr Phe Glu Tyr Pro Ser Asn Ala Val Glu Val Thr Gln Asn
465                 470                 475                 480
Asn Phe Arg Leu Leu Phe Lys Gly Ser Glu Met Val Val Ala Gly Lys
                485                 490                 495
```

```
Leu Gln Asp Arg Gly Pro Asp Val Leu Thr Ala Thr Val Ser Gly Lys
            500                 505                 510

Leu Pro Thr Gln Asn Ile Thr Phe Gln Thr Glu Ser Ser Val Ala Glu
            515                 520                 525

Gln Glu Ala Glu Phe Gln Ser Pro Lys Tyr Ile Phe His Asn Phe Met
        530                 535                 540

Glu Arg Leu Trp Ala Tyr Leu Thr Ile Gln Gln Leu Leu Glu Gln Thr
545                 550                 555                 560

Val Ser Ala Ser Asp Ala Asp Gln Gln Ala Leu Arg Asn Gln Ala Leu
                565                 570                 575

Asn Leu Ser Leu Ala Tyr Ser Phe Val Thr Pro Leu Thr Ser Met Val
            580                 585                 590

Val Thr Lys Pro Asp Asp Gln Glu Gln Ser Gln Val Ala Glu Lys Pro
        595                 600                 605

Met Glu Gly Glu Ser Arg Asn Arg Asn Val His Ser Gly Ser Thr Phe
        610                 615                 620

Phe Lys Tyr Tyr Leu Gln Gly Ala Lys Ile Pro Lys Pro Glu Ala Ser
625                 630                 635                 640

Phe Ser Pro Arg Arg Gly Trp Asn Arg Gln Ala Gly Ala Ala Gly Ser
            645                 650                 655

Arg Met Asn Phe Arg Pro Gly Val Leu Ser Ser Arg Leu Leu Gly Leu
            660                 665                 670

Pro Gly Pro Pro Asp Val Pro Asp His Ala Ala Tyr His Pro Phe Arg
            675                 680                 685

Arg Leu Ala Ile Leu Pro Ala Ser Ala Pro Pro Ala Thr Ser Asn Pro
        690                 695                 700

Asp Pro Ala Val Ser Arg Val Met Asn Ile Lys Ile Glu Glu Thr Thr
705                 710                 715                 720

Met Thr Thr Gln Thr Pro Ala Pro Ile Gln Ala Pro Ser Ala Ile Leu
                725                 730                 735

Pro Leu Pro Gly Gln Ser Val Glu Arg Leu Cys Val Asp Pro Arg His
            740                 745                 750

Arg Gln Gly Pro Val Asn Leu Leu Ser Asp Pro Glu Gln Gly Val Glu
        755                 760                 765

Val Thr Gly Gln Tyr Glu Arg Glu Lys Ala Gly Phe Ser Trp Ile Glu
        770                 775                 780

Val Thr Phe Lys Asn Pro Leu Val Trp Val His Ala Ser Pro Glu His
785                 790                 795                 800

Val Val Val Thr Arg Asn Arg Arg Ser Ser Ala Tyr Lys Trp Lys Glu
                805                 810                 815

Thr Leu Phe Ser Val Met Pro Gly Leu Lys Met Thr Met Asp Lys Thr
            820                 825                 830

Gly Leu Leu Leu Leu Ser Asp Pro Asp Lys Val Thr Ile Gly Leu Leu
        835                 840                 845

Phe Trp Asp Gly Arg Gly Glu Gly Leu Arg Leu Leu Leu Arg Asp Thr
        850                 855                 860

Asp Arg Phe Ser Ser His Val Gly Gly Thr Leu Gly Gln Phe Tyr Gln
865                 870                 875                 880

Glu Val Leu Trp Gly Ser Pro Ala Ala Ser Asp Asp Gly Arg Arg Thr
                885                 890                 895

Leu Arg Val Gln Gly Asn Asp His Ser Ala Thr Arg Glu Arg Arg Leu
            900                 905                 910

Asp Tyr Gln Glu Gly Pro Pro Gly Val Glu Ile Ser Cys Trp Ser Val
            915                 920                 925
```

Glu Leu
    930

<210> SEQ ID NO 5
<211> LENGTH: 420
<212> TYPE: PRT
<213> ORGANISM: Homo sapiens

<400> SEQUENCE: 5

Met Arg Trp Arg Thr Ile Leu Leu Gln Tyr Cys Phe Leu Leu Ile Thr
1               5                   10                  15

Cys Leu Leu Thr Ala Leu Glu Ala Val Pro Ile Asp Ile Asp Lys Thr
            20                  25                  30

Lys Val Gln Asn Ile His Pro Val Glu Ser Ala Lys Ile Glu Pro Pro
        35                  40                  45

Asp Thr Gly Leu Tyr Tyr Asp Glu Tyr Leu Lys Gln Val Ile Asp Val
    50                  55                  60

Leu Glu Thr Asp Lys His Phe Arg Glu Lys Leu Gln Lys Ala Asp Ile
65                  70                  75                  80

Glu Glu Ile Lys Ser Gly Arg Leu Ser Lys Glu Leu Asp Leu Val Ser
                85                  90                  95

His His Val Arg Thr Lys Leu Asp Glu Leu Lys Arg Gln Glu Val Gly
            100                 105                 110

Arg Leu Arg Met Leu Ile Lys Ala Lys Leu Asp Ser Leu Gln Asp Ile
        115                 120                 125

Gly Met Asp His Gln Ala Leu Leu Lys Gln Phe Asp His Leu Asn His
    130                 135                 140

Leu Asn Pro Asp Lys Phe Glu Ser Thr Asp Leu Asp Met Leu Ile Lys
145                 150                 155                 160

Ala Ala Thr Ser Asp Leu Glu His Tyr Asp Lys Thr Arg His Glu Glu
                165                 170                 175

Phe Lys Lys Tyr Glu Met Met Lys Glu His Glu Arg Arg Glu Tyr Leu
            180                 185                 190

Lys Thr Leu Asn Glu Glu Lys Arg Lys Glu Glu Ser Lys Phe Glu
        195                 200                 205

Glu Met Lys Lys Lys His Glu Asn His Pro Lys Val Asn His Pro Gly
    210                 215                 220

Ser Lys Asp Gln Leu Lys Glu Val Trp Glu Glu Thr Asp Gly Leu Asp
225                 230                 235                 240

Pro Asn Asp Phe Asp Pro Lys Thr Phe Lys Leu His Asp Val Asn
                245                 250                 255

Ser Asp Gly Phe Leu Asp Glu Gln Glu Leu Glu Ala Leu Phe Thr Lys
            260                 265                 270

Glu Leu Glu Lys Val Tyr Asp Pro Lys Asn Glu Glu Asp Asp Met Val
        275                 280                 285

Glu Met Glu Glu Glu Arg Leu Arg Met Arg Glu His Val Met Asn Glu
    290                 295                 300

Val Asp Thr Asn Lys Asp Arg Leu Val Thr Leu Glu Glu Phe Leu Lys
305                 310                 315                 320

Ala Thr Glu Lys Lys Glu Phe Leu Glu Pro Asp Ser Trp Glu Thr Leu
                325                 330                 335

Asp Gln Gln Gln Phe Phe Thr Glu Glu Leu Lys Glu Tyr Glu Asn
            340                 345                 350

Ile Ile Ala Leu Gln Glu Asn Glu Leu Lys Lys Lys Ala Asp Glu Leu
        355                 360                 365

```
Gln Lys Gln Lys Glu Leu Gln Arg Gln His Asp Gln Leu Glu Ala
    370                 375                 380

Gln Lys Leu Glu Tyr His Gln Val Ile Gln Met Glu Gln Lys Lys
385                 390                 395                 400

Leu Gln Gln Gly Ile Pro Pro Ser Gly Pro Ala Gly Glu Leu Lys Phe
                405                 410                 415

Glu Pro His Ile
            420

<210> SEQ ID NO 6
<211> LENGTH: 577
<212> TYPE: PRT
<213> ORGANISM: Homo sapiens

<400> SEQUENCE: 6

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320
```

Ala Met Leu Glu Asn Glu Lys Lys Arg Glu Met Ala Lys Glu
            325                 330                 335

Lys Glu Lys Ile Glu Arg Glu Lys Glu Glu Leu Met Glu Arg Leu Lys
            340                 345                 350

Gln Ile Glu Glu Gln Thr Lys Lys Ala Gln Gln Glu Leu Glu Glu Gln
            355                 360                 365

Thr Arg Arg Ala Leu Glu Leu Glu Gln Glu Arg Lys Arg Ala Gln Ser
370                 375                 380

Glu Ala Glu Lys Leu Ala Lys Glu Arg Gln Glu Ala Glu Glu Ala Lys
385                 390                 395                 400

Glu Ala Leu Leu Gln Ala Ser Arg Asp Gln Lys Lys Thr Gln Glu Gln
            405                 410                 415

Leu Ala Leu Glu Met Ala Glu Leu Thr Ala Arg Ile Ser Gln Leu Glu
            420                 425                 430

Met Ala Arg Gln Lys Lys Glu Ser Glu Ala Val Glu Trp Gln Gln Lys
            435                 440                 445

Ala Gln Met Val Gln Glu Asp Leu Glu Lys Thr Arg Ala Glu Leu Lys
450                 455                 460

Thr Ala Met Ser Thr Pro His Val Ala Glu Pro Ala Glu Asn Glu Gln
465                 470                 475                 480

Asp Glu Gln Asp Glu Asn Gly Ala Glu Ala Ser Ala Asp Leu Arg Ala
            485                 490                 495

Asp Ala Met Ala Lys Asp Arg Ser Glu Glu Glu Arg Thr Thr Glu Ala
            500                 505                 510

Glu Lys Asn Glu Arg Val Gln Lys His Leu Lys Ala Leu Thr Ser Glu
            515                 520                 525

Leu Ala Asn Ala Arg Asp Glu Ser Lys Lys Thr Ala Asn Asp Met Ile
            530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
            565                 570                 575

Met

<210> SEQ ID NO 7
<211> LENGTH: 255
<212> TYPE: PRT
<213> ORGANISM: Homo sapiens

<400> SEQUENCE: 7

Met Asp Asp Arg Glu Asp Leu Val Tyr Gln Ala Lys Leu Ala Glu Gln
1               5                   10                  15

Ala Glu Arg Tyr Asp Glu Met Val Glu Ser Met Lys Lys Val Ala Gly
            20                  25                  30

Met Asp Val Glu Leu Thr Val Glu Glu Arg Asn Leu Leu Ser Val Ala
            35                  40                  45

Tyr Lys Asn Val Ile Gly Ala Arg Arg Ala Ser Trp Arg Ile Ile Ser
        50                  55                  60

Ser Ile Glu Gln Lys Glu Glu Asn Lys Gly Gly Glu Asp Lys Leu Lys
65                  70                  75                  80

Met Ile Arg Glu Tyr Arg Gln Met Val Glu Thr Glu Leu Lys Leu Ile
            85                  90                  95

Cys Cys Asp Ile Leu Asp Val Leu Asp Lys His Leu Ile Pro Ala Ala
            100                 105                 110

```
Asn Thr Gly Glu Ser Lys Val Phe Tyr Tyr Lys Met Lys Gly Asp Tyr
            115                 120                 125

His Arg Tyr Leu Ala Glu Phe Ala Thr Gly Asn Asp Arg Lys Glu Ala
130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
            195                 200                 205

Leu Ser Glu Glu Ser Tyr Lys Asp Ser Thr Leu Ile Met Gln Leu Leu
        210                 215                 220

Arg Asp Asn Leu Thr Leu Trp Thr Ser Asp Met Gln Gly Asp Gly Glu
225                 230                 235                 240

Glu Gln Asn Lys Glu Ala Leu Gln Asp Val Asp Glu Asn Gln
                245                 250                 255

<210> SEQ ID NO 8
<211> LENGTH: 98
<212> TYPE: PRT
<213> ORGANISM: Homo sapiens

<400> SEQUENCE: 8

Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 9
<211> LENGTH: 323
<212> TYPE: PRT
<213> ORGANISM: Homo sapiens

<400> SEQUENCE: 9

Met Ala Ser Ile Trp Val Gly His Arg Gly Thr Val Arg Asp Tyr Pro
1               5                   10                  15

Asp Phe Ser Pro Ser Val Asp Ala Glu Ala Ile Gln Lys Ala Ile Arg
            20                  25                  30

Gly Ile Gly Thr Asp Glu Lys Met Leu Ile Ser Ile Leu Thr Glu Arg
        35                  40                  45

Ser Asn Ala Gln Arg Gln Leu Ile Val Lys Glu Tyr Gln Ala Ala Tyr
    50                  55                  60

Gly Lys Glu Leu Lys Asp Asp Leu Lys Gly Asp Leu Ser Gly His Phe
65                  70                  75                  80

Glu His Leu Met Val Ala Leu Val Thr Pro Pro Ala Val Phe Asp Ala
                85                  90                  95
```

Lys Gln Leu Lys Lys Ser Met Lys Gly Ala Gly Thr Asn Glu Asp Ala
                100                 105                 110

Leu Ile Glu Ile Leu Thr Thr Arg Thr Ser Arg Gln Met Lys Asp Ile
            115                 120                 125

Ser Gln Ala Tyr Tyr Thr Val Tyr Lys Lys Ser Leu Gly Asp Asp Ile
    130                 135                 140

Ser Ser Glu Thr Ser Gly Asp Phe Arg Lys Ala Leu Leu Thr Leu Ala
145                 150                 155                 160

Asp Gly Arg Arg Asp Glu Ser Leu Lys Val Asp Glu His Leu Ala Lys
                165                 170                 175

Gln Asp Ala Gln Ile Leu Tyr Lys Ala Gly Glu Asn Arg Trp Gly Thr
            180                 185                 190

Asp Glu Asp Lys Phe Thr Glu Ile Leu Cys Leu Arg Ser Phe Pro Gln
    195                 200                 205

Leu Lys Leu Thr Phe Asp Glu Tyr Arg Asn Ile Ser Gln Lys Asp Ile
            210                 215                 220

Val Asp Ser Ile Lys Gly Glu Leu Ser Gly His Phe Glu Asp Leu Leu
225                 230                 235                 240

Leu Ala Ile Val Asn Cys Val Arg Asn Thr Pro Ala Phe Leu Ala Glu
                245                 250                 255

Arg Leu His Arg Ala Leu Lys Gly Ile Gly Thr Asp Glu Phe Thr Leu
            260                 265                 270

Asn Arg Ile Met Val Ser Arg Ser Glu Ile Asp Leu Leu Asp Ile Arg
    275                 280                 285

Thr Glu Phe Lys Lys His Tyr Gly Tyr Ser Leu Tyr Ser Ala Ile Lys
            290                 295                 300

Ser Asp Thr Ser Gly Asp Tyr Glu Ile Thr Leu Leu Lys Ile Cys Gly
305                 310                 315                 320

Gly Asp Asp

<210> SEQ ID NO 10
<211> LENGTH: 101
<212> TYPE: PRT
<213> ORGANISM: Homo sapiens

<400> SEQUENCE: 10

Met Ser Asn Thr Gln Ala Glu Arg Ser Ile Gly Met Ile Asp Met
1               5                   10                  15

Phe His Lys Tyr Thr Arg Arg Asp Asp Lys Ile Glu Lys Pro Ser Leu
                20                  25                  30

Leu Thr Met Met Lys Glu Asn Phe Pro Asn Phe Leu Ser Ala Cys Asp
            35                  40                  45

Lys Lys Gly Thr Asn Tyr Leu Ala Asp Val Phe Glu Lys Lys Asp Lys
    50                  55                  60

Asn Glu Asp Lys Lys Ile Asp Phe Ser Glu Phe Leu Ser Leu Leu Gly
65                  70                  75                  80

Asp Ile Ala Thr Asp Tyr His Lys Gln Ser His Gly Ala Ala Pro Cys
                85                  90                  95

Ser Gly Gly Ser Gln
            100

<210> SEQ ID NO 11
<211> LENGTH: 417
<212> TYPE: PRT
<213> ORGANISM: Homo sapiens -continued

<400> SEQUENCE: 11

```
Met Ser Leu Ser Asn Lys Leu Thr Leu Asp Lys Leu Asp Val Lys Gly
1               5                   10                  15

Lys Arg Val Val Met Arg Val Asp Phe Asn Val Pro Met Lys Asn Asn
            20                  25                  30

Gln Ile Thr Asn Asn Gln Arg Ile Lys Ala Ala Val Pro Ser Ile Lys
        35                  40                  45

Phe Cys Leu Asp Asn Gly Ala Lys Ser Val Val Leu Met Ser His Leu
50                  55                  60

Gly Arg Pro Asp Gly Val Pro Met Pro Asp Lys Tyr Ser Leu Glu Pro
65                  70                  75                  80

Val Ala Val Glu Leu Lys Ser Leu Leu Gly Lys Asp Val Leu Phe Leu
                85                  90                  95

Lys Asp Cys Val Gly Pro Glu Val Glu Lys Ala Cys Ala Asn Pro Ala
            100                 105                 110

Ala Gly Ser Val Ile Leu Leu Glu Asn Leu Arg Phe His Val Glu Glu
        115                 120                 125

Glu Gly Lys Gly Lys Asp Ala Ser Gly Asn Lys Val Lys Ala Glu Pro
130                 135                 140

Ala Lys Ile Glu Ala Phe Arg Ala Ser Leu Ser Lys Leu Gly Asp Val
145                 150                 155                 160

Tyr Val Asn Asp Ala Phe Gly Thr Ala His Arg Ala His Ser Ser Met
                165                 170                 175

Val Gly Val Asn Leu Pro Gln Lys Ala Gly Gly Phe Leu Met Lys Lys
            180                 185                 190

Glu Leu Asn Tyr Phe Ala Lys Ala Leu Glu Ser Pro Glu Arg Pro Phe
        195                 200                 205

Leu Ala Ile Leu Gly Gly Ala Lys Val Ala Asp Lys Ile Gln Leu Ile
210                 215                 220

Asn Asn Met Leu Asp Lys Val Asn Glu Met Ile Ile Gly Gly Gly Met
225                 230                 235                 240

Ala Phe Thr Phe Leu Lys Val Leu Asn Asn Met Glu Ile Gly Thr Ser
                245                 250                 255

Leu Phe Asp Glu Glu Gly Ala Lys Ile Val Lys Asp Leu Met Ser Lys
            260                 265                 270

Ala Glu Lys Asn Gly Val Lys Ile Thr Leu Pro Val Asp Phe Val Thr
        275                 280                 285

Ala Asp Lys Phe Asp Glu Asn Ala Lys Thr Gly Gln Ala Thr Val Ala
290                 295                 300

Ser Gly Ile Pro Ala Gly Trp Met Gly Leu Asp Cys Gly Pro Glu Ser
305                 310                 315                 320

Ser Lys Lys Tyr Ala Glu Ala Val Thr Arg Ala Lys Gln Ile Val Trp
                325                 330                 335

Asn Gly Pro Val Gly Val Phe Glu Trp Glu Ala Phe Ala Arg Gly Thr
            340                 345                 350

Lys Ala Leu Met Asp Glu Val Val Lys Ala Thr Ser Arg Gly Cys Ile
        355                 360                 365

Thr Ile Ile Gly Gly Gly Asp Thr Ala Thr Cys Cys Ala Lys Trp Asn
370                 375                 380

Thr Glu Asp Lys Val Ser His Val Ser Thr Gly Gly Gly Ala Ser Leu
385                 390                 395                 400

Glu Leu Leu Glu Gly Lys Val Leu Pro Gly Val Asp Ala Leu Ser Asn
                405                 410                 415
```

Ile

<210> SEQ ID NO 12
<211> LENGTH: 346
<212> TYPE: PRT
<213> ORGANISM: Homo sapiens

<400> SEQUENCE: 12

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 13
<211> LENGTH: 284
<212> TYPE: PRT

<213> ORGANISM: Homo sapiens

<400> SEQUENCE: 13

Met Glu Ala Ile Lys Lys Met Gln Met Leu Lys Leu Asp Lys Glu
1               5                   10                  15

Asn Ala Ile Asp Arg Ala Glu Gln Ala Glu Ala Asp Lys Lys Ala Ala
                20                  25                  30

Glu Asp Lys Cys Lys Gln Val Glu Glu Glu Leu Thr His Leu Gln Lys
                35                  40                  45

Lys Leu Lys Gly Thr Glu Asp Glu Leu Asp Lys Tyr Ser Glu Asp Leu
        50                  55                  60

Lys Asp Ala Gln Glu Lys Leu Glu Leu Thr Glu Lys Lys Ala Ser Asp
65                  70                  75                  80

Ala Glu Gly Asp Val Ala Ala Leu Asn Arg Arg Ile Gln Leu Val Glu
                    85                  90                  95

Glu Glu Leu Asp Arg Ala Gln Glu Arg Leu Ala Thr Ala Leu Gln Lys
                100                 105                 110

Leu Glu Glu Ala Glu Lys Ala Ala Asp Glu Ser Glu Arg Gly Met Lys
            115                 120                 125

Val Ile Glu Asn Arg Ala Met Lys Asp Glu Glu Lys Met Glu Ile Gln
130                 135                 140

Glu Met Gln Leu Lys Glu Ala Lys His Ile Ala Glu Glu Ala Asp Arg
145                 150                 155                 160

Lys Tyr Glu Glu Val Ala Arg Lys Leu Val Ile Leu Glu Gly Glu Leu
                165                 170                 175

Glu Arg Ala Glu Glu Arg Ala Glu Val Ser Glu Leu Lys Cys Gly Asp
            180                 185                 190

Leu Glu Glu Glu Leu Lys Asn Val Thr Asn Asn Leu Lys Ser Leu Glu
        195                 200                 205

Ala Ser Glu Glu Lys Tyr Ser Glu Lys Glu Asp Lys Tyr Glu Glu Glu
    210                 215                 220

Ile Lys Leu Leu Ser Asp Lys Leu Lys Glu Ala Glu Thr Arg Ala Glu
225                 230                 235                 240

Phe Ala Glu Arg Thr Val Ala Lys Leu Glu Lys Thr Ile Asp Asp Leu
                245                 250                 255

Glu Glu Lys Leu Ala Gln Ala Lys Glu Glu Asn Val Gly Leu His Gln
            260                 265                 270

Thr Leu Asp Gln Thr Leu Asn Glu Leu Asn Cys Ile
        275                 280

<210> SEQ ID NO 14
<211> LENGTH: 276
<212> TYPE: PRT
<213> ORGANISM: Homo sapiens

<400> SEQUENCE: 14

Met Arg Ala Pro His Leu His Leu Ser Ala Ala Ser Gly Ala Arg Ala
1               5                   10                  15

Leu Ala Lys Leu Leu Pro Leu Leu Met Ala Gln Leu Trp Ala Ala Glu
                20                  25                  30

Ala Ala Leu Leu Pro Gln Asn Asp Thr Arg Leu Asp Pro Glu Ala Tyr
            35                  40                  45

Gly Ala Pro Cys Ala Arg Gly Ser Gln Pro Trp Gln Val Ser Leu Phe
        50                  55                  60

Asn Gly Leu Ser Phe His Cys Ala Gly Val Leu Val Asp Gln Ser Trp
65                  70                  75                  80

```
Val Leu Thr Ala Ala His Cys Gly Asn Lys Pro Leu Trp Ala Arg Val
                85                  90                  95

Gly Asp Asp His Leu Leu Leu Gln Gly Glu Gln Leu Arg Arg Thr
            100                 105                 110

Thr Arg Ser Val Val His Pro Lys Tyr His Gln Gly Ser Gly Pro Ile
            115                 120                 125

Leu Pro Arg Arg Thr Asp Glu His Asp Leu Met Leu Leu Lys Leu Ala
130                 135                 140

Arg Pro Val Val Pro Gly Pro Arg Val Arg Ala Leu Gln Leu Pro Tyr
145                 150                 155                 160

Arg Cys Ala Gln Pro Gly Asp Gln Cys Gln Val Ala Gly Trp Gly Thr
                165                 170                 175

Thr Ala Ala Arg Arg Val Lys Tyr Asn Lys Gly Leu Thr Cys Ser Ser
            180                 185                 190

Ile Thr Ile Leu Ser Pro Lys Glu Cys Glu Val Phe Tyr Pro Gly Val
            195                 200                 205

Val Thr Asn Asn Met Ile Cys Ala Gly Leu Asp Arg Gly Gln Asp Pro
210                 215                 220

Cys Gln Ser Asp Ser Gly Gly Pro Leu Val Cys Asp Glu Thr Leu Gln
225                 230                 235                 240

Gly Ile Leu Ser Trp Gly Val Tyr Pro Cys Gly Ser Ala Gln His Pro
                245                 250                 255

Ala Val Tyr Thr Gln Ile Cys Lys Tyr Met Ser Trp Ile Asn Lys Val
            260                 265                 270

Ile Arg Ser Asn
            275

<210> SEQ ID NO 15
<211> LENGTH: 2871
<212> TYPE: PRT
<213> ORGANISM: Homo sapiens

<400> SEQUENCE: 15

Met Ser Cys Asn Gly Gly Ser His Pro Arg Ile Asn Thr Leu Gly Arg
1               5                   10                  15

Met Ile Arg Ala Glu Ser Gly Pro Asp Leu Arg Tyr Glu Val Thr Ser
            20                  25                  30

Gly Gly Gly Gly Thr Ser Arg Met Tyr Tyr Ser Arg Arg Gly Val Ile
        35                  40                  45

Thr Asp Gln Asn Ser Asp Gly Tyr Cys Gln Thr Gly Thr Met Ser Arg
50                  55                  60

His Gln Asn Gln Asn Thr Ile Gln Glu Leu Leu Gln Asn Cys Ser Asp
65                  70                  75                  80

Cys Leu Met Arg Ala Glu Leu Ile Val Gln Pro Glu Leu Lys Tyr Gly
                85                  90                  95

Asp Gly Ile Gln Leu Thr Arg Ser Arg Glu Leu Asp Glu Cys Phe Ala
            100                 105                 110

Gln Ala Asn Asp Gln Met Glu Ile Leu Asp Ser Leu Ile Arg Glu Met
            115                 120                 125

Arg Gln Met Gly Gln Pro Cys Asp Ala Tyr Gln Lys Arg Leu Leu Gln
130                 135                 140

Leu Gln Glu Gln Met Arg Ala Leu Tyr Lys Ala Ile Ser Val Pro Arg
145                 150                 155                 160

Val Arg Arg Ala Ser Ser Lys Gly Gly Gly Gly Tyr Thr Cys Gln Ser
                165                 170                 175
```

```
Gly Ser Gly Trp Asp Glu Phe Thr Lys His Val Thr Ser Glu Cys Leu
            180                 185                 190
Gly Trp Met Arg Gln Gln Arg Ala Glu Met Asp Met Val Ala Trp Gly
            195                 200                 205
Val Asp Leu Ala Ser Val Glu Gln His Ile Asn Ser His Arg Gly Ile
210                 215                 220
His Asn Ser Ile Gly Asp Tyr Arg Trp Gln Leu Asp Lys Ile Lys Ala
225                 230                 235                 240
Asp Leu Arg Glu Lys Ser Ala Ile Tyr Gln Leu Glu Glu Tyr Glu
            245                 250                 255
Asn Leu Leu Lys Ala Ser Phe Glu Arg Met Asp His Leu Arg Gln Leu
            260                 265                 270
Gln Asn Ile Ile Gln Ala Thr Ser Arg Glu Ile Met Trp Ile Asn Asp
            275                 280                 285
Cys Glu Glu Glu Glu Leu Leu Tyr Asp Trp Ser Asp Lys Asn Thr Asn
            290                 295                 300
Ile Ala Gln Lys Gln Glu Ala Phe Ser Ile Arg Met Ser Gln Leu Glu
305                 310                 315                 320
Val Lys Glu Lys Glu Leu Asn Lys Leu Lys Gln Glu Ser Asp Gln Leu
            325                 330                 335
Val Leu Asn Gln His Pro Ala Ser Asp Lys Ile Glu Ala Tyr Met Asp
            340                 345                 350
Thr Leu Gln Thr Gln Trp Ser Trp Ile Leu Gln Ile Thr Lys Cys Ile
            355                 360                 365
Asp Val His Leu Lys Glu Asn Ala Ala Tyr Phe Gln Phe Phe Glu Glu
            370                 375                 380
Ala Gln Ser Thr Glu Ala Tyr Leu Lys Gly Leu Gln Asp Ser Ile Arg
385                 390                 395                 400
Lys Lys Tyr Pro Cys Asp Lys Asn Met Pro Leu Gln His Leu Leu Glu
            405                 410                 415
Gln Ile Lys Glu Leu Glu Lys Glu Arg Glu Lys Ile Leu Glu Tyr Lys
            420                 425                 430
Arg Gln Val Gln Asn Leu Val Asn Lys Ser Lys Lys Ile Val Gln Leu
            435                 440                 445
Lys Pro Arg Asn Pro Asp Tyr Arg Ser Asn Lys Pro Ile Ile Leu Arg
450                 455                 460
Ala Leu Cys Asp Tyr Lys Gln Asp Gln Lys Ile Val His Lys Gly Asp
465                 470                 475                 480
Glu Cys Ile Leu Lys Asp Asn Asn Glu Arg Ser Lys Trp Tyr Val Thr
            485                 490                 495
Gly Pro Gly Gly Val Asp Met Leu Val Pro Ser Val Gly Leu Ile Ile
            500                 505                 510
Pro Pro Pro Asn Pro Leu Ala Val Asp Leu Ser Cys Lys Ile Glu Gln
            515                 520                 525
Tyr Tyr Glu Ala Ile Leu Ala Leu Trp Asn Gln Leu Tyr Ile Asn Met
            530                 535                 540
Lys Ser Leu Val Ser Trp His Tyr Cys Met Ile Asp Ile Glu Lys Ile
545                 550                 555                 560
Arg Ala Met Thr Ile Ala Lys Leu Lys Thr Met Arg Gln Glu Asp Tyr
            565                 570                 575
Met Lys Thr Ile Ala Asp Leu Glu Leu His Tyr Gln Glu Phe Ile Arg
            580                 585                 590
Asn Ser Gln Gly Ser Glu Met Phe Gly Asp Asp Asp Lys Arg Lys Ile
```

```
                595                 600                 605
Gln Ser Gln Phe Thr Asp Ala Gln Lys His Tyr Gln Thr Leu Val Ile
610                 615                 620

Gln Leu Pro Gly Tyr Pro Gln His Gln Thr Val Thr Thr Thr Glu Ile
625                 630                 635                 640

Thr His His Gly Thr Cys Gln Asp Val Asn His Asn Lys Val Ile Glu
                    645                 650                 655

Thr Asn Arg Glu Asn Asp Lys Gln Glu Thr Trp Met Leu Met Glu Leu
            660                 665                 670

Gln Lys Ile Arg Arg Gln Ile Glu His Cys Glu Gly Arg Met Thr Leu
        675                 680                 685

Lys Asn Leu Pro Leu Ala Asp Gln Gly Ser Ser His His Ile Thr Val
690                 695                 700

Lys Ile Asn Glu Leu Lys Ser Val Gln Asn Asp Ser Gln Ala Ile Ala
705                 710                 715                 720

Glu Val Leu Asn Gln Leu Lys Asp Met Leu Ala Asn Phe Arg Gly Ser
                725                 730                 735

Glu Lys Tyr Cys Tyr Leu Gln Asn Glu Val Phe Gly Leu Phe Gln Lys
            740                 745                 750

Leu Glu Asn Ile Asn Gly Val Thr Asp Gly Tyr Leu Asn Ser Leu Cys
        755                 760                 765

Thr Val Arg Ala Leu Leu Gln Ala Ile Leu Gln Thr Glu Asp Met Leu
770                 775                 780

Lys Val Tyr Glu Ala Arg Leu Thr Glu Glu Thr Val Cys Leu Asp
785                 790                 795                 800

Leu Asp Lys Val Glu Ala Tyr Arg Cys Gly Leu Lys Lys Ile Lys Asn
                805                 810                 815

Asp Leu Asn Leu Lys Lys Ser Leu Leu Ala Thr Met Lys Thr Glu Leu
            820                 825                 830

Gln Lys Ala Gln Gln Ile His Ser Gln Thr Ser Gln Gln Tyr Pro Leu
        835                 840                 845

Tyr Asp Leu Asp Leu Gly Lys Phe Gly Glu Lys Val Thr Gln Leu Thr
850                 855                 860

Asp Arg Trp Gln Arg Ile Asp Lys Gln Ile Asp Phe Arg Leu Trp Asp
865                 870                 875                 880

Leu Glu Lys Gln Ile Lys Gln Leu Arg Asn Tyr Arg Asp Asn Tyr Gln
                885                 890                 895

Ala Phe Cys Lys Trp Leu Tyr Asp Ala Lys Arg Arg Gln Asp Ser Leu
            900                 905                 910

Glu Ser Met Lys Phe Gly Asp Ser Asn Thr Val Met Arg Phe Leu Asn
        915                 920                 925

Glu Gln Lys Asn Leu His Ser Glu Ile Ser Gly Lys Arg Asp Lys Ser
930                 935                 940

Glu Glu Val Gln Lys Ile Ala Glu Leu Cys Ala Asn Ser Ile Lys Asp
945                 950                 955                 960

Tyr Glu Leu Gln Leu Ala Ser Tyr Thr Ser Gly Leu Glu Thr Leu Leu
                965                 970                 975

Asn Ile Pro Ile Lys Arg Thr Met Ile Gln Ser Pro Ser Gly Val Ile
            980                 985                 990

Leu Gln Glu Ala Ala Asp Val His  Ala Arg Tyr Ile Glu  Leu Leu Thr
         995                 1000                1005

Arg Ser Gly Asp Tyr Tyr Arg  Phe Leu Ser Glu Met  Leu Lys Ser
   1010                1015                1020
```

-continued

```
Leu Glu Asp Leu Lys Leu Lys Asn Thr Lys Ile Glu Val Leu Glu
    1025                1030                1035

Glu Glu Leu Arg Leu Ala Arg Asp Ala Asn Ser Glu Asn Cys Asn
    1040                1045                1050

Lys Asn Lys Phe Leu Asp Gln Asn Leu Gln Lys Tyr Gln Ala Glu
    1055                1060                1065

Cys Ser Gln Phe Lys Ala Lys Leu Ala Ser Leu Glu Glu Leu Lys
    1070                1075                1080

Arg Gln Ala Glu Leu Asp Gly Lys Ser Ala Lys Gln Asn Leu Asp
    1085                1090                1095

Lys Cys Tyr Gly Gln Ile Lys Glu Leu Asn Glu Lys Ile Thr Arg
    1100                1105                1110

Leu Thr Tyr Glu Ile Glu Asp Glu Lys Arg Arg Arg Lys Ser Val
    1115                1120                1125

Glu Asp Arg Phe Asp Gln Gln Lys Asn Asp Tyr Asp Gln Leu Gln
    1130                1135                1140

Lys Ala Arg Gln Cys Glu Lys Glu Asn Leu Gly Trp Gln Lys Leu
    1145                1150                1155

Glu Ser Glu Lys Ala Ile Lys Glu Lys Glu Tyr Glu Ile Glu Arg
    1160                1165                1170

Leu Arg Val Leu Leu Gln Glu Glu Gly Thr Arg Lys Arg Glu Tyr
    1175                1180                1185

Glu Asn Glu Leu Ala Lys Val Arg Asn His Tyr Asn Glu Glu Met
    1190                1195                1200

Ser Asn Leu Arg Asn Lys Tyr Glu Thr Glu Ile Asn Ile Thr Lys
    1205                1210                1215

Thr Thr Ile Lys Glu Ile Ser Met Gln Lys Glu Asp Asp Ser Lys
    1220                1225                1230

Asn Leu Arg Asn Gln Leu Asp Arg Leu Ser Arg Glu Asn Arg Asp
    1235                1240                1245

Leu Lys Asp Glu Ile Val Arg Leu Asn Asp Ser Ile Leu Gln Ala
    1250                1255                1260

Thr Glu Gln Arg Arg Arg Ala Glu Glu Asn Ala Leu Gln Gln Lys
    1265                1270                1275

Ala Cys Gly Ser Glu Ile Met Gln Lys Lys Gln His Leu Glu Ile
    1280                1285                1290

Glu Leu Lys Gln Val Met Gln Gln Arg Ser Glu Asp Asn Ala Arg
    1295                1300                1305

His Lys Gln Ser Leu Glu Glu Ala Ala Lys Thr Ile Gln Asp Lys
    1310                1315                1320

Asn Lys Glu Ile Glu Arg Leu Lys Ala Glu Phe Gln Glu Glu Ala
    1325                1330                1335

Lys Arg Arg Trp Glu Tyr Glu Asn Glu Leu Ser Lys Val Arg Asn
    1340                1345                1350

Asn Tyr Asp Glu Glu Ile Ile Ser Leu Lys Asn Gln Phe Glu Thr
    1355                1360                1365

Glu Ile Asn Ile Thr Lys Thr Thr Ile His Gln Leu Thr Met Gln
    1370                1375                1380

Lys Glu Glu Asp Thr Ser Gly Tyr Arg Ala Gln Ile Asp Asn Leu
    1385                1390                1395

Thr Arg Glu Asn Arg Ser Leu Ser Glu Glu Ile Lys Arg Leu Lys
    1400                1405                1410

Asn Thr Leu Thr Gln Thr Thr Glu Asn Leu Arg Arg Val Glu Glu
    1415                1420                1425
```

-continued

```
Asp Ile Gln Gln Gln Lys Ala Thr Gly Ser Glu Val Ser Gln Arg
    1430                1435                1440

Lys Gln Gln Leu Glu Val Glu Leu Arg Gln Val Thr Gln Met Arg
    1445                1450                1455

Thr Glu Glu Ser Val Arg Tyr Lys Gln Ser Leu Asp Asp Ala Ala
    1460                1465                1470

Lys Thr Ile Gln Asp Lys Asn Lys Glu Ile Glu Arg Leu Lys Gln
    1475                1480                1485

Leu Ile Asp Lys Glu Thr Asn Asp Arg Lys Cys Leu Glu Asp Glu
    1490                1495                1500

Asn Ala Arg Leu Gln Arg Val Gln Tyr Asp Leu Gln Lys Ala Asn
    1505                1510                1515

Ser Ser Ala Thr Glu Thr Ile Asn Lys Leu Lys Val Gln Glu Gln
    1520                1525                1530

Glu Leu Thr Arg Leu Arg Ile Asp Tyr Glu Arg Val Ser Gln Glu
    1535                1540                1545

Arg Thr Val Lys Asp Gln Asp Ile Thr Arg Phe Gln Asn Ser Leu
    1550                1555                1560

Lys Glu Leu Gln Leu Gln Lys Gln Lys Val Glu Gln Glu Leu Asn
    1565                1570                1575

Arg Leu Lys Arg Thr Ala Ser Glu Asp Ser Cys Lys Arg Lys Lys
    1580                1585                1590

Leu Glu Glu Glu Leu Glu Gly Met Arg Arg Ser Leu Lys Glu Gln
    1595                1600                1605

Ala Ile Lys Ile Thr Asn Leu Thr Gln Gln Leu Glu Gln Ala Ser
    1610                1615                1620

Ile Val Lys Lys Arg Ser Glu Asp Asp Leu Arg Gln Gln Arg Asp
    1625                1630                1635

Val Leu Asp Gly His Leu Arg Glu Lys Gln Arg Thr Gln Glu Glu
    1640                1645                1650

Leu Arg Arg Leu Ser Ser Glu Val Glu Ala Leu Arg Arg Gln Leu
    1655                1660                1665

Leu Gln Glu Gln Glu Ser Val Lys Gln Ala His Leu Arg Asn Glu
    1670                1675                1680

His Phe Gln Lys Ala Ile Glu Asp Lys Ser Arg Ser Leu Asn Glu
    1685                1690                1695

Ser Lys Ile Glu Ile Glu Arg Leu Gln Ser Leu Thr Glu Asn Leu
    1700                1705                1710

Thr Lys Glu His Leu Met Leu Glu Glu Glu Leu Arg Asn Leu Arg
    1715                1720                1725

Leu Glu Tyr Asp Asp Leu Arg Arg Gly Arg Ser Glu Ala Asp Ser
    1730                1735                1740

Asp Lys Asn Ala Thr Ile Leu Glu Leu Arg Ser Gln Leu Gln Ile
    1745                1750                1755

Ser Asn Asn Arg Thr Leu Glu Leu Gln Gly Leu Ile Asn Asp Leu
    1760                1765                1770

Gln Arg Glu Arg Glu Asn Leu Arg Gln Glu Ile Glu Lys Phe Gln
    1775                1780                1785

Lys Gln Ala Leu Glu Ala Ser Asn Arg Ile Gln Glu Ser Lys Asn
    1790                1795                1800

Gln Cys Thr Gln Val Val Gln Glu Arg Glu Ser Leu Leu Val Lys
    1805                1810                1815

Ile Lys Val Leu Glu Gln Asp Lys Ala Arg Leu Gln Arg Leu Glu
```

-continued

```
            1820                1825                1830

Asp Glu Leu Asn Arg Ala Lys Ser Thr Leu Glu Ala Glu Thr Arg
    1835                1840                1845

Val Lys Gln Arg Leu Glu Cys Glu Lys Gln Gln Ile Gln Asn Asp
    1850                1855                1860

Leu Asn Gln Trp Lys Thr Gln Tyr Ser Arg Lys Glu Glu Ala Ile
    1865                1870                1875

Arg Lys Ile Glu Ser Glu Arg Glu Lys Ser Glu Arg Glu Lys Asn
    1880                1885                1890

Ser Leu Arg Ser Glu Ile Glu Arg Leu Gln Ala Glu Ile Lys Arg
    1895                1900                1905

Ile Glu Glu Arg Cys Arg Arg Lys Leu Glu Asp Ser Thr Arg Glu
    1910                1915                1920

Thr Gln Ser Gln Leu Glu Thr Glu Arg Ser Arg Tyr Gln Arg Glu
    1925                1930                1935

Ile Asp Lys Leu Arg Gln Arg Pro Tyr Gly Ser His Arg Glu Thr
    1940                1945                1950

Gln Thr Glu Cys Glu Trp Thr Val Asp Thr Ser Lys Leu Val Phe
    1955                1960                1965

Asp Gly Leu Arg Lys Lys Val Thr Ala Met Gln Leu Tyr Glu Cys
    1970                1975                1980

Gln Leu Ile Asp Lys Thr Thr Leu Asp Lys Leu Leu Lys Gly Lys
    1985                1990                1995

Lys Ser Val Glu Glu Val Ala Ser Glu Ile Gln Pro Phe Leu Arg
    2000                2005                2010

Gly Ala Gly Ser Ile Ala Gly Ala Ser Ala Ser Pro Lys Glu Lys
    2015                2020                2025

Tyr Ser Leu Val Glu Ala Lys Arg Lys Leu Ile Ser Pro Glu
    2030                2035                2040

Ser Thr Val Met Leu Leu Glu Ala Gln Ala Ala Thr Gly Gly Ile
    2045                2050                2055

Ile Asp Pro His Arg Asn Glu Lys Leu Thr Val Asp Ser Ala Ile
    2060                2065                2070

Ala Arg Asp Leu Ile Asp Phe Asp Asp Arg Gln Gln Ile Tyr Ala
    2075                2080                2085

Ala Glu Lys Ala Ile Thr Gly Phe Asp Asp Pro Phe Ser Gly Lys
    2090                2095                2100

Thr Val Ser Val Ser Glu Ala Ile Lys Lys Asn Leu Ile Asp Arg
    2105                2110                2115

Glu Thr Gly Met Arg Leu Leu Glu Ala Gln Ile Ala Ser Gly Gly
    2120                2125                2130

Val Val Asp Pro Val Asn Ser Val Phe Leu Pro Lys Asp Val Ala
    2135                2140                2145

Leu Ala Arg Gly Leu Ile Asp Arg Asp Leu Tyr Arg Ser Leu Asn
    2150                2155                2160

Asp Pro Arg Asp Ser Gln Lys Asn Phe Val Asp Pro Val Thr Lys
    2165                2170                2175

Lys Lys Val Ser Tyr Val Gln Leu Lys Glu Arg Cys Arg Ile Glu
    2180                2185                2190

Pro His Thr Gly Leu Leu Leu Leu Ser Val Gln Lys Arg Ser Met
    2195                2200                2205

Ser Phe Gln Gly Ile Arg Gln Pro Val Thr Val Thr Glu Leu Val
    2210                2215                2220
```

-continued

Asp Ser Gly Ile Leu Arg Pro Ser Thr Val Asn Glu Leu Glu Ser
2225                2230                2235

Gly Gln Ile Ser Tyr Asp Glu Val Gly Glu Arg Ile Lys Asp Phe
2240                2245                2250

Leu Gln Gly Ser Ser Cys Ile Ala Gly Ile Tyr Asn Glu Thr Thr
2255                2260                2265

Lys Gln Lys Leu Gly Ile Tyr Glu Ala Met Lys Ile Gly Leu Val
2270                2275                2280

Arg Pro Gly Thr Ala Leu Glu Leu Leu Glu Ala Gln Ala Ala Thr
2285                2290                2295

Gly Phe Ile Val Asp Pro Val Ser Asn Leu Arg Leu Pro Val Glu
2300                2305                2310

Glu Ala Tyr Lys Arg Gly Leu Val Gly Ile Glu Phe Lys Glu Lys
2315                2320                2325

Leu Leu Ser Ala Glu Arg Ala Val Thr Gly Tyr Asn Asp Pro Glu
2330                2335                2340

Thr Gly Asn Ile Ile Ser Leu Phe Gln Ala Met Asn Lys Glu Leu
2345                2350                2355

Ile Glu Lys Gly His Gly Ile Arg Leu Leu Glu Ala Gln Ile Ala
2360                2365                2370

Thr Gly Gly Ile Ile Asp Pro Lys Glu Ser His Arg Leu Pro Val
2375                2380                2385

Asp Ile Ala Tyr Lys Arg Gly Tyr Phe Asn Glu Glu Leu Ser Glu
2390                2395                2400

Ile Leu Ser Asp Pro Ser Asp Asp Thr Lys Gly Phe Phe Asp Pro
2405                2410                2415

Asn Thr Glu Glu Asn Leu Thr Tyr Leu Gln Leu Lys Glu Arg Cys
2420                2425                2430

Ile Lys Asp Glu Glu Thr Gly Leu Cys Leu Leu Pro Leu Lys Glu
2435                2440                2445

Lys Lys Lys Gln Val Gln Thr Ser Gln Lys Asn Thr Leu Arg Lys
2450                2455                2460

Arg Arg Val Val Ile Val Asp Pro Glu Thr Asn Lys Glu Met Ser
2465                2470                2475

Val Gln Glu Ala Tyr Lys Lys Gly Leu Ile Asp Tyr Glu Thr Phe
2480                2485                2490

Lys Glu Leu Cys Glu Gln Glu Cys Glu Trp Glu Glu Ile Thr Ile
2495                2500                2505

Thr Gly Ser Asp Gly Ser Thr Arg Val Val Leu Val Asp Arg Lys
2510                2515                2520

Thr Gly Ser Gln Tyr Asp Ile Gln Asp Ala Ile Asp Lys Gly Leu
2525                2530                2535

Val Asp Arg Lys Phe Phe Asp Gln Tyr Arg Ser Gly Ser Leu Ser
2540                2545                2550

Leu Thr Gln Phe Ala Asp Met Ile Ser Leu Lys Asn Gly Val Gly
2555                2560                2565

Thr Ser Ser Ser Met Gly Ser Gly Val Ser Asp Asp Val Phe Ser
2570                2575                2580

Ser Ser Arg His Glu Ser Val Ser Lys Ile Ser Thr Ile Ser Ser
2585                2590                2595

Val Arg Asn Leu Thr Ile Arg Ser Ser Ser Phe Ser Asp Thr Leu
2600                2605                2610

Glu Glu Ser Ser Pro Ile Ala Ala Ile Phe Asp Thr Glu Asn Leu
2615                2620                2625

Glu Lys Ile Ser Ile Thr Glu Gly Ile Glu Arg Gly Ile Val Asp
    2630                2635                2640

Ser Ile Thr Gly Gln Arg Leu Leu Glu Ala Gln Ala Cys Thr Gly
    2645                2650                2655

Gly Ile Ile His Pro Thr Thr Gly Gln Lys Leu Ser Leu Gln Asp
    2660                2665                2670

Ala Val Ser Gln Gly Val Ile Asp Gln Asp Met Ala Thr Arg Leu
    2675                2680                2685

Lys Pro Ala Gln Lys Ala Phe Ile Gly Phe Glu Gly Val Lys Gly
    2690                2695                2700

Lys Lys Lys Met Ser Ala Ala Glu Ala Val Lys Glu Lys Trp Leu
    2705                2710                2715

Pro Tyr Glu Ala Gly Gln Arg Phe Leu Glu Phe Gln Tyr Leu Thr
    2720                2725                2730

Gly Gly Leu Val Asp Pro Glu Val His Gly Arg Ile Ser Thr Glu
    2735                2740                2745

Glu Ala Ile Arg Lys Gly Phe Ile Asp Gly Arg Ala Ala Gln Arg
    2750                2755                2760

Leu Gln Asp Thr Ser Ser Tyr Ala Lys Ile Leu Thr Cys Pro Lys
    2765                2770                2775

Thr Lys Leu Lys Ile Ser Tyr Lys Asp Ala Ile Asn Arg Ser Met
    2780                2785                2790

Val Glu Asp Ile Thr Gly Leu Arg Leu Leu Glu Ala Ala Ser Val
    2795                2800                2805

Ser Ser Lys Gly Leu Pro Ser Pro Tyr Asn Met Ser Ser Ala Pro
    2810                2815                2820

Gly Ser Arg Ser Gly Ser Arg Ser Gly Ser Arg Ser Gly Ser Arg
    2825                2830                2835

Ser Gly Ser Arg Ser Gly Ser Arg Arg Gly Ser Phe Asp Ala Thr
    2840                2845                2850

Gly Asn Ser Ser Tyr Ser Tyr Ser Tyr Ser Phe Ser Ser Ser Ser
    2855                2860                2865

Ile Gly His
    2870

<210> SEQ ID NO 16
<211> LENGTH: 206
<212> TYPE: PRT
<213> ORGANISM: Homo sapiens

<400> SEQUENCE: 16

Met Ala Val Lys Lys Ile Ala Ile Phe Gly Ala Thr Gly Gln Thr Gly
1               5                   10                  15

Leu Thr Thr Leu Ala Gln Ala Val Gln Ala Gly Tyr Glu Val Thr Val
                20                  25                  30

Leu Val Arg Asp Ser Ser Arg Leu Pro Ser Glu Gly Pro Arg Pro Ala
            35                  40                  45

His Val Val Val Gly Asp Val Leu Gln Ala Ala Asp Val Asp Lys Thr
        50                  55                  60

Val Ala Gly Gln Asp Ala Val Ile Val Leu Leu Gly Thr Arg Asn Asp
65                  70                  75                  80

Leu Ser Pro Thr Thr Val Met Ser Glu Gly Ala Arg Asn Ile Val Ala
                85                  90                  95

Ala Met Lys Ala His Gly Val Asp Lys Val Val Ala Cys Thr Ser Ala
                100                 105                 110

```
Phe Leu Leu Trp Asp Pro Thr Lys Val Pro Arg Leu Gln Ala Val
            115                 120                 125

Thr Asp Asp His Ile Arg Met His Lys Val Leu Arg Glu Ser Gly Leu
130                 135                 140

Lys Tyr Val Ala Val Met Pro Pro His Ile Gly Asp Gln Pro Leu Thr
145                 150                 155                 160

Gly Ala Tyr Thr Val Thr Leu Asp Gly Arg Gly Pro Ser Arg Val Ile
                165                 170                 175

Ser Lys His Asp Leu Gly His Phe Met Leu Arg Cys Leu Thr Thr Asp
                180                 185                 190

Glu Tyr Asp Gly His Ser Thr Tyr Pro Ser His Gln Tyr Gln
                195                 200                 205

<210> SEQ ID NO 17
<211> LENGTH: 217
<212> TYPE: PRT
<213> ORGANISM: Homo sapiens

<400> SEQUENCE: 17

Met Ala Tyr Pro Gly Tyr Gly Gly Phe Gly Asn Phe Ser Ile Gln
1               5                   10                  15

Val Pro Gly Met Gln Met Gly Gln Pro Val Pro Glu Thr Gly Pro Ala
                20                  25                  30

Ile Leu Leu Asp Gly Tyr Ser Gly Pro Ala Tyr Ser Asp Thr Tyr Ser
                35                  40                  45

Ser Ala Gly Asp Ser Val Tyr Thr Tyr Phe Ser Ala Val Ala Gly Gln
50                  55                  60

Asp Gly Glu Val Asp Ala Glu Leu Gln Arg Cys Leu Thr Gln Ser
65                  70                  75                  80

Gly Ile Asn Gly Thr Tyr Ser Pro Phe Ser Leu Glu Thr Cys Arg Ile
                85                  90                  95

Met Ile Ala Met Leu Asp Arg Asp His Thr Gly Lys Met Gly Phe Asn
                100                 105                 110

Ala Phe Lys Glu Leu Trp Ala Ala Leu Asn Ala Trp Lys Glu Asn Phe
                115                 120                 125

Met Thr Val Asp Gln Asp Gly Ser Gly Thr Val Glu His His Glu Leu
130                 135                 140

Arg Gln Ala Ile Gly Leu Met Gly Tyr Arg Leu Ser Pro Gln Thr Leu
145                 150                 155                 160

Thr Thr Ile Val Lys Arg Tyr Ser Lys Asn Gly Arg Ile Phe Phe Asp
                165                 170                 175

Asp Tyr Val Ala Cys Cys Val Lys Leu Arg Ala Leu Thr Asp Phe Phe
                180                 185                 190

Arg Lys Arg Asp His Leu Gln Gln Gly Ser Ala Asn Phe Ile Tyr Asp
                195                 200                 205

Asp Phe Leu Gln Gly Thr Met Ala Ile
                210                 215

<210> SEQ ID NO 18
<211> LENGTH: 592
<212> TYPE: PRT
<213> ORGANISM: Homo sapiens

<400> SEQUENCE: 18

Met Glu Gly Lys Trp Leu Leu Cys Met Leu Leu Val Leu Gly Thr Ala
1               5                   10                  15
```

```
Ile Val Glu Ala His Asp Gly His Asp Asp Val Ile Asp Ile Glu
            20                  25                  30

Asp Asp Leu Asp Asp Val Ile Glu Val Glu Asp Ser Lys Pro Asp
        35                  40                  45

Thr Thr Ala Pro Pro Ser Ser Pro Lys Val Thr Tyr Lys Ala Pro Val
 50                  55                  60

Pro Thr Gly Glu Val Tyr Phe Ala Asp Ser Phe Asp Arg Gly Thr Leu
 65                  70                  75                  80

Ser Gly Trp Ile Leu Ser Lys Ala Lys Lys Asp Asp Thr Asp Asp Glu
                85                  90                  95

Ile Ala Lys Tyr Asp Gly Lys Trp Glu Val Glu Glu Met Lys Glu Ser
                100                 105                 110

Lys Leu Pro Gly Asp Lys Gly Leu Val Leu Met Ser Arg Ala Lys His
        115                 120                 125

His Ala Ile Ser Ala Lys Leu Asn Lys Pro Phe Leu Phe Asp Thr Lys
    130                 135                 140

Pro Leu Ile Val Gln Tyr Glu Val Asn Phe Gln Asn Gly Ile Glu Cys
145                 150                 155                 160

Gly Gly Ala Tyr Val Lys Leu Leu Ser Lys Thr Pro Glu Leu Asn Leu
                165                 170                 175

Asp Gln Phe His Asp Lys Thr Pro Tyr Thr Ile Met Phe Gly Pro Asp
                180                 185                 190

Lys Cys Gly Glu Asp Tyr Lys Leu His Phe Ile Phe Arg His Lys Asn
            195                 200                 205

Pro Lys Thr Gly Ile Tyr Glu Glu Lys His Ala Lys Arg Pro Asp Ala
    210                 215                 220

Asp Leu Lys Thr Tyr Phe Thr Asp Lys Lys Thr His Leu Tyr Thr Leu
225                 230                 235                 240

Ile Leu Asn Pro Asp Asn Ser Phe Glu Ile Leu Val Asp Gln Ser Val
                245                 250                 255

Val Asn Ser Gly Asn Leu Leu Asn Asp Met Thr Pro Pro Val Asn Pro
                260                 265                 270

Ser Arg Glu Ile Glu Asp Pro Glu Asp Arg Lys Pro Glu Asp Trp Asp
                275                 280                 285

Glu Arg Pro Lys Ile Pro Asp Pro Glu Ala Val Lys Pro Asp Asp Trp
    290                 295                 300

Asp Glu Asp Ala Pro Ala Lys Ile Pro Asp Glu Glu Ala Thr Lys Pro
305                 310                 315                 320

Glu Gly Trp Leu Asp Asp Glu Pro Glu Tyr Val Pro Asp Pro Asp Ala
                325                 330                 335

Glu Lys Pro Glu Asp Trp Asp Asp Met Asp Gly Glu Trp Glu Ala
            340                 345                 350

Pro Gln Ile Ala Asn Pro Arg Cys Glu Ser Ala Pro Gly Cys Gly Val
    355                 360                 365

Trp Gln Arg Pro Val Ile Asp Asn Pro Asn Tyr Lys Gly Lys Trp Lys
        370                 375                 380

Pro Pro Met Ile Asp Asn Pro Ser Tyr Gln Gly Ile Trp Lys Pro Arg
385                 390                 395                 400

Lys Ile Pro Asn Pro Asp Phe Phe Glu Asp Leu Glu Pro Phe Arg Met
                405                 410                 415

Thr Pro Phe Ser Ala Ile Gly Leu Glu Leu Trp Ser Met Thr Ser Asp
            420                 425                 430

Ile Phe Phe Asp Asn Phe Ile Ile Cys Ala Asp Arg Arg Ile Val Asp
            435                 440                 445
```

```
Asp Trp Ala Asn Asp Gly Trp Gly Leu Lys Lys Ala Ala Asp Gly Ala
    450                 455                 460
Ala Glu Pro Gly Val Val Gly Gln Met Ile Glu Ala Ala Glu Glu Arg
465                 470                 475                 480
Pro Trp Leu Trp Val Val Tyr Ile Leu Thr Val Ala Leu Pro Val Phe
                485                 490                 495
Leu Val Ile Leu Phe Cys Cys Ser Gly Lys Lys Gln Thr Ser Gly Met
            500                 505                 510
Glu Tyr Lys Lys Thr Asp Ala Pro Gln Pro Asp Val Lys Glu Glu Glu
        515                 520                 525
Glu Glu Lys Glu Glu Lys Asp Lys Gly Asp Glu Glu Glu Gly
    530                 535                 540
Glu Glu Lys Leu Glu Glu Lys Gln Lys Ser Asp Ala Glu Glu Asp Gly
545                 550                 555                 560
Gly Thr Val Ser Gln Glu Glu Asp Arg Lys Pro Lys Ala Glu Glu
                565                 570                 575
Asp Glu Ile Leu Asn Arg Ser Pro Arg Asn Arg Lys Pro Arg Arg Glu
            580                 585                 590

<210> SEQ ID NO 19
<211> LENGTH: 91
<212> TYPE: PRT
<213> ORGANISM: Homo sapiens

<400> SEQUENCE: 19

Met Lys Leu Ala Val Thr Leu Thr Leu Val Thr Leu Ala Leu Cys Cys
1               5                   10                  15
Ser Ser Ala Ser Ala Glu Ile Cys Pro Ser Phe Gln Arg Val Ile Glu
            20                  25                  30
Thr Leu Leu Met Asp Thr Pro Ser Ser Tyr Glu Ala Ala Met Glu Leu
        35                  40                  45
Phe Ser Pro Asp Gln Asp Met Arg Glu Ala Gly Ala Gln Leu Lys Lys
    50                  55                  60
Leu Val Asp Thr Leu Pro Gln Lys Pro Arg Glu Ser Ile Ile Lys Leu
65                  70                  75                  80
Met Glu Lys Ile Ala Gln Ser Ser Leu Cys Asn
                85                  90

<210> SEQ ID NO 20
<211> LENGTH: 308
<212> TYPE: PRT
<213> ORGANISM: Homo sapiens

<400> SEQUENCE: 20

Met Arg Ala Leu Val Leu Leu Ser Leu Phe Leu Leu Gly Gly Gln
1               5                   10                  15
Ala Gln His Val Ser Asp Trp Thr Tyr Ser Glu Gly Ala Leu Asp Glu
            20                  25                  30
Ala His Trp Pro Gln His Tyr Pro Ala Cys Gly Gly Gln Arg Gln Ser
        35                  40                  45
Pro Ile Asn Leu Gln Arg Thr Lys Val Arg Tyr Asn Pro Ser Leu Lys
    50                  55                  60
Gly Leu Asn Met Thr Gly Tyr Glu Thr Gln Ala Gly Glu Phe Pro Met
65                  70                  75                  80
Val Asn Asn Gly His Thr Val Gln Ile Ser Leu Pro Ser Thr Met Arg
                85                  90                  95
```

```
Met Thr Val Ala Asp Gly Thr Val Tyr Ile Ala Gln Gln Met His Phe
            100                 105                 110

His Trp Gly Gly Ala Ser Ser Glu Ile Ser Gly Ser Glu His Thr Val
            115                 120                 125

Asp Gly Ile Arg His Val Ile Glu Ile His Ile Val His Tyr Asn Ser
        130                 135                 140

Lys Tyr Lys Ser Tyr Asp Ile Ala Gln Asp Ala Pro Asp Gly Leu Ala
145                 150                 155                 160

Val Leu Ala Ala Phe Val Glu Val Lys Asn Tyr Pro Glu Asn Thr Tyr
                165                 170                 175

Tyr Ser Asn Phe Ile Ser His Leu Ala Asn Ile Lys Tyr Pro Gly Gln
            180                 185                 190

Arg Thr Thr Leu Thr Gly Leu Asp Val Gln Asp Met Leu Pro Arg Asn
        195                 200                 205

Leu Gln His Tyr Tyr Thr Tyr His Gly Ser Leu Thr Thr Pro Pro Cys
210                 215                 220

Thr Glu Asn Val His Trp Phe Val Leu Ala Asp Phe Val Lys Leu Ser
225                 230                 235                 240

Arg Thr Gln Val Trp Lys Leu Glu Asn Ser Leu Asp His Arg Asn
                245                 250                 255

Lys Thr Ile His Asn Asp Tyr Arg Arg Thr Gln Pro Leu Asn His Arg
            260                 265                 270

Val Val Glu Ser Asn Phe Pro Asn Gln Glu Tyr Thr Leu Gly Ser Glu
        275                 280                 285

Phe Gln Phe Tyr Leu His Lys Ile Glu Glu Ile Leu Asp Tyr Leu Arg
290                 295                 300

Arg Ala Leu Asn
305

<210> SEQ ID NO 21
<211> LENGTH: 531
<212> TYPE: PRT
<213> ORGANISM: Homo sapiens

<400> SEQUENCE: 21

Met Ser Lys Pro His Ser Glu Ala Gly Thr Ala Phe Ile Gln Thr Gln
1               5                   10                  15

Gln Leu His Ala Ala Met Ala Asp Thr Phe Leu Glu His Met Cys Arg
            20                  25                  30

Leu Asp Ile Asp Ser Pro Pro Ile Thr Ala Arg Asn Thr Gly Ile Ile
        35                  40                  45

Cys Thr Ile Gly Pro Ala Ser Arg Ser Val Glu Thr Leu Lys Glu Met
    50                  55                  60

Ile Lys Ser Gly Met Asn Val Ala Arg Leu Asn Phe Ser His Gly Thr
65                  70                  75                  80

His Glu Tyr His Ala Glu Thr Ile Lys Asn Val Arg Thr Ala Thr Glu
                85                  90                  95

Ser Phe Ala Ser Asp Pro Ile Leu Tyr Arg Pro Val Ala Val Ala Leu
            100                 105                 110

Asp Thr Lys Gly Pro Glu Ile Arg Thr Gly Leu Ile Lys Gly Ser Gly
        115                 120                 125

Thr Ala Glu Val Glu Leu Lys Lys Gly Ala Thr Leu Lys Ile Thr Leu
    130                 135                 140

Asp Asn Ala Tyr Met Glu Lys Cys Asp Glu Asn Ile Leu Trp Leu Asp
145                 150                 155                 160
```

```
Tyr Lys Asn Ile Cys Lys Val Val Glu Val Gly Ser Lys Ile Tyr Val
            165                 170                 175

Asp Asp Gly Leu Ile Ser Leu Gln Val Lys Gln Lys Gly Ala Asp Phe
            180                 185                 190

Leu Val Thr Glu Val Glu Asn Gly Gly Ser Leu Gly Ser Lys Lys Gly
            195                 200                 205

Val Asn Leu Pro Gly Ala Ala Val Asp Leu Pro Ala Val Ser Glu Lys
        210                 215                 220

Asp Ile Gln Asp Leu Lys Phe Gly Val Glu Gln Asp Val Asp Met Val
225                 230                 235                 240

Phe Ala Ser Phe Ile Arg Lys Ala Ser Asp Val His Glu Val Arg Lys
            245                 250                 255

Val Leu Gly Glu Lys Gly Lys Asn Ile Lys Ile Ile Ser Lys Ile Glu
            260                 265                 270

Asn His Glu Gly Val Arg Arg Phe Asp Glu Ile Leu Glu Ala Ser Asp
            275                 280                 285

Gly Ile Met Val Ala Arg Gly Asp Leu Gly Ile Glu Ile Pro Ala Glu
        290                 295                 300

Lys Val Phe Leu Ala Gln Lys Met Met Ile Gly Arg Cys Asn Arg Ala
305                 310                 315                 320

Gly Lys Pro Val Ile Cys Ala Thr Gln Met Leu Glu Ser Met Ile Lys
            325                 330                 335

Lys Pro Arg Pro Thr Arg Ala Glu Gly Ser Asp Val Ala Asn Ala Val
            340                 345                 350

Leu Asp Gly Ala Asp Cys Ile Met Leu Ser Gly Glu Thr Ala Lys Gly
            355                 360                 365

Asp Tyr Pro Leu Glu Ala Val Arg Met Gln His Leu Ile Ala Arg Glu
        370                 375                 380

Ala Glu Ala Ala Ile Tyr His Leu Gln Leu Phe Glu Glu Leu Arg Arg
385                 390                 395                 400

Leu Ala Pro Ile Thr Ser Asp Pro Thr Glu Ala Thr Ala Val Gly Ala
            405                 410                 415

Val Glu Ala Ser Phe Lys Cys Cys Ser Gly Ala Ile Ile Val Leu Thr
            420                 425                 430

Lys Ser Gly Arg Ser Ala His Gln Val Ala Arg Tyr Arg Pro Arg Ala
            435                 440                 445

Pro Ile Ile Ala Val Thr Arg Asn Pro Gln Thr Ala Arg Gln Ala His
        450                 455                 460

Leu Tyr Arg Gly Ile Phe Pro Val Leu Cys Lys Asp Pro Val Gln Glu
465                 470                 475                 480

Ala Trp Ala Glu Asp Val Asp Leu Arg Val Asn Phe Ala Met Asn Val
            485                 490                 495

Gly Lys Ala Arg Gly Phe Phe Lys Lys Gly Asp Val Val Ile Val Leu
            500                 505                 510

Thr Gly Trp Arg Pro Gly Ser Gly Phe Thr Asn Thr Met Arg Val Val
            515                 520                 525

Pro Val Pro
    530

<210> SEQ ID NO 22
<211> LENGTH: 418
<212> TYPE: PRT
<213> ORGANISM: Homo sapiens

<400> SEQUENCE: 22
```

-continued

```
Met Pro Ser Ser Val Ser Trp Gly Ile Leu Leu Ala Gly Leu Cys
1               5                   10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
            195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
            355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```

<210> SEQ ID NO 23
<211> LENGTH: 467
<212> TYPE: PRT
<213> ORGANISM: Homo sapiens

<400> SEQUENCE: 23

```
Met Phe Ser Leu Lys Thr Leu Pro Phe Leu Leu Leu His Val Gln
1               5                   10                  15

Ile Ser Lys Ala Phe Pro Val Ser Ser Lys Glu Lys Asn Thr Lys Thr
            20                  25                  30

Val Gln Asp Tyr Leu Glu Lys Phe Tyr Gln Leu Pro Ser Asn Gln Tyr
        35                  40                  45

Gln Ser Thr Arg Lys Asn Gly Thr Asn Val Ile Val Glu Lys Leu Lys
    50                  55                  60

Glu Met Gln Arg Phe Phe Gly Leu Asn Val Thr Gly Lys Pro Asn Glu
65                  70                  75                  80

Glu Thr Leu Asp Met Met Lys Lys Pro Arg Cys Gly Val Pro Asp Ser
                85                  90                  95

Gly Gly Phe Met Leu Thr Pro Gly Asn Pro Lys Trp Glu Arg Thr Asn
            100                 105                 110

Leu Thr Tyr Arg Ile Arg Asn Tyr Thr Pro Gln Leu Ser Glu Ala Glu
        115                 120                 125

Val Glu Arg Ala Ile Lys Asp Ala Phe Glu Leu Trp Ser Val Ala Ser
    130                 135                 140

Pro Leu Ile Phe Thr Arg Ile Ser Gln Gly Glu Ala Asp Ile Asn Ile
145                 150                 155                 160

Ala Phe Tyr Gln Arg Asp His Gly Asp Asn Ser Pro Phe Asp Gly Pro
                165                 170                 175

Asn Gly Ile Leu Ala His Ala Phe Gln Pro Gly Gln Gly Ile Gly Gly
            180                 185                 190

Asp Ala His Phe Asp Ala Glu Glu Thr Trp Thr Asn Thr Ser Ala Asn
        195                 200                 205

Tyr Asn Leu Phe Leu Val Ala Ala His Glu Phe Gly His Ser Leu Gly
    210                 215                 220

Leu Ala His Ser Ser Asp Pro Gly Ala Leu Met Tyr Pro Asn Tyr Ala
225                 230                 235                 240

Phe Arg Glu Thr Ser Asn Tyr Ser Leu Pro Gln Asp Asp Ile Asp Gly
                245                 250                 255

Ile Gln Ala Ile Tyr Gly Leu Ser Ser Asn Pro Ile Gln Pro Thr Gly
            260                 265                 270

Pro Ser Thr Pro Lys Pro Cys Asp Pro Ser Leu Thr Phe Asp Ala Ile
        275                 280                 285

Thr Thr Leu Arg Gly Glu Ile Leu Phe Phe Lys Asp Arg Tyr Phe Trp
    290                 295                 300

Arg Arg His Pro Gln Leu Gln Arg Val Glu Met Asn Phe Ile Ser Leu
305                 310                 315                 320

Phe Trp Pro Ser Leu Pro Thr Gly Ile Gln Ala Ala Tyr Glu Asp Phe
                325                 330                 335

Asp Arg Asp Leu Ile Phe Leu Phe Lys Gly Asn Gln Tyr Trp Ala Leu
            340                 345                 350

Ser Gly Tyr Asp Ile Leu Gln Gly Tyr Pro Lys Asp Ile Ser Asn Tyr
        355                 360                 365

Gly Phe Pro Ser Ser Val Gln Ala Ile Asp Ala Ala Val Phe Tyr Arg
    370                 375                 380
```

```
Ser Lys Thr Tyr Phe Phe Val Asn Asp Gln Phe Trp Arg Tyr Asp Asn
385                 390                 395                 400

Gln Arg Gln Phe Met Glu Pro Gly Tyr Pro Lys Ser Ile Ser Gly Ala
            405                 410                 415

Phe Pro Gly Ile Glu Ser Lys Val Asp Ala Val Phe Gln Gln Glu His
        420                 425                 430

Phe Phe His Val Phe Ser Gly Pro Arg Tyr Tyr Ala Phe Asp Leu Ile
        435                 440                 445

Ala Gln Arg Val Thr Arg Val Ala Arg Gly Asn Lys Trp Leu Asn Cys
    450                 455                 460

Arg Tyr Gly
465

<210> SEQ ID NO 24
<211> LENGTH: 1474
<212> TYPE: PRT
<213> ORGANISM: Homo sapiens

<400> SEQUENCE: 24

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
        275                 280                 285
```

```
Lys Phe Ser Gly Gln Leu Asn Ser His Gly Cys Phe Tyr Gln Gln Val
    290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Gly Thr Val Val Glu Leu Thr
                325                 330                 335
Gly Arg Gln Ser Ser Glu Ile Thr Arg Thr Ile Thr Lys Leu Ser Phe
                340                 345                 350
Val Lys Val Asp Ser His Phe Arg Gln Gly Ile Pro Phe Phe Gly Gln
                355                 360                 365
Val Arg Leu Val Asp Gly Lys Gly Val Pro Ile Pro Asn Lys Val Ile
370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                405                 410                 415
Thr Ser Leu Thr Val Arg Val Asn Tyr Lys Asp Arg Ser Pro Cys Tyr
                420                 425                 430
Gly Tyr Gln Trp Val Ser Glu Glu His Glu Glu Ala His His Thr Ala
                435                 440                 445
Tyr Leu Val Phe Ser Pro Ser Lys Ser Phe Val His Leu Glu Pro Met
450                 455                 460
Ser His Glu Leu Pro Cys Gly His Thr Gln Thr Val Gln Ala His Tyr
465                 470                 475                 480
Ile Leu Asn Gly Gly Thr Leu Leu Gly Leu Lys Lys Leu Ser Phe Tyr
                485                 490                 495
Tyr Leu Ile Met Ala Lys Gly Gly Ile Val Arg Thr Gly Thr His Gly
                500                 505                 510
Leu Leu Val Lys Gln Glu Asp Met Lys Gly His Phe Ser Ile Ser Ile
                515                 520                 525
Pro Val Lys Ser Asp Ile Ala Pro Val Ala Arg Leu Leu Ile Tyr Ala
530                 535                 540
Val Leu Pro Thr Gly Asp Val Ile Gly Asp Ser Ala Lys Tyr Asp Val
545                 550                 555                 560
Glu Asn Cys Leu Ala Asn Lys Val Asp Leu Ser Phe Ser Pro Ser Gln
                565                 570                 575
Ser Leu Pro Ala Ser His Ala His Leu Arg Val Thr Ala Ala Pro Gln
                580                 585                 590
Ser Val Cys Ala Leu Arg Ala Val Asp Gln Ser Val Leu Leu Met Lys
                595                 600                 605
Pro Asp Ala Glu Leu Ser Ala Ser Ser Val Tyr Asn Leu Leu Pro Glu
610                 615                 620
Lys Asp Leu Thr Gly Phe Pro Gly Pro Leu Asn Asp Gln Asp Asp Glu
625                 630                 635                 640
Asp Cys Ile Asn Arg His Asn Val Tyr Ile Asn Gly Ile Thr Tyr Thr
                645                 650                 655
Pro Val Ser Ser Thr Asn Glu Lys Asp Met Tyr Ser Phe Leu Glu Asp
                660                 665                 670
Met Gly Leu Lys Ala Phe Thr Asn Ser Lys Ile Arg Lys Pro Lys Met
                675                 680                 685
Cys Pro Gln Leu Gln Gln Tyr Glu Met His Gly Pro Glu Gly Leu Arg
                690                 695                 700
Val Gly Phe Tyr Glu Ser Asp Val Met Gly Arg Gly His Ala Arg Leu
705                 710                 715                 720
```

Val His Val Glu Glu Pro His Thr Glu Thr Val Arg Lys Tyr Phe Pro
            725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
            755                 760                 765

Ala Phe Cys Leu Ser Glu Asp Ala Gly Leu Gly Ile Ser Ser Thr Ala
            770                 775                 780

Ser Leu Arg Ala Phe Gln Pro Phe Val Glu Leu Thr Met Pro Tyr
785                 790                 795                 800

Ser Val Ile Arg Gly Glu Ala Phe Thr Leu Lys Ala Thr Val Leu Asn
            805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
            850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
            885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Glu Glu Ser Ala
            930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
            965                 970                 975

Met Val Leu Phe Ala Pro Asn Ile Tyr Val Leu Asp Tyr Leu Asn Glu
            980                 985                 990

Thr Gln Gln Leu Thr Pro Glu Val Lys Ser Lys Ala Ile Gly Tyr Leu
            995                 1000                1005

Asn Thr Gly Tyr Gln Arg Gln Leu Asn Tyr Lys His Tyr Asp Gly
    1010                1015                1020

Ser Tyr Ser Thr Phe Gly Glu Arg Tyr Gly Arg Asn Gln Gly Asn
    1025                1030                1035

Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
    1055                1060                1065

Trp Leu Ser Gln Arg Gln Lys Asp Asn Gly Cys Phe Arg Ser Ser
    1070                1075                1080

Gly Ser Leu Leu Asn Asn Ala Ile Lys Gly Gly Val Glu Asp Glu
    1085                1090                1095

Val Thr Leu Ser Ala Tyr Ile Thr Ile Ala Leu Leu Glu Ile Pro
    1100                1105                1110

Leu Thr Val Thr His Pro Val Val Arg Asn Ala Leu Phe Cys Leu
    1115                1120                1125

Glu Ser Ala Trp Lys Thr Ala Gln Glu Gly Asp His Gly Ser His

```
                    1130                1135                1140

Val Tyr Thr Lys Ala Leu Leu Ala Tyr Ala Phe Ala Leu Ala Gly
    1145                1150                1155

Asn Gln Asp Lys Arg Lys Glu Val Leu Lys Ser Leu Asn Glu Glu
    1160                1165                1170

Ala Val Lys Lys Asp Asn Ser Val His Trp Glu Arg Pro Gln Lys
    1175                1180                1185

Pro Lys Ala Pro Val Gly His Phe Tyr Glu Pro Gln Ala Pro Ser
    1190                1195                1200

Ala Glu Val Glu Met Thr Ser Tyr Val Leu Leu Ala Tyr Leu Thr
    1205                1210                1215

Ala Gln Pro Ala Pro Thr Ser Glu Asp Leu Thr Ser Ala Thr Asn
    1220                1225                1230

Ile Val Lys Trp Ile Thr Lys Gln Gln Asn Ala Gln Gly Gly Phe
    1235                1240                1245

Ser Ser Thr Gln Asp Thr Val Val Ala Leu His Ala Leu Ser Lys
    1250                1255                1260

Tyr Gly Ala Ala Thr Phe Thr Arg Thr Gly Lys Ala Ala Gln Val
    1265                1270                1275

Thr Ile Gln Ser Ser Gly Thr Phe Ser Ser Lys Phe Gln Val Asp
    1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
    1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
    1340                1345                1350

Glu Pro Lys Ala His Thr Ser Phe Gln Ile Ser Leu Ser Val Ser
    1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425

Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala

<210> SEQ ID NO 25
<211> LENGTH: 146
<212> TYPE: PRT
<213> ORGANISM: Homo sapiens

<400> SEQUENCE: 25

Met Ala Gly Pro Leu Arg Ala Pro Leu Leu Leu Leu Ala Ile Leu Ala
1               5                   10                  15
```

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
 50                  55                  60

Asn Asp Met Tyr His Ser Arg Ala Leu Gln Val Val Arg Ala Arg Lys
 65                  70                  75                  80

Gln Ile Val Ala Gly Val Asn Tyr Phe Leu Asp Val Glu Leu Gly Arg
            85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
 130                 135                 140

Asp Ala
145

<210> SEQ ID NO 26
<211> LENGTH: 289
<212> TYPE: PRT
<213> ORGANISM: Homo sapiens

<400> SEQUENCE: 26

Met Glu Asn Gly Tyr Thr Tyr Glu Asp Tyr Lys Asn Thr Ala Glu Trp
 1               5                  10                  15

Leu Leu Ser His Thr Lys His Arg Pro Gln Val Ala Ile Ile Cys Gly
            20                  25                  30

Ser Gly Leu Gly Gly Leu Thr Asp Lys Leu Thr Gln Ala Gln Ile Phe
            35                  40                  45

Asp Tyr Gly Glu Ile Pro Asn Phe Pro Arg Ser Thr Val Pro Gly His
 50                  55                  60

Ala Gly Arg Leu Val Phe Gly Phe Leu Asn Gly Arg Ala Cys Val Met
 65                  70                  75                  80

Met Gln Gly Arg Phe His Met Tyr Glu Gly Tyr Pro Leu Trp Lys Val
            85                  90                  95

Thr Phe Pro Val Arg Val Phe His Leu Leu Gly Val Asp Thr Leu Val
            100                 105                 110

Val Thr Asn Ala Ala Gly Gly Leu Asn Pro Lys Phe Glu Val Gly Asp
            115                 120                 125

Ile Met Leu Ile Arg Asp His Ile Asn Leu Pro Gly Phe Ser Gly Gln
 130                 135                 140

Asn Pro Leu Arg Gly Pro Asn Asp Glu Arg Phe Gly Asp Arg Phe Pro
145                 150                 155                 160

Ala Met Ser Asp Ala Tyr Asp Arg Thr Met Arg Gln Arg Ala Leu Ser
                165                 170                 175

Thr Trp Lys Gln Met Gly Glu Gln Arg Glu Leu Gln Glu Gly Thr Tyr
            180                 185                 190

Val Met Val Ala Gly Pro Ser Phe Glu Thr Val Ala Glu Cys Arg Val
            195                 200                 205

Leu Gln Lys Leu Gly Ala Asp Ala Val Gly Met Ser Thr Val Pro Glu
 210                 215                 220

Val Ile Val Ala Arg His Cys Gly Leu Arg Val Phe Gly Phe Ser Leu
225                 230                 235                 240

```
Ile Thr Asn Lys Val Ile Met Asp Tyr Glu Ser Leu Glu Lys Ala Asn
                245                 250                 255

His Glu Glu Val Leu Ala Ala Gly Lys Gln Ala Ala Gln Lys Leu Glu
            260                 265                 270

Gln Phe Val Ser Ile Leu Met Ala Ser Ile Pro Leu Pro Asp Lys Ala
        275                 280                 285

Ser

<210> SEQ ID NO 27
<211> LENGTH: 453
<212> TYPE: PRT
<213> ORGANISM: Homo sapiens

<400> SEQUENCE: 27

Met Ser Lys Ile Ser Glu Ala Val Lys Arg Ala Arg Ala Ala Phe Ser
1               5                   10                  15

Ser Gly Arg Thr Arg Pro Leu Gln Phe Arg Ile Gln Gln Leu Glu Ala
            20                  25                  30

Leu Gln Arg Leu Ile Gln Glu Gln Glu Gln Glu Leu Val Gly Ala Leu
        35                  40                  45

Ala Ala Asp Leu His Lys Asn Glu Trp Asn Ala Tyr Tyr Glu Glu Val
    50                  55                  60

Val Tyr Val Leu Glu Glu Ile Glu Tyr Met Ile Gln Lys Leu Pro Glu
65                  70                  75                  80

Trp Ala Ala Asp Glu Pro Val Gly Lys Thr Pro Gln Thr Gln Gln Asp
                85                  90                  95

Glu Leu Tyr Ile His Ser Glu Pro Leu Gly Val Val Leu Val Ile Gly
            100                 105                 110

Thr Trp Asn Tyr Pro Phe Asn Leu Thr Ile Gln Pro Met Val Gly Ala
        115                 120                 125

Ile Ala Ala Gly Asn Ala Val Val Leu Lys Pro Ser Glu Leu Ser Glu
    130                 135                 140

Asn Met Ala Ser Leu Leu Ala Thr Ile Ile Pro Gln Tyr Leu Asp Lys
145                 150                 155                 160

Asp Leu Tyr Pro Val Ile Asn Gly Gly Val Pro Glu Thr Thr Glu Leu
                165                 170                 175

Leu Lys Glu Arg Phe Asp His Ile Leu Tyr Thr Gly Ser Thr Gly Val
            180                 185                 190

Gly Lys Ile Ile Met Thr Ala Ala Lys His Leu Thr Pro Val Thr
        195                 200                 205

Leu Glu Leu Gly Gly Lys Ser Pro Cys Tyr Val Asp Lys Asn Cys Asp
    210                 215                 220

Leu Asp Val Ala Cys Arg Arg Ile Ala Trp Gly Lys Phe Met Asn Ser
225                 230                 235                 240

Gly Gln Thr Cys Val Ala Pro Asp Tyr Ile Leu Cys Asp Pro Ser Ile
                245                 250                 255

Gln Asn Gln Ile Val Glu Lys Leu Lys Lys Ser Leu Lys Glu Phe Tyr
            260                 265                 270

Gly Glu Asp Ala Lys Lys Ser Arg Asp Tyr Gly Arg Ile Ile Ser Ala
        275                 280                 285

Arg His Phe Gln Arg Val Met Gly Leu Ile Glu Gly Gln Lys Val Ala
    290                 295                 300

Tyr Gly Gly Thr Gly Asp Ala Ala Thr Arg Tyr Ile Ala Pro Thr Ile
305                 310                 315                 320
```

```
Leu Thr Asp Val Asp Pro Gln Ser Pro Val Met Gln Glu Glu Ile Phe
            325                 330                 335
Gly Pro Val Leu Pro Ile Val Cys Val Arg Ser Leu Glu Glu Ala Ile
                340                 345                 350
Gln Phe Ile Asn Gln Arg Glu Lys Pro Leu Ala Leu Tyr Met Phe Ser
            355                 360                 365
Ser Asn Asp Lys Val Ile Lys Lys Met Ile Ala Glu Thr Ser Ser Gly
        370                 375                 380
Gly Val Ala Ala Asn Asp Val Ile Val His Ile Thr Leu His Ser Leu
385                 390                 395                 400
Pro Phe Gly Gly Val Gly Asn Ser Gly Met Gly Ser Tyr His Gly Lys
                405                 410                 415
Lys Ser Phe Glu Thr Phe Ser His Arg Arg Ser Cys Leu Val Arg Pro
            420                 425                 430
Leu Met Asn Asp Glu Gly Leu Lys Val Arg Tyr Pro Pro Ser Pro Ala
        435                 440                 445
Lys Met Thr Gln His
    450
```

<210> SEQ ID NO 28
<211> LENGTH: 135
<212> TYPE: PRT
<213> ORGANISM: Homo sapiens

<400> SEQUENCE: 28

```
Met Ala Thr Val Gln Gln Leu Glu Gly Arg Trp Arg Leu Val Asp Ser
1               5                   10                  15
Lys Gly Phe Asp Glu Tyr Met Lys Glu Leu Gly Val Gly Ile Ala Leu
                20                  25                  30
Arg Lys Met Gly Ala Met Ala Lys Pro Asp Cys Ile Ile Thr Cys Asp
            35                  40                  45
Gly Lys Asn Leu Thr Ile Lys Thr Glu Ser Thr Leu Lys Thr Thr Gln
        50                  55                  60
Phe Ser Cys Thr Leu Gly Glu Lys Phe Glu Glu Thr Thr Ala Asp Gly
65                  70                  75                  80
Arg Lys Thr Gln Thr Val Cys Asn Phe Thr Asp Gly Ala Leu Val Gln
                85                  90                  95
His Gln Glu Trp Asp Gly Lys Glu Ser Thr Ile Thr Arg Lys Leu Lys
            100                 105                 110
Asp Gly Lys Leu Val Val Glu Cys Val Met Asn Asn Val Thr Cys Thr
        115                 120                 125
Arg Ile Tyr Glu Lys Val Glu
    130                 135
```

<210> SEQ ID NO 29
<211> LENGTH: 199
<212> TYPE: PRT
<213> ORGANISM: Homo sapiens

<400> SEQUENCE: 29

```
Met Ser Ser Gly Asn Ala Lys Ile Gly His Pro Ala Pro Asn Phe Lys
1               5                   10                  15
Ala Thr Ala Val Met Pro Asp Gly Gln Phe Lys Asp Ile Ser Leu Ser
                20                  25                  30
Asp Tyr Lys Gly Lys Tyr Val Val Phe Phe Tyr Pro Leu Asp Phe
            35                  40                  45
Thr Phe Val Cys Pro Thr Glu Ile Ile Ala Phe Ser Asp Arg Ala Glu
```

```
                50                  55                  60
Glu Phe Lys Lys Leu Asn Cys Gln Val Ile Gly Ala Ser Val Asp Ser
 65                  70                  75                  80

His Phe Cys His Leu Ala Trp Val Asn Thr Pro Lys Lys Gln Gly Gly
                 85                  90                  95

Leu Gly Pro Met Asn Ile Pro Leu Val Ser Asp Pro Lys Arg Thr Ile
            100                 105                 110

Ala Gln Asp Tyr Gly Val Leu Lys Ala Asp Glu Gly Ile Ser Phe Arg
        115                 120                 125

Gly Leu Phe Ile Ile Asp Asp Lys Gly Ile Leu Arg Gln Ile Thr Val
130                 135                 140

Asn Asp Leu Pro Val Gly Arg Ser Val Asp Glu Thr Leu Arg Leu Val
145                 150                 155                 160

Gln Ala Phe Gln Phe Thr Asp Lys His Gly Glu Val Cys Pro Ala Gly
                165                 170                 175

Trp Lys Pro Gly Ser Asp Thr Ile Lys Pro Asp Val Gln Lys Ser Lys
            180                 185                 190

Glu Tyr Phe Ser Lys Gln Lys
        195

<210> SEQ ID NO 30
<211> LENGTH: 491
<212> TYPE: PRT
<213> ORGANISM: Homo sapiens

<400> SEQUENCE: 30

Met Gln Pro Leu Leu Cys Leu Gly Asn Leu Glu Asp Ala Arg Glu Arg
 1               5                  10                  15

Thr Gly Thr Leu Leu Ala Gln His Pro Ala Trp Gly Arg Thr Arg Ala
             20                  25                  30

Lys Pro Gly Ser Pro Leu Asn Thr Lys Lys Glu Gly Asp Leu Ile Ala
         35                  40                  45

Ala Gln Ala Arg Leu Lys Asp Leu Glu Ala Leu Leu Asn Ser Lys Glu
     50                  55                  60

Ala Ala Leu Ser Thr Ala Leu Ser Glu Lys Arg Thr Leu Glu Gly Glu
 65                  70                  75                  80

Leu His Asp Leu Arg Gly Gln Val Ala Lys Leu Glu Ala Ala Leu Gly
                 85                  90                  95

Glu Ala Lys Lys Gln Leu Gln Asp Glu Met Leu Arg Arg Val Asp Ala
            100                 105                 110

Glu Asn Arg Leu Gln Thr Met Lys Glu Glu Leu Asp Phe Gln Lys Asn
        115                 120                 125

Ile Tyr Ser Glu Glu Leu Arg Glu Thr Lys Arg Arg His Glu Thr Arg
    130                 135                 140

Leu Val Glu Ile Asp Asn Gly Lys Gln Arg Glu Phe Glu Ser Arg Leu
145                 150                 155                 160

Ala Asp Ala Leu Gln Glu Leu Arg Ala Gln His Glu Asp Gln Val Glu
                165                 170                 175

Gln Tyr Lys Lys Glu Leu Glu Lys Thr Tyr Ser Ala Lys Leu Asp Asn
            180                 185                 190

Ala Arg Gln Ser Ala Glu Arg Asn Ser Asn Leu Val Gly Ala Ala His
        195                 200                 205

Glu Glu Leu Gln Gln Ser Arg Ile Arg Ile Asp Ser Leu Ser Ala Gln
    210                 215                 220

Leu Ser Gln Leu Gln Lys Gln Leu Ala Ala Lys Glu Ala Lys Leu Arg
```

```
                225                 230                 235                 240
Asp Leu Glu Asp Ser Leu Ala Arg Glu Arg Asp Thr Ser Arg Arg Leu
                245                 250                 255

Leu Ala Glu Lys Glu Arg Glu Met Ala Glu Met Arg Ala Arg Met Gln
                260                 265                 270

Gln Gln Leu Asp Glu Tyr Gln Glu Leu Leu Asp Ile Lys Leu Ala Leu
                275                 280                 285

Asp Met Glu Ile His Ala Tyr Arg Lys Leu Leu Glu Gly Glu Glu Glu
            290                 295                 300

Arg Leu Arg Leu Ser Pro Ser Pro Thr Ser Gln Arg Ser Arg Gly Arg
305                 310                 315                 320

Ala Ser Ser His Ser Ser Gln Thr Gln Gly Gly Gly Ser Val Thr Lys
                325                 330                 335

Lys Arg Lys Leu Glu Ser Thr Glu Ser Arg Ser Ser Phe Ser Gln His
                340                 345                 350

Ala Arg Thr Ser Gly Arg Val Ala Val Glu Glu Val Asp Glu Glu Gly
                355                 360                 365

Lys Phe Val Arg Leu Arg Asn Lys Ser Asn Glu Asp Gln Ser Met Gly
            370                 375                 380

Asn Trp Gln Ile Lys Arg Gln Asn Gly Asp Asp Pro Leu Leu Thr Tyr
385                 390                 395                 400

Arg Phe Pro Pro Lys Phe Thr Leu Lys Ala Gly Gln Val Val Thr Ile
                405                 410                 415

Trp Ala Ala Gly Ala Gly Ala Thr His Ser Pro Pro Thr Asp Leu Val
                420                 425                 430

Trp Lys Ala Gln Asn Thr Trp Gly Cys Gly Asn Ser Leu Arg Thr Ala
                435                 440                 445

Leu Ile Asn Ser Thr Gly Glu Glu Val Ala Met Arg Lys Leu Val Arg
            450                 455                 460

Ser Val Thr Val Val Glu Asp Asp Glu Asp Gly Asp Asp Leu
465                 470                 475                 480

Leu His His His His Val Ser Gly Ser Arg Arg
                485                 490

<210> SEQ ID NO 31
<211> LENGTH: 4563
<212> TYPE: PRT
<213> ORGANISM: Homo sapiens

<400> SEQUENCE: 31

Met Asp Pro Pro Arg Pro Ala Leu Leu Ala Leu Leu Ala Leu Pro Ala
1               5                   10                  15

Leu Leu Leu Leu Leu Leu Ala Gly Ala Arg Ala Glu Glu Glu Met Leu
                20                  25                  30

Glu Asn Val Ser Leu Val Cys Pro Lys Asp Ala Thr Arg Phe Lys His
                35                  40                  45

Leu Arg Lys Tyr Thr Tyr Asn Tyr Glu Ala Glu Ser Ser Ser Gly Val
            50                  55                  60

Pro Gly Thr Ala Asp Ser Arg Ser Ala Thr Arg Ile Asn Cys Lys Val
65                  70                  75                  80

Glu Leu Glu Val Pro Gln Leu Cys Ser Phe Ile Leu Lys Thr Ser Gln
                85                  90                  95

Cys Thr Leu Lys Glu Val Tyr Gly Phe Asn Pro Glu Gly Lys Ala Leu
                100                 105                 110

Leu Lys Lys Thr Lys Asn Ser Glu Glu Phe Ala Ala Ala Met Ser Arg
```

```
            115                 120                 125
Tyr Glu Leu Lys Leu Ala Ile Pro Glu Gly Lys Gln Val Phe Leu Tyr
    130                 135                 140
Pro Glu Lys Asp Glu Pro Thr Tyr Ile Leu Asn Ile Lys Arg Gly Ile
145                 150                 155                 160
Ile Ser Ala Leu Leu Val Pro Pro Glu Thr Glu Ala Lys Gln Val
                165                 170                 175
Leu Phe Leu Asp Thr Val Tyr Gly Asn Cys Ser Thr His Phe Thr Val
                180                 185                 190
Lys Thr Arg Lys Gly Asn Val Ala Thr Glu Ile Ser Thr Glu Arg Asp
            195                 200                 205
Leu Gly Gln Cys Asp Arg Phe Lys Pro Ile Arg Thr Gly Ile Ser Pro
    210                 215                 220
Leu Ala Leu Ile Lys Gly Met Thr Arg Pro Leu Ser Thr Leu Ile Ser
225                 230                 235                 240
Ser Ser Gln Ser Cys Gln Tyr Thr Leu Asp Ala Lys Arg Lys His Val
                245                 250                 255
Ala Glu Ala Ile Cys Lys Glu Gln His Leu Phe Leu Pro Phe Ser Tyr
                260                 265                 270
Asn Asn Lys Tyr Gly Met Val Ala Gln Val Thr Gln Thr Leu Lys Leu
            275                 280                 285
Glu Asp Thr Pro Lys Ile Asn Ser Arg Phe Phe Gly Glu Gly Thr Lys
    290                 295                 300
Lys Met Gly Leu Ala Phe Glu Ser Thr Lys Ser Thr Ser Pro Pro Lys
305                 310                 315                 320
Gln Ala Glu Ala Val Leu Lys Thr Leu Gln Glu Leu Lys Lys Leu Thr
                325                 330                 335
Ile Ser Glu Gln Asn Ile Gln Arg Ala Asn Leu Phe Asn Lys Leu Val
                340                 345                 350
Thr Glu Leu Arg Gly Leu Ser Asp Glu Ala Val Thr Ser Leu Leu Pro
            355                 360                 365
Gln Leu Ile Glu Val Ser Ser Pro Ile Thr Leu Gln Ala Leu Val Gln
    370                 375                 380
Cys Gly Gln Pro Gln Cys Ser Thr His Ile Leu Gln Trp Leu Lys Arg
385                 390                 395                 400
Val His Ala Asn Pro Leu Leu Ile Asp Val Val Thr Tyr Leu Val Ala
                405                 410                 415
Leu Ile Pro Glu Pro Ser Ala Gln Gln Leu Arg Glu Ile Phe Asn Met
                420                 425                 430
Ala Arg Asp Gln Arg Ser Arg Ala Thr Leu Tyr Ala Leu Ser His Ala
            435                 440                 445
Val Asn Asn Tyr His Lys Thr Asn Pro Thr Gly Thr Gln Glu Leu Leu
    450                 455                 460
Asp Ile Ala Asn Tyr Leu Met Glu Gln Ile Gln Asp Asp Cys Thr Gly
465                 470                 475                 480
Asp Glu Asp Tyr Thr Tyr Leu Ile Leu Arg Val Ile Gly Asn Met Gly
                485                 490                 495
Gln Thr Met Glu Gln Leu Thr Pro Glu Leu Lys Ser Ser Ile Leu Lys
                500                 505                 510
Cys Val Gln Ser Thr Lys Pro Ser Leu Met Ile Gln Lys Ala Ala Ile
            515                 520                 525
Gln Ala Leu Arg Lys Met Glu Pro Lys Asp Lys Asp Gln Glu Val Leu
    530                 535                 540
```

-continued

```
Leu Gln Thr Phe Leu Asp Asp Ala Ser Pro Gly Asp Lys Arg Leu Ala
545                 550                 555                 560

Ala Tyr Leu Met Leu Met Arg Ser Pro Ser Gln Ala Asp Ile Asn Lys
                565                 570                 575

Ile Val Gln Ile Leu Pro Trp Glu Gln Asn Glu Gln Val Lys Asn Phe
            580                 585                 590

Val Ala Ser His Ile Ala Asn Ile Leu Asn Ser Glu Glu Leu Asp Ile
        595                 600                 605

Gln Asp Leu Lys Lys Leu Val Lys Glu Ala Leu Lys Glu Ser Gln Leu
    610                 615                 620

Pro Thr Val Met Asp Phe Arg Lys Phe Ser Arg Asn Tyr Gln Leu Tyr
625                 630                 635                 640

Lys Ser Val Ser Leu Pro Ser Leu Asp Pro Ala Ser Ala Lys Ile Glu
                645                 650                 655

Gly Asn Leu Ile Phe Asp Pro Asn Asn Tyr Leu Pro Lys Glu Ser Met
            660                 665                 670

Leu Lys Thr Thr Leu Thr Ala Phe Gly Phe Ala Ser Ala Asp Leu Ile
        675                 680                 685

Glu Ile Gly Leu Glu Gly Lys Gly Phe Glu Pro Thr Leu Glu Ala Leu
    690                 695                 700

Phe Gly Lys Gln Gly Phe Phe Pro Asp Ser Val Asn Lys Ala Leu Tyr
705                 710                 715                 720

Trp Val Asn Gly Gln Val Pro Asp Gly Val Ser Lys Val Leu Val Asp
                725                 730                 735

His Phe Gly Tyr Thr Lys Asp Asp Lys His Glu Gln Asp Met Val Asn
            740                 745                 750

Gly Ile Met Leu Ser Val Glu Lys Leu Ile Lys Asp Leu Lys Ser Lys
        755                 760                 765

Glu Val Pro Glu Ala Arg Ala Tyr Leu Arg Ile Leu Gly Glu Glu Leu
    770                 775                 780

Gly Phe Ala Ser Leu His Asp Leu Gln Leu Leu Gly Lys Leu Leu Leu
785                 790                 795                 800

Met Gly Ala Arg Thr Leu Gln Gly Ile Pro Gln Met Ile Gly Glu Val
                805                 810                 815

Ile Arg Lys Gly Ser Lys Asn Asp Phe Phe Leu His Tyr Ile Phe Met
            820                 825                 830

Glu Asn Ala Phe Glu Leu Pro Thr Gly Ala Gly Leu Gln Leu Gln Ile
        835                 840                 845

Ser Ser Ser Gly Val Ile Ala Pro Gly Ala Lys Ala Gly Val Lys Leu
    850                 855                 860

Glu Val Ala Asn Met Gln Ala Glu Leu Val Ala Lys Pro Ser Val Ser
865                 870                 875                 880

Val Glu Phe Val Thr Asn Met Gly Ile Ile Pro Asp Phe Ala Arg
                885                 890                 895

Ser Gly Val Gln Met Asn Thr Asn Phe Phe His Glu Ser Gly Leu Glu
            900                 905                 910

Ala His Val Ala Leu Lys Ala Gly Lys Leu Lys Phe Ile Ile Pro Ser
        915                 920                 925

Pro Lys Arg Pro Val Lys Leu Leu Ser Gly Gly Asn Thr Leu His Leu
    930                 935                 940

Val Ser Thr Thr Lys Thr Glu Val Ile Pro Pro Leu Ile Glu Asn Arg
945                 950                 955                 960

Gln Ser Trp Ser Val Cys Lys Gln Val Phe Pro Gly Leu Asn Tyr Cys
                965                 970                 975
```

```
Thr Ser Gly Ala Tyr Ser Asn Ala Ser Ser Thr Asp Ser Ala Ser Tyr
            980                 985                 990

Tyr Pro Leu Thr Gly Asp Thr Arg  Leu Glu Leu Glu Leu Arg Pro Thr
        995                 1000                1005

Gly Glu Ile Glu Gln Tyr Ser Val Ser Ala Thr Tyr Glu Leu Gln
    1010                1015                1020

Arg Glu Asp Arg Ala Leu Val Asp Thr Leu Lys Phe Val Thr Gln
    1025                1030                1035

Ala Glu Gly Ala Lys Gln Thr Glu Ala Thr Met Thr Phe Lys Tyr
    1040                1045                1050

Asn Arg Gln Ser Met Thr Leu Ser Ser Glu Val Gln Ile Pro Asp
    1055                1060                1065

Phe Asp Val Asp Leu Gly Thr Ile Leu Arg Val Asn Asp Glu Ser
    1070                1075                1080

Thr Glu Gly Lys Thr Ser Tyr Arg Leu Thr Leu Asp Ile Gln Asn
    1085                1090                1095

Lys Lys Ile Thr Glu Val Ala Leu Met Gly His Leu Ser Cys Asp
    1100                1105                1110

Thr Lys Glu Glu Arg Lys Ile Lys Gly Val Ile Ser Ile Pro Arg
    1115                1120                1125

Leu Gln Ala Glu Ala Arg Ser Glu Ile Leu Ala His Trp Ser Pro
    1130                1135                1140

Ala Lys Leu Leu Leu Gln Met Asp Ser Ser Ala Thr Ala Tyr Gly
    1145                1150                1155

Ser Thr Val Ser Lys Arg Val Ala Trp His Tyr Asp Glu Glu Lys
    1160                1165                1170

Ile Glu Phe Glu Trp Asn Thr Gly Thr Asn Val Asp Thr Lys Lys
    1175                1180                1185

Met Thr Ser Asn Phe Pro Val Asp Leu Ser Asp Tyr Pro Lys Ser
    1190                1195                1200

Leu His Met Tyr Ala Asn Arg Leu Leu Asp His Arg Val Pro Glu
    1205                1210                1215

Thr Asp Met Thr Phe Arg His Val Gly Ser Lys Leu Ile Val Ala
    1220                1225                1230

Met Ser Ser Trp Leu Gln Lys Ala Ser Gly Ser Leu Pro Tyr Thr
    1235                1240                1245

Gln Thr Leu Gln Asp His Leu Asn Ser Leu Lys Glu Phe Asn Leu
    1250                1255                1260

Gln Asn Met Gly Leu Pro Asp Phe His Ile Pro Glu Asn Leu Phe
    1265                1270                1275

Leu Lys Ser Asp Gly Arg Val Lys Tyr Thr Leu Asn Lys Asn Ser
    1280                1285                1290

Leu Lys Ile Glu Ile Pro Leu Pro Phe Gly Gly Lys Ser Ser Arg
    1295                1300                1305

Asp Leu Lys Met Leu Glu Thr Val Arg Thr Pro Ala Leu His Phe
    1310                1315                1320

Lys Ser Val Gly Phe His Leu Pro Ser Arg Glu Phe Gln Val Pro
    1325                1330                1335

Thr Phe Thr Ile Pro Lys Leu Tyr Gln Leu Gln Val Pro Leu Leu
    1340                1345                1350

Gly Val Leu Asp Leu Ser Thr Asn Val Tyr Ser Asn Leu Tyr Asn
    1355                1360                1365

Trp Ser Ala Ser Tyr Ser Gly Gly Asn Thr Ser Thr Asp His Phe
```

-continued

```
               1370                1375              1380

Ser Leu Arg Ala Arg Tyr His Met Lys Ala Asp Ser Val Val Asp
    1385                1390              1395

Leu Leu Ser Tyr Asn Val Gln Gly Ser Gly Glu Thr Thr Tyr Asp
    1400                1405              1410

His Lys Asn Thr Phe Thr Leu Ser Cys Asp Gly Ser Leu Arg His
    1415                1420              1425

Lys Phe Leu Asp Ser Asn Ile Lys Phe Ser His Val Glu Lys Leu
    1430                1435              1440

Gly Asn Asn Pro Val Ser Lys Gly Leu Leu Ile Phe Asp Ala Ser
    1445                1450              1455

Ser Ser Trp Gly Pro Gln Met Ser Ala Ser Val His Leu Asp Ser
    1460                1465              1470

Lys Lys Lys Gln His Leu Phe Val Lys Glu Val Lys Ile Asp Gly
    1475                1480              1485

Gln Phe Arg Val Ser Ser Phe Tyr Ala Lys Gly Thr Tyr Gly Leu
    1490                1495              1500

Ser Cys Gln Arg Asp Pro Asn Thr Gly Arg Leu Asn Gly Glu Ser
    1505                1510              1515

Asn Leu Arg Phe Asn Ser Ser Tyr Leu Gln Gly Thr Asn Gln Ile
    1520                1525              1530

Thr Gly Arg Tyr Glu Asp Gly Thr Leu Ser Leu Thr Ser Thr Ser
    1535                1540              1545

Asp Leu Gln Ser Gly Ile Ile Lys Asn Thr Ala Ser Leu Lys Tyr
    1550                1555              1560

Glu Asn Tyr Glu Leu Thr Leu Lys Ser Asp Thr Asn Gly Lys Tyr
    1565                1570              1575

Lys Asn Phe Ala Thr Ser Asn Lys Met Asp Met Thr Phe Ser Lys
    1580                1585              1590

Gln Asn Ala Leu Leu Arg Ser Glu Tyr Gln Ala Asp Tyr Glu Ser
    1595                1600              1605

Leu Arg Phe Phe Ser Leu Leu Ser Gly Ser Leu Asn Ser His Gly
    1610                1615              1620

Leu Glu Leu Asn Ala Asp Ile Leu Gly Thr Asp Lys Ile Asn Ser
    1625                1630              1635

Gly Ala His Lys Ala Thr Leu Arg Ile Gly Gln Asp Gly Ile Ser
    1640                1645              1650

Thr Ser Ala Thr Thr Asn Leu Lys Cys Ser Leu Leu Val Leu Glu
    1655                1660              1665

Asn Glu Leu Asn Ala Glu Leu Gly Leu Ser Gly Ala Ser Met Lys
    1670                1675              1680

Leu Thr Thr Asn Gly Arg Phe Arg Glu His Asn Ala Lys Phe Ser
    1685                1690              1695

Leu Asp Gly Lys Ala Ala Leu Thr Glu Leu Ser Leu Gly Ser Ala
    1700                1705              1710

Tyr Gln Ala Met Ile Leu Gly Val Asp Ser Lys Asn Ile Phe Asn
    1715                1720              1725

Phe Lys Val Ser Gln Glu Gly Leu Lys Leu Ser Asn Asp Met Met
    1730                1735              1740

Gly Ser Tyr Ala Glu Met Lys Phe Asp His Thr Asn Ser Leu Asn
    1745                1750              1755

Ile Ala Gly Leu Ser Leu Asp Phe Ser Ser Lys Leu Asp Asn Ile
    1760                1765              1770
```

-continued

Tyr Ser Ser Asp Lys Phe Tyr Lys Gln Thr Val Asn Leu Gln Leu
1775             1780              1785

Gln Pro Tyr Ser Leu Val Thr Thr Leu Asn Ser Asp Leu Lys Tyr
1790             1795              1800

Asn Ala Leu Asp Leu Thr Asn Asn Gly Lys Leu Arg Leu Glu Pro
1805             1810              1815

Leu Lys Leu His Val Ala Gly Asn Leu Lys Gly Ala Tyr Gln Asn
1820             1825              1830

Asn Glu Ile Lys His Ile Tyr Ala Ile Ser Ser Ala Ala Leu Ser
1835             1840              1845

Ala Ser Tyr Lys Ala Asp Thr Val Ala Lys Val Gln Gly Val Glu
1850             1855              1860

Phe Ser His Arg Leu Asn Thr Asp Ile Ala Gly Leu Ala Ser Ala
1865             1870              1875

Ile Asp Met Ser Thr Asn Tyr Asn Ser Asp Ser Leu His Phe Ser
1880             1885              1890

Asn Val Phe Arg Ser Val Met Ala Pro Phe Thr Met Thr Ile Asp
1895             1900              1905

Ala His Thr Asn Gly Asn Gly Lys Leu Ala Leu Trp Gly Glu His
1910             1915              1920

Thr Gly Gln Leu Tyr Ser Lys Phe Leu Leu Lys Ala Glu Pro Leu
1925             1930              1935

Ala Phe Thr Phe Ser His Asp Tyr Lys Gly Ser Thr Ser His His
1940             1945              1950

Leu Val Ser Arg Lys Ser Ile Ser Ala Ala Leu Glu His Lys Val
1955             1960              1965

Ser Ala Leu Leu Thr Pro Ala Glu Gln Thr Gly Thr Trp Lys Leu
1970             1975              1980

Lys Thr Gln Phe Asn Asn Asn Glu Tyr Ser Gln Asp Leu Asp Ala
1985             1990              1995

Tyr Asn Thr Lys Asp Lys Ile Gly Val Glu Leu Thr Gly Arg Thr
2000             2005              2010

Leu Ala Asp Leu Thr Leu Leu Asp Ser Pro Ile Lys Val Pro Leu
2015             2020              2025

Leu Leu Ser Glu Pro Ile Asn Ile Ile Asp Ala Leu Glu Met Arg
2030             2035              2040

Asp Ala Val Glu Lys Pro Gln Glu Phe Thr Ile Val Ala Phe Val
2045             2050              2055

Lys Tyr Asp Lys Asn Gln Asp Val His Ser Ile Asn Leu Pro Phe
2060             2065              2070

Phe Glu Thr Leu Gln Glu Tyr Phe Glu Arg Asn Arg Gln Thr Ile
2075             2080              2085

Ile Val Val Val Glu Asn Val Gln Arg Asn Leu Lys His Ile Asn
2090             2095              2100

Ile Asp Gln Phe Val Arg Lys Tyr Arg Ala Ala Leu Gly Lys Leu
2105             2110              2115

Pro Gln Gln Ala Asn Asp Tyr Leu Asn Ser Phe Asn Trp Glu Arg
2120             2125              2130

Gln Val Ser His Ala Lys Glu Lys Leu Thr Ala Leu Thr Lys Lys
2135             2140              2145

Tyr Arg Ile Thr Glu Asn Asp Ile Gln Ile Ala Leu Asp Asp Ala
2150             2155              2160

Lys Ile Asn Phe Asn Glu Lys Leu Ser Gln Leu Gln Thr Tyr Met
2165             2170              2175

```
Ile Gln Phe Asp Gln Tyr Ile Lys Asp Ser Tyr Asp Leu His Asp
    2180                2185                2190

Leu Lys Ile Ala Ile Ala Asn Ile Ile Asp Glu Ile Ile Glu Lys
    2195                2200                2205

Leu Lys Ser Leu Asp Glu His Tyr His Ile Arg Val Asn Leu Val
    2210                2215                2220

Lys Thr Ile His Asp Leu His Leu Phe Ile Glu Asn Ile Asp Phe
    2225                2230                2235

Asn Lys Ser Gly Ser Ser Thr Ala Ser Trp Ile Gln Asn Val Asp
    2240                2245                2250

Thr Lys Tyr Gln Ile Arg Ile Gln Ile Gln Glu Lys Leu Gln Gln
    2255                2260                2265

Leu Lys Arg His Ile Gln Asn Ile Asp Ile Gln His Leu Ala Gly
    2270                2275                2280

Lys Leu Lys Gln His Ile Glu Ala Ile Asp Val Arg Val Leu Leu
    2285                2290                2295

Asp Gln Leu Gly Thr Thr Ile Ser Phe Glu Arg Ile Asn Asp Val
    2300                2305                2310

Leu Glu His Val Lys His Phe Val Ile Asn Leu Ile Gly Asp Phe
    2315                2320                2325

Glu Val Ala Glu Lys Ile Asn Ala Phe Arg Ala Lys Val His Glu
    2330                2335                2340

Leu Ile Glu Arg Tyr Glu Val Asp Gln Gln Ile Gln Val Leu Met
    2345                2350                2355

Asp Lys Leu Val Glu Leu Thr His Gln Tyr Lys Leu Lys Glu Thr
    2360                2365                2370

Ile Gln Lys Leu Ser Asn Val Leu Gln Gln Val Lys Ile Lys Asp
    2375                2380                2385

Tyr Phe Glu Lys Leu Val Gly Phe Ile Asp Asp Ala Val Lys Lys
    2390                2395                2400

Leu Asn Glu Leu Ser Phe Lys Thr Phe Ile Glu Asp Val Asn Lys
    2405                2410                2415

Phe Leu Asp Met Leu Ile Lys Lys Leu Lys Ser Phe Asp Tyr His
    2420                2425                2430

Gln Phe Val Asp Glu Thr Asn Asp Lys Ile Arg Glu Val Thr Gln
    2435                2440                2445

Arg Leu Asn Gly Glu Ile Gln Ala Leu Glu Leu Pro Gln Lys Ala
    2450                2455                2460

Glu Ala Leu Lys Leu Phe Leu Glu Glu Thr Lys Ala Thr Val Ala
    2465                2470                2475

Val Tyr Leu Glu Ser Leu Gln Asp Thr Lys Ile Thr Leu Ile Ile
    2480                2485                2490

Asn Trp Leu Gln Glu Ala Leu Ser Ser Ala Ser Leu Ala His Met
    2495                2500                2505

Lys Ala Lys Phe Arg Glu Thr Leu Glu Asp Thr Arg Asp Arg Met
    2510                2515                2520

Tyr Gln Met Asp Ile Gln Gln Glu Leu Gln Arg Tyr Leu Ser Leu
    2525                2530                2535

Val Gly Gln Val Tyr Ser Thr Leu Val Thr Tyr Ile Ser Asp Trp
    2540                2545                2550

Trp Thr Leu Ala Ala Lys Asn Leu Thr Asp Phe Ala Glu Gln Tyr
    2555                2560                2565

Ser Ile Gln Asp Trp Ala Lys Arg Met Lys Ala Leu Val Glu Gln
```

```
                    2570                2575                2580

Gly Phe Thr Val Pro Glu Ile Lys Thr Ile Leu Gly Thr Met Pro
        2585                2590                2595

Ala Phe Glu Val Ser Leu Gln Ala Leu Gln Lys Ala Thr Phe Gln
    2600                2605                2610

Thr Pro Asp Phe Ile Val Pro Leu Thr Asp Leu Arg Ile Pro Ser
    2615                2620                2625

Val Gln Ile Asn Phe Lys Asp Leu Lys Asn Ile Lys Ile Pro Ser
    2630                2635                2640

Arg Phe Ser Thr Pro Glu Phe Thr Ile Leu Asn Thr Phe His Ile
    2645                2650                2655

Pro Ser Phe Thr Ile Asp Phe Val Glu Met Lys Val Lys Ile Ile
    2660                2665                2670

Arg Thr Ile Asp Gln Met Gln Asn Ser Glu Leu Gln Trp Pro Val
    2675                2680                2685

Pro Asp Ile Tyr Leu Arg Asp Leu Lys Val Glu Asp Ile Pro Leu
    2690                2695                2700

Ala Arg Ile Thr Leu Pro Asp Phe Arg Leu Pro Glu Ile Ala Ile
    2705                2710                2715

Pro Glu Phe Ile Ile Pro Thr Leu Asn Leu Asn Asp Phe Gln Val
    2720                2725                2730

Pro Asp Leu His Ile Pro Glu Phe Gln Leu Pro His Ile Ser His
    2735                2740                2745

Thr Ile Glu Val Pro Thr Phe Gly Lys Leu Tyr Ser Ile Leu Lys
    2750                2755                2760

Ile Gln Ser Pro Leu Phe Thr Leu Asp Ala Asn Ala Asp Ile Gly
    2765                2770                2775

Asn Gly Thr Thr Ser Ala Asn Glu Ala Gly Ile Ala Ala Ser Ile
    2780                2785                2790

Thr Ala Lys Gly Glu Ser Lys Leu Glu Val Leu Asn Phe Asp Phe
    2795                2800                2805

Gln Ala Asn Ala Gln Leu Ser Asn Pro Lys Ile Asn Pro Leu Ala
    2810                2815                2820

Leu Lys Glu Ser Val Lys Phe Ser Ser Lys Tyr Leu Arg Thr Glu
    2825                2830                2835

His Gly Ser Glu Met Leu Phe Phe Gly Asn Ala Ile Glu Gly Lys
    2840                2845                2850

Ser Asn Thr Val Ala Ser Leu His Thr Glu Lys Asn Thr Leu Glu
    2855                2860                2865

Leu Ser Asn Gly Val Ile Val Lys Ile Asn Asn Gln Leu Thr Leu
    2870                2875                2880

Asp Ser Asn Thr Lys Tyr Phe His Lys Leu Asn Ile Pro Lys Leu
    2885                2890                2895

Asp Phe Ser Ser Gln Ala Asp Leu Arg Asn Glu Ile Lys Thr Leu
    2900                2905                2910

Leu Lys Ala Gly His Ile Ala Trp Thr Ser Ser Gly Lys Gly Ser
    2915                2920                2925

Trp Lys Trp Ala Cys Pro Arg Phe Ser Asp Glu Gly Thr His Glu
    2930                2935                2940

Ser Gln Ile Ser Phe Thr Ile Glu Gly Pro Leu Thr Ser Phe Gly
    2945                2950                2955

Leu Ser Asn Lys Ile Asn Ser Lys His Leu Arg Val Asn Gln Asn
    2960                2965                2970
```

```
Leu Val Tyr Glu Ser Gly Ser Leu Asn Phe Ser Lys Leu Glu Ile
2975             2980                 2985

Gln Ser Gln Val Asp Ser Gln His Val Gly His Ser Val Leu Thr
2990             2995                 3000

Ala Lys Gly Met Ala Leu Phe Gly Glu Gly Lys Ala Glu Phe Thr
3005             3010                 3015

Gly Arg His Asp Ala His Leu Asn Gly Lys Val Ile Gly Thr Leu
3020             3025                 3030

Lys Asn Ser Leu Phe Phe Ser Ala Gln Pro Phe Glu Ile Thr Ala
3035             3040                 3045

Ser Thr Asn Asn Glu Gly Asn Leu Lys Val Arg Phe Pro Leu Arg
3050             3055                 3060

Leu Thr Gly Lys Ile Asp Phe Leu Asn Asn Tyr Ala Leu Phe Leu
3065             3070                 3075

Ser Pro Ser Ala Gln Gln Ala Ser Trp Gln Val Ser Ala Arg Phe
3080             3085                 3090

Asn Gln Tyr Lys Tyr Asn Gln Asn Phe Ser Ala Gly Asn Asn Glu
3095             3100                 3105

Asn Ile Met Glu Ala His Val Gly Ile Asn Gly Glu Ala Asn Leu
3110             3115                 3120

Asp Phe Leu Asn Ile Pro Leu Thr Ile Pro Glu Met Arg Leu Pro
3125             3130                 3135

Tyr Thr Ile Ile Thr Thr Pro Pro Leu Lys Asp Phe Ser Leu Trp
3140             3145                 3150

Glu Lys Thr Gly Leu Lys Glu Phe Leu Lys Thr Thr Lys Gln Ser
3155             3160                 3165

Phe Asp Leu Ser Val Lys Ala Gln Tyr Lys Lys Asn Lys His Arg
3170             3175                 3180

His Ser Ile Thr Asn Pro Leu Ala Val Leu Cys Glu Phe Ile Ser
3185             3190                 3195

Gln Ser Ile Lys Ser Phe Asp Arg His Phe Glu Lys Asn Arg Asn
3200             3205                 3210

Asn Ala Leu Asp Phe Val Thr Lys Ser Tyr Asn Glu Thr Lys Ile
3215             3220                 3225

Lys Phe Asp Lys Tyr Lys Ala Glu Lys Ser His Asp Glu Leu Pro
3230             3235                 3240

Arg Thr Phe Gln Ile Pro Gly Tyr Thr Val Pro Val Val Asn Val
3245             3250                 3255

Glu Val Ser Pro Phe Thr Ile Glu Met Ser Ala Phe Gly Tyr Val
3260             3265                 3270

Phe Pro Lys Ala Val Ser Met Pro Ser Phe Ser Ile Leu Gly Ser
3275             3280                 3285

Asp Val Arg Val Pro Ser Tyr Thr Leu Ile Leu Pro Ser Leu Glu
3290             3295                 3300

Leu Pro Val Leu His Val Pro Arg Asn Leu Lys Leu Ser Leu Pro
3305             3310                 3315

His Phe Lys Glu Leu Cys Thr Ile Ser His Ile Phe Ile Pro Ala
3320             3325                 3330

Met Gly Asn Ile Thr Tyr Asp Phe Ser Phe Lys Ser Ser Val Ile
3335             3340                 3345

Thr Leu Asn Thr Asn Ala Glu Leu Phe Asn Gln Ser Asp Ile Val
3350             3355                 3360

Ala His Leu Leu Ser Ser Ser Ser Ser Val Ile Asp Ala Leu Gln
3365             3370                 3375
```

-continued

Tyr Lys Leu Glu Gly Thr Thr Arg Leu Thr Arg Lys Arg Gly Leu
3380            3385                3390

Lys Leu Ala Thr Ala Leu Ser Leu Ser Asn Lys Phe Val Glu Gly
3395            3400                3405

Ser His Asn Ser Thr Val Ser Leu Thr Thr Lys Asn Met Glu Val
3410            3415                3420

Ser Val Ala Lys Thr Thr Lys Ala Glu Ile Pro Ile Leu Arg Met
3425            3430                3435

Asn Phe Lys Gln Glu Leu Asn Gly Asn Thr Lys Ser Lys Pro Thr
3440            3445                3450

Val Ser Ser Ser Met Glu Phe Lys Tyr Asp Phe Asn Ser Ser Met
3455            3460                3465

Leu Tyr Ser Thr Ala Lys Gly Ala Val Asp His Lys Leu Ser Leu
3470            3475                3480

Glu Ser Leu Thr Ser Tyr Phe Ser Ile Glu Ser Ser Thr Lys Gly
3485            3490                3495

Asp Val Lys Gly Ser Val Leu Ser Arg Glu Tyr Ser Gly Thr Ile
3500            3505                3510

Ala Ser Glu Ala Asn Thr Tyr Leu Asn Ser Lys Ser Thr Arg Ser
3515            3520                3525

Ser Val Lys Leu Gln Gly Thr Ser Lys Ile Asp Asp Ile Trp Asn
3530            3535                3540

Leu Glu Val Lys Glu Asn Phe Ala Gly Glu Ala Thr Leu Gln Arg
3545            3550                3555

Ile Tyr Ser Leu Trp Glu His Ser Thr Lys Asn His Leu Gln Leu
3560            3565                3570

Glu Gly Leu Phe Phe Thr Asn Gly Glu His Thr Ser Lys Ala Thr
3575            3580                3585

Leu Glu Leu Ser Pro Trp Gln Met Ser Ala Leu Val Gln Val His
3590            3595                3600

Ala Ser Gln Pro Ser Ser Phe His Asp Phe Pro Asp Leu Gly Gln
3605            3610                3615

Glu Val Ala Leu Asn Ala Asn Thr Lys Asn Gln Lys Ile Arg Trp
3620            3625                3630

Lys Asn Glu Val Arg Ile His Ser Gly Ser Phe Gln Ser Gln Val
3635            3640                3645

Glu Leu Ser Asn Asp Gln Glu Lys Ala His Leu Asp Ile Ala Gly
3650            3655                3660

Ser Leu Glu Gly His Leu Arg Phe Leu Lys Asn Ile Ile Leu Pro
3665            3670                3675

Val Tyr Asp Lys Ser Leu Trp Asp Phe Leu Lys Leu Asp Val Thr
3680            3685                3690

Thr Ser Ile Gly Arg Arg Gln His Leu Arg Val Ser Thr Ala Phe
3695            3700                3705

Val Tyr Thr Lys Asn Pro Asn Gly Tyr Ser Phe Ser Ile Pro Val
3710            3715                3720

Lys Val Leu Ala Asp Lys Phe Ile Thr Pro Gly Leu Lys Leu Asn
3725            3730                3735

Asp Leu Asn Ser Val Leu Val Met Pro Thr Phe His Val Pro Phe
3740            3745                3750

Thr Asp Leu Gln Val Pro Ser Cys Lys Leu Asp Phe Arg Glu Ile
3755            3760                3765

Gln Ile Tyr Lys Lys Leu Arg Thr Ser Ser Phe Ala Leu Asn Leu

```
                  3770              3775              3780
Pro Thr Leu Pro Glu Val Lys Phe Pro Glu Val Asp Val Leu Thr
    3785              3790              3795
Lys Tyr Ser Gln Pro Glu Asp Ser Leu Ile Pro Phe Phe Glu Ile
    3800              3805              3810
Thr Val Pro Glu Ser Gln Leu Thr Val Ser Gln Phe Thr Leu Pro
    3815              3820              3825
Lys Ser Val Ser Asp Gly Ile Ala Ala Leu Asp Leu Asn Ala Val
    3830              3835              3840
Ala Asn Lys Ile Ala Asp Phe Glu Leu Pro Thr Ile Ile Val Pro
    3845              3850              3855
Glu Gln Thr Ile Glu Ile Pro Ser Ile Lys Phe Ser Val Pro Ala
    3860              3865              3870
Gly Ile Val Ile Pro Ser Phe Gln Ala Leu Thr Ala Arg Phe Glu
    3875              3880              3885
Val Asp Ser Pro Val Tyr Asn Ala Thr Trp Ser Ala Ser Leu Lys
    3890              3895              3900
Asn Lys Ala Asp Tyr Val Glu Thr Val Leu Asp Ser Thr Cys Ser
    3905              3910              3915
Ser Thr Val Gln Phe Leu Glu Tyr Glu Leu Asn Val Leu Gly Thr
    3920              3925              3930
His Lys Ile Glu Asp Gly Thr Leu Ala Ser Lys Thr Lys Gly Thr
    3935              3940              3945
Leu Ala His Arg Asp Phe Ser Ala Glu Tyr Glu Glu Asp Gly Lys
    3950              3955              3960
Phe Glu Gly Leu Gln Glu Trp Glu Gly Lys Ala His Leu Asn Ile
    3965              3970              3975
Lys Ser Pro Ala Phe Thr Asp Leu His Leu Arg Tyr Gln Lys Asp
    3980              3985              3990
Lys Lys Gly Ile Ser Thr Ser Ala Ala Ser Pro Ala Val Gly Thr
    3995              4000              4005
Val Gly Met Asp Met Asp Glu Asp Asp Asp Phe Ser Lys Trp Asn
    4010              4015              4020
Phe Tyr Tyr Ser Pro Gln Ser Ser Pro Asp Lys Lys Leu Thr Ile
    4025              4030              4035
Phe Lys Thr Glu Leu Arg Val Arg Glu Ser Asp Glu Thr Gln
    4040              4045              4050
Ile Lys Val Asn Trp Glu Glu Glu Ala Ala Ser Gly Leu Leu Thr
    4055              4060              4065
Ser Leu Lys Asp Asn Val Pro Lys Ala Thr Gly Val Leu Tyr Asp
    4070              4075              4080
Tyr Val Asn Lys Tyr His Trp Glu His Thr Gly Leu Thr Leu Arg
    4085              4090              4095
Glu Val Ser Ser Lys Leu Arg Arg Asn Leu Gln Asn Asn Ala Glu
    4100              4105              4110
Trp Val Tyr Gln Gly Ala Ile Arg Gln Ile Asp Asp Ile Asp Val
    4115              4120              4125
Arg Phe Gln Lys Ala Ala Ser Gly Thr Thr Gly Thr Tyr Gln Glu
    4130              4135              4140
Trp Lys Asp Lys Ala Gln Asn Leu Tyr Gln Glu Leu Leu Thr Gln
    4145              4150              4155
Glu Gly Gln Ala Ser Phe Gln Gly Leu Lys Asp Asn Val Phe Asp
    4160              4165              4170
```

-continued

```
Gly Leu Val Arg Val Thr Gln Lys Phe His Met Lys Val Lys His
4175                4180                4185

Leu Ile Asp Ser Leu Ile Asp Phe Leu Asn Phe Pro Arg Phe Gln
4190                4195                4200

Phe Pro Gly Lys Pro Gly Ile Tyr Thr Arg Glu Glu Leu Cys Thr
4205                4210                4215

Met Phe Ile Arg Glu Val Gly Thr Val Leu Ser Gln Val Tyr Ser
4220                4225                4230

Lys Val His Asn Gly Ser Glu Ile Leu Phe Ser Tyr Phe Gln Asp
4235                4240                4245

Leu Val Ile Thr Leu Pro Phe Glu Leu Arg Lys His Lys Leu Ile
4250                4255                4260

Asp Val Ile Ser Met Tyr Arg Glu Leu Leu Lys Asp Leu Ser Lys
4265                4270                4275

Glu Ala Gln Glu Val Phe Lys Ala Ile Gln Ser Leu Lys Thr Thr
4280                4285                4290

Glu Val Leu Arg Asn Leu Gln Asp Leu Leu Gln Phe Ile Phe Gln
4295                4300                4305

Leu Ile Glu Asp Asn Ile Lys Gln Leu Lys Glu Met Lys Phe Thr
4310                4315                4320

Tyr Leu Ile Asn Tyr Ile Gln Asp Glu Ile Asn Thr Ile Phe Asn
4325                4330                4335

Asp Tyr Ile Pro Tyr Val Phe Lys Leu Leu Lys Glu Asn Leu Cys
4340                4345                4350

Leu Asn Leu His Lys Phe Asn Glu Phe Ile Gln Asn Glu Leu Gln
4355                4360                4365

Glu Ala Ser Gln Glu Leu Gln Gln Ile His Gln Tyr Ile Met Ala
4370                4375                4380

Leu Arg Glu Glu Tyr Phe Asp Pro Ser Ile Val Gly Trp Thr Val
4385                4390                4395

Lys Tyr Tyr Glu Leu Glu Glu Lys Ile Val Ser Leu Ile Lys Asn
4400                4405                4410

Leu Leu Val Ala Leu Lys Asp Phe His Ser Glu Tyr Ile Val Ser
4415                4420                4425

Ala Ser Asn Phe Thr Ser Gln Leu Ser Ser Gln Val Glu Gln Phe
4430                4435                4440

Leu His Arg Asn Ile Gln Glu Tyr Leu Ser Ile Leu Thr Asp Pro
4445                4450                4455

Asp Gly Lys Gly Lys Glu Lys Ile Ala Glu Leu Ser Ala Thr Ala
4460                4465                4470

Gln Glu Ile Ile Lys Ser Gln Ala Ile Ala Thr Lys Lys Ile Ile
4475                4480                4485

Ser Asp Tyr His Gln Gln Phe Arg Tyr Lys Leu Gln Asp Phe Ser
4490                4495                4500

Asp Gln Leu Ser Asp Tyr Tyr Glu Lys Phe Ile Ala Glu Ser Lys
4505                4510                4515

Arg Leu Ile Asp Leu Ser Ile Gln Asn Tyr His Thr Phe Leu Ile
4520                4525                4530

Tyr Ile Thr Glu Leu Leu Lys Lys Leu Gln Ser Thr Thr Val Met
4535                4540                4545

Asn Pro Tyr Met Lys Leu Ala Pro Gly Glu Leu Thr Ile Ile Leu
4550                4555                4560
```

<210> SEQ ID NO 32

```
<211> LENGTH: 339
<212> TYPE: PRT
<213> ORGANISM: Homo sapiens

<400> SEQUENCE: 32

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp

<210> SEQ ID NO 33
<211> LENGTH: 261
<212> TYPE: PRT
<213> ORGANISM: Homo sapiens

<400> SEQUENCE: 33

Met Ala Ser Pro Asp Trp Gly Tyr Asp Asp Lys Asn Gly Pro Glu Gln
```

```
                1               5                  10                 15
Trp Ser Lys Leu Tyr Pro Ile Ala Asn Gly Asn Asn Gln Ser Pro Val
                20                 25                 30

Asp Ile Lys Thr Ser Glu Thr Lys His Asp Thr Ser Leu Lys Pro Ile
                35                 40                 45

Ser Val Ser Tyr Asn Pro Ala Thr Ala Lys Glu Ile Ile Asn Val Gly
                50                 55                 60

His Ser Phe His Val Asn Phe Glu Asp Asn Asp Asn Arg Ser Val Leu
65                                 70                 75                                  80

Lys Gly Gly Pro Phe Ser Asp Ser Tyr Arg Leu Phe Gln Phe His Phe
                                   85                 90                 95

His Trp Gly Ser Thr Asn Glu His Gly Ser Glu His Thr Val Asp Gly
                                   100                105                110

Val Lys Tyr Ser Ala Glu Leu His Val Ala His Trp Asn Ser Ala Lys
                                   115                120                125

Tyr Ser Ser Leu Ala Glu Ala Ala Ser Lys Ala Asp Gly Leu Ala Val
                                   130                135                140

Ile Gly Val Leu Met Lys Val Gly Glu Ala Asn Pro Lys Leu Gln Lys
145                                150                155                               160

Val Leu Asp Ala Leu Gln Ala Ile Lys Thr Lys Gly Lys Arg Ala Pro
                                   165                170                175

Phe Thr Asn Phe Asp Pro Ser Thr Leu Leu Pro Ser Ser Leu Asp Phe
                                   180                185                190

Trp Thr Tyr Pro Gly Ser Leu Thr His Pro Pro Leu Tyr Glu Ser Val
                                   195                200                205

Thr Trp Ile Ile Cys Lys Glu Ser Ile Ser Val Ser Ser Glu Gln Leu
                                   210                215                220

Ala Gln Phe Arg Ser Leu Leu Ser Asn Val Glu Gly Asp Asn Ala Val
225                                230                235                               240

Pro Met Gln His Asn Asn Arg Pro Thr Gln Pro Leu Lys Gly Arg Thr
                                   245                250                255

Val Arg Ala Ser Phe
                                   260

<210> SEQ ID NO 34
<211> LENGTH: 260
<212> TYPE: PRT
<213> ORGANISM: Homo sapiens

<400> SEQUENCE: 34

Met Ser His His Trp Gly Tyr Gly Lys His Asn Gly Pro Glu His Trp
1               5                  10                 15

His Lys Asp Phe Pro Ile Ala Lys Gly Glu Arg Gln Ser Pro Val Asp
                20                 25                 30

Ile Asp Thr His Thr Ala Lys Tyr Asp Pro Ser Leu Lys Pro Leu Ser
                35                 40                 45

Val Ser Tyr Asp Gln Ala Thr Ser Leu Arg Ile Leu Asn Asn Gly His
                50                 55                 60

Ala Phe Asn Val Glu Phe Asp Asp Ser Gln Asp Lys Ala Val Leu Lys
65                                 70                 75                                  80

Gly Gly Pro Leu Asp Gly Thr Tyr Arg Leu Ile Gln Phe His Phe His
                                   85                 90                 95

Trp Gly Ser Leu Asp Gly Gln Gly Ser Glu His Thr Val Asp Lys Lys
                                   100                105                110

Lys Tyr Ala Ala Glu Leu His Leu Val His Trp Asn Thr Lys Tyr Gly
```

```
                    115                 120                 125
Asp Phe Gly Lys Ala Val Gln Gln Pro Asp Gly Leu Ala Val Leu Gly
        130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
        180                 185                 190

Tyr Pro Gly Ser Leu Thr Thr Pro Pro Leu Leu Glu Cys Val Thr Trp
                195                 200                 205

Ile Val Leu Lys Glu Pro Ile Ser Val Ser Ser Glu Gln Val Leu Lys
        210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
        260

<210> SEQ ID NO 35
<211> LENGTH: 201
<212> TYPE: PRT
<213> ORGANISM: Homo sapiens

<400> SEQUENCE: 35

Met Ala Leu Ser Trp Val Leu Thr Val Leu Ser Leu Leu Pro Leu Leu
1               5                   10                  15

Glu Ala Gln Ile Pro Leu Cys Ala Asn Leu Val Pro Val Pro Ile Thr
                20                  25                  30

Asn Ala Thr Leu Asp Gln Ile Thr Gly Lys Trp Phe Tyr Ile Ala Ser
            35                  40                  45

Ala Phe Arg Asn Glu Glu Tyr Asn Lys Ser Val Gln Glu Ile Gln Ala
        50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125

Met Leu Ala Phe Asp Val Asn Asp Glu Lys Asn Trp Gly Leu Ser Val
        130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser
        195                 200

<210> SEQ ID NO 36
<211> LENGTH: 198
<212> TYPE: PRT
```

<213> ORGANISM: Homo sapiens

<400> SEQUENCE: 36

```
Met Pro Leu Gly Leu Leu Trp Leu Gly Leu Ala Leu Leu Gly Ala Leu
1               5                   10                  15
His Ala Gln Ala Gln Asp Ser Thr Ser Asp Leu Ile Pro Ala Pro Pro
            20                  25                  30
Leu Ser Lys Val Pro Leu Gln Gln Asn Phe Gln Asp Asn Gln Phe Gln
        35                  40                  45
Gly Lys Trp Tyr Val Val Gly Leu Ala Gly Asn Ala Ile Leu Arg Glu
    50                  55                  60
Asp Lys Asp Pro Gln Lys Met Tyr Ala Thr Ile Tyr Glu Leu Lys Glu
65                  70                  75                  80
Asp Lys Ser Tyr Asn Val Thr Ser Val Leu Phe Arg Lys Lys Lys Cys
                85                  90                  95
Asp Tyr Trp Ile Arg Thr Phe Val Pro Gly Cys Gln Pro Gly Glu Phe
            100                 105                 110
Thr Leu Gly Asn Ile Lys Ser Tyr Pro Gly Leu Thr Ser Tyr Leu Val
        115                 120                 125
Arg Val Val Ser Thr Asn Tyr Asn Gln His Ala Met Val Phe Phe Lys
    130                 135                 140
Lys Val Ser Gln Asn Arg Glu Tyr Phe Lys Ile Thr Leu Tyr Gly Arg
145                 150                 155                 160
Thr Lys Glu Leu Thr Ser Glu Leu Lys Glu Asn Phe Ile Arg Phe Ser
                165                 170                 175
Lys Ser Leu Gly Leu Pro Glu Asn His Ile Val Phe Pro Val Pro Ile
            180                 185                 190
Asp Gln Cys Ile Asp Gly
        195
```

<210> SEQ ID NO 37
<211> LENGTH: 277
<212> TYPE: PRT
<213> ORGANISM: Homo sapiens

<400> SEQUENCE: 37

```
Met Ala Ala Val Ser Val Tyr Ala Pro Pro Val Gly Gly Phe Ser Phe
1               5                   10                  15
Asp Asn Cys Arg Arg Asn Ala Val Leu Glu Ala Asp Phe Ala Lys Arg
            20                  25                  30
Gly Tyr Lys Leu Pro Lys Val Arg Lys Thr Gly Thr Thr Ile Ala Gly
        35                  40                  45
Val Val Tyr Lys Asp Gly Ile Val Leu Gly Ala Asp Thr Arg Ala Thr
    50                  55                  60
Glu Gly Met Val Val Ala Asp Lys Asn Arg Ser Lys Ile His Phe Ile
65                  70                  75                  80
Ser Pro Asn Ile Tyr Cys Cys Gly Ala Gly Thr Ala Ala Asp Thr Asp
                85                  90                  95
Met Thr Thr Gln Leu Ile Ser Ser Asn Leu Glu Leu His Ser Leu Ser
            100                 105                 110
Thr Gly Arg Leu Pro Arg Val Val Thr Ala Asn Arg Met Leu Lys Gln
        115                 120                 125
Met Leu Phe Arg Tyr Gln Gly Tyr Ile Gly Ala Ala Leu Val Leu Gly
    130                 135                 140
Gly Val Asp Val Thr Gly Pro His Leu Tyr Ser Ile Tyr Pro His Gly
145                 150                 155                 160
```

```
Ser Thr Asp Lys Leu Pro Tyr Val Thr Met Gly Ser Gly Ser Leu Ala
            165                 170                 175

Ala Met Ala Val Phe Glu Asp Lys Phe Arg Pro Asp Met Glu Glu Glu
            180                 185                 190

Glu Ala Lys Asn Leu Val Ser Glu Ala Ile Ala Ala Gly Ile Phe Asn
            195                 200                 205

Asp Leu Gly Ser Gly Ser Asn Ile Asp Leu Cys Val Ile Ser Lys Asn
            210                 215                 220

Lys Leu Asp Phe Leu Arg Pro Tyr Thr Val Pro Asn Lys Lys Gly Thr
225                 230                 235                 240

Arg Leu Gly Arg Tyr Arg Cys Glu Lys Gly Thr Thr Ala Val Leu Thr
            245                 250                 255

Glu Lys Ile Thr Pro Leu Glu Ile Glu Val Leu Glu Glu Thr Val Gln
            260                 265                 270

Thr Met Asp Thr Ser
            275

<210> SEQ ID NO 38
<211> LENGTH: 316
<212> TYPE: PRT
<213> ORGANISM: Homo sapiens

<400> SEQUENCE: 38

Met Ala Thr Phe Val Glu Leu Ser Thr Lys Ala Lys Met Pro Ile Val
1               5                   10                  15

Gly Leu Gly Thr Trp Lys Ser Pro Leu Gly Lys Val Lys Glu Ala Val
            20                  25                  30

Lys Val Ala Ile Asp Ala Gly Tyr Arg His Ile Asp Cys Ala Tyr Val
            35                  40                  45

Tyr Gln Asn Glu His Glu Val Gly Glu Ala Ile Gln Glu Lys Ile Gln
        50                  55                  60

Glu Lys Ala Val Lys Arg Glu Asp Leu Phe Ile Val Ser Lys Leu Trp
65                  70                  75                  80

Pro Thr Phe Phe Glu Arg Pro Leu Val Arg Lys Ala Phe Glu Lys Thr
            85                  90                  95

Leu Lys Asp Leu Lys Leu Ser Tyr Leu Asp Val Tyr Leu Ile His Trp
            100                 105                 110

Pro Gln Gly Phe Lys Ser Gly Asp Asp Leu Phe Pro Lys Asp Asp Lys
            115                 120                 125

Gly Asn Ala Ile Gly Gly Lys Ala Thr Phe Leu Asp Ala Trp Glu Ala
        130                 135                 140

Met Glu Glu Leu Val Asp Glu Gly Leu Val Lys Ala Leu Gly Val Ser
145                 150                 155                 160

Asn Phe Ser His Phe Gln Ile Glu Lys Leu Leu Asn Lys Pro Gly Leu
            165                 170                 175

Lys Tyr Lys Pro Val Thr Asn Gln Val Glu Cys His Pro Tyr Leu Thr
            180                 185                 190

Gln Glu Lys Leu Ile Gln Tyr Cys His Ser Lys Gly Ile Thr Val Thr
            195                 200                 205

Ala Tyr Ser Pro Leu Gly Ser Pro Asp Arg Pro Trp Ala Lys Pro Glu
        210                 215                 220

Asp Pro Ser Leu Leu Glu Asp Pro Lys Ile Lys Glu Ile Ala Ala Lys
225                 230                 235                 240

His Lys Lys Thr Ala Ala Gln Val Leu Ile Arg Phe His Ile Gln Arg
            245                 250                 255
```

```
Asn Val Ile Val Ile Pro Lys Ser Val Thr Pro Ala Arg Ile Val Glu
            260                 265                 270

Asn Ile Gln Val Phe Asp Phe Lys Leu Ser Asp Glu Glu Met Ala Thr
            275                 280                 285

Ile Leu Ser Phe Asn Arg Asn Trp Arg Ala Cys Asn Val Leu Gln Ser
            290                 295                 300

Ser His Leu Glu Asp Tyr Pro Phe Asp Ala Glu Tyr
305                 310                 315

<210> SEQ ID NO 39
<211> LENGTH: 303
<212> TYPE: PRT
<213> ORGANISM: Homo sapiens

<400> SEQUENCE: 39

Met Ala Arg Arg Gly Pro Gly Trp Arg Pro Leu Leu Leu Leu Val Leu
1               5                   10                  15

Leu Ala Gly Ala Ala Gln Gly Gly Leu Tyr Phe Arg Arg Gly Gln Thr
            20                  25                  30

Cys Tyr Arg Pro Leu Arg Gly Asp Gly Leu Ala Pro Leu Gly Arg Ser
            35                  40                  45

Thr Tyr Pro Arg Pro His Glu Tyr Leu Ser Pro Ala Asp Leu Pro Lys
        50                  55                  60

Ser Trp Asp Trp Arg Asn Val Asp Gly Val Asn Tyr Ala Ser Ile Thr
65                  70                  75                  80

Arg Asn Gln His Ile Pro Gln Tyr Cys Gly Ser Cys Trp Ala His Ala
                85                  90                  95

Ser Thr Ser Ala Met Ala Asp Arg Ile Asn Ile Lys Arg Lys Gly Ala
            100                 105                 110

Trp Pro Ser Thr Leu Leu Ser Val Gln Asn Val Ile Asp Cys Gly Asn
            115                 120                 125

Ala Gly Ser Cys Glu Gly Gly Asn Asp Leu Ser Val Trp Asp Tyr Ala
        130                 135                 140

His Gln His Gly Ile Pro Asp Glu Thr Cys Asn Asn Tyr Gln Ala Lys
145                 150                 155                 160

Asp Gln Glu Cys Asp Lys Phe Asn Gln Cys Gly Thr Cys Asn Glu Phe
                165                 170                 175

Lys Glu Cys His Ala Ile Arg Asn Tyr Thr Leu Trp Arg Val Gly Asp
            180                 185                 190

Tyr Gly Ser Leu Ser Gly Arg Glu Lys Met Met Ala Glu Ile Tyr Ala
            195                 200                 205

Asn Gly Pro Ile Ser Cys Gly Ile Met Ala Thr Glu Arg Leu Ala Asn
        210                 215                 220

Tyr Thr Gly Gly Ile Tyr Ala Glu Tyr Gln Asp Thr Thr Tyr Ile Asn
225                 230                 235                 240

His Val Val Ser Val Ala Gly Trp Gly Ile Ser Asp Gly Thr Glu Tyr
                245                 250                 255

Trp Ile Val Arg Asn Ser Trp Gly Glu Pro Trp Gly Glu Arg Gly Trp
            260                 265                 270

Leu Arg Ile Val Thr Ser Thr Tyr Lys Asp Gly Lys Gly Ala Arg Tyr
            275                 280                 285

Asn Leu Ala Ile Glu Glu His Cys Thr Phe Gly Asp Pro Ile Val
        290                 295                 300

<210> SEQ ID NO 40
```

-continued

```
<211> LENGTH: 437
<212> TYPE: PRT
<213> ORGANISM: Homo sapiens

<400> SEQUENCE: 40

Met Val Arg Ser Val Ala Trp Ala Gly Phe Met Val Leu Leu Met Ile
1               5                   10                  15

Pro Trp Gly Ser Ala Ala Lys Leu Val Cys Tyr Phe Thr Asn Trp Ala
            20                  25                  30

Gln Tyr Arg Gln Gly Glu Ala Arg Phe Leu Pro Lys Asp Leu Asp Pro
        35                  40                  45

Ser Leu Cys Thr His Leu Ile Tyr Ala Phe Ala Gly Met Thr Asn His
    50                  55                  60

Gln Leu Ser Thr Thr Glu Trp Asn Asp Glu Thr Leu Tyr Gln Glu Phe
65                  70                  75                  80

Asn Gly Leu Lys Lys Met Asn Pro Lys Leu Lys Thr Leu Leu Ala Ile
                85                  90                  95

Gly Gly Trp Asn Phe Gly Thr Gln Lys Phe Thr Asp Met Val Ala Thr
            100                 105                 110

Ala Asn Asn Arg Gln Thr Phe Val Asn Ser Ala Ile Arg Phe Leu Arg
        115                 120                 125

Lys Tyr Ser Phe Asp Gly Leu Asp Leu Asp Trp Glu Tyr Pro Gly Ser
130                 135                 140

Gln Gly Ser Pro Ala Val Asp Lys Glu Arg Phe Thr Thr Leu Val Gln
145                 150                 155                 160

Asp Leu Ala Asn Ala Phe Gln Gln Glu Ala Gln Thr Ser Gly Lys Glu
                165                 170                 175

Arg Leu Leu Leu Ser Ala Ala Val Pro Ala Gly Gln Thr Tyr Val Asp
            180                 185                 190

Ala Gly Tyr Glu Val Asp Lys Ile Ala Gln Asn Leu Asp Phe Val Asn
        195                 200                 205

Leu Met Ala Tyr Asp Phe His Gly Ser Trp Glu Lys Val Thr Gly His
    210                 215                 220

Asn Ser Pro Leu Tyr Lys Arg Gln Glu Glu Ser Gly Ala Ala Ala Ser
225                 230                 235                 240

Leu Asn Val Asp Ala Ala Val Gln Gln Trp Leu Gln Lys Gly Thr Pro
                245                 250                 255

Ala Ser Lys Leu Ile Leu Gly Met Pro Thr Tyr Gly Arg Ser Phe Thr
            260                 265                 270

Leu Ala Ser Ser Ser Asp Thr Arg Val Gly Ala Pro Ala Thr Gly Ser
        275                 280                 285

Gly Thr Pro Gly Pro Phe Thr Lys Glu Gly Gly Met Leu Ala Tyr Tyr
    290                 295                 300

Glu Val Cys Ser Trp Lys Gly Ala Thr Lys Gln Arg Ile Gln Asp Gln
305                 310                 315                 320

Lys Val Pro Tyr Ile Phe Arg Asp Asn Gln Trp Val Gly Phe Asp Asp
                325                 330                 335

Val Glu Ser Phe Lys Thr Lys Gly Arg Tyr Pro Leu Ile Gln Thr Leu
            340                 345                 350

Arg Gln Glu Leu Ser Leu Pro Tyr Leu Pro Ser Gly Thr Pro Glu Leu
        355                 360                 365

Glu Val Pro Lys Pro Gly Gln Pro Ser Glu Pro Glu His Gly Pro Ser
    370                 375                 380

Pro Gly Gln Asp Thr Phe Cys Gln Gly Lys Ala Asp Gly Leu Tyr Pro
385                 390                 395                 400
```

```
Asn Pro Arg Glu Arg Ser Ser Phe Tyr Ser Cys Ala Ala Gly Arg Leu
            405                 410                 415

Phe Gln Gln Ser Cys Pro Thr Gly Leu Val Phe Ser Asn Ser Cys Lys
            420                 425                 430

Cys Cys Thr Trp Asn
            435

<210> SEQ ID NO 41
<211> LENGTH: 418
<212> TYPE: PRT
<213> ORGANISM: Homo sapiens

<400> SEQUENCE: 41

Met Tyr Arg Pro Ala Arg Val Thr Ser Thr Ser Arg Phe Leu Asn Pro
1               5                   10                  15

Tyr Val Val Cys Phe Ile Val Ala Gly Val Val Ile Leu Ala Val
                20                  25                  30

Thr Ile Ala Leu Leu Val Tyr Phe Leu Ala Phe Asp Gln Lys Ser Tyr
            35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335
```

```
Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile

<210> SEQ ID NO 42
<211> LENGTH: 147
<212> TYPE: PRT
<213> ORGANISM: Homo sapiens

<400> SEQUENCE: 42

Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145

<210> SEQ ID NO 43
<211> LENGTH: 847
<212> TYPE: PRT
<213> ORGANISM: Homo sapiens

<400> SEQUENCE: 43

Met Ala Lys Pro Leu Thr Asp Gln Glu Lys Arg Arg Gln Ile Ser Ile
1               5                   10                  15

Arg Gly Ile Val Gly Val Glu Asn Val Ala Glu Leu Lys Lys Ser Phe
            20                  25                  30

Asn Arg His Leu His Phe Thr Leu Val Lys Asp Arg Asn Val Ala Thr
        35                  40                  45

Thr Arg Asp Tyr Tyr Phe Ala Leu Ala His Thr Val Arg Asp His Leu
    50                  55                  60

Val Gly Arg Trp Ile Arg Thr Gln Gln His Tyr Tyr Asp Lys Cys Pro
65                  70                  75                  80

Lys Arg Val Tyr Tyr Leu Ser Leu Glu Phe Tyr Met Gly Arg Thr Leu
```

```
                    85                  90                  95
Gln Asn Thr Met Ile Asn Leu Gly Leu Gln Asn Ala Cys Asp Glu Ala
                100                 105                 110

Ile Tyr Gln Leu Gly Leu Asp Ile Glu Glu Leu Glu Glu Ile Glu Glu
                115                 120                 125

Asp Ala Gly Leu Gly Asn Gly Gly Leu Gly Arg Leu Ala Ala Cys Phe
                130                 135                 140

Leu Asp Ser Met Ala Thr Leu Gly Leu Ala Ala Tyr Gly Tyr Gly Ile
145                 150                 155                 160

Arg Tyr Glu Tyr Gly Ile Phe Asn Gln Lys Ile Arg Asp Gly Trp Gln
                165                 170                 175

Val Glu Glu Ala Asp Asp Trp Leu Arg Tyr Gly Asn Pro Trp Glu Lys
                180                 185                 190

Ser Arg Pro Glu Phe Met Leu Pro Val His Phe Tyr Gly Lys Val Glu
                195                 200                 205

His Thr Asn Thr Gly Thr Lys Trp Ile Asp Thr Gln Val Val Leu Ala
                210                 215                 220

Leu Pro Tyr Asp Thr Pro Val Pro Gly Tyr Met Asn Asn Thr Val Asn
225                 230                 235                 240

Thr Met Arg Leu Trp Ser Ala Arg Ala Pro Asn Asp Phe Asn Leu Arg
                245                 250                 255

Asp Phe Asn Val Gly Asp Tyr Ile Gln Ala Val Leu Asp Arg Asn Leu
                260                 265                 270

Ala Glu Asn Ile Ser Arg Val Leu Tyr Pro Asn Asp Asn Phe Phe Glu
                275                 280                 285

Gly Lys Glu Leu Arg Leu Lys Gln Glu Tyr Phe Val Val Ala Ala Thr
                290                 295                 300

Leu Gln Asp Ile Ile Arg Arg Phe Lys Ala Ser Lys Phe Gly Ser Thr
305                 310                 315                 320

Arg Gly Ala Gly Thr Val Phe Asp Ala Phe Pro Asp Gln Val Ala Ile
                325                 330                 335

Gln Leu Asn Asp Thr His Pro Ala Leu Ala Ile Pro Glu Leu Met Arg
                340                 345                 350

Ile Phe Val Asp Ile Glu Lys Leu Pro Trp Ser Lys Ala Trp Glu Leu
                355                 360                 365

Thr Gln Lys Thr Phe Ala Tyr Thr Asn His Thr Val Leu Pro Glu Ala
                370                 375                 380

Leu Glu Arg Trp Pro Val Asp Leu Val Glu Lys Leu Leu Pro Arg His
385                 390                 395                 400

Leu Glu Ile Ile Tyr Glu Ile Asn Gln Lys His Leu Asp Arg Ile Val
                405                 410                 415

Ala Leu Phe Pro Lys Asp Val Asp Arg Leu Arg Arg Met Ser Leu Ile
                420                 425                 430

Glu Glu Glu Gly Ser Lys Arg Ile Asn Met Ala His Leu Cys Ile Val
                435                 440                 445

Gly Ser His Ala Val Asn Gly Val Ala Lys Ile His Ser Asp Ile Val
                450                 455                 460

Lys Thr Lys Val Phe Lys Asp Phe Ser Glu Leu Glu Pro Asp Lys Phe
465                 470                 475                 480

Gln Asn Lys Thr Asn Gly Ile Thr Pro Arg Arg Trp Leu Leu Leu Cys
                485                 490                 495

Asn Pro Gly Leu Ala Glu Leu Ile Ala Glu Lys Ile Gly Glu Asp Tyr
                500                 505                 510
```

```
Val Lys Asp Leu Ser Gln Leu Thr Lys Leu His Ser Phe Leu Gly Asp
        515                 520                 525

Asp Val Phe Leu Arg Glu Leu Ala Lys Val Lys Gln Glu Asn Lys Leu
    530                 535                 540

Lys Phe Ser Gln Phe Leu Glu Thr Glu Tyr Lys Val Lys Ile Asn Pro
545                 550                 555                 560

Ser Ser Met Phe Asp Val Gln Val Lys Arg Ile His Glu Tyr Lys Arg
                565                 570                 575

Gln Leu Leu Asn Cys Leu His Val Ile Thr Met Tyr Asn Arg Ile Lys
            580                 585                 590

Lys Asp Pro Lys Lys Leu Phe Val Pro Arg Thr Val Ile Ile Gly Gly
        595                 600                 605

Lys Ala Ala Pro Gly Tyr His Met Ala Lys Met Ile Ile Lys Leu Ile
    610                 615                 620

Thr Ser Val Ala Asp Val Val Asn Asn Asp Pro Met Val Gly Ser Lys
625                 630                 635                 640

Leu Lys Val Ile Phe Leu Glu Asn Tyr Arg Val Ser Leu Ala Glu Lys
                645                 650                 655

Val Ile Pro Ala Thr Asp Leu Ser Glu Gln Ile Ser Thr Ala Gly Thr
            660                 665                 670

Glu Ala Ser Gly Thr Gly Asn Met Lys Phe Met Leu Asn Gly Ala Leu
        675                 680                 685

Thr Ile Gly Thr Met Asp Gly Ala Asn Val Glu Met Ala Glu Glu Ala
    690                 695                 700

Gly Glu Glu Asn Leu Phe Ile Phe Gly Met Arg Ile Asp Asp Val Ala
705                 710                 715                 720

Ala Leu Asp Lys Lys Gly Tyr Glu Ala Lys Glu Tyr Tyr Glu Ala Leu
                725                 730                 735

Pro Glu Leu Lys Leu Val Ile Asp Gln Ile Asp Asn Gly Phe Phe Ser
            740                 745                 750

Pro Lys Gln Pro Asp Leu Phe Lys Asp Ile Ile Asn Met Leu Phe Tyr
        755                 760                 765

His Asp Arg Phe Lys Val Phe Ala Asp Tyr Glu Ala Tyr Val Lys Cys
    770                 775                 780

Gln Asp Lys Val Ser Gln Leu Tyr Met Asn Pro Lys Ala Trp Asn Thr
785                 790                 795                 800

Met Val Leu Lys Asn Ile Ala Ala Ser Gly Lys Phe Ser Ser Asp Arg
                805                 810                 815

Thr Ile Lys Glu Tyr Ala Gln Asn Ile Trp Asn Val Glu Pro Ser Asp
            820                 825                 830

Leu Lys Ile Ser Leu Ser Asn Glu Ser Asn Lys Val Asn Gly Asn
        835                 840                 845

<210> SEQ ID NO 44
<211> LENGTH: 353
<212> TYPE: PRT
<213> ORGANISM: Homo sapiens

<400> SEQUENCE: 44

Met Glu Lys Thr Leu Glu Thr Val Pro Leu Glu Arg Lys Lys Arg Glu
1               5                   10                  15

Lys Glu Gln Phe Arg Lys Leu Phe Ile Gly Gly Leu Ser Phe Glu Thr
                20                  25                  30

Thr Glu Glu Ser Leu Arg Asn Tyr Tyr Glu Gln Trp Gly Lys Leu Thr
            35                  40                  45
```

Asp Cys Val Val Met Arg Asp Pro Ala Ser Lys Arg Ser Arg Gly Phe
          50                  55                  60

Gly Phe Val Thr Phe Ser Ser Met Ala Glu Val Asp Ala Ala Met Ala
 65                  70                  75                  80

Ala Arg Pro His Ser Ile Asp Gly Arg Val Val Glu Pro Lys Arg Ala
                     85                  90                  95

Val Ala Arg Glu Glu Ser Gly Lys Pro Gly Ala His Val Thr Val Lys
                100                 105                 110

Lys Leu Phe Val Gly Gly Ile Lys Glu Asp Thr Glu Glu His His Leu
            115                 120                 125

Arg Asp Tyr Phe Glu Glu Tyr Gly Lys Ile Asp Thr Ile Glu Ile Ile
        130                 135                 140

Thr Asp Arg Gln Ser Gly Lys Lys Arg Gly Phe Gly Phe Val Thr Phe
145                 150                 155                 160

Asp Asp His Asp Pro Val Asp Lys Ile Val Leu Gln Lys Tyr His Thr
                165                 170                 175

Ile Asn Gly His Asn Ala Glu Val Arg Lys Ala Leu Ser Arg Gln Glu
                180                 185                 190

Met Gln Glu Val Gln Ser Ser Arg Ser Gly Arg Gly Gly Asn Phe Gly
            195                 200                 205

Phe Gly Asp Ser Arg Gly Gly Gly Asn Phe Gly Pro Gly Pro Gly
        210                 215                 220

Ser Asn Phe Arg Gly Gly Ser Asp Gly Tyr Gly Ser Gly Arg Gly Phe
225                 230                 235                 240

Gly Asp Gly Tyr Asn Gly Tyr Gly Gly Pro Gly Gly Gly Asn Phe
                245                 250                 255

Gly Gly Ser Pro Gly Tyr Gly Gly Arg Gly Gly Tyr Gly Gly Gly
            260                 265                 270

Gly Pro Gly Tyr Gly Asn Gln Gly Gly Gly Tyr Gly Gly Gly Tyr Asp
        275                 280                 285

Asn Tyr Gly Gly Gly Asn Tyr Gly Ser Gly Asn Tyr Asn Asp Phe Gly
        290                 295                 300

Asn Tyr Asn Gln Gln Pro Ser Asn Tyr Gly Pro Met Lys Ser Gly Asn
305                 310                 315                 320

Phe Gly Gly Ser Arg Asn Met Gly Gly Pro Tyr Gly Gly Gly Asn Tyr
                325                 330                 335

Gly Pro Gly Gly Ser Gly Gly Ser Gly Gly Tyr Gly Gly Arg Ser Arg
                340                 345                 350

Tyr

<210> SEQ ID NO 45
<211> LENGTH: 379
<212> TYPE: PRT
<213> ORGANISM: Homo sapiens

<400> SEQUENCE: 45

Met Glu Gln Leu Ser Ser Ala Asn Thr Arg Phe Ala Leu Asp Leu Phe
 1               5                  10                  15

Leu Ala Leu Ser Glu Asn Asn Pro Ala Gly Asn Ile Phe Ile Ser Pro
                 20                  25                  30

Phe Ser Ile Ser Ser Ala Met Ala Met Val Phe Leu Gly Thr Arg Gly
             35                  40                  45

Asn Thr Ala Ala Gln Leu Ser Lys Thr Phe His Phe Asn Thr Val Glu
         50                  55                  60

Glu Val His Ser Arg Phe Gln Ser Leu Asn Ala Asp Ile Asn Lys Arg

```
                65                  70                  75                  80
Gly Ala Ser Tyr Ile Leu Lys Leu Ala Asn Arg Leu Tyr Gly Glu Lys
                    85                  90                  95

Thr Tyr Asn Phe Leu Pro Glu Phe Leu Val Ser Thr Gln Lys Thr Tyr
                100                 105                 110

Gly Ala Asp Leu Ala Ser Val Asp Phe Gln His Ala Ser Glu Asp Ala
                115                 120                 125

Arg Lys Thr Ile Asn Gln Trp Val Lys Gly Thr Glu Gly Lys Ile
    130                 135                 140

Pro Glu Leu Leu Ala Ser Gly Met Val Asp Asn Met Thr Lys Leu Val
145                 150                 155                 160

Leu Val Asn Ala Ile Tyr Phe Lys Gly Asn Trp Lys Asp Lys Phe Met
                165                 170                 175

Lys Glu Ala Thr Thr Asn Ala Pro Phe Arg Leu Asn Lys Lys Asp Arg
                180                 185                 190

Lys Thr Val Lys Met Met Tyr Gln Lys Lys Phe Ala Tyr Gly Tyr
                195                 200                 205

Ile Glu Asp Leu Lys Cys Arg Val Leu Glu Leu Pro Tyr Gln Gly Glu
    210                 215                 220

Glu Leu Ser Met Val Ile Leu Leu Pro Asp Asp Ile Glu Asp Glu Ser
225                 230                 235                 240

Thr Gly Leu Lys Lys Ile Glu Glu Gln Leu Thr Leu Glu Lys Leu His
                245                 250                 255

Glu Trp Thr Lys Pro Glu Asn Leu Asp Phe Ile Glu Val Asn Val Ser
                260                 265                 270

Leu Pro Arg Phe Lys Leu Glu Glu Ser Tyr Thr Leu Asn Ser Asp Leu
                275                 280                 285

Ala Arg Leu Gly Val Gln Asp Leu Phe Asn Ser Ser Lys Ala Asp Leu
    290                 295                 300

Ser Gly Met Ser Gly Ala Arg Asp Ile Phe Ile Ser Lys Ile Val His
305                 310                 315                 320

Lys Ser Phe Val Glu Val Asn Glu Glu Gly Thr Glu Ala Ala Ala Ala
                325                 330                 335

Thr Ala Gly Ile Ala Thr Phe Cys Met Leu Met Pro Glu Glu Asn Phe
                340                 345                 350

Thr Ala Asp His Pro Phe Leu Phe Ile Arg His Asn Ser Ser Gly
                355                 360                 365

Ser Ile Leu Phe Leu Gly Arg Phe Ser Ser Pro
    370                 375

<210> SEQ ID NO 46
<211> LENGTH: 934
<212> TYPE: PRT
<213> ORGANISM: Homo sapiens

<400> SEQUENCE: 46

Met Ala Arg Arg Ser Val Leu Tyr Phe Ile Leu Leu Asn Ala Leu Ile
1               5                   10                  15

Asn Lys Gly Gln Ala Cys Phe Cys Asp His Tyr Ala Trp Thr Gln Trp
                20                  25                  30

Thr Ser Cys Ser Lys Thr Cys Asn Ser Gly Thr Gln Ser Arg His Arg
            35                  40                  45

Gln Ile Val Val Asp Lys Tyr Tyr Gln Glu Asn Phe Cys Glu Gln Ile
    50                  55                  60

Cys Ser Lys Gln Glu Thr Arg Glu Cys Asn Trp Gln Arg Cys Pro Ile
```

```
              65                  70                  75                  80
Asn Cys Leu Leu Gly Asp Phe Gly Pro Trp Ser Asp Cys Asp Pro Cys
                    85                  90                  95
Ile Glu Lys Gln Ser Lys Val Arg Ser Val Leu Arg Pro Ser Gln Phe
                100                 105                 110
Gly Gly Gln Pro Cys Thr Ala Pro Leu Val Ala Phe Gln Pro Cys Ile
                115                 120                 125
Pro Ser Lys Leu Cys Lys Ile Glu Glu Ala Asp Cys Lys Asn Lys Phe
            130                 135                 140
Arg Cys Asp Ser Gly Arg Cys Ile Ala Arg Lys Leu Glu Cys Asn Gly
145                 150                 155                 160
Glu Asn Asp Cys Gly Asp Asn Ser Asp Glu Arg Asp Cys Gly Arg Thr
                165                 170                 175
Lys Ala Val Cys Thr Arg Lys Tyr Asn Pro Ile Pro Ser Val Gln Leu
                180                 185                 190
Met Gly Asn Gly Phe His Phe Leu Ala Gly Glu Pro Arg Gly Glu Val
                195                 200                 205
Leu Asp Asn Ser Phe Thr Gly Gly Ile Cys Lys Thr Val Lys Ser Ser
            210                 215                 220
Arg Thr Ser Asn Pro Tyr Arg Val Pro Ala Asn Leu Glu Asn Val Gly
225                 230                 235                 240
Phe Glu Val Gln Thr Ala Glu Asp Asp Leu Lys Thr Asp Phe Tyr Lys
                245                 250                 255
Asp Leu Thr Ser Leu Gly His Asn Glu Asn Gln Gln Gly Ser Phe Ser
                260                 265                 270
Ser Gln Gly Gly Ser Ser Phe Ser Val Pro Ile Phe Tyr Ser Ser Lys
            275                 280                 285
Arg Ser Glu Asn Ile Asn His Asn Ser Ala Phe Lys Gln Ala Ile Gln
            290                 295                 300
Ala Ser His Lys Lys Asp Ser Ser Phe Ile Arg Ile His Lys Val Met
305                 310                 315                 320
Lys Val Leu Asn Phe Thr Thr Lys Ala Lys Asp Leu His Leu Ser Asp
                325                 330                 335
Val Phe Leu Lys Ala Leu Asn His Leu Pro Leu Glu Tyr Asn Ser Ala
                340                 345                 350
Leu Tyr Ser Arg Ile Phe Asp Asp Phe Gly Thr His Tyr Phe Thr Ser
            355                 360                 365
Gly Ser Leu Gly Gly Val Tyr Asp Leu Leu Tyr Gln Phe Ser Ser Glu
            370                 375                 380
Glu Leu Lys Asn Ser Gly Leu Thr Glu Glu Ala Lys His Cys Val
385                 390                 395                 400
Arg Ile Glu Thr Lys Lys Arg Val Leu Phe Ala Lys Lys Thr Lys Val
                405                 410                 415
Glu His Arg Cys Thr Thr Asn Lys Leu Ser Glu Lys His Glu Gly Ser
            420                 425                 430
Phe Ile Gln Gly Ala Glu Lys Ser Ile Ser Leu Ile Arg Gly Gly Arg
            435                 440                 445
Ser Glu Tyr Gly Ala Ala Leu Ala Trp Glu Lys Gly Ser Ser Gly Leu
            450                 455                 460
Glu Glu Lys Thr Phe Ser Glu Trp Leu Glu Ser Val Lys Glu Asn Pro
465                 470                 475                 480
Ala Val Ile Asp Phe Glu Leu Ala Pro Ile Val Asp Leu Val Arg Asn
                485                 490                 495
```

-continued

```
Ile Pro Cys Ala Val Thr Lys Arg Asn Asn Leu Arg Lys Ala Leu Gln
            500                 505                 510

Glu Tyr Ala Ala Lys Phe Asp Pro Cys Gln Cys Ala Pro Cys Pro Asn
        515                 520                 525

Asn Gly Arg Pro Thr Leu Ser Gly Thr Glu Cys Leu Cys Val Cys Gln
    530                 535                 540

Ser Gly Thr Tyr Gly Glu Asn Cys Glu Lys Gln Ser Pro Asp Tyr Lys
545                 550                 555                 560

Ser Asn Ala Val Asp Gly Gln Trp Gly Cys Trp Ser Ser Trp Ser Thr
                565                 570                 575

Cys Asp Ala Thr Tyr Lys Arg Ser Arg Thr Arg Glu Cys Asn Asn Pro
            580                 585                 590

Ala Pro Gln Arg Gly Gly Lys Arg Cys Glu Gly Glu Lys Arg Gln Glu
        595                 600                 605

Glu Asp Cys Thr Phe Ser Ile Met Glu Asn Asn Gly Gln Pro Cys Ile
    610                 615                 620

Asn Asp Asp Glu Glu Met Lys Glu Val Asp Leu Pro Glu Ile Glu Ala
625                 630                 635                 640

Asp Ser Gly Cys Pro Gln Pro Val Pro Pro Glu Asn Gly Phe Ile Arg
                645                 650                 655

Asn Glu Lys Gln Leu Tyr Leu Val Gly Glu Asp Val Glu Ile Ser Cys
            660                 665                 670

Leu Thr Gly Phe Glu Thr Val Gly Tyr Gln Tyr Phe Arg Cys Leu Pro
        675                 680                 685

Asp Gly Thr Trp Arg Gln Gly Asp Val Glu Cys Gln Arg Thr Glu Cys
    690                 695                 700

Ile Lys Pro Val Val Gln Glu Val Leu Thr Ile Thr Pro Phe Gln Arg
705                 710                 715                 720

Leu Tyr Arg Ile Gly Glu Ser Ile Glu Leu Thr Cys Pro Lys Gly Phe
                725                 730                 735

Val Val Ala Gly Pro Ser Arg Tyr Thr Cys Gln Gly Asn Ser Trp Thr
            740                 745                 750

Pro Pro Ile Ser Asn Ser Leu Thr Cys Glu Lys Asp Thr Leu Thr Lys
        755                 760                 765

Leu Lys Gly His Cys Gln Leu Gly Gln Lys Gln Ser Gly Ser Glu Cys
    770                 775                 780

Ile Cys Met Ser Pro Glu Glu Asp Cys Ser His His Ser Glu Asp Leu
785                 790                 795                 800

Cys Val Phe Asp Thr Asp Ser Asn Asp Tyr Phe Thr Ser Pro Ala Cys
                805                 810                 815

Lys Phe Leu Ala Glu Lys Cys Leu Asn Asn Gln Gln Leu His Phe Leu
            820                 825                 830

His Ile Gly Ser Cys Gln Asp Gly Arg Gln Leu Glu Trp Gly Leu Glu
        835                 840                 845

Arg Thr Arg Leu Ser Ser Asn Ser Thr Lys Lys Glu Ser Cys Gly Tyr
    850                 855                 860

Asp Thr Cys Tyr Asp Trp Glu Lys Cys Ser Ala Ser Thr Ser Lys Cys
865                 870                 875                 880

Val Cys Leu Leu Pro Pro Gln Cys Phe Lys Gly Gly Asn Gln Leu Tyr
                885                 890                 895

Cys Val Lys Met Gly Ser Ser Thr Ser Glu Lys Thr Leu Asn Ile Cys
            900                 905                 910

Glu Val Gly Thr Ile Arg Cys Ala Asn Arg Lys Met Glu Ile Leu His
        915                 920                 925
```

```
Pro Gly Lys Cys Leu Ala
        930

<210> SEQ ID NO 47
<211> LENGTH: 397
<212> TYPE: PRT
<213> ORGANISM: Homo sapiens

<400> SEQUENCE: 47

Met Asp Ser Leu Ala Thr Ser Ile Asn Gln Phe Ala Leu Glu Leu Ser
1               5                   10                  15

Lys Lys Leu Ala Glu Ser Ala Gln Gly Lys Asn Ile Phe Phe Ser Ser
            20                  25                  30

Trp Ser Ile Ser Thr Ser Leu Thr Met Val Tyr Leu Gly Ala Lys Gly
        35                  40                  45

Thr Thr Ala Ala Gln Met Ala Gln Val Leu Gln Phe Asn Arg Asp Gln
    50                  55                  60

Gly Val Lys Cys Asp Pro Glu Ser Glu Lys Lys Arg Lys Met Glu Phe
65                  70                  75                  80

Asn Leu Ser Asn Ser Glu Glu Ile His Ser Asp Phe Gln Thr Leu Ile
                85                  90                  95

Ser Glu Ile Leu Lys Pro Asn Asp Asp Tyr Leu Leu Lys Thr Ala Asn
            100                 105                 110

Ala Ile Tyr Gly Glu Lys Thr Tyr Ala Phe His Asn Lys Tyr Leu Glu
        115                 120                 125

Asp Met Lys Thr Tyr Phe Asp Ala Glu Pro Gln Ser Val Asn Phe Val
    130                 135                 140

Glu Ala Ser Asp Gln Ile Arg Lys Asp Ile Asn Ser Trp Val Glu Arg
145                 150                 155                 160

Gln Thr Glu Gly Lys Ile Gln Asn Leu Leu Pro Asp Asp Ser Val Asp
                165                 170                 175

Ser Thr Thr Arg Met Ile Leu Val Asn Ala Leu Tyr Phe Lys Gly Ile
            180                 185                 190

Trp Glu His Gln Phe Leu Val Gln Asn Thr Thr Glu Lys Pro Phe Arg
        195                 200                 205

Ile Asn Glu Thr Thr Ser Lys Pro Val Gln Met Met Phe Met Lys Lys
    210                 215                 220

Lys Leu His Ile Phe His Ile Glu Lys Pro Lys Ala Val Gly Leu Gln
225                 230                 235                 240

Leu Tyr Tyr Lys Ser Cys Asp Leu Ser Leu Ile Leu Leu Pro Glu
                245                 250                 255

Asp Ile Asn Gly Leu Glu Gln Leu Glu Lys Ala Ile Thr Tyr Glu Lys
            260                 265                 270

Leu Asn Glu Trp Thr Ser Ala Asp Met Met Glu Leu Tyr Glu Val Gln
        275                 280                 285

Leu His Leu Pro Lys Phe Lys Leu Glu Asp Ser Tyr Asp Leu Lys Ser
    290                 295                 300

Thr Leu Ser Ser Met Gly Met Ser Asp Ala Phe Ser Gln Ser Lys Ala
305                 310                 315                 320

Asp Phe Ser Gly Met Ser Ser Ala Arg Asn Leu Phe Leu Ser Asn Val
                325                 330                 335

Phe His Lys Ala Phe Val Glu Ile Asn Glu Gln Gly Thr Glu Ala Ala
            340                 345                 350

Ala Gly Ser Gly Ser Glu Ile Asp Ile Arg Ile Arg Val Pro Ser Ile
        355                 360                 365
```

Glu Phe Asn Ala Asn His Pro Phe Leu Phe Phe Ile Arg His Asn Lys
    370                 375                 380

Thr Asn Thr Ile Leu Phe Tyr Gly Arg Leu Cys Ser Pro
385                 390                 395

<210> SEQ ID NO 48
<211> LENGTH: 72
<212> TYPE: PRT
<213> ORGANISM: Homo sapiens

<400> SEQUENCE: 48

Met Ser Tyr Gln Gln Gln Cys Lys Gln Pro Cys Gln Pro Pro Pro Pro
1               5                   10                  15

Val Cys Pro Ala Pro Lys Cys Pro Glu Pro Cys Pro Pro Pro Lys Cys
            20                  25                  30

Pro Glu Pro Cys Pro Pro Ser Lys Cys Pro Gln Ser Cys Pro Pro Gln
        35                  40                  45

Gln Cys Gln Gln Lys Cys Pro Pro Val Thr Pro Ser Pro Pro Cys Gln
    50                  55                  60

Pro Lys Cys Pro Pro Lys Ser Lys
65                  70

<210> SEQ ID NO 49
<211> LENGTH: 146
<212> TYPE: PRT
<213> ORGANISM: Homo sapiens

<400> SEQUENCE: 49

Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
            20                  25                  30

Leu Gly Ala Ala Leu Lys Ala Thr Gly Lys Asn Leu Ser Glu Ala Gln
        35                  40                  45

Leu Arg Lys Leu Ile Ser Glu Val Asp Ser Gly Asp Gly Glu Ile
    50                  55                  60

Ser Phe Gln Glu Phe Leu Thr Ala Ala Arg Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
                100                 105                 110

Pro Leu Pro Gln Glu Glu Leu Asp Ala Met Ile Arg Glu Ala Asp Val
            115                 120                 125

Asp Gln Asp Gly Arg Val Asn Tyr Glu Glu Phe Ala Arg Met Leu Ala
        130                 135                 140

Gln Glu
145

<210> SEQ ID NO 50
<211> LENGTH: 5890
<212> TYPE: PRT
<213> ORGANISM: Homo sapiens

<400> SEQUENCE: 50

Met Glu Lys Glu Glu Thr Thr Arg Glu Leu Leu Leu Pro Asn Trp Gln
1               5                   10                  15

Gly Ser Gly Ser His Gly Leu Thr Ile Ala Gln Arg Asp Asp Gly Val

-continued

```
                20                  25                  30
Phe Val Gln Glu Val Thr Gln Asn Ser Pro Ala Ala Arg Thr Gly Val
             35                  40                  45
Val Lys Glu Gly Asp Gln Ile Val Gly Ala Thr Ile Tyr Phe Asp Asn
         50                  55                  60
Leu Gln Ser Gly Glu Val Thr Gln Leu Leu Asn Thr Met Gly His His
 65                  70                  75                  80
Thr Val Gly Leu Lys Leu His Arg Lys Gly Asp Arg Ser Pro Glu Pro
                 85                  90                  95
Gly Gln Thr Trp Thr Arg Glu Val Phe Ser Ser Cys Ser Ser Glu Val
                100                 105                 110
Val Leu Ser Gly Asp Asp Glu Tyr Gln Arg Ile Tyr Thr Thr Lys
            115                 120                 125
Ile Lys Pro Arg Leu Lys Ser Glu Asp Gly Val Glu Gly Asp Leu Gly
            130                 135                 140
Glu Thr Gln Ser Arg Thr Ile Thr Val Thr Arg Arg Val Thr Ala Tyr
145                 150                 155                 160
Thr Val Asp Val Thr Gly Arg Glu Gly Ala Lys Asp Ile Asp Ile Ser
                165                 170                 175
Ser Pro Glu Phe Lys Ile Lys Ile Pro Arg His Glu Leu Thr Glu Ile
                180                 185                 190
Ser Asn Val Asp Val Glu Thr Gln Ser Gly Lys Thr Val Ile Arg Leu
            195                 200                 205
Pro Ser Gly Ser Gly Ala Ala Ser Pro Thr Gly Ser Ala Val Asp Ile
210                 215                 220
Arg Ala Gly Ala Ile Ser Ala Ser Gly Pro Glu Leu Gln Gly Ala Gly
225                 230                 235                 240
His Ser Lys Leu Gln Val Thr Met Pro Gly Ile Lys Val Gly Gly Ser
                245                 250                 255
Gly Val Asn Val Asn Ala Lys Gly Leu Asp Leu Gly Gly Arg Gly Gly
            260                 265                 270
Val Gln Val Pro Ala Val Asp Ile Ser Ser Ser Leu Gly Gly Arg Ala
        275                 280                 285
Val Glu Val Gln Gly Pro Ser Leu Glu Ser Gly Asp His Gly Lys Ile
290                 295                 300
Lys Phe Pro Thr Met Lys Val Pro Lys Phe Gly Val Ser Thr Gly Arg
305                 310                 315                 320
Glu Gly Gln Thr Pro Lys Ala Gly Leu Arg Val Ser Ala Pro Glu Val
                325                 330                 335
Ser Val Gly His Lys Gly Gly Lys Pro Gly Leu Thr Ile Gln Ala Pro
            340                 345                 350
Gln Leu Glu Val Ser Val Pro Ser Ala Asn Ile Glu Gly Leu Glu Gly
        355                 360                 365
Lys Leu Lys Gly Pro Gln Ile Thr Gly Pro Ser Leu Glu Gly Asp Leu
370                 375                 380
Gly Leu Lys Gly Ala Lys Pro Gln Gly His Ile Gly Val Asp Ala Ser
385                 390                 395                 400
Ala Pro Gln Ile Gly Gly Ser Ile Thr Gly Pro Ser Val Glu Val Gln
                405                 410                 415
Ala Pro Asp Ile Asp Val Gln Gly Pro Gly Ser Lys Leu Asn Val Pro
            420                 425                 430
Lys Met Lys Val Pro Lys Phe Ser Val Ser Gly Ala Lys Gly Glu Glu
        435                 440                 445
```

```
Thr Gly Ile Asp Val Thr Leu Pro Thr Gly Glu Val Thr Pro Gly
    450                 455                 460

Val Ser Gly Asp Val Ser Leu Pro Glu Ile Ala Thr Gly Gly Leu Glu
465                 470                 475                 480

Gly Lys Met Lys Gly Thr Lys Val Lys Thr Pro Glu Met Ile Ile Gln
                485                 490                 495

Lys Pro Lys Ile Ser Met Gln Asp Val Asp Leu Ser Leu Gly Ser Pro
                500                 505                 510

Lys Leu Lys Gly Asp Ile Lys Val Ser Ala Pro Gly Val Gln Gly Asp
            515                 520                 525

Val Lys Gly Pro Gln Val Ala Leu Lys Gly Ser Arg Val Asp Ile Glu
    530                 535                 540

Thr Pro Asn Leu Glu Gly Thr Leu Thr Gly Pro Arg Leu Gly Ser Pro
545                 550                 555                 560

Ser Gly Lys Thr Gly Thr Cys Arg Ile Ser Met Ser Glu Val Asp Leu
                565                 570                 575

Asn Val Ala Ala Pro Lys Val Lys Gly Gly Val Asp Val Thr Leu Pro
            580                 585                 590

Arg Val Glu Gly Lys Val Lys Val Pro Glu Val Asp Val Arg Gly Pro
    595                 600                 605

Lys Val Asp Val Ser Ala Pro Asp Val Glu Ala His Gly Pro Glu Trp
    610                 615                 620

Asn Leu Lys Met Pro Lys Met Lys Met Pro Thr Phe Ser Thr Pro Gly
625                 630                 635                 640

Ala Lys Gly Glu Gly Pro Asp Val His Met Thr Leu Pro Lys Gly Asp
                645                 650                 655

Ile Ser Ile Ser Gly Pro Lys Val Asn Val Glu Ala Pro Asp Val Asn
                660                 665                 670

Leu Glu Gly Leu Gly Gly Lys Leu Lys Gly Pro Asp Val Lys Leu Pro
            675                 680                 685

Asp Met Ser Val Lys Thr Pro Lys Ile Ser Met Pro Asp Val Asp Leu
    690                 695                 700

His Val Lys Gly Thr Lys Val Lys Gly Glu Tyr Asp Val Thr Val Pro
705                 710                 715                 720

Lys Leu Glu Gly Glu Leu Lys Gly Pro Lys Val Asp Ile Asp Ala Pro
                725                 730                 735

Asp Val Asp Val His Gly Pro Asp Trp His Leu Lys Met Pro Lys Met
                740                 745                 750

Lys Met Pro Lys Phe Ser Val Pro Gly Phe Lys Ala Glu Gly Pro Glu
            755                 760                 765

Val Asp Val Asn Leu Pro Lys Ala Asp Val Asp Ile Ser Gly Pro Lys
    770                 775                 780

Ile Asp Val Thr Ala Pro Asp Val Ser Ile Glu Glu Pro Glu Gly Lys
785                 790                 795                 800

Leu Lys Gly Pro Lys Phe Lys Met Pro Glu Met Asn Ile Lys Val Pro
                805                 810                 815

Lys Ile Ser Met Pro Asp Val Asp Leu His Leu Lys Gly Pro Asn Val
            820                 825                 830

Lys Gly Glu Tyr Asp Val Thr Met Pro Lys Val Glu Ser Glu Ile Lys
            835                 840                 845

Val Pro Asp Val Glu Leu Lys Ser Ala Lys Met Asp Ile Asp Val Pro
    850                 855                 860

Asp Val Glu Val Gln Gly Pro Asp Trp His Leu Lys Met Pro Lys Met
865                 870                 875                 880
```

-continued

```
Lys Met Pro Lys Phe Ser Met Pro Gly Phe Lys Ala Glu Gly Pro Glu
            885                 890                 895
Val Asp Val Asn Leu Pro Lys Ala Asp Val Asp Ile Ser Gly Pro Lys
            900                 905                 910
Val Gly Val Glu Val Pro Asp Val Asn Ile Glu Gly Pro Glu Gly Lys
            915                 920                 925
Leu Lys Gly Pro Lys Phe Lys Met Pro Glu Met Asn Ile Lys Ala Pro
    930                 935                 940
Lys Ile Ser Met Pro Asp Val Asp Leu His Met Lys Gly Pro Lys Val
945                 950                 955                 960
Lys Gly Glu Tyr Asp Met Thr Val Pro Lys Leu Glu Gly Asp Leu Lys
                965                 970                 975
Gly Pro Lys Val Asp Val Ser Ala Pro Asp Val Glu Met Gln Gly Pro
            980                 985                 990
Asp Trp Asn Leu Lys Met Pro Lys Ile Lys Met Pro Lys Phe Ser Met
        995                 1000                1005
Pro Ser Leu Lys Gly Glu Gly Pro Glu Phe Asp Val Asn Leu Ser
    1010                1015                1020
Lys Ala Asn Val Asp Ile Ser Ala Pro Lys Val Asp Thr Asn Ala
    1025                1030                1035
Pro Asp Leu Ser Leu Glu Gly Pro Glu Gly Lys Leu Lys Gly Pro
    1040                1045                1050
Lys Phe Lys Met Pro Glu Met His Phe Arg Ala Pro Lys Met Ser
    1055                1060                1065
Leu Pro Asp Val Asp Leu Asp Leu Lys Gly Pro Lys Met Lys Gly
    1070                1075                1080
Asn Val Asp Ile Ser Ala Pro Lys Ile Glu Gly Glu Met Gln Val
    1085                1090                1095
Pro Asp Val Asp Ile Arg Gly Pro Lys Val Asp Ile Lys Ala Pro
    1100                1105                1110
Asp Val Glu Gly Gln Gly Leu Asp Trp Ser Leu Lys Ile Pro Lys
    1115                1120                1125
Met Lys Met Pro Lys Phe Ser Met Pro Ser Leu Lys Gly Glu Gly
    1130                1135                1140
Pro Glu Val Asp Val Asn Leu Pro Lys Ala Asp Val Val Val Ser
    1145                1150                1155
Gly Pro Lys Val Asp Ile Glu Ala Pro Asp Val Ser Leu Glu Gly
    1160                1165                1170
Pro Glu Gly Lys Leu Lys Gly Pro Lys Phe Lys Met Pro Glu Met
    1175                1180                1185
His Phe Lys Thr Pro Lys Ile Ser Met Pro Asp Val Asp Leu His
    1190                1195                1200
Leu Lys Gly Pro Lys Val Lys Gly Asp Val Asp Val Ser Val Pro
    1205                1210                1215
Lys Val Glu Gly Glu Met Lys Val Pro Asp Val Glu Ile Lys Gly
    1220                1225                1230
Pro Lys Met Asp Ile Asp Ala Pro Asp Val Glu Val Gln Gly Pro
    1235                1240                1245
Asp Trp His Leu Lys Met Pro Lys Met Lys Met Pro Lys Phe Ser
    1250                1255                1260
Met Pro Gly Phe Lys Gly Glu Gly Arg Glu Val Asp Val Asn Leu
    1265                1270                1275
Pro Lys Ala Asp Ile Asp Val Ser Gly Pro Lys Val Asp Val Glu
```

```
              1280              1285              1290

Val Pro Asp Val Ser Leu Glu Gly Pro Glu Gly Lys  Leu Lys Gly
    1295              1300              1305

Pro Lys Phe Lys Met Pro Glu Met His Phe Lys Ala  Pro Lys Ile
    1310              1315              1320

Ser Met Pro Asp Val Asp Leu Asn Leu Lys Gly Pro  Lys Leu Lys
    1325              1330              1335

Gly Asp Val Asp Val Ser Leu Pro Glu Val Glu Gly  Glu Met Lys
    1340              1345              1350

Val Pro Asp Val Asp Ile Lys Gly Pro Lys Val Asp  Ile Ser Ala
    1355              1360              1365

Pro Asp Val Asp Val His Gly Pro Asp Trp His Leu  Lys Met Pro
    1370              1375              1380

Lys Val Lys Met Pro Lys Phe Ser Met Pro Gly Phe  Lys Gly Glu
    1385              1390              1395

Gly Pro Glu Val Asp Val Lys Leu Pro Lys Ala Asp  Val Asp Val
    1400              1405              1410

Ser Gly Pro Lys Met Asp Ala Glu Val Pro Asp Val  Asn Ile Glu
    1415              1420              1425

Gly Pro Asp Ala Lys Leu Lys Gly Pro Lys Phe Lys  Met Pro Glu
    1430              1435              1440

Met Ser Ile Lys Pro Gln Lys Ile Ser Ile Pro Asp  Val Gly Leu
    1445              1450              1455

His Leu Lys Gly Pro Lys Met Lys Gly Asp Tyr Asp  Val Thr Val
    1460              1465              1470

Pro Lys Val Glu Gly Glu Ile Lys Ala Pro Asp Val  Asp Ile Lys
    1475              1480              1485

Gly Pro Lys Val Asp Ile Asn Ala Pro Asp Val Glu  Val His Gly
    1490              1495              1500

Pro Asp Trp His Leu Lys Met Pro Lys Val Lys Met  Pro Lys Phe
    1505              1510              1515

Ser Met Pro Gly Phe Lys Gly Glu Gly Pro Glu Val  Asp Met Asn
    1520              1525              1530

Leu Pro Lys Ala Asp Leu Gly Val Ser Gly Pro Lys  Val Asp Ile
    1535              1540              1545

Asp Val Pro Asp Val Asn Leu Glu Ala Pro Glu Gly  Lys Leu Lys
    1550              1555              1560

Gly Pro Lys Phe Lys Met Pro Ser Met Asn Ile Gln  Thr His Lys
    1565              1570              1575

Ile Ser Met Pro Asp Val Gly Leu Asn Leu Lys Ala  Pro Lys Leu
    1580              1585              1590

Lys Thr Asp Val Asp Val Ser Leu Pro Lys Val Glu  Gly Asp Leu
    1595              1600              1605

Lys Gly Pro Glu Ile Asp Val Lys Ala Pro Lys Met  Asp Val Asn
    1610              1615              1620

Val Gly Asp Ile Asp Ile Glu Gly Pro Glu Gly Lys  Leu Lys Gly
    1625              1630              1635

Pro Lys Phe Lys Met Pro Glu Met His Phe Lys Ala  Pro Lys Ile
    1640              1645              1650

Ser Met Pro Asp Val Asp Leu His Leu Lys Gly Pro  Lys Val Lys
    1655              1660              1665

Gly Asp Met Asp Val Ser Val Pro Lys Val Glu Gly  Glu Met Lys
    1670              1675              1680
```

-continued

```
Val Pro Asp Val Asp Ile Lys Gly Pro Lys Val Asp Ile Asp Ala
1685                1690                1695

Pro Asp Val Glu Val His Asp Pro Asp Trp His Leu Lys Met Pro
1700                1705                1710

Lys Met Lys Met Pro Lys Phe Ser Met Pro Gly Phe Lys Ala Glu
1715                1720                1725

Gly Pro Glu Val Asp Val Asn Leu Pro Lys Ala Asp Ile Asp Val
1730                1735                1740

Ser Gly Pro Ser Val Asp Thr Asp Ala Pro Asp Leu Asp Ile Glu
1745                1750                1755

Gly Pro Glu Gly Lys Leu Lys Gly Ser Lys Phe Lys Met Pro Lys
1760                1765                1770

Leu Asn Ile Lys Ala Pro Lys Val Ser Met Pro Asp Val Asp Leu
1775                1780                1785

Asn Leu Lys Gly Pro Lys Leu Lys Gly Glu Ile Asp Ala Ser Val
1790                1795                1800

Pro Glu Leu Glu Gly Asp Leu Arg Gly Pro Gln Val Asp Val Lys
1805                1810                1815

Gly Pro Phe Val Glu Ala Glu Val Pro Asp Val Asp Leu Glu Cys
1820                1825                1830

Pro Asp Ala Lys Leu Lys Gly Pro Lys Phe Lys Met Pro Glu Met
1835                1840                1845

His Phe Lys Ala Pro Lys Ile Ser Met Pro Asp Val Asp Leu His
1850                1855                1860

Leu Lys Gly Pro Lys Val Lys Gly Asp Ala Asp Val Ser Val Pro
1865                1870                1875

Lys Leu Glu Gly Asp Leu Thr Gly Pro Ser Val Gly Val Glu Val
1880                1885                1890

Pro Asp Val Glu Leu Glu Cys Pro Asp Ala Lys Leu Lys Gly Pro
1895                1900                1905

Lys Phe Lys Met Pro Asp Met His Phe Lys Ala Pro Lys Ile Ser
1910                1915                1920

Met Pro Asp Val Asp Leu His Leu Lys Gly Pro Lys Val Lys Gly
1925                1930                1935

Asp Val Asp Val Ser Val Pro Lys Leu Glu Gly Asp Leu Thr Gly
1940                1945                1950

Pro Ser Val Gly Val Glu Val Pro Asp Val Glu Leu Glu Cys Pro
1955                1960                1965

Asp Ala Lys Leu Lys Gly Pro Lys Phe Lys Met Pro Glu Met His
1970                1975                1980

Phe Lys Thr Pro Lys Ile Ser Met Pro Asp Val Asp Leu His Leu
1985                1990                1995

Lys Gly Pro Lys Val Lys Gly Asp Met Asp Val Ser Val Pro Lys
2000                2005                2010

Val Glu Gly Glu Met Lys Val Pro Asp Val Asp Ile Lys Gly Pro
2015                2020                2025

Lys Met Asp Ile Asp Ala Pro Asp Val Asp Val His Gly Pro Asp
2030                2035                2040

Trp His Leu Lys Met Pro Lys Met Lys Met Pro Lys Phe Ser Met
2045                2050                2055

Pro Gly Phe Lys Ala Glu Gly Pro Glu Val Asp Val Asn Leu Pro
2060                2065                2070

Lys Ala Asp Val Val Val Ser Gly Pro Lys Val Asp Val Glu Val
2075                2080                2085
```

-continued

```
Pro Asp Val Ser Leu Glu Gly Pro Glu Gly Lys Leu  Lys Gly Pro
    2090            2095                2100

Lys Leu Lys Met Pro Glu Met His Phe Lys Ala Pro  Lys Ile Ser
    2105            2110                2115

Met Pro Asp Val Asp Leu His Leu Lys Gly Pro Lys  Val Lys Gly
    2120            2125                2130

Asp Val Asp Val Ser Leu Pro Lys Leu Glu Gly Asp  Leu Thr Gly
    2135            2140                2145

Pro Ser Val Asp Val Glu Val Pro Asp Val Glu Leu  Glu Cys Pro
    2150            2155                2160

Asp Ala Lys Leu Lys Gly Pro Lys Phe Lys Met Pro  Glu Met His
    2165            2170                2175

Phe Lys Thr Pro Lys Ile Ser Met Pro Asp Val Asn  Leu Asn Leu
    2180            2185                2190

Lys Gly Pro Lys Val Lys Gly Asp Met Asp Val Ser  Val Pro Lys
    2195            2200                2205

Val Glu Gly Glu Met Lys Val Pro Asp Val Asp Ile  Arg Gly Pro
    2210            2215                2220

Lys Val Asp Ile Asp Ala Pro Asp Val Asp Val His  Gly Pro Asp
    2225            2230                2235

Trp His Leu Lys Met Pro Lys Met Lys Met Pro Lys  Phe Ser Met
    2240            2245                2250

Pro Gly Phe Lys Gly Glu Gly Pro Glu Val Asp Val  Asn Leu Pro
    2255            2260                2265

Lys Ala Asp Val Asp Val Ser Gly Pro Lys Val Asp  Val Glu Val
    2270            2275                2280

Pro Asp Val Ser Leu Glu Gly Pro Glu Gly Lys Leu  Lys Gly Pro
    2285            2290                2295

Lys Phe Lys Met Pro Glu Met His Phe Lys Thr Pro  Lys Ile Ser
    2300            2305                2310

Met Pro Asp Val Asp Phe Asn Leu Lys Gly Pro Lys  Ile Lys Gly
    2315            2320                2325

Asp Val Asp Val Ser Ala Pro Lys Leu Glu Gly Glu  Leu Lys Gly
    2330            2335                2340

Pro Glu Leu Asp Val Lys Gly Pro Lys Leu Asp Ala  Asp Met Pro
    2345            2350                2355

Glu Val Ala Val Glu Gly Pro Asn Gly Lys Trp Lys  Thr Pro Lys
    2360            2365                2370

Phe Lys Met Pro Asp Met His Phe Lys Ala Pro Lys  Ile Ser Met
    2375            2380                2385

Pro Asp Leu Asp Leu His Leu Lys Ser Pro Lys Ala  Lys Gly Glu
    2390            2395                2400

Val Asp Val Asp Val Pro Lys Leu Glu Gly Asp Leu  Lys Gly Pro
    2405            2410                2415

His Val Asp Val Ser Gly Pro Asp Ile Asp Ile Glu  Gly Pro Glu
    2420            2425                2430

Gly Lys Leu Lys Gly Pro Lys Phe Lys Met Pro Asp  Met His Phe
    2435            2440                2445

Lys Ala Pro Asn Ile Ser Met Pro Asp Val Asp Leu  Asn Leu Lys
    2450            2455                2460

Gly Pro Lys Ile Lys Gly Asp Val Asp Val Ser Val  Pro Glu Val
    2465            2470                2475

Glu Gly Lys Leu Glu Val Pro Asp Met Asn Ile Arg  Gly Pro Lys
```

```
                    2480                2485                2490

Val Asp Val Asn Ala Pro Asp Val Gln Ala Pro Asp Trp His Leu
2495                2500                2505

Lys Met Pro Lys Met Lys Met Pro Lys Phe Ser Met Pro Gly Phe
2510                2515                2520

Lys Ala Glu Gly Pro Glu Val Asp Val Asn Leu Pro Lys Ala Asp
2525                2530                2535

Val Asp Ile Ser Gly Pro Lys Val Asp Ile Glu Gly Pro Asp Val
2540                2545                2550

Asn Ile Glu Gly Pro Glu Gly Lys Leu Lys Gly Pro Lys Leu Lys
2555                2560                2565

Met Pro Glu Met Asn Ile Lys Ala Pro Lys Ile Ser Met Pro Asp
2570                2575                2580

Phe Asp Leu His Leu Lys Gly Pro Lys Val Lys Gly Asp Val Asp
2585                2590                2595

Val Ser Leu Pro Lys Val Glu Gly Asp Leu Lys Gly Pro Glu Val
2600                2605                2610

Asp Ile Lys Gly Pro Lys Val Asp Ile Asn Ala Pro Asp Val Gly
2615                2620                2625

Val Gln Gly Pro Asp Trp His Leu Lys Met Pro Lys Val Lys Met
2630                2635                2640

Pro Lys Phe Ser Met Pro Gly Phe Lys Gly Glu Gly Pro Asp Gly
2645                2650                2655

Asp Val Lys Leu Pro Lys Ala Asp Ile Asp Val Ser Gly Pro Lys
2660                2665                2670

Val Asp Ile Glu Gly Pro Asp Val Asn Ile Glu Gly Pro Glu Gly
2675                2680                2685

Lys Leu Lys Gly Pro Lys Phe Lys Met Pro Glu Met Asn Ile Lys
2690                2695                2700

Ala Pro Lys Ile Ser Met Pro Asp Ile Asp Leu Asn Leu Lys Gly
2705                2710                2715

Pro Lys Val Lys Gly Asp Val Asp Val Ser Leu Pro Lys Val Glu
2720                2725                2730

Gly Asp Leu Lys Gly Pro Glu Val Asp Ile Lys Gly Pro Lys Val
2735                2740                2745

Asp Ile Asp Ala Pro Asp Val Asp Val His Gly Pro Asp Trp His
2750                2755                2760

Leu Lys Met Pro Lys Ile Lys Met Pro Lys Ile Ser Met Pro Gly
2765                2770                2775

Phe Lys Gly Glu Gly Pro Asp Val Asp Val Asn Leu Pro Lys Ala
2780                2785                2790

Asp Ile Asp Val Ser Gly Pro Lys Val Asp Val Glu Cys Pro Asp
2795                2800                2805

Val Asn Ile Glu Gly Pro Glu Gly Lys Trp Lys Ser Pro Lys Phe
2810                2815                2820

Lys Met Pro Glu Met His Phe Lys Thr Pro Lys Ile Ser Met Pro
2825                2830                2835

Asp Ile Asp Leu Asn Leu Thr Gly Pro Lys Ile Lys Gly Asp Val
2840                2845                2850

Asp Val Thr Gly Pro Lys Val Glu Gly Asp Leu Lys Gly Pro Glu
2855                2860                2865

Val Asp Leu Lys Gly Pro Lys Val Asp Ile Asp Val Pro Asp Val
2870                2875                2880
```

```
Asn Val Gln Gly Pro Asp Trp His Leu Lys Met Pro Lys Met Lys
2885                    2890                2895

Met Pro Lys Phe Ser Met Pro Gly Phe Lys Ala Glu Gly Pro Glu
2900                    2905                2910

Val Asp Val Asn Leu Pro Lys Ala Asp Val Asp Val Ser Gly Pro
2915                    2920                2925

Lys Val Asp Val Glu Gly Pro Asp Val Asn Ile Glu Gly Pro Glu
2930                    2935                2940

Gly Lys Leu Lys Gly Pro Lys Phe Lys Met Pro Glu Met Asn Ile
2945                    2950                2955

Lys Ala Pro Lys Ile Pro Met Pro Asp Phe Asp Leu His Leu Lys
2960                    2965                2970

Gly Pro Lys Val Lys Gly Asp Val Asp Ile Ser Leu Pro Lys Val
2975                    2980                2985

Glu Gly Asp Leu Lys Gly Pro Glu Val Asp Ile Arg Gly Pro Gln
2990                    2995                3000

Val Asp Ile Asp Val Pro Asp Val Gly Val Gln Gly Pro Asp Trp
3005                    3010                3015

His Leu Lys Met Pro Lys Val Lys Met Pro Lys Phe Ser Met Pro
3020                    3025                3030

Gly Phe Lys Gly Glu Gly Pro Asp Val Asp Val Asn Leu Pro Lys
3035                    3040                3045

Ala Asp Leu Asp Val Ser Gly Pro Lys Val Asp Ile Asp Val Pro
3050                    3055                3060

Asp Val Asn Ile Glu Gly Pro Glu Gly Lys Leu Lys Gly Pro Lys
3065                    3070                3075

Phe Lys Met Pro Glu Met Asn Ile Lys Ala Pro Lys Ile Ser Met
3080                    3085                3090

Pro Asp Ile Asp Leu Asn Leu Lys Gly Pro Lys Val Lys Gly Asp
3095                    3100                3105

Met Asp Val Ser Leu Pro Lys Val Glu Gly Asp Met Lys Val Pro
3110                    3115                3120

Asp Val Asp Ile Lys Gly Pro Lys Val Asp Ile Asn Ala Pro Asp
3125                    3130                3135

Val Asp Val Gln Gly Pro Asp Trp His Leu Lys Met Pro Lys Ile
3140                    3145                3150

Lys Met Pro Lys Ile Ser Met Pro Gly Phe Lys Gly Glu Gly Pro
3155                    3160                3165

Glu Val Asp Val Asn Leu Pro Lys Ala Asp Leu Asp Val Ser Gly
3170                    3175                3180

Pro Lys Val Asp Val Asp Val Pro Asp Val Asn Ile Glu Gly Pro
3185                    3190                3195

Asp Ala Lys Leu Lys Gly Pro Lys Phe Lys Met Pro Glu Met Asn
3200                    3205                3210

Ile Lys Ala Pro Lys Ile Ser Met Pro Asp Leu Asp Leu Asn Leu
3215                    3220                3225

Lys Gly Pro Lys Met Lys Gly Glu Val Asp Val Ser Leu Ala Asn
3230                    3235                3240

Val Glu Gly Asp Leu Lys Gly Pro Ala Leu Asp Ile Lys Gly Pro
3245                    3250                3255

Lys Ile Asp Val Asp Ala Pro Asp Ile Asp Ile His Gly Pro Asp
3260                    3265                3270

Ala Lys Leu Lys Gly Pro Lys Leu Lys Met Pro Asp Met His Val
3275                    3280                3285
```

```
Asn Met Pro Lys Ile Ser Met Pro Glu Ile Asp Leu Asn Leu Lys
    3290            3295            3300

Gly Ser Lys Leu Lys Gly Asp Val Asp Val Ser Gly Pro Lys Leu
    3305            3310            3315

Glu Gly Asp Ile Lys Ala Pro Ser Leu Asp Ile Lys Gly Pro Glu
    3320            3325            3330

Val Asp Val Ser Gly Pro Lys Leu Asn Ile Glu Gly Lys Ser Lys
    3335            3340            3345

Lys Ser Arg Phe Lys Leu Pro Lys Phe Asn Phe Ser Gly Ser Lys
    3350            3355            3360

Val Gln Thr Pro Glu Val Asp Val Lys Gly Lys Lys Pro Asp Ile
    3365            3370            3375

Asp Ile Thr Gly Pro Lys Val Asp Ile Asn Ala Pro Asp Val Glu
    3380            3385            3390

Val Gln Gly Lys Val Lys Gly Ser Lys Phe Lys Met Pro Phe Leu
    3395            3400            3405

Ser Ile Ser Ser Pro Lys Val Ser Met Pro Asp Val Glu Leu Asn
    3410            3415            3420

Leu Lys Ser Pro Lys Val Lys Gly Asp Leu Asp Ile Ala Gly Pro
    3425            3430            3435

Asn Leu Glu Gly Asp Phe Lys Gly Pro Lys Val Asp Ile Lys Ala
    3440            3445            3450

Pro Glu Val Asn Leu Asn Ala Pro Asp Val Asp Val His Gly Pro
    3455            3460            3465

Asp Trp Asn Leu Lys Met Pro Lys Met Lys Met Pro Lys Phe Ser
    3470            3475            3480

Val Ser Gly Leu Lys Ala Glu Gly Pro Asp Val Ala Val Asp Leu
    3485            3490            3495

Pro Lys Gly Asp Ile Asn Ile Glu Gly Pro Ser Met Asn Ile Glu
    3500            3505            3510

Gly Pro Asp Leu Asn Val Glu Gly Pro Glu Gly Leu Lys Gly
    3515            3520            3525

Pro Lys Phe Lys Met Pro Asp Met Asn Ile Lys Ala Pro Lys Ile
    3530            3535            3540

Ser Met Pro Asp Ile Asp Leu Asn Leu Lys Gly Pro Lys Val Lys
    3545            3550            3555

Gly Asp Val Asp Ile Ser Leu Pro Lys Leu Glu Gly Asp Leu Lys
    3560            3565            3570

Gly Pro Glu Val Asp Ile Lys Gly Pro Lys Val Asp Ile Asn Ala
    3575            3580            3585

Pro Asp Val Asp Val His Gly Pro Asp Trp His Leu Lys Met Pro
    3590            3595            3600

Lys Val Lys Met Pro Lys Phe Ser Met Pro Gly Phe Lys Gly Glu
    3605            3610            3615

Gly Pro Glu Val Asp Val Thr Leu Pro Lys Ala Asp Ile Asp Ile
    3620            3625            3630

Ser Gly Pro Asn Val Asp Val Asp Val Pro Asp Val Asn Ile Glu
    3635            3640            3645

Gly Pro Asp Ala Lys Leu Lys Gly Pro Lys Phe Lys Met Pro Glu
    3650            3655            3660

Met Asn Ile Lys Ala Pro Lys Ile Ser Met Pro Asp Phe Asp Leu
    3665            3670            3675

Asn Leu Lys Gly Pro Lys Met Lys Gly Asp Val Val Val Ser Leu
```

-continued

```
                3680                3685                3690

Pro Lys Val Glu Gly Asp Leu Lys Gly Pro Glu Val Asp Ile Lys
    3695                3700                3705

Gly Pro Lys Val Asp Ile Asp Thr Pro Asp Ile Asn Ile Glu Gly
    3710                3715                3720

Ser Glu Gly Lys Phe Lys Gly Pro Lys Phe Lys Ile Pro Glu Met
    3725                3730                3735

His Leu Lys Ala Pro Lys Ile Ser Met Pro Asp Ile Asp Leu Asn
    3740                3745                3750

Leu Lys Gly Pro Lys Val Lys Gly Asp Val Asp Val Ser Leu Pro
    3755                3760                3765

Lys Met Glu Gly Asp Leu Lys Gly Pro Glu Val Asp Ile Lys Gly
    3770                3775                3780

Pro Lys Val Asp Ile Asn Ala Pro Asp Val Asp Val Gln Gly Pro
    3785                3790                3795

Asp Trp His Leu Lys Met Pro Lys Val Lys Met Pro Lys Phe Ser
    3800                3805                3810

Met Pro Gly Phe Lys Gly Glu Gly Pro Asp Val Asp Val Asn Leu
    3815                3820                3825

Pro Lys Ala Asp Leu Asp Val Ser Gly Pro Lys Val Asp Ile Asp
    3830                3835                3840

Val Pro Asp Val Asn Ile Glu Gly Pro Glu Gly Lys Leu Lys Gly
    3845                3850                3855

Pro Lys Phe Lys Met Pro Glu Met Asn Ile Lys Ala Pro Lys Ile
    3860                3865                3870

Ser Met Pro Asp Ile Asp Leu Asn Leu Lys Gly Pro Lys Val Lys
    3875                3880                3885

Gly Asp Met Asp Val Ser Leu Pro Lys Val Glu Gly Asp Met Gln
    3890                3895                3900

Val Pro Asp Leu Asp Ile Lys Gly Pro Lys Val Asp Ile Asn Ala
    3905                3910                3915

Pro Asp Val Asp Val Arg Gly Pro Asp Trp His Leu Lys Met Pro
    3920                3925                3930

Lys Ile Lys Met Pro Lys Ile Ser Met Pro Gly Phe Lys Gly Glu
    3935                3940                3945

Gly Pro Glu Val Asp Val Asn Leu Pro Lys Ala Asp Leu Asp Val
    3950                3955                3960

Ser Gly Pro Lys Val Asp Val Asp Val Pro Asp Val Asn Ile Glu
    3965                3970                3975

Gly Pro Asp Ala Lys Leu Lys Gly Pro Lys Phe Lys Met Pro Glu
    3980                3985                3990

Met Asn Ile Lys Ala Pro Lys Ile Ser Met Pro Asp Phe Asp Leu
    3995                4000                4005

His Leu Lys Gly Pro Lys Val Lys Gly Asp Val Asp Val Ser Leu
    4010                4015                4020

Pro Lys Met Glu Gly Asp Leu Lys Ala Pro Glu Val Asp Ile Lys
    4025                4030                4035

Gly Pro Lys Val Asp Ile Asp Ala Pro Asp Val Asp Val His Gly
    4040                4045                4050

Pro Asp Trp His Leu Lys Met Pro Lys Val Lys Met Pro Lys Phe
    4055                4060                4065

Ser Met Pro Gly Phe Lys Gly Glu Gly Pro Glu Val Asp Val Asn
    4070                4075                4080
```

```
Leu Pro Lys Ala Asp Ile Asp Val Ser Gly Pro Lys Val Asp Ile
    4085            4090                4095
Asp Thr Pro Asp Ile Asp Ile His Gly Pro Glu Gly Lys Leu Lys
    4100            4105                4110
Gly Pro Lys Phe Lys Met Pro Asp Leu His Leu Lys Ala Pro Lys
    4115            4120                4125
Ile Ser Met Pro Glu Val Asp Leu Asn Leu Lys Gly Pro Lys Met
    4130            4135                4140
Lys Gly Asp Val Asp Val Ser Leu Pro Lys Val Glu Gly Asp Leu
    4145            4150                4155
Lys Gly Pro Glu Val Asp Ile Lys Gly Pro Lys Val Asp Ile Asp
    4160            4165                4170
Val Pro Asp Val Asp Val Gln Gly Pro Asp Trp His Leu Lys Met
    4175            4180                4185
Pro Lys Val Lys Met Pro Lys Phe Ser Met Pro Gly Phe Lys Gly
    4190            4195                4200
Glu Gly Pro Asp Val Asp Val Asn Leu Pro Lys Ala Asp Leu Asp
    4205            4210                4215
Val Ser Gly Pro Lys Val Asp Ile Asp Val Pro Asp Val Asn Ile
    4220            4225                4230
Glu Gly Pro Asp Ala Lys Leu Lys Gly Pro Lys Phe Lys Met Pro
    4235            4240                4245
Glu Met Asn Ile Lys Ala Pro Lys Ile Ser Met Pro Asp Phe Asp
    4250            4255                4260
Leu His Leu Lys Gly Pro Lys Val Lys Gly Asp Val Asp Val Ser
    4265            4270                4275
Leu Pro Lys Val Glu Gly Asp Leu Lys Gly Pro Glu Val Asp Ile
    4280            4285                4290
Lys Gly Pro Lys Val Asp Ile Asp Ala Pro Asp Val Asp Val His
    4295            4300                4305
Gly Pro Asp Trp His Leu Lys Met Pro Lys Val Lys Met Pro Lys
    4310            4315                4320
Phe Ser Met Pro Gly Phe Lys Gly Glu Gly Pro Asp Val Asp Val
    4325            4330                4335
Thr Leu Pro Lys Ala Asp Ile Glu Ile Ser Gly Pro Lys Val Asp
    4340            4345                4350
Ile Asp Ala Pro Asp Val Ser Ile Glu Gly Pro Asp Ala Lys Leu
    4355            4360                4365
Lys Gly Pro Lys Phe Lys Met Pro Glu Met Asn Ile Lys Ala Pro
    4370            4375                4380
Lys Ile Ser Met Pro Asp Ile Asp Phe Asn Leu Lys Gly Pro Lys
    4385            4390                4395
Val Lys Gly Asp Val Asp Val Ser Leu Pro Lys Val Glu Gly Asp
    4400            4405                4410
Leu Lys Gly Pro Glu Ile Asp Ile Lys Gly Pro Ser Leu Asp Ile
    4415            4420                4425
Asp Thr Pro Asp Val Asn Ile Glu Gly Pro Glu Gly Lys Leu Lys
    4430            4435                4440
Gly Pro Lys Phe Lys Met Pro Glu Met Asn Ile Lys Ala Pro Lys
    4445            4450                4455
Ile Ser Met Pro Asp Phe Asp Leu His Leu Lys Gly Pro Lys Val
    4460            4465                4470
Lys Gly Asp Val Asp Val Ser Leu Pro Lys Val Glu Ser Asp Leu
    4475            4480                4485
```

```
Lys Gly Pro Glu Val Asp Ile Glu Gly Pro Gly Lys Leu Lys
    4490                4495            4500

Gly Pro Lys Phe Lys Met Pro Asp Val His Phe Lys Ser Pro Gln
    4505                4510            4515

Ile Ser Met Ser Asp Ile Asp Leu Asn Leu Lys Gly Pro Lys Ile
    4520                4525            4530

Lys Gly Asp Met Asp Ile Ser Val Pro Lys Leu Glu Gly Asp Leu
    4535                4540            4545

Lys Gly Pro Lys Val Asp Val Lys Gly Pro Lys Val Gly Ile Asp
    4550                4555            4560

Thr Pro Asp Ile Asp Ile His Gly Pro Glu Gly Lys Leu Lys Gly
    4565                4570            4575

Pro Lys Phe Lys Met Pro Asp Leu His Leu Lys Ala Pro Lys Ile
    4580                4585            4590

Ser Met Pro Glu Val Asp Leu Asn Leu Lys Gly Pro Lys Val Lys
    4595                4600            4605

Gly Asp Met Asp Ile Ser Leu Pro Lys Val Glu Gly Asp Leu Lys
    4610                4615            4620

Gly Pro Glu Val Asp Ile Arg Asp Pro Lys Val Asp Ile Asp Val
    4625                4630            4635

Pro Asp Val Asp Val Gln Gly Pro Asp Trp His Leu Lys Met Pro
    4640                4645            4650

Lys Val Lys Met Pro Lys Phe Ser Met Pro Gly Phe Lys Gly Glu
    4655                4660            4665

Gly Pro Asp Val Asp Val Asn Leu Pro Lys Ala Asp Ile Asp Val
    4670                4675            4680

Ser Gly Pro Lys Val Asp Val Asp Val Pro Asp Val Asn Ile Glu
    4685                4690            4695

Gly Pro Asp Ala Lys Leu Lys Gly Pro Lys Phe Lys Met Pro Glu
    4700                4705            4710

Met Ser Ile Lys Ala Pro Lys Ile Ser Met Pro Asp Ile Asp Leu
    4715                4720            4725

Asn Leu Lys Gly Pro Lys Val Lys Gly Asp Val Asp Val Thr Leu
    4730                4735            4740

Pro Lys Val Glu Gly Asp Leu Lys Gly Pro Glu Ala Asp Ile Lys
    4745                4750            4755

Gly Pro Lys Val Asp Ile Asn Thr Pro Asp Val Asp Val His Gly
    4760                4765            4770

Pro Asp Trp His Leu Lys Met Pro Lys Val Lys Met Pro Lys Phe
    4775                4780            4785

Ser Met Pro Gly Phe Lys Gly Glu Gly Pro Asp Val Asp Val Ser
    4790                4795            4800

Leu Pro Lys Ala Asp Ile Asp Val Ser Gly Pro Lys Val Asp Val
    4805                4810            4815

Asp Ile Pro Asp Val Asn Ile Glu Gly Pro Asp Ala Lys Leu Lys
    4820                4825            4830

Gly Pro Lys Phe Lys Met Pro Glu Ile Asn Ile Lys Ala Pro Lys
    4835                4840            4845

Ile Ser Ile Pro Asp Val Asp Leu Asp Leu Lys Gly Pro Lys Val
    4850                4855            4860

Lys Gly Asp Phe Asp Val Ser Val Pro Lys Val Glu Gly Thr Leu
    4865                4870            4875

Lys Gly Pro Glu Val Asp Leu Lys Gly Pro Arg Leu Asp Phe Glu
```

```
                    4880            4885            4890

Gly Pro Asp Ala Lys Leu Ser Gly Pro Ser Leu Lys Met Pro Ser
    4895            4900            4905

Leu Glu Ile Ser Ala Pro Lys Val Thr Ala Pro Asp Val Asp Leu
    4910            4915            4920

His Leu Lys Ala Pro Lys Ile Gly Phe Ser Gly Pro Lys Leu Glu
    4925            4930            4935

Gly Gly Glu Val Asp Leu Lys Gly Pro Lys Val Glu Ala Pro Ser
    4940            4945            4950

Leu Asp Val His Met Asp Ser Pro Asp Ile Asn Ile Glu Gly Pro
    4955            4960            4965

Asp Val Lys Ile Pro Lys Phe Lys Lys Pro Lys Phe Gly Phe Gly
    4970            4975            4980

Ala Lys Ser Pro Lys Ala Asp Ile Lys Ser Pro Ser Leu Asp Val
    4985            4990            4995

Thr Val Pro Glu Ala Glu Leu Asn Leu Glu Thr Pro Glu Ile Ser
    5000            5005            5010

Val Gly Gly Lys Gly Lys Lys Ser Lys Phe Lys Met Pro Lys Ile
    5015            5020            5025

His Met Ser Gly Pro Lys Ile Lys Ala Lys Lys Gln Gly Phe Asp
    5030            5035            5040

Leu Asn Val Pro Gly Gly Glu Ile Asp Ala Ser Leu Lys Ala Pro
    5045            5050            5055

Asp Val Asp Val Asn Ile Ala Gly Pro Asp Ala Ala Leu Lys Val
    5060            5065            5070

Asp Val Lys Ser Pro Lys Thr Lys Lys Thr Met Phe Gly Lys Met
    5075            5080            5085

Tyr Phe Pro Asp Val Glu Phe Asp Ile Lys Ser Pro Lys Phe Lys
    5090            5095            5100

Ala Glu Ala Pro Leu Pro Ser Pro Lys Leu Glu Gly Glu Leu Gln
    5105            5110            5115

Ala Pro Asp Leu Glu Leu Ser Leu Pro Ala Ile His Val Glu Gly
    5120            5125            5130

Leu Asp Ile Lys Ala Lys Ala Pro Lys Val Lys Met Pro Asp Val
    5135            5140            5145

Asp Ile Ser Val Pro Lys Ile Glu Gly Asp Leu Lys Gly Pro Lys
    5150            5155            5160

Val Gln Ala Asn Leu Gly Ala Pro Asp Ile Asn Ile Glu Gly Leu
    5165            5170            5175

Asp Ala Lys Val Lys Thr Pro Ser Phe Gly Ile Ser Ala Pro Gln
    5180            5185            5190

Val Ser Ile Pro Asp Val Asn Val Asn Leu Lys Gly Pro Lys Ile
    5195            5200            5205

Lys Gly Asp Val Pro Ser Val Gly Leu Glu Gly Pro Asp Val Asp
    5210            5215            5220

Leu Gln Gly Pro Glu Ala Lys Ile Lys Phe Pro Lys Phe Ser Met
    5225            5230            5235

Pro Lys Ile Gly Ile Pro Gly Val Lys Met Glu Gly Gly Gly Ala
    5240            5245            5250

Glu Val His Ala Gln Leu Pro Ser Leu Glu Gly Asp Leu Arg Gly
    5255            5260            5265

Pro Asp Val Lys Leu Glu Gly Pro Asp Val Ser Leu Lys Gly Pro
    5270            5275            5280
```

```
Gly Val Asp Leu Pro Ser Val Asn Leu Ser Met Pro Lys Val Ser
    5285              5290              5295

Gly Pro Asp Leu Asp Leu Asn Leu Lys Gly Pro Ser Leu Lys Gly
    5300              5305              5310

Asp Leu Asp Ala Ser Val Pro Ser Met Lys Val His Ala Pro Gly
    5315              5320              5325

Leu Asn Leu Ser Gly Val Gly Gly Lys Met Gln Val Gly Gly Asp
    5330              5335              5340

Gly Val Lys Val Pro Gly Ile Asp Ala Thr Thr Lys Leu Asn Val
    5345              5350              5355

Gly Ala Pro Asp Val Thr Leu Arg Gly Pro Ser Leu Gln Gly Asp
    5360              5365              5370

Leu Ala Val Ser Gly Asp Ile Lys Cys Pro Lys Val Ser Val Gly
    5375              5380              5385

Ala Pro Asp Leu Ser Leu Glu Ala Ser Glu Gly Ser Ile Lys Leu
    5390              5395              5400

Pro Lys Met Lys Leu Pro Gln Phe Gly Ile Ser Thr Pro Gly Ser
    5405              5410              5415

Asp Leu His Val Asn Ala Lys Gly Pro Gln Val Ser Gly Glu Leu
    5420              5425              5430

Lys Gly Pro Gly Val Asp Val Asn Leu Lys Gly Pro Arg Ile Ser
    5435              5440              5445

Ala Pro Asn Val Asp Phe Asn Leu Glu Gly Pro Lys Val Lys Gly
    5450              5455              5460

Ser Leu Gly Ala Thr Gly Glu Ile Lys Gly Pro Thr Val Gly Gly
    5465              5470              5475

Gly Leu Pro Gly Ile Gly Val Gln Gly Leu Glu Gly Asn Leu Gln
    5480              5485              5490

Met Pro Gly Ile Lys Ser Ser Gly Cys Asp Val Asn Leu Pro Gly
    5495              5500              5505

Val Asn Val Lys Leu Pro Thr Gly Gln Ile Ser Gly Pro Glu Ile
    5510              5515              5520

Lys Gly Gly Leu Lys Gly Ser Glu Val Gly Phe His Gly Ala Ala
    5525              5530              5535

Pro Asp Ile Ser Val Lys Gly Pro Ala Phe Asn Met Ala Ser Pro
    5540              5545              5550

Glu Ser Asp Phe Gly Ile Asn Leu Lys Gly Pro Lys Ile Lys Gly
    5555              5560              5565

Gly Ala Asp Val Ser Gly Gly Val Ser Ala Pro Asp Ile Ser Leu
    5570              5575              5580

Gly Glu Gly His Leu Ser Val Lys Gly Ser Gly Gly Glu Trp Lys
    5585              5590              5595

Gly Pro Gln Val Ser Ser Ala Leu Asn Leu Asp Thr Ser Lys Phe
    5600              5605              5610

Ala Gly Gly Leu His Phe Ser Gly Pro Lys Val Glu Gly Gly Val
    5615              5620              5625

Lys Gly Gly Gln Ile Gly Leu Gln Ala Pro Gly Leu Ser Val Ser
    5630              5635              5640

Gly Pro Gln Gly His Leu Glu Ser Gly Ser Gly Lys Val Thr Phe
    5645              5650              5655

Pro Lys Met Lys Ile Pro Lys Phe Thr Phe Ser Gly Arg Glu Leu
    5660              5665              5670

Val Gly Arg Glu Met Gly Val Asp Val His Phe Pro Lys Ala Glu
    5675              5680              5685
```

Ala Ser Ile Gln Ala Gly Ala Gly Asp Gly Glu Trp Glu Glu Ser
            5690                5695                5700

Glu Val Lys Leu Lys Lys Ser Lys Ile Lys Met Pro Lys Phe Asn
        5705                5710                5715

Phe Ser Lys Pro Lys Gly Lys Gly Gly Val Thr Gly Ser Pro Glu
    5720                5725                5730

Ala Ser Ile Ser Gly Ser Lys Gly Asp Leu Lys Ser Ser Lys Ala
        5735                5740                5745

Ser Leu Gly Ser Leu Glu Gly Glu Ala Glu Ala Glu Ala Ser Ser
    5750                5755                5760

Pro Lys Gly Lys Phe Ser Leu Phe Lys Ser Lys Lys Pro Arg His
    5765                5770                5775

Arg Ser Asn Ser Phe Ser Asp Glu Arg Glu Phe Ser Gly Pro Ser
    5780                5785                5790

Thr Pro Thr Gly Thr Leu Glu Phe Glu Gly Gly Glu Val Ser Leu
5795                5800                5805

Glu Gly Gly Lys Val Lys Gly Lys His Gly Lys Leu Lys Phe Gly
    5810                5815                5820

Thr Phe Gly Gly Leu Gly Ser Lys Ser Lys Gly His Tyr Glu Val
    5825                5830                5835

Thr Gly Ser Asp Asp Glu Thr Gly Lys Leu Gln Gly Ser Gly Val
    5840                5845                5850

Ser Leu Ala Ser Lys Lys Ser Arg Leu Ser Ser Ser Ser Ser Asn
    5855                5860                5865

Asp Ser Gly Asn Lys Val Gly Ile Gln Leu Pro Glu Val Glu Leu
    5870                5875                5880

Ser Val Ser Thr Lys Lys Glu
    5885                5890

<210> SEQ ID NO 51
<211> LENGTH: 219
<212> TYPE: PRT
<213> ORGANISM: Homo sapiens

<400> SEQUENCE: 51

Met Ser Glu Thr Ala Pro Ala Ala Pro Ala Ala Pro Ala Pro Ala Glu
1               5                   10                  15

Lys Thr Pro Val Lys Lys Lys Ala Arg Lys Ser Ala Gly Ala Ala Lys
            20                  25                  30

Arg Lys Ala Ser Gly Pro Pro Val Ser Glu Leu Ile Thr Lys Val Val
        35                  40                  45

Ala Ala Ser Lys Glu Arg Ser Gly Val Ser Leu Ala Ala Leu Lys Lys
    50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
            100                 105                 110

Ser Gly Glu Ala Lys Pro Lys Ala Lys Lys Ala Gly Ala Ala Lys Ala
        115                 120                 125

Lys Lys Pro Ala Gly Ala Ala Lys Lys Pro Lys Lys Ala Thr Gly Ala
    130                 135                 140

Ala Thr Pro Lys Lys Ser Ala Lys Lys Thr Pro Lys Lys Ala Lys Lys
145                 150                 155                 160

```
Pro Ala Ala Ala Gly Ala Lys Lys Ala Lys Ser Pro Lys Ala
                165                 170                 175

Lys Ala Ala Lys Pro Lys Lys Ala Pro Lys Ser Pro Ala Lys Ala Lys
            180                 185                 190

Ala Val Lys Pro Lys Ala Ala Lys Pro Lys Thr Ala Lys Pro Lys Ala
        195                 200                 205

Ala Lys Pro Lys Lys Ala Ala Lys Lys Lys
        210                 215
```

<210> SEQ ID NO 52
<211> LENGTH: 277
<212> TYPE: PRT
<213> ORGANISM: Homo sapiens

<400> SEQUENCE: 52

```
Met Trp Pro Leu Ala Leu Val Ile Ala Ser Leu Thr Leu Ala Leu Ser
1               5                   10                  15

Gly Gly Val Ser Gln Glu Ser Ser Lys Val Leu Asn Thr Asn Gly Thr
            20                  25                  30

Ser Gly Phe Leu Pro Gly Gly Tyr Thr Cys Phe Pro His Ser Gln Pro
        35                  40                  45

Trp Gln Ala Ala Leu Leu Val Gln Gly Arg Leu Leu Cys Gly Gly Val
    50                  55                  60

Leu Val His Pro Lys Trp Val Leu Thr Ala Ala His Cys Leu Lys Glu
65                  70                  75                  80

Gly Leu Lys Val Tyr Leu Gly Lys His Ala Leu Gly Arg Val Glu Ala
                85                  90                  95

Gly Glu Gln Val Arg Glu Val Val His Ser Ile Pro His Pro Glu Tyr
            100                 105                 110

Arg Arg Ser Pro Thr His Leu Asn His Asp His Asp Ile Met Leu Leu
        115                 120                 125

Glu Leu Gln Ser Pro Val Gln Leu Thr Gly Tyr Ile Gln Thr Leu Pro
    130                 135                 140

Leu Ser His Asn Asn Arg Leu Thr Pro Gly Thr Thr Cys Arg Val Ser
145                 150                 155                 160

Gly Trp Gly Thr Thr Ser Pro Gln Val Asn Tyr Pro Lys Thr Leu
                165                 170                 175

Gln Cys Ala Asn Ile Gln Leu Arg Ser Asp Glu Cys Arg Gln Val
            180                 185                 190

Tyr Pro Gly Lys Ile Thr Asp Asn Met Leu Cys Ala Gly Thr Lys Glu
        195                 200                 205

Gly Gly Lys Asp Ser Cys Glu Gly Asp Ser Gly Gly Pro Leu Val Cys
    210                 215                 220

Asn Arg Thr Leu Tyr Gly Ile Val Ser Trp Gly Asp Phe Pro Cys Gly
225                 230                 235                 240

Gln Pro Asp Arg Pro Gly Val Tyr Thr Arg Val Ser Arg Tyr Val Leu
                245                 250                 255

Trp Ile Arg Glu Thr Ile Arg Lys Tyr Glu Thr Gln Gln Gln Lys Trp
            260                 265                 270

Leu Lys Gly Pro Gln
        275
```

<210> SEQ ID NO 53
<211> LENGTH: 383
<212> TYPE: PRT
<213> ORGANISM: Homo sapiens

<400> SEQUENCE: 53

```
Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380
```

<210> SEQ ID NO 54
<211> LENGTH: 946
<212> TYPE: PRT
<213> ORGANISM: Homo sapiens

<400> SEQUENCE: 54

| | | | | | | | | | | | | | | |
|---|---|---|---|---|---|---|---|---|---|---|---|---|---|---|
| Met | Lys | Arg | Leu | Thr | Cys | Phe | Phe | Ile | Cys | Phe | Phe | Leu | Ser | Glu | Val |
| 1 | | | | 5 | | | | | 10 | | | | | 15 | |
| Ser | Gly | Phe | Glu | Ile | Pro | Ile | Asn | Gly | Leu | Ser | Glu | Phe | Val | Asp | Tyr |
| | | | 20 | | | | | 25 | | | | | 30 | | |
| Glu | Asp | Leu | Val | Glu | Leu | Ala | Pro | Gly | Lys | Phe | Gln | Leu | Val | Ala | Glu |
| | | | 35 | | | | | 40 | | | | | 45 | | |
| Asn | Arg | Arg | Tyr | Gln | Arg | Ser | Leu | Pro | Gly | Glu | Ser | Glu | Met | Met | |
| | 50 | | | | | 55 | | | | | 60 | | | | |
| Glu | Glu | Val | Asp | Gln | Val | Thr | Leu | Tyr | Ser | Tyr | Lys | Val | Gln | Ser | Thr |
| 65 | | | | | 70 | | | | | 75 | | | | | 80 |
| Ile | Thr | Ser | Arg | Met | Ala | Thr | Thr | Met | Ile | Gln | Ser | Lys | Val | Val | Asn |
| | | | | 85 | | | | | 90 | | | | | 95 | |
| Asn | Ser | Pro | Gln | Pro | Gln | Asn | Val | Val | Phe | Asp | Val | Gln | Ile | Pro | Lys |
| | | | 100 | | | | | 105 | | | | | 110 | | |
| Gly | Ala | Phe | Ile | Ser | Asn | Phe | Ser | Met | Thr | Val | Asp | Gly | Lys | Thr | Phe |
| | | | 115 | | | | | 120 | | | | | 125 | | |
| Arg | Ser | Ser | Ile | Lys | Glu | Lys | Thr | Val | Gly | Arg | Ala | Leu | Tyr | Ala | Gln |
| | 130 | | | | | 135 | | | | | 140 | | | | |
| Ala | Arg | Ala | Lys | Gly | Lys | Thr | Ala | Gly | Leu | Val | Arg | Ser | Ser | Ala | Leu |
| 145 | | | | | 150 | | | | | 155 | | | | | 160 |
| Asp | Met | Glu | Asn | Phe | Arg | Thr | Glu | Val | Asn | Val | Leu | Pro | Gly | Ala | Lys |
| | | | | 165 | | | | | 170 | | | | | 175 | |
| Val | Gln | Phe | Glu | Leu | His | Tyr | Gln | Glu | Val | Lys | Trp | Arg | Lys | Leu | Gly |
| | | | 180 | | | | | 185 | | | | | 190 | | |
| Ser | Tyr | Glu | His | Arg | Ile | Tyr | Leu | Gln | Pro | Gly | Arg | Leu | Ala | Lys | His |
| | | | 195 | | | | | 200 | | | | | 205 | | |
| Leu | Glu | Val | Asp | Val | Trp | Val | Ile | Glu | Pro | Gln | Gly | Leu | Arg | Phe | Leu |
| | 210 | | | | | 215 | | | | | 220 | | | | |
| His | Val | Pro | Asp | Thr | Phe | Glu | Gly | His | Phe | Asp | Gly | Val | Pro | Val | Ile |
| 225 | | | | | 230 | | | | | 235 | | | | | 240 |
| Ser | Lys | Gly | Gln | Gln | Lys | Ala | His | Val | Ser | Phe | Lys | Pro | Thr | Val | Ala |
| | | | | 245 | | | | | 250 | | | | | 255 | |
| Gln | Gln | Arg | Ile | Cys | Pro | Ser | Cys | Arg | Glu | Thr | Ala | Val | Asp | Gly | Glu |
| | | | 260 | | | | | 265 | | | | | 270 | | |
| Leu | Val | Val | Leu | Tyr | Asp | Val | Lys | Arg | Glu | Glu | Lys | Ala | Gly | Glu | Leu |
| | | | 275 | | | | | 280 | | | | | 285 | | |
| Glu | Val | Phe | Asn | Gly | Tyr | Phe | Val | His | Phe | Phe | Ala | Pro | Asp | Asn | Leu |
| | 290 | | | | | 295 | | | | | 300 | | | | |
| Asp | Pro | Ile | Pro | Lys | Asn | Ile | Leu | Phe | Val | Ile | Asp | Val | Ser | Gly | Ser |
| 305 | | | | | 310 | | | | | 315 | | | | | 320 |
| Met | Trp | Gly | Val | Lys | Met | Lys | Gln | Thr | Val | Glu | Ala | Met | Lys | Thr | Ile |
| | | | | 325 | | | | | 330 | | | | | 335 | |
| Leu | Asp | Asp | Leu | Arg | Ala | Glu | Asp | His | Phe | Ser | Val | Ile | Asp | Phe | Asn |
| | | | 340 | | | | | 345 | | | | | 350 | | |
| Gln | Asn | Ile | Arg | Thr | Trp | Arg | Asn | Asp | Leu | Ile | Ser | Ala | Thr | Lys | Thr |
| | | | 355 | | | | | 360 | | | | | 365 | | |
| Gln | Val | Ala | Asp | Ala | Lys | Arg | Tyr | Ile | Glu | Lys | Ile | Gln | Pro | Ser | Gly |
| | 370 | | | | | 375 | | | | | 380 | | | | |
| Gly | Thr | Asn | Ile | Asn | Glu | Ala | Leu | Leu | Arg | Ala | Ile | Phe | Ile | Leu | Asn |
| 385 | | | | | 390 | | | | | 395 | | | | | 400 |
| Glu | Ala | Asn | Asn | Leu | Gly | Leu | Leu | Asp | Pro | Asn | Ser | Val | Ser | Leu | Ile |
| | | | | 405 | | | | | 410 | | | | | 415 | |

```
Ile Leu Val Ser Asp Gly Asp Pro Thr Val Gly Glu Leu Lys Leu Ser
            420                 425                 430

Lys Ile Gln Lys Asn Val Lys Glu Asn Ile Gln Asp Asn Ile Ser Leu
        435                 440                 445

Phe Ser Leu Gly Met Gly Phe Asp Val Asp Tyr Asp Phe Leu Lys Arg
450                 455                 460

Leu Ser Asn Glu Asn His Gly Ile Ala Gln Arg Ile Tyr Gly Asn Gln
465                 470                 475                 480

Asp Thr Ser Ser Gln Leu Lys Lys Phe Tyr Asn Gln Val Ser Thr Pro
                485                 490                 495

Leu Leu Arg Asn Val Gln Phe Asn Tyr Pro His Thr Ser Val Thr Asp
                500                 505                 510

Val Thr Gln Asn Asn Phe His Asn Tyr Phe Gly Gly Ser Glu Ile Val
            515                 520                 525

Val Ala Gly Lys Phe Asp Pro Ala Lys Leu Asp Gln Ile Glu Ser Val
530                 535                 540

Ile Thr Ala Thr Ser Ala Asn Thr Gln Leu Val Leu Glu Thr Leu Ala
545                 550                 555                 560

Gln Met Asp Asp Leu Gln Asp Phe Leu Ser Lys Asp Lys His Ala Asp
                565                 570                 575

Pro Asp Phe Thr Arg Lys Leu Trp Ala Tyr Leu Thr Ile Asn Gln Leu
                580                 585                 590

Leu Ala Glu Arg Ser Leu Ala Pro Thr Ala Ala Lys Arg Arg Ile
            595                 600                 605

Thr Arg Ser Ile Leu Gln Met Ser Leu Asp His His Ile Val Thr Pro
610                 615                 620

Leu Thr Ser Leu Val Ile Glu Asn Glu Ala Gly Asp Glu Arg Met Leu
625                 630                 635                 640

Ala Asp Ala Pro Pro Gln Asp Pro Ser Cys Cys Ser Gly Ala Leu Tyr
                645                 650                 655

Tyr Gly Ser Lys Val Val Pro Asp Ser Thr Pro Ser Trp Ala Asn Pro
                660                 665                 670

Ser Pro Thr Pro Val Ile Ser Met Leu Ala Gln Gly Ser Gln Val Leu
            675                 680                 685

Glu Ser Thr Pro Pro His Val Met Arg Val Glu Asn Asp Pro His
690                 695                 700

Phe Ile Ile Tyr Leu Pro Lys Ser Gln Lys Asn Ile Cys Phe Asn Ile
705                 710                 715                 720

Asp Ser Glu Pro Gly Lys Ile Leu Asn Leu Val Ser Asp Pro Glu Ser
                725                 730                 735

Gly Ile Val Val Asn Gly Gln Leu Val Gly Ala Lys Lys Pro Asn Asn
            740                 745                 750

Gly Lys Leu Ser Thr Tyr Phe Gly Lys Leu Gly Phe Tyr Phe Gln Ser
            755                 760                 765

Glu Asp Ile Lys Ile Glu Ile Ser Thr Glu Thr Ile Thr Leu Ser His
        770                 775                 780

Gly Ser Ser Thr Phe Ser Leu Ser Trp Ser Asp Thr Ala Gln Val Thr
785                 790                 795                 800

Asn Gln Arg Val Gln Ile Ser Val Lys Glu Lys Val Thr Ile
                805                 810                 815

Thr Leu Asp Lys Glu Met Ser Phe Ser Val Leu Leu His Arg Val Trp
            820                 825                 830

Lys Lys His Pro Val Asn Val Asp Phe Leu Gly Ile Tyr Ile Pro Pro
```

```
                    835                 840                 845
Thr Asn Lys Phe Ser Pro Lys Ala His Gly Leu Ile Gly Gln Phe Met
    850                 855                 860

Gln Glu Pro Lys Ile His Ile Phe Asn Glu Arg Pro Gly Lys Asp Pro
865                 870                 875                 880

Glu Lys Pro Glu Ala Ser Met Glu Val Lys Gly Gln Lys Leu Ile Ile
                885                 890                 895

Thr Arg Gly Leu Gln Lys Asp Tyr Arg Thr Asp Leu Val Phe Gly Thr
            900                 905                 910

Asp Val Thr Cys Trp Phe Val His Asn Ser Gly Lys Gly Phe Ile Asp
        915                 920                 925

Gly His Tyr Lys Asp Tyr Phe Val Pro Gln Leu Tyr Ser Phe Leu Lys
    930                 935                 940

Arg Pro
945

<210> SEQ ID NO 55
<211> LENGTH: 246
<212> TYPE: PRT
<213> ORGANISM: Homo sapiens

<400> SEQUENCE: 55

Met Gly Asp Arg Glu Gln Leu Leu Gln Arg Ala Arg Leu Ala Glu Gln
1               5                   10                  15

Ala Glu Arg Tyr Asp Asp Met Ala Ser Ala Met Lys Ala Val Thr Glu
                20                  25                  30

Leu Asn Glu Pro Leu Ser Asn Glu Asp Arg Asn Leu Leu Ser Val Ala
            35                  40                  45

Tyr Lys Asn Val Val Gly Ala Arg Arg Ser Ser Trp Arg Val Ile Ser
        50                  55                  60

Ser Ile Glu Gln Lys Thr Met Ala Asp Gly Asn Glu Lys Lys Leu Glu
65                  70                  75                  80

Lys Val Lys Ala Tyr Arg Glu Lys Ile Glu Lys Glu Leu Glu Thr Val
                85                  90                  95

Cys Asn Asp Val Leu Ser Leu Leu Asp Lys Phe Leu Ile Lys Asn Cys
            100                 105                 110

Asn Asp Phe Gln Tyr Glu Ser Lys Val Phe Tyr Leu Lys Met Lys Gly
        115                 120                 125

Asp Tyr Tyr Arg Tyr Leu Ala Glu Val Ala Ser Gly Glu Lys Lys Asn
    130                 135                 140

Ser Val Val Glu Ala Ser Glu Ala Ala Tyr Lys Glu Ala Phe Glu Ile
145                 150                 155                 160

Ser Lys Glu Gln Met Gln Pro Thr His Pro Ile Arg Leu Gly Leu Ala
                165                 170                 175

Leu Asn Phe Ser Val Phe Tyr Tyr Glu Ile Gln Asn Ala Pro Glu Gln
            180                 185                 190

Ala Cys Leu Leu Ala Lys Gln Ala Phe Asp Asp Ala Ile Ala Glu Leu
        195                 200                 205

Asp Thr Leu Asn Glu Asp Ser Tyr Lys Asp Ser Thr Leu Ile Met Gln
    210                 215                 220

Leu Leu Arg Asp Asn Leu Thr Leu Trp Thr Ser Asp Gln Gln Asp Glu
225                 230                 235                 240

Glu Ala Gly Glu Gly Asn
                245
```

```
<210> SEQ ID NO 56
<211> LENGTH: 166
<212> TYPE: PRT
<213> ORGANISM: Homo sapiens

<400> SEQUENCE: 56

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
130                 135                 140

Asp Arg Cys Thr Leu Ala Glu Lys Leu Gly Gly Ser Ala Val Ile Ser
145                 150                 155                 160

Leu Glu Gly Lys Pro Leu
                165

<210> SEQ ID NO 57
<211> LENGTH: 199
<212> TYPE: PRT
<213> ORGANISM: Homo sapiens

<400> SEQUENCE: 57

Met Asn Tyr Ser Lys Ile Pro Ala Gln Val Asp Leu Arg Arg Gln Ala
1               5                   10                  15

Glu Arg Asp Cys Arg Val Ser Ser Phe Arg Val Lys Glu Asn Phe Asp
            20                  25                  30

Lys Ala Arg Phe Ser Gly Thr Trp Tyr Ala Met Ala Lys Lys Asp Pro
        35                  40                  45

Glu Gly Leu Phe Leu Gln Asp Asn Ile Val Ala Glu Phe Ser Val Asp
    50                  55                  60

Glu Thr Gly Gln Met Ser Ala Thr Ala Lys Gly Arg Val Arg Leu Leu
65                  70                  75                  80

Asn Asn Trp Asp Val Cys Ala Asp Met Val Gly Thr Phe Thr Asp Thr
                85                  90                  95

Glu Asp Pro Ala Lys Phe Lys Met Lys Tyr Trp Gly Val Ala Ser Phe
            100                 105                 110

Leu Gln Lys Gly Asn Asp Asp His Trp Ile Val Asp Thr Asp Tyr Asp
        115                 120                 125

Thr Tyr Ala Val Gln Tyr Ser Cys Arg Leu Leu Asn Leu Asp Gly Thr
    130                 135                 140

Cys Ala Asp Ser Tyr Ser Phe Val Phe Ser Arg Asp Pro Asn Gly Leu
145                 150                 155                 160

Pro Pro Glu Ala Gln Lys Ile Val Arg Gln Arg Gln Glu Glu Leu Cys
                165                 170                 175
```

```
Leu Ala Arg Gln Tyr Arg Leu Ile Val His Asn Gly Tyr Cys Asp Gly
            180                 185                 190

Arg Ser Glu Arg Asn Leu Leu
            195

<210> SEQ ID NO 58
<211> LENGTH: 128
<212> TYPE: PRT
<213> ORGANISM: Homo sapiens

<400> SEQUENCE: 58

Ser Pro Pro Gly Lys Pro Gln Gly Pro Pro Gln Gly Gly Asn Gln
1               5                   10                  15

Pro Gln Gly Pro Pro Pro Pro Gly Lys Pro Gln Gly Pro Pro Pro
            20                  25                  30

Gln Gly Gly Asn Lys Pro Gln Gly Pro Pro Pro Gly Lys Pro Gln
            35                  40                  45

Gly Pro Pro Gln Gly Asp Asn Lys Ser Gln Ser Ala Lys Pro Gln
    50                  55                  60

Gly Pro Pro Gln Gly Gly Lys Pro Gln Gly Pro Pro Gln Gly
65                  70                  75                  80

Gly Asn Lys Pro Gln Gly Pro Pro Pro Gln Gly Lys Ser Ala Arg Ser
            85                  90                  95

Pro Pro Gly Lys Pro Gln Gly Pro Pro Gln Gln Glu Gly Asn Asn Pro
            100                 105                 110

Gln Gly Pro Pro Pro Ala Gly Gly Asn Pro Gly Ser Lys Ser Arg
            115                 120                 125

<210> SEQ ID NO 59
<211> LENGTH: 191
<212> TYPE: PRT
<213> ORGANISM: Homo sapiens

<400> SEQUENCE: 59

Met Gln Thr Ile Lys Cys Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
            35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
            85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
            115                 120                 125

Leu Ala Lys Asn Lys Gln Lys Pro Ile Thr Pro Glu Thr Ala Glu Lys
            130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
            165                 170                 175
```

Leu Glu Pro Pro Glu Pro Lys Lys Ser Arg Arg Cys Val Leu Leu
            180                 185                 190

<210> SEQ ID NO 60
<211> LENGTH: 151
<212> TYPE: PRT
<213> ORGANISM: Homo sapiens

<400> SEQUENCE: 60

Met Ser Lys Asn Thr Val Ser Ser Ala Arg Phe Arg Lys Val Asp Val
1               5                   10                  15

Asp Glu Tyr Asp Glu Asn Lys Phe Val Asp Glu Glu Asp Gly Gly Asp
            20                  25                  30

Gly Gln Ala Gly Pro Asp Glu Gly Val Asp Ser Cys Leu Arg Gln
            35                  40                  45

Gly Asn Met Thr Ala Ala Leu Gln Ala Ala Leu Lys Asn Pro Pro Ile
        50                  55                  60

Asn Thr Lys Ser Gln Ala Val Lys Asp Arg Ala Gly Ser Ile Val Leu
65                  70                  75                  80

Lys Val Leu Ile Ser Phe Lys Ala Asn Asp Ile Glu Lys Ala Val Gln
                85                  90                  95

Ser Leu Asp Lys Asn Gly Val Asp Leu Leu Met Lys Tyr Ile Tyr Lys
            100                 105                 110

Gly Phe Glu Ser Pro Ser Asp Asn Ser Ser Ala Met Leu Leu Gln Trp
            115                 120                 125

His Glu Lys Ala Leu Ala Ala Gly Gly Val Gly Ser Ile Val Arg Val
        130                 135                 140

Leu Thr Ala Arg Lys Thr Val
145                 150

<210> SEQ ID NO 61
<211> LENGTH: 346
<212> TYPE: PRT
<213> ORGANISM: Homo sapiens

<400> SEQUENCE: 61

Met Asp Pro Ala Arg Lys Ala Gly Ala Gln Ala Met Ile Trp Thr Ala
1               5                   10                  15

Gly Trp Leu Leu Leu Leu Leu Leu Arg Gly Gly Ala Gln Ala Leu Glu
            20                  25                  30

Cys Tyr Ser Cys Val Gln Lys Ala Asp Asp Gly Cys Ser Pro Asn Lys
            35                  40                  45

Met Lys Thr Val Lys Cys Ala Pro Gly Val Asp Val Cys Thr Glu Ala
        50                  55                  60

Val Gly Ala Val Glu Thr Ile His Gly Gln Phe Ser Leu Ala Val Arg
65                  70                  75                  80

Gly Cys Gly Ser Gly Leu Pro Gly Lys Asn Asp Arg Gly Leu Asp Leu
                85                  90                  95

His Gly Leu Leu Ala Phe Ile Gln Leu Gln Gln Cys Ala Gln Asp Arg
            100                 105                 110

Cys Asn Ala Lys Leu Asn Leu Thr Ser Arg Ala Leu Asp Pro Ala Gly
            115                 120                 125

Asn Glu Ser Ala Tyr Pro Pro Asn Gly Val Glu Cys Tyr Ser Cys Val
        130                 135                 140

Gly Leu Ser Arg Glu Ala Cys Gln Gly Thr Ser Pro Pro Val Val Ser
145                 150                 155                 160

Cys Tyr Asn Ala Ser Asp His Val Tyr Lys Gly Cys Phe Asp Gly Asn

```
            165                 170                 175
Val Thr Leu Thr Ala Ala Asn Val Thr Val Ser Leu Pro Val Arg Gly
            180                 185                 190

Cys Val Gln Asp Glu Phe Cys Thr Arg Asp Gly Val Thr Gly Pro Gly
            195                 200                 205

Phe Thr Leu Ser Gly Ser Cys Cys Gln Gly Ser Arg Cys Asn Ser Asp
            210                 215                 220

Leu Arg Asn Lys Thr Tyr Phe Ser Pro Arg Ile Pro Pro Leu Val Arg
225                 230                 235                 240

Leu Pro Pro Glu Pro Thr Thr Val Ala Ser Thr Thr Ser Val Thr
                245                 250                 255

Thr Ser Thr Ser Ala Pro Val Arg Pro Thr Ser Thr Thr Lys Pro Met
            260                 265                 270

Pro Ala Pro Thr Ser Gln Thr Pro Arg Gln Gly Val Glu His Glu Ala
            275                 280                 285

Ser Arg Asp Glu Glu Pro Arg Leu Thr Gly Gly Ala Ala Gly His Gln
            290                 295                 300

Asp Arg Ser Asn Ser Gly Gln Tyr Pro Ala Lys Gly Gly Pro Gln Gln
305                 310                 315                 320

Pro His Asn Lys Gly Cys Val Ala Pro Thr Ala Gly Leu Ala Ala Leu
                325                 330                 335

Leu Leu Ala Val Ala Ala Gly Val Leu Leu
            340                 345

<210> SEQ ID NO 62
<211> LENGTH: 394
<212> TYPE: PRT
<213> ORGANISM: Homo sapiens

<400> SEQUENCE: 62

Met Asp Ser Gln Gly Arg Lys Val Val Cys Asp Asn Gly Thr Gly
1               5                   10                  15

Phe Val Lys Cys Gly Tyr Ala Gly Ser Asn Phe Pro Glu His Ile Phe
                20                  25                  30

Pro Ala Leu Val Gly Arg Pro Ile Ile Arg Ser Thr Thr Lys Val Gly
            35                  40                  45

Asn Ile Glu Ile Lys Asp Leu Met Val Gly Asp Glu Ala Ser Glu Leu
        50                  55                  60

Arg Ser Met Leu Glu Val Asn Tyr Pro Met Glu Asn Gly Ile Val Arg
65                  70                  75                  80

Asn Trp Asp Asp Met Lys His Leu Trp Asp Tyr Thr Phe Gly Pro Glu
                85                  90                  95

Lys Leu Asn Ile Asp Thr Arg Asn Cys Lys Ile Leu Leu Thr Glu Pro
            100                 105                 110

Pro Met Asn Pro Thr Lys Asn Arg Glu Lys Ile Val Glu Val Met Phe
        115                 120                 125

Glu Thr Tyr Gln Phe Ser Gly Val Tyr Val Ala Ile Gln Ala Val Leu
    130                 135                 140

Thr Leu Tyr Ala Gln Gly Leu Leu Thr Gly Val Val Asp Ser Gly
145                 150                 155                 160

Asp Gly Val Thr His Ile Cys Pro Val Tyr Glu Gly Phe Ser Leu Pro
                165                 170                 175

His Leu Thr Arg Arg Leu Asp Ile Ala Gly Arg Asp Ile Thr Arg Tyr
            180                 185                 190

Leu Ile Lys Leu Leu Leu Leu Arg Gly Tyr Ala Phe Asn His Ser Ala
```

```
                195                 200                 205
Asp Phe Glu Thr Val Arg Met Ile Lys Glu Lys Leu Cys Tyr Val Gly
210                 215                 220

Tyr Asn Ile Glu Gln Glu Gln Lys Leu Ala Leu Glu Thr Thr Val Leu
225                 230                 235                 240

Val Glu Ser Tyr Thr Leu Pro Asp Gly Arg Ile Ile Lys Val Gly Gly
                245                 250                 255

Glu Arg Phe Glu Ala Pro Glu Ala Leu Phe Gln Pro His Leu Ile Asn
            260                 265                 270

Val Glu Gly Val Gly Val Ala Glu Leu Leu Phe Asn Thr Ile Gln Ala
        275                 280                 285

Ala Asp Ile Asp Thr Arg Ser Glu Phe Tyr Lys His Ile Val Leu Ser
290                 295                 300

Gly Gly Ser Thr Met Tyr Pro Gly Leu Pro Ser Arg Leu Glu Arg Glu
305                 310                 315                 320

Leu Lys Gln Leu Tyr Leu Glu Arg Val Leu Lys Gly Asp Val Glu Lys
                325                 330                 335

Leu Ser Lys Phe Lys Ile Arg Ile Glu Asp Pro Pro Arg Arg Lys His
            340                 345                 350

Met Val Phe Leu Gly Gly Ala Val Leu Ala Asp Ile Met Lys Asp Lys
        355                 360                 365

Asp Asn Phe Trp Met Thr Arg Gln Glu Tyr Gln Glu Lys Gly Val Arg
370                 375                 380

Val Leu Glu Lys Leu Gly Val Thr Val Arg
385                 390

<210> SEQ ID NO 63
<211> LENGTH: 86
<212> TYPE: PRT
<213> ORGANISM: Homo sapiens

<400> SEQUENCE: 63

Ser Cys Arg Ser Ser Gln Ser Leu Val Tyr Ser Asp Gly Asn Thr Tyr
1               5                   10                  15

Leu Asn Trp Phe Gln Gln Arg Pro Gly Gln Ser Pro Arg Arg Leu Ile
            20                  25                  30

Tyr Lys Val Ser Asn Arg Asp Ser Gly Val Pro Asp Arg Phe Ser Gly
        35                  40                  45

Ser Gly Ser Gly Thr Asp Phe Thr Leu Lys Ile Ser Arg Val Glu Ala
    50                  55                  60

Glu Asp Val Gly Val Tyr Tyr Cys Met Gln Gly Thr His Trp Pro Pro
65                  70                  75                  80

Ile Met Val Phe Thr Phe
            85

<210> SEQ ID NO 64
<211> LENGTH: 227
<212> TYPE: PRT
<213> ORGANISM: Homo sapiens

<400> SEQUENCE: 64

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45
```

```
Ala Glu Ala Lys Glu Gly Lys Glu Lys Pro Asp Gln Asp Ala Glu Gly
 50                  55                  60

Lys Ala Glu Glu Lys Glu Gly Glu Lys Asp Ala Ala Ala Lys Glu
65                   70                  75                  80

Glu Ala Pro Lys Ala Glu Pro Glu Lys Thr Glu Gly Ala Ala Glu Ala
                 85                  90                  95

Lys Ala Glu Pro Pro Lys Ala Pro Glu Gln Glu Gln Ala Ala Pro Gly
            100                 105                 110

Pro Ala Gly Gly Glu Ala Pro Lys Ala Ala Glu Ala Ala Ala
        115                 120                 125

Pro Ala Glu Ser Ala Ala Pro Ala Ala Gly Glu Glu Pro Ser Lys Glu
        130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205

Pro Lys Pro Val Glu Ala Pro Ala Ala Asn Ser Asp Gln Thr Val Thr
210                 215                 220

Val Lys Glu
225

<210> SEQ ID NO 65
<211> LENGTH: 401
<212> TYPE: PRT
<213> ORGANISM: Homo sapiens

<400> SEQUENCE: 65

Met Met Gly Leu Gly Asn Gly Arg Arg Ser Met Lys Ser Pro Pro Leu
1               5                   10                  15

Val Leu Ala Ala Leu Val Ala Cys Ile Ile Val Leu Gly Phe Asn Tyr
            20                  25                  30

Trp Ile Ala Ser Ser Arg Ser Val Asp Leu Gln Thr Arg Ile Met Glu
        35                  40                  45

Leu Glu Gly Arg Val Arg Ala Ala Glu Arg Gly Ala Val Glu
 50                  55                  60

Leu Lys Lys Asn Glu Phe Gln Gly Glu Leu Glu Lys Gln Arg Glu Gln
65                  70                  75                  80

Leu Asp Lys Ile Gln Ser Ser His Asn Phe Gln Leu Glu Ser Val Asn
                85                  90                  95

Lys Leu Tyr Gln Asp Glu Lys Ala Val Leu Val Asn Asn Ile Thr Thr
            100                 105                 110

Gly Glu Arg Leu Ile Arg Val Leu Gln Asp Gln Leu Lys Thr Leu Gln
        115                 120                 125

Arg Asn Tyr Gly Arg Leu Gln Gln Asp Val Leu Gln Phe Gln Lys Asn
        130                 135                 140

Gln Thr Asn Leu Glu Arg Lys Phe Ser Tyr Asp Leu Ser Gln Cys Ile
145                 150                 155                 160

Asn Gln Met Lys Glu Val Lys Glu Gln Cys Glu Glu Arg Ile Glu Glu
                165                 170                 175

Val Thr Lys Lys Gly Asn Glu Ala Val Ala Ser Arg Asp Leu Ser Glu
            180                 185                 190
```

Asn Asn Asp Gln Arg Gln Gln Leu Gln Ala Leu Ser Glu Pro Gln Pro
            195                 200                 205

Arg Leu Gln Ala Ala Gly Leu Pro His Thr Glu Val Pro Gln Gly Lys
    210                 215                 220

Gly Asn Val Leu Gly Asn Ser Lys Ser Gln Thr Pro Ala Pro Ser Ser
225                 230                 235                 240

Glu Val Val Leu Asp Ser Lys Arg Gln Val Glu Lys Glu Glu Thr Asn
                245                 250                 255

Glu Ile Gln Val Val Asn Glu Glu Pro Gln Arg Asp Arg Leu Pro Gln
            260                 265                 270

Glu Pro Gly Arg Glu Gln Val Glu Asp Arg Pro Val Gly Gly Arg
        275                 280                 285

Gly Phe Gly Gly Ala Gly Glu Leu Gly Gln Thr Pro Gln Val Gln Ala
    290                 295                 300

Ala Leu Ser Val Ser Gln Glu Asn Pro Glu Met Glu Gly Pro Glu Arg
305                 310                 315                 320

Asp Gln Leu Val Ile Pro Asp Gly Gln Glu Glu Gln Glu Ala Ala
                325                 330                 335

Gly Glu Gly Arg Asn Gln Gln Lys Leu Arg Gly Glu Asp Tyr Asn
            340                 345                 350

Met Asp Glu Asn Glu Ala Glu Ser Glu Thr Asp Lys Gln Ala Ala Leu
        355                 360                 365

Ala Gly Asn Asp Arg Asn Ile Asp Val Phe Asn Val Glu Asp Gln Lys
    370                 375                 380

Arg Asp Thr Ile Asn Leu Leu Asp Gln Arg Glu Lys Arg Asn His Thr
385                 390                 395                 400

Leu

<210> SEQ ID NO 66
<211> LENGTH: 324
<212> TYPE: PRT
<213> ORGANISM: Homo sapiens

<400> SEQUENCE: 66

Met Gly Asn Leu Leu Lys Val Leu Thr Cys Thr Asp Leu Glu Gln Gly
1               5                   10                  15

Pro Asn Phe Phe Leu Asp Phe Glu Asn Ala Gln Pro Thr Glu Ser Glu
            20                  25                  30

Lys Glu Ile Tyr Asn Gln Val Asn Val Leu Lys Asp Ala Glu Gly
        35                  40                  45

Ile Leu Glu Asp Leu Gln Ser Tyr Arg Gly Ala Gly His Glu Ile Arg
    50                  55                  60

Glu Ala Ile Gln His Pro Ala Asp Glu Lys Leu Gln Glu Lys Ala Trp
65                  70                  75                  80

Gly Ala Val Val Pro Leu Val Gly Lys Leu Lys Phe Tyr Glu Phe
                85                  90                  95

Ser Gln Arg Leu Glu Ala Ala Leu Arg Gly Leu Leu Gly Ala Leu Thr
            100                 105                 110

Ser Thr Pro Tyr Ser Pro Thr Gln His Leu Glu Arg Glu Gln Ala Leu
        115                 120                 125

Ala Lys Gln Phe Ala Glu Ile Leu His Phe Thr Leu Arg Phe Asp Glu
    130                 135                 140

Leu Lys Met Thr Asn Pro Ala Ile Gln Asn Asp Phe Ser Tyr Tyr Arg
145                 150                 155                 160

```
Arg Thr Leu Ser Arg Met Arg Ile Asn Asn Val Pro Ala Glu Gly Glu
            165                 170                 175

Asn Glu Val Asn Asn Glu Leu Ala Asn Arg Met Ser Leu Phe Tyr Ala
        180                 185                 190

Glu Ala Thr Pro Met Leu Lys Thr Leu Ser Asp Ala Thr Thr Lys Phe
        195                 200                 205

Val Ser Glu Asn Lys Asn Leu Pro Ile Glu Asn Thr Thr Asp Cys Leu
    210                 215                 220

Ser Thr Met Ala Ser Val Cys Arg Val Met Leu Glu Thr Pro Glu Tyr
225                 230                 235                 240

Arg Ser Arg Phe Thr Asn Glu Glu Thr Val Ser Phe Cys Leu Arg Val
            245                 250                 255

Met Val Gly Val Ile Ile Leu Tyr Asp His Val His Pro Val Gly Ala
        260                 265                 270

Phe Ala Lys Thr Ser Lys Ile Asp Met Lys Gly Cys Ile Lys Val Leu
        275                 280                 285

Lys Asp Gln Pro Pro Asn Ser Val Glu Gly Leu Leu Asn Ala Leu Arg
    290                 295                 300

Tyr Thr Thr Lys His Leu Asn Asp Glu Thr Thr Ser Lys Gln Ile Lys
305                 310                 315                 320

Ser Met Leu Gln

<210> SEQ ID NO 67
<211> LENGTH: 249
<212> TYPE: PRT
<213> ORGANISM: Homo sapiens

<400> SEQUENCE: 67

Met Glu Met Gly Arg Arg Ile His Leu Glu Leu Arg Asn Arg Thr Pro
1               5                   10                  15

Ser Asp Val Lys Glu Leu Val Leu Asp Asn Ser Arg Ser Asn Glu Gly
            20                  25                  30

Lys Leu Glu Gly Leu Thr Asp Glu Phe Glu Glu Leu Glu Phe Leu Ser
        35                  40                  45

Thr Ile Asn Val Gly Leu Thr Ser Ile Ala Asn Leu Pro Lys Leu Asn
    50                  55                  60

Lys Leu Lys Lys Leu Glu Leu Ser Asp Asn Arg Val Ser Gly Gly Leu
65                  70                  75                  80

Glu Val Leu Ala Glu Lys Cys Pro Asn Leu Thr His Leu Asn Leu Ser
                85                  90                  95

Gly Asn Lys Ile Lys Asp Leu Ser Thr Ile Glu Pro Leu Lys Lys Leu
            100                 105                 110

Glu Asn Leu Lys Ser Leu Asp Leu Phe Asn Cys Glu Val Thr Asn Leu
        115                 120                 125

Asn Asp Tyr Arg Glu Asn Val Phe Lys Leu Leu Pro Gln Leu Thr Tyr
    130                 135                 140

Leu Asp Gly Tyr Asp Arg Asp Asp Lys Glu Ala Pro Asp Ser Asp Ala
145                 150                 155                 160

Glu Gly Tyr Val Glu Gly Leu Asp Asp Glu Glu Asp Glu
                165                 170                 175

Glu Glu Tyr Asp Glu Asp Ala Gln Val Val Asp Glu Glu Asp
        180                 185                 190

Asp Glu Glu Glu Glu Gly Glu Glu Asp Val Ser Gly Glu Glu
    195                 200                 205

Glu Asp Glu Glu Gly Tyr Asn Asp Gly Glu Val Asp Asp Glu Glu Asp
```

```
              210                 215                 220
Glu Glu Glu Leu Gly Glu Glu Arg Gly Gln Lys Arg Lys Arg Glu
225                 230                 235                 240

Pro Glu Asp Glu Gly Glu Asp Asp Asp
                    245
```

METHODS FOR DETECTING PRE-DIABETES AND DIABETES

CROSS REFERENCE TO RELATED APPLICATION

This application is a National Stage application filed under Rule 371 based on PCT/US09/51578 filed Jul. 23, 2009 which claims the benefit of U.S. Provisional Application No. 61/083,096, filed Jul. 23, 2008, which is incorporated herein in its entirety.

FIELD

This relates to the field of diabetes, specifically to the identification of subjects who have diabetes or pre-diabetes, who are at risk of developing diabetes or pre-diabetes and/or to monitoring the effectiveness of treatments for diabetes.

BACKGROUND

Diabetes mellitus is a metabolic disorder characterized by chronic hyperglycemia with disturbances of carbohydrate, fat and protein metabolism that result from defects in insulin secretion, insulin action, or both. Diabetes can present with characteristic symptoms such as thirst, polyuria, blurring of vision, chronic infections, slow wound healing, and weight loss. In its most severe forms, ketoacidosis or a non-ketotic hyperosmolar state may develop and lead to stupor, coma and, in the absence of effective treatment, death.

Diabetes mellitus is subdivided into type 1 diabetes and type 2 diabetes. Type 1 diabetes results from autoimmune mediated destruction of the beta cells of the pancreas. Patients with type 1 diabetes exhibit little or no insulin secretion as manifested by low or undetectable levels of insulin or plasma C-peptide (also known in the art as "soluble C-peptide"). Type 2 diabetes is characterized by disorders of insulin action and insulin secretion, either of which may be the predominant feature. Type 2 diabetes patients can be both insulin deficient and insulin resistant. At least initially, and often throughout their lifetime, these individuals do not need supplemental insulin treatment to survive. Type 2 diabetes accounts for 90-95% of all cases of diabetes and can go undiagnosed for many years because the hyperglycemia is often not severe enough to provoke noticeable symptoms of diabetes or symptoms are simply not recognized. The majority of patients with type 2 diabetes are obese, and obesity itself may cause or aggravate insulin resistance. Many of those who are not obese by traditional weight criteria may have an increased percentage of body fat distributed predominantly in the abdominal region (visceral fat).

The symptoms of the early stages of diabetes often are not severe, not recognized, or may be absent. Consequently, hyperglycemia sufficient to cause pathological and functional changes may be present for a long time, occasionally up to ten years, before a diagnosis is made, usually by the detection of high levels of glucose in urine after overnight fasting during a routine medical work-up. The long-term effects of diabetes include progressive development of complications such as retinopathy with potential blindness, nephropathy that may lead to renal failure, neuropathy, microvascular changes, and autonomic dysfunction. People with diabetes are also at increased risk of cardiovascular, peripheral vascular, and cerebrovascular disease, as well as an increased risk of cancer. Several pathogenic processes are involved in the development of diabetes, including processes which destroy the insulin-secreting beta cells of the pancreas with consequent insulin deficiency, and changes in liver and smooth muscle cells that result in the resistance to insulin uptake. The abnormalities of carbohydrate, fat and protein metabolism are due to deficient action of insulin on target tissues resulting from insensitivity to insulin (insulin resistance) or lack of insulin (loss of beta cell function).

Over 18 million people in the United States have type 2 diabetes, and of these, about 5 million do not know they have the disease. These persons, who do not know they have the disease and who do not exhibit the classic symptoms of diabetes, present a major diagnostic and therapeutic challenge. Nearly 41 million persons in the United States are at significant risk of developing type 2 diabetes. These persons are broadly referred to as "pre-diabetics." The risk of developing type 2 diabetes increases with age, obesity, and lack of physical activity. It occurs more frequently in women with prior gestational diabetes, and in individuals with hypertension and/or dyslipidemia. As intervention early in the development of diabetes can substantially affect the long-term prognosis of the disease, a need remains to identify individuals who are pre-diabetic or those subjects who will become diabetic. In addition, a need remains for monitoring therapeutic interventions, to determine if they are effective.

SUMMARY

Pre-diabetes can be present for ten or more years before the detection of glycemic abnormalities and the development of actual diabetes. Treatment of pre-diabetics with drugs such as acarbose, metformin, troglitazone and rosiglitazone can postpone or prevent diabetes; yet few pre-diabetics are treated. A major reason is that no simple and unambiguous laboratory test has existed that can be used to identify those subjects at risk for developing diabetes or pre-diabetes. In addition, there is a need for a test that can determine the effectiveness of therapy for pre-diabetes and/or diabetes. There also is a need to identify subjects with a diabetic condition, including both pre-diabetic and diabetic subjects, so that they can obtain treatment early, and also to monitor the progression of the disease over time non-invasively.

Methods for identifying individuals who are not yet diabetics (pre-diabetic), but who are at significant risk of developing diabetes, such as type 2 diabetes, are disclosed herein. Methods are also provided for the identification of diabetic subjects. These methods can be used to select subjects for therapeutic or lifestyle intervention. In additional embodiments, the methods can be used to identify diabetes type 2 in a subject (as compared to pre-diabetes). In further embodiments, the methods can be used to identify the efficacy of a therapeutic intervention, such as to manage dosage over time of anti-diabetic medication, or to asses the success of lifestyle interventions or other treatments to modify disease progression. The methods include the identification of biomarkers such as proteins in a biological fluid, such as saliva. In some embodiments, these biomarkers are identified using antibody-based methods, such as, but not limited to, an enzyme-linked immunosorbant assay (ELISA), a radioimmunoassay (RIA), a lateral flow immunoassay, or proteomic approaches that utilize various detection methods.

In several embodiments, methods are provided for the diagnosis of pre-diabetes, determining if a subject is at risk for developing pre-diabetes, or monitoring the efficacy of therapy, including lifestyle modifications and preventative treatments, in a human subject of interest. The methods include testing in a biological sample (such as saliva) obtained from said subject the abundance (amount) of one or more proteins relative to the abundance (amount) in a biological sample (such as saliva) from a pre-diabetic subject or a control subject. In some examples, the control is a sample from a subject not known to have impaired glucose tolerance, impaired fasting glucose regulation, or both. The subject of interest is diagnosed with pre-diabetes or diabetes, determined to be at risk for developing pre-diabetes, or having an effective therapeutic regimen if the abundance (amount) is not statistically significantly different relative to abundance in the saliva from the pre-diabetic or diabetic subject, respectively, or is statistically increased relative to abundance in a saliva sample from the control subject.

The foregoing and other features will become more apparent from the following detailed description of several embodiments, which proceeds with reference to the accompanying figures.

BRIEF DESCRIPTION OF THE FIGURES

FIG. 3A is a perspective view of a physical embodiment of a lateral flow test strip showing the basic components of the device and their relationship to each other.

FIG. 3B is a perspective view of a physical embodiment of a lateral flow test strip for the detection of multiple analytes.

SEQUENCE LISTING

Figure 1:
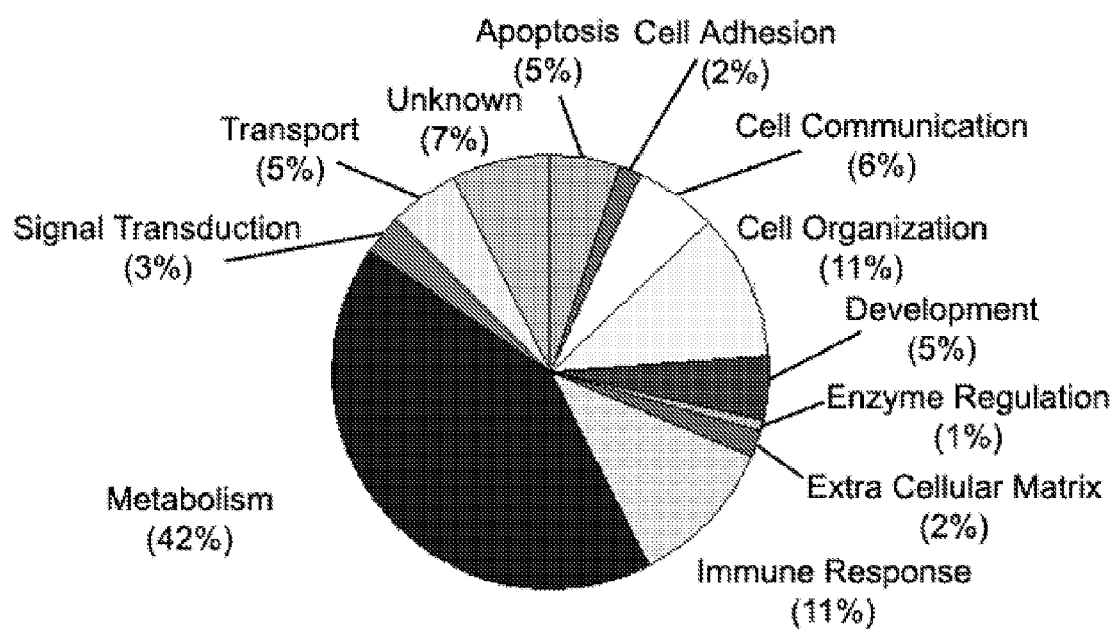
FIG. 1 is a pie chart showing the functional annotation of type 2 diabetes human whole saliva proteome. Salivary proteins were functionally annotated using DAVID™ and Bio-Harvester informatics resources. The majority of the proteins are predicted to have metabolic and immune response functions.

Any nucleic acid and amino acid sequences listed herein or in the accompanying sequence listing are shown using standard letter abbreviations for nucleotide bases, and three letter code for amino acids, as defined in 37 C.F.R. 1.822. In at least some cases, only one strand of each nucleic acid sequence is shown, but the complementary strand is understood as included by any reference to the displayed strand.

SEQ ID NOs: 1-67 show exemplary amino acid sequences of salivary proteome proteins differentially abundant in pre-diabetes and diabetes relative to normal.

DETAILED DESCRIPTION

The twin epidemics of obesity and diabetes threaten to overwhelm healthcare systems in the US and worldwide (Smyth and Heron, Nat Med 12:75-80, 2005). Over the last several years, the number of persons in the United States diagnosed with diabetes has reached almost epidemic proportions, with about 18 million affected individuals in the United States alone, at a cost of 174 billion dollars for 2007 (American Diabetes Association, Diabetes Care 31:596-615, 2008) Improved detection techniques and biomarkers are urgently needed across the entire spectrum of diabetes initiation and progression. Since 70% of pre-diabetics will progress to frank diabetes (Nathan et al., Diabetes Care 30:753-759, 2007), and 7% of newly diagnosed type 2 diabetes mellitus patients in the US have been diabetic for approximately 4 to 7 years before diagnosis (Harris et al., Diabetes Care 15:815-819, 1992), the ability to ascertain those individuals at risk for the development of clinically apparent diabetes is critical to effectively focus potentially limited clinical resources. In particular, it is desirable to screen and start treating glucose-intolerant individuals as early as possible since, even before the onset of diabetes, vascular lesions gradually develop with deterioration of glucose tolerance. Additionally, beta-cell function is seriously compromised by the time that overt alterations in glucose homeostasis, such as impaired glucose tolerance (IGT) and impaired fasting glucose (IFG), are manifest; thus, timely intervention is important to maintain residual insulin secretory capacity.

The effectiveness of early intervention with lifestyle modification or medication in arresting disease progression has been demonstrated by the Diabetes Prevention Program (Diabetes Prevention Program Research Group. NEJM 346:393-403, 2002). However, the determination of IGT and IFG is itself an issue due to the relatively invasive nature of these assessments, particularly that of IGT by an oral glucose tolerance test (OGTT). In addition, an important additional diagnostic problem is monitoring of glucose homeostasis for confirming diabetes. Compliance with glucose monitoring is poor because of the pain and inconvenience of conventional blood collection using lancets. Furthermore, non-invasive monitoring techniques for diabetes, and to determine the efficacy of therapy, are desirable. Finally, assessment of progression of frank diabetes to complications is only feasible after complications are well established. Thus, it would be beneficial to have methods for assessing the development of diabetes from pre-diabetes, and for monitoring the course of the disease.

Saliva has a number of advantages as a diagnostic fluid. These include: non-invasive collection; feasible without special training or equipment; especially advantageous for pediatric or elderly populations; and amenable to large-scale population studies. The salivary proteome is derived from a number of sources, including major and minor salivary gland secretions, oral bacterial products, and gingival crevicular fluid (GCF) (Humphrey et al., J Pros Dent 85:162-169, 2001). Although the majority of salivary protein by amount is comprised of the major classes of salivary protein families such as the acidic and basic proline-rich proteins, amylase, and various mucins, the salivary proteome as a whole is dynamic and complex (for discussion, see Helmerhorst and Oppenheim, Crit. Rev Oral Biol Med 680-693, 2007). Of particular interest is GCF, which is considered a transudate or ultrafiltrate of serum. Although the proportional contribution of GCF to saliva is small, it allows saliva to exhibit levels of serum-derived proteins that may reflect their circulating levels.

Thus, saliva can be used to determine the effect of a treatment protocol or a disease process in an individual of interest. For example, it is possible to measure proteins such as insulin and GIP (Messenger et al., J Endocrinol 177:407-412, 2003), prolactin (Huang, Arch Oral Biol 49:951-962, 2004) and GH (Rantonen et al., Acta Odontol Scand 58:299-303, 2000) in saliva. Previous studies have described the salivary proteome (Yamguchi et al., Biomed Microdev 7:53-58, 2005; see also, for example, Hu et al., Proteomics 5:1714-1728, 2005) while other studies have described alterations in salivary dynamics (Dodds et al., Community Dent Oral Epidemiol 28:373-381, 2000; Bernardi et al., Oral Health Prev Dent 5:73-78, 2007) or the differential abundance in saliva of single factors, such as MMP-8 (Collin et al., J Periodontal Res 35:259-265, 2000) and EGF (Oxford et al., J Diabetes Complications 14:140-145, 2000).

Presented below is the first comprehensive analysis of the salivary proteome in diabetes. In some embodiments of the methods disclosed herein, this proteome can be used to diagnose diabetes and pre-diabetes, as well as to monitor the progression of the disease and to assess the efficacy of a particular therapeutic intervention. Thus, non-invasive methods are provided herein for the diagnosis of pre-diabetes and diabetes using biomarkers identified in a biological fluid, such as saliva. Non-invasive methods are also provided to identify those subjects at risk of developing pre-diabetes and diabetes using these biomarkers. Additionally, non-invasive methods are provided for evaluating the efficacy of a therapy using the biomarkers. These biomarkers also can be identified using antibody-based methods, such as, but not limited to, an enzyme-linked immunosorbant assay (ELISA), a radioimmunoassay (RIA), or lateral flow immunoassay, and other proteomic approaches with or without use of antibodies Terms Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). All the amino acid sequences identified herein, as set forth in GENBANK® on Mar. 10, 2008, are incorporated by reference herein. This includes all those shown in the tables, as well as described in the examples section.

In order to facilitate review of the various embodiments of this disclosure, the following explanations of specific terms are provided:

Alpha-1-antitrypsin: A 52 kDa serine protease inhibitor that is considered the most prominent serpin. The protein was called "antitrypsin" because of its ability to covalently bind and irreversibly inactivate the enzyme trypsin in vitro. The term alpha-1 refers to the enzyme's behavior on protein electrophoresis. There are several "clusters" of proteins in electrophoresis, the first being albumin, the second being the alpha, the third beta and the fourth gamma (immunoglobulins). The non-albumin proteins are referred to as globulins. The alpha region can be further divided into two sub-regions, termed "1" and "2". Alpha 1-antitrypsin is the main enzyme of the alpha-globulin 1 region. An exemplary amino acid sequence is shown in GENBANK® Accession No. P01009 (Mar. 10, 2008), incorporated by reference herein.

Alpha-2-macroglobulin: A large plasma protein found in the blood. It is produced by the liver, and is a major component of the alpha-2 band in protein electrophoresis. Alpha-2 macroglobulin is able to inactivate an enormous variety of proteinases (including serine-, cysteine-, aspartic- and metalloproteinases). Alpha-2 macroglobulin has in its structure a 35 amino acid "bait" region. Proteinases binding and cleaving the bait region become bound to α2M. The proteinase-α2M complex is recognized by macrophage receptors and cleared from the system. It functions as an inhibitor of coagulation by inhibiting thrombin and it functions as an inhibitor of fibrinolysis by inhibiting plasmin. An exemplary amino acid sequence is shown in GENBANK® Accession No. P01023 (Mar. 10, 2008), incorporated by reference herein.

Animal: Living multi-cellular vertebrate organisms, a category that includes, for example, mammals and birds. The term mammal includes both human and non-human mammals. Similarly, the term "subject" includes both human and veterinary subjects, for example mice.

Antibody: A polypeptide ligand comprising at least a light chain or heavy chain immunoglobulin variable region which specifically binds an epitope of a protein listed in the tables below, or a fragment of any of these proteins. The term "specifically binds" refers to, with respect to an antigen such the proteins listed in the tables below, the preferential association of an antibody or other ligand, in whole or part, with the protein. A specific binding agent binds substantially only to a defined target, such as protein of interest. Thus, as a non-limiting example, an alpha-1-antitrypsin specific binding agent is an agent that binds substantially to an alpha-1-antitrypsin polypeptide. If an agent, such as an antibody, specifically binds alpha-1-antitrypsin it does not specifically bind other peptides including cystatin C, alpha-2-macroglobulin or transthyretin, or any of the other proteins listed in the tables below. A minor degree of non-specific interaction may occur between a molecule, such as a specific binding agent, and a non-target polypeptide. Specific binding can be distinguished as mediated through specific recognition of the antigen.

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that can be used to determine specific immunoreactivity.

Antibodies can include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Anti-diabetic agent: A chemical or pharmaceutical anti-hyperglycemic agent or drug capable of treating diabetes, including, but not limited to agents for alleviating the symptoms associated with type 2 diabetes or slowing the progression or onset of type 2 diabetes. Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. The anti-diabetic agents include those agents disclosed in *Diabetes Care,* 22(4):623-34, herein incorporated by reference. One common class of anti-diabetic agents is the sulfonylureas, which are believed to increase secretion of insulin, decrease hepatic glucogenesis, and increase insulin receptor sensitivity.

Another class of anti-diabetic agents is the biguanide anti-hyperglycemics, which decrease hepatic glucose production and intestinal absorption, and increase peripheral glucose uptake and utilization, without inducing hyperinsulinemia.

The biguanide anti-diabetic agents include compounds defined by the chemical formula of Formula 1 (see below), such as the biguanides disclosed in U.S. Pat. Nos. 3,960,949; 4,017,539; and 6,011,049, herein incorporated by reference. One specific, non-limiting example of a biguanide antidiabetic agent is metformin.

Incretins are another class of anti-diabetic agents. These agents are described in further detail below.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care,* 22(4):623-34 at pages 626-27, herein incorporated by reference.

Binding: A specific interaction between two or more molecules, such as the binding of an antibody and an antigen (for example an antibody to an antigen). In one embodiment, specific binding is identified by a dissociation constant (Kd). In one embodiment, binding affinity is calculated by a modification of the Scatchard method described by Frankel et al., *Mol. Immunol.,* 16:101-106, 1979. In another embodiment, binding affinity is measured by an antigen/antibody dissociation rate. In yet another embodiment, a high binding affinity is measured by a competition radioimmunoassay (RIA). In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Body mass index (BMI): A mathematical formula for measuring body mass in humans, also sometimes called Quetelet's Index. BMI is calculated by dividing weight (in kg) by height$^2$ (in meters$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (also called "overweight") corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J. Clin. Nutr.,* 45:1035-47, 1987). Ideal body weight will vary among species and individuals based on height, body build, bone structure, and sex.

Chromatography: The process of separating a mixture, for example a mixture containing the proteins listed in the tables below. It involves passing a mixture through a stationary phase, which separates molecules of interest from other molecules in the mixture and allows one or more molecules of interest to be isolated. Examples of methods of chromatographic separation include capillary-action chromatography, such as paper chromatography, thin layer chromatography (TLC), column chromatography, fast protein liquid chromatography (FPLC), nano-reversed phase liquid chromatography, ion exchange chromatography, gel chromatography, such as gel filtration chromatography, size exclusion chromatography, affinity chromatography, high performance liquid chromatography (HPLC), and reverse phase high performance liquid chromatography (RP-HPLC) amongst others.

Contacting: "Contacting" includes in solution and solid phase, for example contacting a salivary protein with a test agent. The test agent may also be a combinatorial library for screening a plurality of compounds. In another example, contacting includes contacting a sample with an antibody, for example contacting a sample that contains a protein of interest such as those listed in the tables below.

Cystatin-C: A serum protein used mainly as a measure of glomerular filtration rate. It is a single 120-residue polypeptide belonging to the type 2 cystatin gene family. Studies have shown that Cystatin C allows a more precise testing of kidney function than creatinine. The type 2 cystatin proteins are a class of cysteine proteinase inhibitors found in a variety of human fluids and secretions, where they appear to provide protective functions. The cystatin locus on chromosome 20 contains the majority of the type 2 cystatin genes and pseudogenes. This gene is located in the cystatin locus and encodes the most abundant extracellular inhibitor of cysteine proteases, which is found in high concentrations in biological fluids. An exemplary amino acid sequence is shown in GENBANK® Accession No. P01034.

Diabetes mellitus: A disease caused by a relative or absolute lack of insulin leading to uncontrolled carbohydrate metabolism, commonly simplified to "diabetes," though diabetes mellitus should not be confused with diabetes insipidus. As used herein, "diabetes" refers to diabetes mellitus, unless otherwise indicated. A "diabetic condition" includes pre-diabetes and diabetes. Type 1 diabetes (sometimes referred to as "insulin dependent diabetes" or "juvenile onset diabetes") is an autoimmune disease characterized by destruction of the pancreatic β cells that leads to a total or near total lack of insulin. In diabetes type 2 (sometimes referred to as "non-insulin dependent diabetes" or "adult onset diabetes"), the body does not respond to insulin, though it is present.

Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine,* J. B. Wyngaarden, et al., eds. (W.B. Saunders Co., Philadelphia, 1992, 19$^{th}$ ed.).

A subject exhibiting one or more of the following risk factors is considered to have a heightened or substantial risk of developing diabetes type 2:

1. Obesity, such as a BMI greater than or equal to about 30 kg/m$^2$;

2. Elevated fasting blood glucose (FPG) levels;
3. Impaired glucose tolerance (IGT);
4. Non-caucasian ethnicity;
5. Hyperinsulinemia;
6. Hypertriglyceridemia;
7. Family history of diabetes;
8. History of gestational diabetes;
9. Sedentary lifestyle;
10. In humans, middle age or elderly status (i.e., 40 years old and older).

The methods disclosed herein provide a means of identifying s subject who has diabetes or pre-diabetes, or who is at increased risk of developing diabetes, including both type 1 and type 2 diabetes. A "non-diabetic" or "normal" subject does not have any form of diabetes, such as type 1 diabetes, type 2 diabetes, or pre-diabetes.

Fasting plasma glucose (FPG): A diagnostic test for diabetes or pre-diabetes. The blood glucose concentration or level of a subject is analyzed in a blood sample obtained from a subject after the subject has fasted overnight or undergone a fast of at least 8 hours. A diabetic subject will often show a heightened blood glucose level, compared to a non-diabetic subject. Generally, a fasting plasma glucose test (FPG) is used to determine if a subject has impaired fasting glucose. An FPG of greater than 100 mg/dl and less than 126 mg/dl indicates that a subject has pre-diabetes. A FPG greater than or equal to 126 mg/dl indicates that a subject has frank diabetes, and an FPG of equal to or less than 100 mg/dl indices that subject is normal (healthy) and does not have pre-diabetes or diabetes. For example, the subject is not known to have diabetes type 2, and/or does not satisfy diagnostic criteria for diabetes type 2 and pre-diabetes.

Food intake: The amount of food consumed by an individual. Food intake can be measured by volume or by weight. In one embodiment, food intake is the total amount of food consumed by an individual. In another embodiment, food intake is the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Hyperglycemia: An above-normal level of glucose (sugar) in the blood, and an indicator of diabetes. Hyperglycemia occurs when the body either lacks sufficient insulin or cannot use available insulin to metabolize glucose. Symptoms of hyperglycemia include excessive thirst, a dry mouth, and frequent urination.

Isolated: An isolated biological component (such as a nucleic acid, peptide or protein) has been substantially separated, produced apart from, or purified away from other biological components in the cell of the organism in which the component naturally occurs, for example the separation of a peptide from a sample, such as saliva, serum or blood. Peptides and proteins that have been isolated include nucleic acids and proteins purified by standard purification methods, such as chromatography, for example high performance liquid chromatography (HPLC) and the like. The term also embraces peptides, and proteins prepared by recombinant expression in a host cell as well as chemically synthesized peptide and nucleic acids. It is understood that the term "isolated" does not imply that the biological component is free of trace contamination, and can include molecules that are at least 50% isolated, such as at least 50%, 55%, 60%, 65%, 70%, 75%, 80%, 85%, 90%, 95%, 98%, 99%, or even 100% isolated.

Immunoassay: A biochemical test that measures the presence or concentration of a substance in a sample, such as a biological sample, using the reaction of an antibody to its cognate antigen, for example the specific binding of an antibody to a protein. Both the presence of antigen or the amount of antigen present can be measured. For measuring proteins, for each the antigen and the presence and amount (abundance) of the protein can determined or measured.

Measuring the quantity of antigen (such as any of the proteins listed in the Tables herein) can be achieved by a variety of methods. One of the most common is to label either the antigen or antibody with a detectable label. Specific, non-limiting examples of labels include fluorescent tags, enzymatic linkages, and radioactive isotopes (for example $^{14}C$, $^{32}P$, $^{125}I$ and $^{3}H$ isotopes and the like). In some examples alpha-1-antitrypsin, cystatin C, alpha-2-macroglobulin or transthyretin is labeled with a radioactive isotope, such as $^{14}C$, $^{32}P$, $^{125}I$, $^{3}H$ isotope. In other examples an antibody that specifically binds one of an antigen of interest is labeled. Methods for labeling and guidance in the choice of labels appropriate for various purposes are discussed for example in Sambrook et al. (Molecular Cloning: *A Laboratory Manual*, Cold Spring Harbor, N.Y., 1989) Ausubel et al. (In Current Protocols in Molecular Biology, John Wiley & Sons, New York, 1998), and Harlow & Lane, (Antibodies, *A Laboratory Manual*, Cold Spring Harbor Publications, New York, 1988)), A "competitive radioimmunoassay (RIA)" is a type of immunoassay used to test for antigens (for example, proteins present in a sample, such as a biological sample). In some examples it involves mixing known quantities of radioactive antigen (for example a radioactively labeled protein, such as a $^{125}I$ labeled protein) with antibody to that antigen, then adding unlabeled or "cold" antigen (for example unlabeled antigen present in a sample, such as biological sample obtained from a subject, such as saliva) and measuring the amount of labeled antigen displaced by the unlabeled antigen.

Initially, the radioactive antigen is bound to the antibodies. When "cold" (i.e. unlabeled) antigen is added, the two compete for antibody binding sites at higher concentrations of "cold" antigen, more of it binds to the antibody, displacing the radioactive variant. The bound antigens are isolated from the unbound ones and the amount of radioactivity measured. A radioimmunoassay can be used to calculate the amount of an antigen in a sample.

Incretin: Gastrointestinal peptides that affect glycemic control, including amylin, gastric inhibitory peptide (GIP), and glucagon-like peptide 1 (GLP-1). During the past few years, analogs of these hormones have become available for use in controlling diabetes. One incretin, pramlintide, is an analog of amylin, a naturally occurring hormone produced along with insulin by pancreatic β-cells. Levels increase postprandially and typically correlate with insulin levels. As with insulin, amylin levels are very low in type 1 diabetes; however, levels may be elevated in patients with insulin resistance. Administration of exogenous amylin in the form of pramlintide has been shown to decrease postprandial hyperglycemia in patients with type 1 or type 2 diabetes who are treated with insulin. The major mechanism of action appears to be inhibition of gastric emptying and suppression of glucagon release. Clinically, it also suppresses the appetite in those who receive it.

Exenatide is an analog of GLP-1, a naturally occurring incretin produced by the L-cells of the distal ileum. GLP-1 acts to stimulate insulin release from the pancreatic β-cells, suppress glucagon release from the pancreatic α-cells, slow gastric emptying, and increase satiety. Administration of exenatide in patients with type 2 diabetes has similar effects to pramlintide. Clinically, the result is a reduction in A1C of ~1%. Preliminary studies suggest that a significant proportion of patients with type 2 diabetes using insulin may be successfully transitioned from insulin to exenatide in addition to their oral agents.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes (for example $^{14}C$, $^{32}P$, $^{125}I$, $^{3}H$ isotopes and the like). In some examples a protein, such as one of the proteins listed in the Tables herein, is labeled with a radioactive isotope, such as $^{14}C$, $^{32}P$, $^{125}I$, $^{3}H$ isotope. In some examples an antibody that specifically binds the protein is labeled. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998), Harlow & Lane (Antibodies, *A Laboratory Manual*, Cold Spring Harbor Publications, New York, 1988).

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):515-209S, 1998). Excess body fat is a result of an imbalance of energy intake and energy expenditure. In one embodiment in humans, the Body Mass Index (BMI) is used to assess obesity. In one embodiment, a BMI of 25.0 kg/m$^2$ to 29.9 kg/m$^2$ is overweight (also called grade I obesity), while a BMI of 30 kg/m$^2$ is truly obese (also called grade II obesity).

In another embodiment in humans, waist circumference is used to assess obesity. In this embodiment, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Oral glucose tolerance test (OGTT): A diagnostic test for diabetes. After fasting overnight, a subject is provided a concentrated sugar solution to drink, usually containing 50 to 100 grams of glucose. The subject's blood is sampled periodically over the next few to several hours to test blood glucose levels over time. In a non-diabetic subject, blood glucose concentration shows a slight upward shift and returns to normal within 2-3 hours. In a diabetic subject, blood glucose concentration is generally higher than normal after fasting, rises more after the subject drinks the glucose solution, and may take several hours to return to normal. An OGTT of greater than or equal to 140 mg/dl and less than 200 mg/dl indicates that a subject has pre-diabetes. An OGTT of greater than or equal to 200 mg/dl indicates that a subject has frank diabetes, and an OGTT of less than 140 mg/dl indicates that a subject is normal (healthy) and does not have pre-diabetes or diabetes.

Overweight: An individual who weighs more than their ideal body weight. An overweight individual can be obese, but is not necessarily obese. In one embodiment, an overweight human individual is any individual who desires to decrease their weight. In another embodiment, an overweight human individual is an individual with a BMI of 25.0 kg/m$^2$ to 29.9 kg/m$^2$.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated forms.

Pre-diabetes: A condition identified in a subject by impaired glucose tolerance, alone or in combination with impaired fasting glucose regulation. An oral glucose tolerance test (OGTT) can be used to determine if a subject has impaired glucose tolerance. An OGTT of greater than or equal to 140 mg/dl and less than 200 mg/dl indicates that a subject has pre-diabetes. An OGTT of greater than or equal to 200 mg/dl indicates that a subject has frank diabetes, and an OGTT of less than 140 mg/dl indicates that a subject is normal (healthy) and does not have pre-diabetes or diabetes. Generally, a fasting plasma glucose test (FPG) can also be used to identify a subject as pre-diabetic. A FPG of greater than 100 mg/dl and less than 126 mg/dl indicates that a subject has pre-diabetes. A FPG greater than or equal to 126 mg/dl indicates that a subject has frank diabetes, and an FPG of equal to or less than 100 mg/dl indicates that subject is normal (healthy) and does not have pre-diabetes or diabetes.

Pharmaceutical agent: A chemical compound or composition capable of inducing a desired therapeutic (including a prophylactic effect) when properly administered to a subject. The pharmaceutically acceptable salts of the compounds of this invention include, but are not limited to, those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. This term refers to pharmaceutical agents, pharmaceutical compositions, and drugs acceptable for both human and veterinary uses.

Proteome: A significant portion of proteins in a biological sample at a given time. The concept of proteome is fundamentally different from the genome. While the genome is virtually static, the proteome continually changes in response to internal and external events. A "proteomic profile" is a representation of the expression pattern of a plurality of proteins in a biological sample, such as saliva, at a given time. The proteomic profile can, for example, be represented as a mass spectrum, but other representations based on any physicochemical or biochemical properties of the proteins are also included. Thus the proteomic profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Differential expression profiles may have important diagnostic value, even in the absence of specifically identified proteins. Single protein spots can then be detected, for example, by immunoblotting, multiple spots or proteins using protein microarrays. The proteomic profile typically represents or contains information that could range from a few peaks to a complex profile representing 50 or more peaks. Thus, for example, the proteomic profile may contain or represent at least 2, or at least 5 or at least 10 or at least 15, or at least 20, or at least 25, or at least 30, or at least 35, or at least 40, or at least 45, or at least 50 proteins. A "unique expression signature" is a unique feature or motif within the proteomic profile of a biological sample (such as a reference sample) that differs from the proteomic profile of a corresponding normal biological sample (obtained from the same type of biological fluid) in a statistically significant manner.

Subject: A term that includes both human and veterinary individuals, for example mammals, such as humans.

Therapeutic agent: A substance that demonstrates some therapeutic effect by restoring or maintaining health, such as by alleviating the symptoms associated with a disease or physiological disorder, or delaying (including preventing) progression or onset of a disease. In some instances, the therapeutic agent is a chemical or pharmaceutical agent, or a prodrug. A therapeutic agent may be an antidiabetic agent, which includes an antihyperglycemic agent, such as an agent capable of regulating insulin levels or glucose tolerance. As one non-limiting example, the antidiabetic agent is a biguanide antidiabetic agent suitable for administration to humans. Another non-limiting example of a therapeutic agent is an incretin.

A "therapeutically effective amount" or "therapeutically effective dose" is that amount or dose sufficient to inhibit or prevent onset or advancement, to treat outward symptoms, or to cause regression, of a disease. The therapeutically effective amount or dose also can be considered as that amount or dose capable of relieving symptoms caused by the disease. Thus, a therapeutically effective amount or dose of an antidiabetic agent is that amount or dose sufficient to achieve a stated therapeutic effect. As one specific, non-limiting example, a therapeutically effective amount of an antidiabetic agent is an amount that reduces the signs of, symptoms of, or laboratory findings associated with pre-diabetes; delays the progression of pre-diabetes to diabetes; or lowers FPG or OGTT plasma glucose levels.

Transthyretin: A serum and cerebrospinal fluid carrier of the thyroid hormone tyroxine (T4), originally called prealbumin. TTR is a 55 kDa homotetramer with a dimer of dimers configuration that is synthesized in the liver, choroid plexus and retinal pigment epithelium. Each monomer is a 127 residue polypeptide rich in beta sheet structure. Association of two monomers forms an extended beta sandwich. Further association of another identical set of monomers produces the homotetrameric structure. An exemplary amino acid sequence is set forth as GENBANK® Accession No. Q549C7, incorporated by reference herein.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Methods for Detecting Diabetes and Pre-Diabetes and for Monitoring the Efficacy of a Therapeutic Regimen Methods are disclosed herein that are of use to determine if a subject has a diabetic condition, including pre-diabetes or diabetes, or to monitor the efficacy of therapy. The methods can be used to determine if a subject has type 1 or type 2 diabetes, or to monitor the efficacy of a therapy for either type 1 diabetes or type 2 diabetes. These methods utilize a biological fluid, such as, but not limited to saliva, for the detection of biomarkers. These biomarkers can be proteins, including any naturally occurring forms of the proteins, such as but not limited to glycosylated forms. In some embodiments the subject is obese or overweight. The method can also include measuring blood hemoglobin A1C as an adjunct to the detection of other biomarkers.

In some embodiments, the methods disclosed herein are used to identify a subject as having pre-diabetes. In some embodiments, a fasting plasma glucose (FPG) test or an oral glucose tolerance test (OGTT) is also performed. In some embodiments, the methods can be used to confirm that a subject has pre-diabetes, such as a subject who has a FPG of about 100 mg/dl to about 126 mg/dl and/or an OGTT of about 140 to about 200 mg/dl. The present methods can also be used to detect pre-diabetes in a subject who is at risk for developing diabetes, such as a in an obese or overweight subject. Thus, in some embodiments, the subject of interest has a body mass index (BMI) greater than or equal to about 30 kg/m$^2$, has a family history of diabetes, or who has had gestational diabetes. The methods can be used to detect pre-diabetes in a subject who has not had a FPG or an OGTT, or a subject who has a FPG of about 90 mg/dl to about 110 mg/dl, such as about 100 mg/dl, or an OGTT of about 135 mg/dl to about 145 mg/dl, such as about 140 mg/dl. Alternatively (or in addition) the method is used in subjects with an elevated serum hemoglobin A1C level, such as greater than about 6%. However, in other embodiments, an FPG or an OGTT is not performed on the subject. These methods can be performed over time, to monitor the progression of diabetes in a subject, or to assess for the development of diabetes from a pre-diabetic condition.

Methods are also provided for determining the efficacy of a therapy, including lifestyle modifications, for the treatment of diabetes or pre-diabetes, or preventing the development of diabetes or pre-diabetes. In one embodiment, the therapeutic regimen includes the use of at least one of metformin, insulin, incretin, lifestyle modification or dipetidyl peptidase-4 (DPP-4) inhibitors. In one embodiment, methods are provided for managing a therapeutic intervention over time. For example, the method can be used to determine whether lifestyle modifications alone are sufficient treatment, or whether pharmaceutical intervention needs to be added to a therapeutic plan.

Methods are disclosed herein that include testing a biological sample, such as a saliva sample, obtained from the subject. In one example, the biological sample is a biological fluid, such as saliva. However, other biological fluids are also of use, such as blood, GCF, serum, amniotic fluid, urine or tears. The methods include detecting, or determining the abundance (amount) of one or more proteins from Table 1 below.

TABLE 1

Exemplary proteins of a pre-diabetes or diabetes proteomic profile

| Swiss Prot # | Name | SEQ ID NO: |
|---|---|---|
| Q9NP55 | Protein Plunc | 1 |
| P07998 | Pancreatic ribonuclease | 2 |
| P19827 | Inter-α-trypsin inhibitor heavy chain H1 | 3 |
| Q14624 | Inter-α-trypsin inhibitor heavy chain H4 | 4 |
| P80303 | Nucleobindin-2 | 5 |
| P26038 | Moesin | 6 |
| P62258 | 14-3-3 epsilon | 7 |
| P01040 | Cystatin A | 8 |
| P12429 | Annexin A3 | 9 |
| P31151 | Protein S100-A7 | 10 |
| P00558 | Phosphoglycerate kinase 1 | 11 |
| P04083 | Annexin A1 | 12 |
| P67936-2 | Isoform2 of P67936 Tropomyosin α-4 | 13 |
| O43240 | Kallikrein-10 | 14 |
| P15924 | Desmoplakin | 15 |
| P30043 | Flavin reductase | 16 |
| P28676 | Grancalcin | 17 |
| P27824 | Calnexin | 18 |

For each of these proteins, an exemplary GENBANK® Accession number is listed. The amino acid sequences, set forth in GENBANK® on Mar. 10, 2008, are incorporated by reference herein. The methods can include detecting at least one, two, three, four, five, at least ten, or at least fifteen of these proteins. In some examples, the methods include determining a proteomic profile. In other examples, the methods include detecting a proteomic profile including at least 1, 2, 3, 4, 5, 6, 7, 8, 9, 10, 11, 12, 13, 14, 15, 16, 17, or all of these proteins, including any of the proteins set forth in the tables herein.

In some examples, the proteomic profile includes at least two of the proteins of Table 1 (such as protein plunc and pancreatic ribonuclease; inter-α-trypsin inhibitor heavy chain H1 and inter-α-trypsin inhibitor heavy chain H4; nucleobindin-2 and moesin; and so on). In other examples, the proteomic profile includes at least three of the proteins of Table 1 (for example, protein plunc, pancreatic ribonuclease and inter-α-trypsin inhibitor heavy chain H1; inter-α-trypsin inhibitor heavy chain H4, nucleobindin-2, and moesin; 14-3-3 epsilon, cystatin A, and annexin A3; and so on). In further examples, the proteomic profile includes at least four of the proteins of Table 1 (such as protein plunc, pancreatic ribonuclease inter-α-trypsin inhibitor heavy chain H1, and inter-α-trypsin inhibitor heavy chain H4; nucleobindin-2, moesin, 14-3-3 epsilon, and cystatin A; annexin A3, protein S100-A7, phosphoglycerate kinase 1, and annexin A1; and so on). It is understood that any combination of any number of the proteins of Table 1 are contemplated herein.

In some embodiments, the method includes detecting an increase, such as a statistically significant increase, such as at least a 2, 3, 4, 5, 6 or 7 fold increase, in the amount of protein plunc, pancreatic ribonuclease, inter-α-trypsin inhibitor heavy chain H1, inter-α-trypsin heavy chain H4, nucleobindin-2, and/or moesin as compared to a reference sample. In additional embodiments, the method includes detecting a decrease, such as a significantly significant increase, such as at least a 2, 3, 4, 5, 6 or 7 fold decrease in the amount of 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and/or calnexin as compared to a reference sample.

In one embodiment, the method includes comparing a proteomic profile of a test sample of saliva from a subject of interest comprising at least one of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin, such as 2, 3, 4, 5, 6, 7, 8, 9, 10, 11, 12, 13, 14, 15, 16, 17, or all of these proteins with a proteomic profile from of a reference sample.

In one embodiment, the method determines if the subject has pre-diabetes or diabetes. If the reference sample is a normal sample, and the proteomic profile of the test sample is essentially the same as the proteomic profile of the normal sample the subject is determined not to have pre-diabetes or diabetes, respectively. However, if the proteomic profile of the test sample has a unique expression signature relative to the proteomic profile of the normal sample the subject is determined to have pre-diabetes or diabetes, respectively.

In another embodiment, if the reference sample is a sample from a subject with pre-diabetes or diabetes, and its proteomic profile shares at least one unique expression signature characteristic with the reference sample, then the subject is determined to have pre-diabetes or diabetes, respectively. If the proteomic profile of the test sample has a unique expression signature relative to the reference sample the subject is determined not to have pre-diabetes or diabetes, respectively. Hence, the proteomic profile provides an additional diagnostic criterion for these disorders.

In another embodiment, the method is a method to determine if a therapy is effective for the treatment of the subject by detecting the presence of at least one protein from Table 1. The methods can include detecting at least one, two, three, four, five, at least ten, at least fifteen of these proteins. In some examples, the methods include determining a proteomic profile. In other examples, the methods include detecting a proteomic profile including at least 1, 2, 3, 4, 5, 6, 7, 8, 9, 10, 11, 12, 13, 14, 15, 16, 17, or all of these proteins. The method can be performed multiple times over a specified time period, such as days, weeks, months or years. In several examples, the therapy includes treatment with metformin, dipeptidyl peptidase-4 inhibitors, or an incretin. If the reference sample is a normal sample, and the proteomic profile of the test sample is essentially the same as the proteomic profile of the normal sample the subject is determined to have an effective therapy, while if the proteomic profile of the test sample has a unique expression signature relative to the proteomic profile of the normal sample to have an ineffective therapy. If the reference sample is a sample from a subject with pre-diabetes or diabetes, and proteomic profile shares at least one unique expression signature characteristic with the reference sample then the subject is determined to have an ineffective therapy, while if the proteomic profile of the test sample has a unique expression signature relative to the reference sample the subject is determined to have an effective therapy. In several examples, the therapy includes treatment with metformin, dipeptidyl peptidase-4 inhibitors, or an incretin. Changes in the profile can also represent the progression (or regression) of the disease process.

In some embodiments, the method also includes detecting, or determining the abundance (amount) of one or more proteins from Table 2 below.

TABLE 2

Exemplary proteins of a pre-diabetes or diabetes proteomic profile

| Swiss Prot # | Name | SEQ ID NO: |
|---|---|---|
| Q6FHH3 | Uteroglobin | 19 |
| P23280 | Carbonic anhydrase 6 | 20 |
| P14618 | Pyruvate kinase isozymes M1/M2 | 21 |
| P01009 | Alpha-1-antitrypsin | 22 |
| P22894 | Neutrophil collagenase | 23 |
| P01023 | Alpha 2-macroglobulin | 24 |
| P01034 | Cystatin C | 25 |
| P00491 | Purine nucleoside phosphorylase | 26 |
| P30838 | Aldehyde dehydrogenase | 27 |
| Q01469 | Fatty acid binding protein, epidermal | 28 |
| Q06830 | Peroxiredoxin-1, -2, + -6 | 29 |
| Q5TC18 | Lamin A/C | 30 |
| Q13787 | Apolipoprotein B-100 | 31 |
| P07355 | Annexin A2 | 32 |
| P00915 | Carbonic anhydrase 1 | 33 |
| P00918 | Carbonic anhydrase 2 | 34 |
| P02763 | Alpha 1 acid glycoprotein | 35 |
| P80188 | Lipocalin 2 | 36 |

For each of these proteins, an exemplary GENBANK® Accession number is listed. The amino acid sequences, set forth in GENBANK® on Mar. 10, 2008, are incorporated by reference herein. The methods can include detecting at least one, two, three, four, five, at least ten, at least fifteen of these proteins. In some examples, the methods include determining a proteomic profile. In one embodiment, the method includes comparing a proteomic profile of a test sample of saliva from a subject of interest comprising at least one of uteroglobin, carbonic anhydrase 6, pyruvate kinase isozymes M1/M2, alpha-1-antitrypsin, neutrophil collagenase, alpha 2-macroglobulin, cystatin C, purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, carbonic anhydrase 2, alpha 1 acid glycoprotein, and lipocalin 2 as compared to the proteomic profile of a reference sample. In some examples, the proteomic profile includes all of these proteins. In other examples, the methods include detecting a proteomic profile including at least 1, 2, 3, 4, 5, 6, 7, 8, 9, 10, 11, 12, 13, 14, 15, 16, 17, or all of these proteins.

In some examples, the proteomic profile includes at least two of the proteins of Table 2 (such as uteroglobin and carbonic anhydrase 6; pyruvate kinase isozymes M1/M2 and alpha-1-antitrypsin; neutrophil collagenase and alpha 2-macroglobulin; cystatin C and purine nucleoside phosphorylase; aldehyde dehydrogenase and fatty acid binding protein, epidermal; peroxiredoxin-1, -2, -6 and lamin A/C; apolipoprotein B-100 and annexin A2; carbonic anhydrase 1 and carbonic anhydrase 2; or alpha 1 acid glycoprotein and lipocalin 2). In other examples, the proteomic profile includes at least three of the proteins of Table 2 (for example, uteroglobin, carbonic anhydrase 6, and pyruvate kinase isozymes M1/M2; alpha-1-antitrypsin, neutrophil collagenase, and alpha 2-macroglobulin; cystatin C, purine nucleoside phosphorylase, and aldehyde dehydrogenase; fatty acid binding protein, epidermal, peroxiredoxin-1, -2, -6, and lamin A/C; apolipoprotein B-100, annexin A2, and carbonic anhydrase 1; or carbonic anhydrase 2, alpha 1 acid glycoprotein, and lipocalin 2). In further examples, the proteomic profile includes at least four of the proteins of Table 2 (such as uteroglobin, carbonic anhydrase 6, pyruvate kinase isozymes M1/M2, and alpha-1-antitrypsin; neutrophil collagenase, alpha 2-macroglobulin, cystatin C, and purine nucleoside phosphorylase; aldehyde dehydrogenase, fatty acid binding protein, epidermal, peroxiredoxin-1, -2, -6, and lamin A/C; apolipoprotein B-100, annexin A2, carbonic anhydrase 1 and carbonic anhydrase 2 or carbonic anhydrase 1, carbonic anhydrase 2, alpha 1 acid glycoprotein, and lipocalin 2). In additional examples, the proteomic profile includes at least five of the proteins of Table 2 (for example, uteroglobin, carbonic anhydrase 6, pyruvate kinase isozymes M1/M2, alpha-1-antitrypsin, and neutrophil collagenase; alpha 2-macroglobulin, cystatin C, purine nucleoside phosphorylase, aldehyde dehydrogenase, and fatty acid binding protein, epidermal; peroxiredoxin-1, -2, -6, lamin A/C, apolipoprotein B-100, annexin A2, and carbonic anhydrase 1; or annexin A2, carbonic anhydrase 1, carbonic anhydrase 2, alpha 1 acid glycoprotein, and lipocalin 2). In further examples, the proteomic profile includes at least six of the proteins of Table 2 (for example, uteroglobin, carbonic anhydrase 6, pyruvate kinase isozymes M1/M2, alpha-1-antitrypsin, neutrophil collagenase, and alpha 2-macroglobulin; cystatin C, purine nucleoside phosphorylase, aldehyde dehydrogenase, fatty acid binding protein, epidermal, peroxiredoxin-1, -2, -6, and lamin A/C; apolipoprotein B-100, annexin A2, carbonic anhydrase 1, carbonic anhydrase 2 alpha 1 acid glycoprotein, and lipocalin 2) or at least nine of the proteins of Table 2 (for example, uteroglobin, carbonic anhydrase 6, pyruvate kinase isozymes M1/M2, alpha-1-antitrypsin, neutrophil collagenase, alpha 2-macroglobulin, cystatin C, purine nucleoside phosphorylase, and aldehyde dehydrogenase; or fatty acid binding protein, epidermal, peroxiredoxin-1, -2, -6, lamin A/C; apolipoprotein B-100, annexin A2, carbonic anhydrase 1, carbonic anhydrase 2 alpha 1 acid glycoprotein, and lipocalin 2). It is understood that any combination of any number of the proteins of Table 2 are contemplated herein.

In some embodiments, the method includes detecting an increase, such as a statistically significant increase, such as at least a 1.5, 2, 3, 4, or 5 fold increase in the amount of uteroglobin, carbonic anhydrase 6, pyruvate kinase isozymes M1/M2, alpha-1-antitrypsin, neutrophil collagenase, alpha 2-macroglobulin, cystatin C, alpha 1 acid glycoprotein and/or lipocalin 2 as compared to a reference sample. In some embodiments, the method includes detecting an decrease, such as a statistically significant decrease, such as at least a 2, 3, 4, or 5 fold decrease in the amount of purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, and/or carbonic anhydrase 2 as compared to a reference sample.

In one embodiment, the method includes comparing a proteomic profile of a test sample of saliva from a subject of interest comprising at least one of uteroglobin, carbonic anhydrase 6, pyruvate kinase isozymes M1/M2, alpha-1-antitrypsin, neutrophil collagenase, alpha 2-macroglobulin, cystatin C, purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, carbonic anhydrase 2, alpha 1 acid glycoprotein, and lipocalin 2. Statistical methods for determining if the abundance of a protein of interest is increased relative to a control are well known in the art, and are described below.

In one embodiment, the method determines if the subject has pre-diabetes or diabetes comprising detecting the presence of at least one protein listed in Table 2. In other examples, the methods include detecting a proteomic profile including at least 1, 2, 3, 4, 5, 6, 7, 8, 9, 10, 11, 12, 13, 14, 15, 16, 17, or all of these proteins and comparing the profile to a reference sample. If the reference sample is a normal sample, and the proteomic profile of the test sample is essentially the same as the proteomic profile of the normal sample the subject is determined not to have pre-diabetes or diabetes, respectively. However, if the proteomic profile of the test sample has a unique expression signature relative to the proteomic profile of the normal sample the subject is determined to have pre-diabetes or diabetes, respectively. If the reference sample is a sample from a subject with pre-diabetes or diabetes, and the proteomic profile shares at least one unique expression signature characteristic with the reference sample then the subject is determined to have pre-diabetes or diabetes, respectively. If the proteomic profile of the test sample has a unique expression signature relative to the reference sample the subject is determined not to have pre-diabetes or diabetes, respectively.

In another embodiment, the method determines if a therapy is effective for the treatment of the subject. Thus, the method can be performed multiple times over a specified time period, such as days, weeks, months or years. If the reference sample is a normal sample, and the proteomic profile of the test sample is essentially the same as the proteomic profile of the normal sample the subject is determined to have an effective therapy, while if the proteomic profile of the test sample has a unique expression signature relative to the proteomic profile of the normal sample to have an ineffective therapy. In another embodiment, if the reference sample is a sample from a subject with pre-diabetes or diabetes, and proteomic profile shares at least one unique expression signature characteristic with the reference sample then the subject is determined to have an ineffective therapy, while if the proteomic profile of the test sample has a unique expression signature relative to the reference sample the subject is determined to have an effective therapy. In several examples, the therapy includes treatment with metformin, dipeptidyl peptidase-4 inhibitors, or an incretin.

In further embodiments, the method includes detecting the presence or abundance (amount) of one or more of the proteins of Table 3, below.

TABLE 3

Exemplary proteins of a pre-diabetes or diabetes proteomic profile

| Swiss Prot # | Name | SEQ ID NO: |
|---|---|---|
| Q86U62 | Proteasome subunit | 37 |
| O60218 | Aldo-keto reductase family 1 member B10 | 38 |
| Q9UBR2 | Cathepsin Z | 39 |
| Q13231-3 | Chitotriosidase isoform 2, 3, + 4 | 40 |
| O60235 | Transmembrane protease, serine 11D | 41 |
| Q549C7 | Transthyretin | 42 |
| P06737 | Glycogen phosphorylase, liver form | 43 |
| P22626 | Heterogeneous nuclear RNPs A2/B1 | 44 |
| P30740 | Leukocyte elastase inhibitor | 45 |
| P13671 | Complement component C6 | 46 |
| Q4VAX6 | Serpin peptidase inhibitor | 47 |
| Q96RM1 | Small proline-rich protein 2F | 48 |
| Q9NZT1 | Calmodulin-like protein 5 | 49 |
| Q09666 | Neuroblast differentiation AHNAK | 50 |
| Q4VB24 | Histone cluster 1, H1e | 51 |
| Q9UKR3 | Kallikrein-13 | 52 |
| P36222 | Chitinase-3-like protein 1 | 53 |
| A2RTY6 | Inter-alpha (Globulin) inhibitor H2 | 54 |
| Q04917 | 14-3-3 protein eta | 55 |
| P23528 | Cofilin-1 | 56 |
| Q5VY30 | Retinol binding protein 4, plasma | 57 |
| Q7M4Q5 | Basic proline-rich peptide 1B-8a | 58 |
| P60953-2 | Isoform 2 of P60953 cdc 42 homolog | 59 |
| O15511 | Actin-related protein 2/3 complex subunit 5 | 60 |
| O95274 | Ly6/PLAUR domain-containing protein 3 | 61 |
| P61160 | Actin-like protein 2 | 62 |
| Q7Z3Y5 | Rearranged VKA17 V gene segment | 63 |
| P80723 | Brain acid soluble protein 1 | 64 |

TABLE 3-continued

Exemplary proteins of a pre-diabetes or diabetes proteomic profile

| Swiss Prot # | Name | SEQ ID NO: |
|---|---|---|
| Q8NBJ4 | Golgi phosphoprotein 2 | 65 |
| Q9NUQ9 | Protein FAM49B (L1) | 66 |
| P39687 | Acidic leucine-rich nuclear phosphoprotein 32 | 67 |

For each of these proteins, an exemplary GENBANK® Accession number is listed. The amino acid sequences, set forth in GENBANK® on Mar. 10, 2008, are incorporated by reference herein. The methods can include detecting at least one, two, three, four, five, at least ten, fifteen, twenty, twenty-five, thirty, or all of these proteins. In some examples, the methods include determining a proteomic profile. In additional examples, the methods include detecting all of these proteins, such as a proteomic profile including at least 1, 2, 3, 4, 5, 6, 7, 8, 9, 10, 11, 12, 13, 14, 15 or all of these proteins. In one embodiment, the method includes comparing a proteomic profile of a test sample of saliva from a subject of interest comprising at least one of proteasome subunit, aldo-keto reductase family 1 member B 10, cathepsin Z, chitotriosidase isoform 2, 3, +4, transmembrane protease, serine 11D, transthyretin, glycogen phosphorylase, heterogeneous nuclear RNPs A2/B1, leukocyte elastase inhibitor, small proline-rich protein 2F, calmodulin-like protein 5, neuroblast differentiation AHNAK, histone cluster 1, H1e, kallikrein-13, chitinase-3-like protein 1, inter-alpha (Globulin) inhibitor H2, 14-3-3 protein eta, cofilin-1, retinol binding protein 4, plasma, basic proline-rich peptide 1B-8a, isoform 2 of P60953 cdc 42 homolog, actin-related protein 2/3 complex subunit 5, ly6/PLAUR domain-containing protein 3, actin-like protein 2, Rearranged VKA17V gene segment, brain acid soluble protein 1, golgi phosphoprotein 2, protein FAM49B (L1), and acidic leucine-rich nuclear phosphoprotein 32 as compared to the proteomic profile of a reference sample.

In some examples, the proteomic profile includes at least two of the proteins of Table 3 (such as proteasome subunit and aldo-keto reductase family 1 member B10; cathepsin Z and chitotriosidase isoform 2, 3, +4; transmembrane protease, serine 11D and transthyretin; and so on). In other examples, the proteomic profile includes at least three of the proteins of Table 3 (for example, proteasome subunit, aldo-keto reductase family 1 member B 10, and cathepsin Z; chitotriosidase isoform 2, 3, +4; transmembrane protease, serine 11D, and transthyretin; glycogen phosphorylase, liver form, heterogeneous nuclear RNPs A2/B1, and leukocyte elastase inhibitor; and so on). In further examples, the proteomic profile includes at least four of the proteins of Table 3 (such as proteasome subunit, aldo-keto reductase family 1 member B10, cathepsin Z, and chitotriosidase isoform 2, 3, +4; transmembrane protease, serine 11D, transthyretin, glycogen phosphorylase, liver form, and heterogeneous nuclear RNPs A2/B1; leukocyte elastase inhibitor, complement component C6, serpin peptidase inhibitor, and small proline-rich protein 2F; and so on). It is understood that any combination of any number of the proteins of Table 3 are contemplated herein.

In one embodiment, the method is a method to determine if the subject has pre-diabetes or diabetes comprising detecting at least one protein listed in Table 3. If the reference sample is a normal sample, and the proteomic profile of the test sample is essentially the same as the proteomic profile of the normal sample the subject is determined not to have pre-diabetes or diabetes, respectively. However, if the proteomic profile of the test sample has a unique expression signature relative to the proteomic profile of the normal sample the subject is determined to have pre-diabetes or diabetes, respectively. If the reference sample is a sample from a subject with pre-diabetes or diabetes, and proteomic profile shares at least one unique expression signature characteristic with the reference sample then the subject is determined to have pre-diabetes or diabetes, respectively. If the proteomic profile of the test sample has a unique expression signature relative to the reference sample the subject is determined not to have pre-diabetes or diabetes, respectively.

In another embodiment, the method is a method to determine if a therapy is effective for the treatment of the subject. Thus, the method can be performed multiple times over a specified time period, such as days, weeks, months or years. If the reference sample is a normal sample, and the proteomic profile of the test sample is essentially the same as the proteomic profile of the normal sample the subject is determined to have an effective therapy, while if the proteomic profile of the test sample has a unique expression signature relative to the proteomic profile of the normal sample to have an ineffective therapy. If the reference sample is a sample from a subject with pre-diabetes or diabetes, and proteomic profile shares at least one unique expression signature characteristic with the reference sample then the subject is determined to have an ineffective therapy, while if the proteomic profile of the test sample has a unique expression signature relative to the reference sample the subject is determined to have an effective therapy. In several examples, the therapy includes treatment with metformin, dipeptidyl peptidase-4 inhibitors, or an incretin. Methods for monitoring the efficacy of therapeutic agents are described below.

Monitoring

The diagnostic methods of the present invention are valuable tools for practicing physicians to make quick treatment decisions for diabetic conditions, including both pre-diabetes and diabetes. These treatment decisions can include the administration of an anti-diabetic agent and decisions to monitor a subject for onset and/or advancement of diabetes. The treatment decisions can also include lifestyle monitoring. The method disclosed herein can also be used to monitor the effectiveness of a therapy.

Following the measurement of the expression levels of one or more of the proteins identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the biomarkers herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

In several embodiments, identification of a subject as being pre-diabetic or diabetic results in the physician treating the subject, such as prescribing an anti-hyperglycemic or an anti-diabetic agent to inhibit or delay the onset or progression of type II diabetes. In additional embodiment, the dose or dosing regimen is modified based on the information obtained using the methods disclosed herein. In some embodiments, the anti-diabetic agent contains a biguanide of the formula:

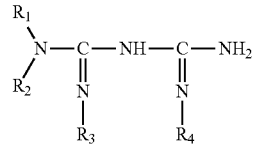

Formula 1 wherein $R_1$ and $R_2$ are independently selected from alkyl, lower alkyl, alkenyl, lower alkenyl, cycloalkyl, aryl, or an arylalkyl of the formula:

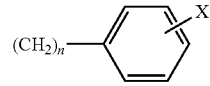

wherein X is hydrogen or halogen and n=0, 1 or 2; $R_3$ and $R_4$ are independently selected from hydrogen, alkyl, lower alkyl, alkenyl, lower alkenyl, cycloalkyl, alkoxy, lower alkoxy, alkoxyalkyl; and pharmaceutically acceptable salts thereof. In particular embodiments, the biguanide antidiabetic agent is metformin Metformin is manufactured by Lyonnaise Industrielle Pharmaceutique SA (Lyons, France), also known by its acronym LIPHA SA, and commercially distributed in the United States as a hydrochloride salt by the Bristol-Myers Squibb Company (Princeton, N.J.) as GLUCOPHAGE® XR. Additionally, Bristol-Myers Squibb distributes a pharmaceutical having a combination of metformin and glyburide as GLUCOVANCE®.

Anti-diabetic agents other than biguanides can also be administered to the identified subject. For example, in alternative embodiments, the anti-diabetic agent is a thiazolidinedione, such as troglitazone. In some examples, the anti-diabetic agent is an incretin or dipeptidyl peptidase-4 inhibitor, but the anti-diabetic agent can be any agent of interest.

A therapeutically effective amount of an anti-diabetic agent may be administered in a single dose, or in several doses, for example daily, during a course of treatment. The course of treatment may last for any length of time, such as a day or several days, a week or several weeks, a month or several months, or a year or several years, so long as the therapeutic effect is observed, such as inhibiting the onset of type II diabetes in a subject diagnosed with pre-diabetes, or inducing a subject diagnosed with type 2 diabetes or pre-diabetes to a normal glucose tolerance. The subject can be monitored while undergoing treatment using the methods described herein in order to assess the efficacy of the treatment protocol. In this manner, the length of time or the amount give to the subject can be modified based on the results obtained using the methods disclosed herein.

The therapeutically effective amount will depend on the anti-diabetic agent being used, the characteristics of the subject being treated (such as age, BMI, physiological condition, etc.), the severity and type of the affliction, and the manner of administration of the agent. The therapeutically effective dose can be determined by various methods, including generating an empirical dose-response curve, predicting potency and efficacy by using quantitative structure activity relationships (QSAR) methods or molecular modeling, and other methods used in the pharmaceutical sciences. In certain, non-limiting examples, the therapeutically effective amount of metformin (or a related biguanide analog or homolog) is at least about 1000 mg per day, such as at least about 1500 mg per day, or even at least about 1700 mg per day. In certain other, non-limiting examples, the total amount of metformin is divided into smaller doses, such as two or three doses per day, for example 850 mg twice a day (b.i.d.) or 500 mg three times a day (t.i.d.). In alternative, non-limiting examples, the total amount of metformin is about 500 mg or less per day. The subject can be monitored at different doses of an agent using the assays described herein, in order to determine a therapeutically effective amount for the subject of interest.

For administration to animals, purified therapeutically active agents are generally combined with a pharmaceutically acceptable carrier. Pharmaceutical preparations may contain only one type of anti-diabetic agent, or may be composed of a combination of several types of anti-diabetic agents, such as a combination of two or more anti-diabetic agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Anti-diabetic agents may be administered by any means that achieve their intended purpose. For example, the anti-diabetic agents may be administered to a subject through systemic administration, such as intravenous or intraperitoneal administration; intralesionally; by suppository; or orally.

The anti-diabetic agent can be administered alone or in combination with another anti-diabetic agent. In certain embodiments, the anti-diabetic agent is administered in the absence of administering any other anti-diabetic agent.

Other measures may be taken to inhibit or delay the onset of type II diabetes in subjects at a heightened risk of developing the disease. For example, in some embodiments, a subject may be instructed, trained, or induced to adopt anti-diabetic lifestyle modifications. For example, the subject can be counseled to reduce caloric intake or to exercise. The methods disclosed herein can be used to monitor the effectiveness of these alternative measures, to determine if pharmaceutical intervention is warranted for a subject of interest.

Methods for Determining Risk

Methods are provided herein to determine if a subject is at risk for developing a diabetic condition, such as pre-diabetes or diabetes. These methods utilize a biological fluid, such as, but not limited to saliva, for the detection of biomarkers. These biomarkers can be proteins, including any naturally occurring forms of the proteins, such as but not limited to glycosylated forms. The method can detect the risk for developing type 1 or type 2 diabetes. In some embodiments the subject is obese or overweight. These biomarkers can be proteins, including any naturally occurring forms of the proteins, such as but not limited to glycosylated forms. In some embodiments the subject is obese or overweight. The method can also include measuring blood hemoglobin A1C as an adjunct to the detection of other biomarkers.

In some embodiments, the methods disclosed herein are used to identify a subject as having pre-diabetes. In some embodiments, an FPG or an OGTT is not performed on the subject. These methods can be performed over time, to determine if the subject is at increased or decreased risk for developing pre-diabetes or diabetes. For example, the methods can be performed after an environmental exposure to determine if the exposure increases the subject's risk for developing diabetes. The methods can also be performed over time, to determine if a subject's risk for developing diabetes or pre-diabetes has increased or decreased over time. In some examples, the method is used in a subject with an elevated serum A1C level, such as greater than about 5%.

Methods are disclosed herein that include testing in a biological sample, such as a saliva sample, obtained from the subject. In one example, the biological sample is a biological fluid, such as saliva. However, other biological fluids are also of use, such as blood, GCF, serum, amniotic fluid, urine or tears.

The methods include detecting, or determining the abundance (amount) of one or more proteins from Table 1 above. The methods can include detecting at least one, two, three, four, five, at least ten, or at least fifteen of these proteins. In some examples, the methods include determining a proteomic profile. In other examples, the methods include detecting all of these proteins, such as a proteomic profile including at least 1, 2, 3, 4, 5, 6, 7, 8, 9, 10, 11, 12, 13, 14, 15, 16, 17, or all of these proteins.

In some embodiments, the method includes detecting an increase, such as a significantly significant increase, such as at least a 2, 3, 4, 5, 6 or 7 fold increase in the amount of protein plunc, pancreatic ribonuclease, inter-α-trypsin inhibitor heavy chain H1, inter-α-trypsin heavy chain H4, nucleobindin-2, and/or moesin as compared to a reference sample. In additional embodiments, the method includes detecting a decrease, such as a statistically significant decrease, such as at least a 2, 3, 4, 5, 6 or 7 fold decrease in the amount of 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and/or calnexin as compared to a reference sample, such as a sample from a subject that does not have diabetes and/or is known not to be at risk for developing diabetes.

In one embodiment, the method includes comparing a proteomic profile of a test sample of saliva from a subject of interest comprising at least one of protein plunc, pancreatic ribonuclease, inter-α-trypsin inhibitor heavy chain H1, inter- α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin, such as 2, 3, 4, 5, 6, 7, 8, 9, 10, 11, 12, 13, 14, 15, 16, 17, or all of these proteins with a proteomic profile from of a reference sample.

In one embodiment, if the reference sample is a normal sample, or a sample from a subject known not to be at risk for developing diabetes or pre-diabetes, and the proteomic profile of the test sample is essentially the same as the proteomic profile of the normal sample the subject is determined not to be at risk for pre-diabetes or diabetes, respectively. However, if the proteomic profile of the test sample has a unique expression signature relative to the proteomic profile of the reference sample the subject is determined to be at risk for pre-diabetes or diabetes, respectively.

If the reference sample is a sample from a subject with pre-diabetes or diabetes, or a subject known to be at risk for developing pre-diabetes or diabetes, and its proteomic profile shares at least one unique expression signature characteristic with the reference sample, then the subject is determined to be at risk for pre-diabetes or diabetes, respectively. If the proteomic profile of the test sample has a unique expression signature relative to the reference sample the subject is determined not to be at risk for pre-diabetes or diabetes, respectively. The proteomic profile can provide an additional criterion for the identification of a subject at risk for a diabetic condition.

In some embodiments, the method also includes detecting, or determining the abundance (amount) of one or more proteins from Table 2 above. The methods can include detecting at least one, two, three, four, five, at least ten, at least fifteen or all of these proteins. In some examples, the methods include determining a proteomic profile. In other examples, the methods include a proteomic profile including at least 1, 2, 3, 4, 5, 6, 7, 8, 9, 10, 11, 12, 13, 14, 15, 16, 17, or all of these proteins (for example, one or more of the combinations described above). In one embodiment, the method includes comparing a proteomic profile of a test sample of saliva from a subject of interest comprising at least one of uteroglobin, carbonic anhydrase 6, pyruvate kinase isozymes M1/M2, alpha-1-antitrypsin, neutrophil collagenase, alpha 2-macroglobulin, cystatin C, purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, carbonic anhydrase 2, alpha 1 acid glycoprotein, and lipocalin 2. In some embodiments, the method includes detecting an increase, such as a statistically significant increase, such as at least a 1.5, 2, 3, 4, or 5 fold increase, in the amount of uteroglobin, carbonic anhydrase C, pyruvate kinase isozymes M1/M2, alpha-1-antitrypsin, neutrophil collagenase, alpha 2-macroglobulin, cystatin C, alpha 1 acid glycoprotein, and/or lipocalin 2 as compared to a reference sample. In some embodiments, the method includes detecting an decrease, such as a statistically significant decrease, such as at least a 2, 3, 4, or 5 fold decrease in the amount of purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, and/or carbonic anhydrase 2 as compared to a reference sample. In one embodiment, the method includes comparing a proteomic profile of a test sample of saliva from a subject of interest comprising at least one of uteroglobin, carbonic anhydrase C, pyruvate kinase isozymes M1/M2, alpha-1-antitrypsin, neutrophil collagenase, alpha 2-macroglobulin, cystatin C, purine nucleoside phosphorylase, aldehyde dehydrogenase, fatty acid biding protein (epidermal), peroxiredoxin-1, -2, +-6, lamin A/C, apolipoprotein B-100, annexin A2, carbonic anhydrase 1, carbonic anhydrase 2, alpha 1 acid glycoprotein, and lipocalin 2.

Statistical methods for determining if the abundance of a protein of interest is increased relative to a reference sample are well known in the art, and are described below. If the reference sample is a normal sample, or a sample from a subject known not to be at risk for pre-diabetes and/or diabetes, and the proteomic profile of the test sample is essentially the same as the proteomic profile of the reference sample the subject is determined not to be at risk for pre-diabetes or diabetes, respectively. However, if the proteomic profile of the test sample has a unique expression signature relative to the proteomic profile of the reference sample the subject is determined to be at risk for pre-diabetes or diabetes, respectively. If the reference sample is a sample from a subject with pre-diabetes or diabetes, or known to be at risk for pre-diabetes and/or diabetes, and the proteomic profile shares at least one unique expression signature characteristic with the reference sample then the subject is determined to be at risk for pre-diabetes or diabetes, respectively. If the proteomic profile of the test sample has a unique expression signature relative to the reference sample the subject is determined not to be at risk for pre-diabetes or diabetes, respectively. The expression signature can include a difference in a single or multiple proteins in comparison to a control subject.

In yet further embodiments, the method includes detecting the presence or abundance (amount) of one or more of the proteins of Table 3 above. The methods can include detecting at least one, two, three, four, five, at least ten, fifteen, twenty, twenty-five, thirty, or all of these proteins. In some examples, the methods include determining a proteomic profile. In other examples, the methods include detecting all of these proteins, such as a proteomic profile including at least 1, 2, 3, 4, 5, 6, 7, 8, 9, 10, 11, 12, 13, 14, 15 or all of these proteins.

In another example, the methods include detecting all of these proteins. In one embodiment, the method includes comparing a proteomic profile of a test sample of saliva from a subject of interest comprising at least one of proteasome subunit, aldo-keto reductase family 1 member B10, cathepsin Z, chitotriosidase isoform 2, 3, +4, transmembrane protease, serine 11D, transthyretin, glycogen phosphorylase, heterogeneous nuclear RNPs A2/B1, leukocyte elastase inhibitor, small proline-rich protein 2F, calmodulin-like protein 5, neuroblast differentiation AHNAK, histone cluster 1, H1e, kallikrein-13, chitinase-3-like protein 1, inter-alpha (Globulin) inhibitor H2, 14-3-3 protein eta, cofilin-1, retinol binding protein 4, plasma, basic proline-rich peptide 1B-8a, isoform 2 of P60953 cdc 42 homolog, actin-related protein 2/3 complex subunit 5, ly6/PLAUR domain-containing protein 3, actin-like protein 2, Rearranged VKA17V gene segment, brain acid soluble protein 1, golgi phosphoprotein 2, protein FAM49B (L1), and acidic leucine-rich nuclear phosphoprotein 32.

If the reference sample is a normal sample or a sample from a subject known not to be at risk for pre-diabetes and/or diabetes, and the proteomic profile of the test sample is essentially the same as the proteomic profile of the reference sample the subject is determined not to be at risk for pre-diabetes or diabetes, respectively. However, if the proteomic profile of the test sample has a unique expression signature relative to the proteomic profile of the reference sample the subject is determined to be at risk for pre-diabetes or diabetes, respectively. If the reference sample is a sample from a subject with pre-diabetes or diabetes, or known to be at risk for pre-diabetes and/or diabetes, and the proteomic profile shares at least one unique expression signature characteristic with the reference sample then the subject is determined to be at risk for pre-diabetes or diabetes, respectively. If the proteomic profile of the test sample has a unique expression signature relative to the reference sample the subject is determined not to be at risk for pre-diabetes or diabetes, respectively.

Proteomic Identification of Proteins and Polypeptides Expressed in Biological Fluids Proteomic analysis of biological fluids, such as saliva or serum, can be performed using a variety of methods known in the art, and are of use in the methods disclosed herein. The biological fluid can be saliva, such as from a subject of interest, and/or a subject with diabetes, and/or a subject with pre-diabetes and/or a control subject without diabetes (or pre-diabetes). Typically, protein patterns (proteome maps) of samples from different sources, such as normal biological fluid (normal sample) and a test biological fluid (test sample), are compared to detect proteins that are up- or down-regulated in a disease, such as diabetes. These proteins can then be excised for identification and full characterization, such as by using peptide-mass fingerprinting and/or mass spectrometry and sequencing methods, or the normal and/or disease-specific proteome map can be used directly for the diagnosis of the disease of interest, or to confirm the presence or absence of the disease, such as pre-diabetes or diabetes.

In a direct comparative analysis, the reference, such as a normal (such as a sample from a non-diabetic subject) or known (such as a sample from a subject known to have diabetes or pre-diabetes) and test samples are treated exactly the same way, in order to correctly represent the relative abundance of proteins, and obtain accurate results. The required amount of total proteins depends on the analytical technique used, and can be readily determined by one skilled in the art. The proteins present in the biological samples are typically separated by two-dimensional gel electrophoresis (2-DE) according to their pI and molecular weight. The proteins are first separated by their charge using isoelectric focusing (one-dimensional gel electrophoresis). This step can, for example, be carried out using immobilized pH-gradient (IPG) strips, which are commercially available. The second dimension is a normal SDS-PAGE analysis, where the focused IPG strip is used as the sample. After 2-DE separation, proteins can be visualized with conventional dyes, like Coomassie Blue or silver staining, and imaged using known techniques and equipment, such as, for example Bio-Rad GS800 densitometer and PDQUEST™ software, both of which are commercially available. Individual spots are then cut from the gel, destained, and subjected to tryptic digestion. The peptide mixtures can be analyzed by mass spectrometry (MS). Alternatively, the peptides can be separated, for example by capillary high pressure liquid chromatography (HPLC) and can be analyzed by MS either individually, or in pools.

Mass spectrometers consist of an ion source, mass analyzer, ion detector, and data acquisition unit. First, the peptides are ionized in the ion source. The ionized peptides then are separated according to their mass-to-charge ratio in the mass analyzer and the separate ions are detected. Mass spectrometry has been widely used in protein analysis, especially since the invention of matrix-assisted laser-desorption ionisation/time-of-flight (MALDI-TOF) and electrospray ionisation (ESI) methods. There are several versions of mass analyzer, including, for example, MALDI-TOF and triple or quadrupole-TOF, or ion trap mass analyzer coupled to ESI. Thus, for example, a Q-Tof-2 mass spectrometer utilizes an orthogonal time-of-flight analyzer that allows the simultaneous detection of ions across the full mass spectrum range (see, for example, Chemusevich et al., *J. Mass Spectrom.* 36:849-865, 2001, incorporated herein by reference).

If desired, the amino acid sequences of the peptide fragments and eventually the proteins from which they derived can be determined by techniques known in the art, such as certain variations of mass spectrometry, or Edman degradation. A "proteomic profile" refers to a representation of the expression pattern of a plurality of proteins in a biological sample, such as biological fluid (for example, saliva, blood or serum) at a given time. The proteomic profile can, for example, be represented as a mass spectrum, but other representations based on any physicochemical or biochemical properties of the proteins are also included. Although it is possible to identify and sequence all or some of the proteins present in the proteome of a biological fluid, this is not necessary for the diagnostic use of the proteomic profiles.

Diagnosis of a diabetes or pre-diabetes can be based on characteristic differences (unique expression signatures) between a normal proteomic profile (a profile from a non-diabetic subject, who does not have pre-diabetes or diabetes), and the proteomic profile of the same biological fluid obtained under the same experimental conditions. Diagnosis of a diabetes or pre-diabetes can be based on characteristic similarities (unique expression signatures) between a diabetic or pre-diabetic proteomic profile respectively, and the proteomic profile of the test biological fluid obtained under the same experimental conditions.

The unique expression signature can be any unique feature or motif within the proteomic profile of a test or reference biological sample that differs from the proteomic profile of a corresponding normal biological sample obtained from the same type of source, in a statistically significant manner. For example, if the proteomic profile is presented in the form of a mass spectrum, the unique expression signature is typically a peak or a combination of peaks that differ, qualitatively or quantitatively, from the mass spectrum of a corresponding normal sample. Thus, the appearance of a new peak or a combination of new peaks in the mass spectrum, or any statistically significant change in the amplitude or shape of an existing peak or combination of existing peaks, or the disappearance of an existing peak, in the mass spectrum can be considered a unique expression signature.

When the proteomic profile of the test sample obtained from a subject of interest is compared with the proteomic profile of a reference sample comprising a unique expression signature characteristic of a pre-diabetic or diabetic subject, the subject of interest is diagnosed with diabetes or pre-diabetes if it shares the unique expression signature with the reference sample. For example a profile that does not have any statistically significant change in the amplitude or shape of an existing peak representing one or more of alpha-1-antitrypsin (A1AT), cystatin C (CysC), alpha-2-macroglobulin (A2MG), and transthyretin (TTR) from a sample from a subject with pre-diabetes or diabetes, detects pre-diabetes or diabetes in the subject, respectively. In one example, if the proteomic profile of the test sample shows a unique expression signature, such as an increase in the abundance of one, two, three or four of alpha-1-antitrypsin (A1AT), cystatin C (CysC), alpha-2-macroglobulin (A2MG), and transthyretin (TTR) relative to the proteomic profile of the normal biological fluid, then the subject has pre-diabetes. In a specific, non-limiting example, if the proteomic profile of a test sample shows a unique expression signature, such as an increase in the abundance of one, two, three or four of alpha-1-antitrypsin (A1AT), cystatin C (CysC), alpha-2-macroglobulin (A2MG), and transthyretin (TTR) relative to the proteomic profile of a biological subject with pre-diabetes, then the subject has diabetes. Other combinations (such as those as described above) can also be used to detect a proteomic profile from a subject of interest to diagnose whether the subject has pre-diabetes or diabetes.

Pre-diabetes or diabetes also can be diagnosed by comparing the proteomic profile of a biological fluid obtained from the subject to be diagnosed with the proteomic profile of a normal biological fluid of the same kind, obtained and treated the same manner. If the proteomic profile of the test sample is essentially the same as the proteomic profile of the normal sample (from a subject without diabetes or pre-diabetes), the subject is considered not to have pre-diabetes or diabetes, respectively). If the proteomic profile of the test sample shows a unique expression signature, such as an increase in the abundance of one, two, three or four of alpha-1-antitrypsin (A1AT), cystatin C (CysC), alpha-2-macroglobulin (A2MG), and transthyretin (TTR) relative to the proteomic profile of the normal biological fluid, then the subject has pre-diabetes. If the proteomic profile of the test sample shows a unique expression signature, such as an increase in the abundance of one, two, three or four of alpha-1-antitrypsin (A1AT), cystatin C (CysC), alpha-2-macroglobulin (A2MG), and transthyretin (TTR) relative to the proteomic profile of the biological fluid from a subject with pre-diabetes, then the subject has diabetes.

Alternatively or in addition, the proteomic profile of the test sample may be compared with the proteomic profile of a reference standard, such as a previously established proteomic profile or a set of values from a subject with pre-diabetes or diabetes. In this case, the subject is diagnosed with the pathologic condition if the proteomic profile of the test sample shares at least one feature, or a combination of features representing a unique expression signature, with the proteomic profile of the reference sample from the subject with pre-diabetes or diabetes.

Statistical methods for comparing proteomic profiles are well known in the art. For example, in the case of a mass spectrum, the proteomic profile is defined by the peak amplitude values at key mass/charge (M/Z) positions along the horizontal axis of the spectrum. Accordingly, a characteristic proteomic profile can, for example, be characterized by the pattern formed by the combination of spectral amplitudes at given M/Z vales. The presence or absence of a characteristic expression signature, or the substantial identity of two profiles can be determined by matching the proteomic profile (pattern) of a test sample with the proteomic profile (pattern) of a reference or normal sample, with an appropriate algorithm. Statistical methods for analyzing proteomic patterns is disclosed, for example, in Petricoin III, et al., *The Lancet* 359:572-77, 2002; Issaq et al., *Biochem Biophys Commun* 292:587-92 (2002); Ball et al., *Bioinformatics* 18:395-404, 2002; and Li et al., *Clinical Chemistry Journal*, 48:1296-1304, 2002.

Protein Arrays

The disclosed methods can utilize protein arrays, which can be used to detect proteins, monitor their expression levels, and investigate protein interactions and functions. The use of protein arrays enables high-throughput protein analysis, when large numbers of determinations can be performed simultaneously, using automated means. In the microarray or chip format, that was originally developed for DNA arrays, such determinations can be carried out with minimum use of materials while generating large amounts of data. Protein microarrays, in addition to their high efficiency, provide very high sensitivity.

Protein arrays are formed by immobilizing proteins on a solid surface, such as glass, silicon, micro-wells, nitrocellulose, PVDF membranes, and microbeads, using a variety of covalent and non-covalent attachment chemistries well known in the art. The solid support is chemically stable before and after the coupling procedure, allow good spot morphology, display minimal nonspecific binding, should not contribute a background in detection systems, and should be compatible with different detection systems. In general, protein microarrays use the same detection methods commonly used for the reading of DNA arrays. Similarly, the same instrumentation as used for reading DNA microarrays is applicable to protein arrays.

Thus, capture arrays (such as antibody arrays) can be probed with fluorescently labeled proteins from two different sources, such as normal and diabetic and/or pre-diabetic biological fluids. In this case, the readout is based on the change in the fluorescent signal as a reflection of changes in the expression level of a target protein. Alternative readouts include, without limitation, fluorescence resonance energy transfer, surface plasmon resonance, mass spectrometry, resonance light scattering, and atomic force microscopy (see Zhou H, et al., *Trends Biotechnol.* 19:S34-9, 2001; Zhu et al., *Current Opin. Chem. Biol.* 5:40-45, 2001; Wilson and Nock, *Angew Chem Int Ed Engl* 42:494-500, 2003); and Schweitzer and Kingsmore, *Curr Opin Biotechnol* 13:14-9, 2002). Biomolecule arrays are also disclosed in U.S. Pat. No. 6,406,921, issued Jun. 18, 2002, the entire disclosure of which is hereby incorporated by reference. In some embodiments the capture arrays include antibodies to two, three or four of alpha-1-antitrypsin (A1AT), cystatin C (CysC), alpha-2-macroglobulin (A2MG), and transthyretin (TTR). The capture arrays can also include antibodies that specifically bind a protein listed in Table 2. An additional, two, three, four, five, ten, twenty, thirty, forty or fifty antibodies can be included on a capture array.

Immunoassays

The methods disclosed herein can also be performed in the form of various immunoassay formats, which are well known in the art. There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the proteins listed in Tables 1, 2 or 3. In addition, immunoassays can be used to detect any of the proteins listed in Table 5.

ELISA is a heterogeneous immunoassay, which has been widely used in laboratory practice since the early 1970s, and can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a saliva sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogenous immunoassay, such as an ELISA, can be used to detect any of the proteins listed in Tables 1, 2, 3 or 5.

In another example, immuno-PCR can be used to detect any of the proteins listed in Tables 1, 2, 3, or 5 Immuno-PCR is a modification of the conventional ELISA format in which the detecting antibody is labeled with a DNA label, and is applicable to the analysis of biological samples (see, e.g., U.S. Pat. No. 5,665,539 and U.S. Patent Application Publication No. 2005/0239108; all herein incorporated by reference). The amplification ability of PCR provides large amounts of the DNA label which can be detected by various methods, typically gel electrophoresis with conventional staining (e.g., Sano et al., *Science*, 258:120-122, 1992). This method can also include the direct conjugation of the DNA label to the antibody and replacement of gel electrophoresis by using labeled primers to generate a PCR product that can be assayed by ELISA or using real time quantitative PCR. In an example of the real-time PCR method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the proteins to be detected, such proteins bind to the antibodies. A measured amount of the corresponding enzyme-labeled proteins is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the proteins listed in Tables 1, 2, 3 or 5.

Immunoassay kits are also disclosed herein. These kits include, in separate containers (a) monoclonal antibodies having binding specificity for the polypeptides used in the diagnosis of a pre-diabetes or diabetes; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art. In several embodiments, the immunoassay kit includes two, three or four of: antibodies that specifically bind a protein listed in Table 1. The immunoassay kit can also include one or more antibodies that specifically bind a protein listed in Table 2. The immunoassay kit can also include one or more antibodies that specifically bind a protein listed in Table 3. In one example, the immunoassay kit includes antibodies that specifically bind one, two or three of: antibodies that specifically bind different proteins listed in Table 1, antibodies that specifically bind a protein listed in Table 2, and antibodies that specifically bind a protein listed in Table 3. Thus, the kits can be used to detect two or more different proteins listed in Tables 1, 2 and/or 3.

Capture Device Methods

The disclosed methods can be carried out using a sample capture device, such as a lateral flow device (for example a lateral flow test strip) that allows detection of one or more proteins, such as those described herein.

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and 5,073,484 (incorporated herein by reference). The test strips include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853; WO 88/08534; and EP-A 0 299 428 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645; 4,168,146; 4,366,241; 4,855,240; 4,861,711; 5,120,643; European Patent No. 0296724; WO 97/06439; WO 98/36278; and WO 08/030,546 (each of which are herein incorporated by reference). Multiple zone lateral flow test strips are disclosed in U.S. Pat. Nos. 5,451,504, 5,451,507, and 5,798,273 (incorporated by reference herein). U.S. Pat. No. 6,656,744 (incorporated by reference) discloses a lateral flow test strip in which a label binds to an antibody through a streptavidin-biotin interaction.

In particular examples, the methods disclosed herein include application of a biological sample (such as saliva or urine) from a test subject to a lateral flow test device for the detection of one or more proteins (such as one or more proteins listed in Tables 1, 2, 3, and 5, for example, combinations of proteins as described above) in the sample. The lateral flow test device includes one or more antibodies (such as antibodies that bind one or more of the proteins listed in Tables 1, 2, 3, and 5) at an addressable location. In a particular example, the lateral flow test device includes antibodies that bind A1AT and A1AG. The addressable locations can be, for example, a linear array or other geometric pattern that provides diagnostic information to the user. The binding of one or more proteins in the sample to the antibodies present in the test device is detected and the presence or amount of one or more proteins in the sample of the test subject is compared to a control, wherein a change in the presence or amount of one or more proteins in the sample from the test subject as compared to the control indicates that the subject has pre-diabetes or diabetes.

Flow-through Devices

Flow-through type assay devices were designed, in part, to obviate the need for incubation and washing steps associated with dipstick assays. Flow-through immunoassay devices involve a capture reagent (such as one or more antibodies) bound to a porous membrane or filter to which a liquid sample is added. As the liquid flows through the membrane, target analyte (such as protein) binds to the capture reagent. The addition of sample is followed by (or made concurrent with) addition of detector reagent, such as labeled (e.g., gold-conjugated or colored latex particle-conjugated protein). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277,560; 4,632,901; 4,812,293; 4,920,046; and 5,279,935; U.S. Patent Application Publication Nos. 20030049857 and 20040241876; and WO 08/030,546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; European Patent No. 0296724; WO 97/06439; WO 98/36278; and WO 08/030,546.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as non-woven polyester), for example, to provide increased rigidity to the strip. Zones within each strip may differentially contain the specific binding partner(s) and/or other reagents required for the detection and/or quantification of the particular analyte being tested for, for example, one or more proteins disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular proteins to be detected may be obtained from any biological source. Examples of biological sources include blood serum, blood plasma, urine, spinal fluid, saliva, fermentation fluid, lymph fluid, tissue culture fluid and ascites fluid of a human or animal. In a particular example, the biological source is saliva. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

Another common feature to be considered in the use of assay devices is a means to detect the formation of a complex between an analyte (such as one or more proteins described herein) and a capture reagent (such as one or more antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest, for example those described herein).

In other instances, a detector reagent collectively includes an unlabeled first binding partner specific for the analyte and a labeled second binding partner specific for the first binding partner and so forth. Thus, the detector can be a labeled antibody specific for a protein described herein. The detector can also be an unlabeled first antibody specific for the protein of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Flow-Through Device Construction and Design

A flow-through device involves a capture reagent (such as one or more antibodies) immobilized on a solid support, typically, microtiter plate or a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize non-specific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more proteins described herein) can specifically bind to the immobilized capture reagent (such as one or more antibodies). Where detection of an analyte-capture reagent complex is desired, a detector reagent (such as labeled antibodies that specifically bind one or more proteins) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; 6,368,876 and 7,517,699; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more proteins) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more proteins) in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810; both of which are incorporated herein by reference.

Lateral flow devices have a wide variety of physical formats that are equally well known in the art. Any physical format that supports and/or houses the basic components of a lateral flow device in the proper function relationship is contemplated by this disclosure.

The basic components of a particular embodiment of a lateral flow device are illustrated in FIG. 3A, which shows a particular embodiment of a bibulous lateral flow strip 12. Lateral flow strip 12 is divided into a proximal sample application pad 14, an intermediate test result zone 16, and a distal absorbent pad 18. Flow strip 12 is interrupted by a conjugate pad 19 that contains labeled conjugate (such as gold- or latex-conjugated antibody specific for the target analyte or an analyte analog). A flow path along strip 12 passes from proximal pad 14, through conjugate pad 19, into test result zone 16, for eventual collection in absorbent pad 18. Selective binding agents are positioned on a proximal test line 20 in test result membrane 16. A control line 22 is provided in test result zone 16, slightly distal to test line 20. For example, in a competitive assay, the binding agent in test line 20 specifically binds the target analyte, while control line 22 less specifically binds the target analyte.

In operation of the particular embodiment of a lateral flow device illustrated in FIG. 3A, a fluid sample containing an analyte of interest, such as one or more proteins described herein (for example, A1AT or A1AG, or other combinations of proteins, as discussed above), is applied to the sample pad 14. In some examples, the sample may be applied to the sample pad 14 by dipping the end of the device containing the sample pad 14 into the sample (such as saliva or urine) or by applying the sample directly onto the sample pad 14 (for example by placing the sample pad 14 in the mouth of the subject). In other examples where a sample is whole blood, an optional developer fluid is added to the blood sample to cause hemolysis of the red blood cells and, in some cases, to make an appropriate dilution of the whole blood sample.

From the sample pad 14, the sample passes, for instance by capillary action, to the conjugate pad 19. In the conjugate pad 19, the analyte of interest, such as a protein of interest, may bind (or be bound by) a mobilized or mobilizable detector reagent, such as an antibody (such as antibody that recognizes one or more of the proteins described herein). For example, a protein analyte may bind to a labeled (e.g., gold-conjugated or colored latex particle-conjugated) antibody contained in the conjugate pad. The analyte complexed with the detector reagent may subsequently flow to the test result zone 16 where the complex may further interact with an analyte-specific binding partner (such as an antibody that binds a particular protein, an anti-hapten antibody, or streptavidin), which is immobilized at the proximal test line 20. In some examples, a protein complexed with a detector reagent (such as gold-conjugated antibody) may further bind to unlabeled, oxidized antibodies immobilized at the proximal test line 20. The formation of a complex, which results from the accumulation of the label (e.g., gold or colored latex) in the localized region of the proximal test line 20 is detected. The control line 22 may contain an immobilized, detector-reagent-specific binding partner, which can bind the detector reagent in the presence or absence of the analyte. Such binding at the control line 22 indicates proper performance of the test, even in the absence of the analyte of interest. The test results may be visualized directly, or may measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line 20 in test result zone 16 (for example test lines 20a, 20b, and 20c in FIG. 3B). The operation of this particular embodiment is similar to that described in the immediately preceding paragraph with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

1. Sample Pad

The sample pad (such as sample pad 14 in FIG. 3A) is a component of a lateral flow device that initially receives the sample, and may serve to remove particulates from the sample. Among the various materials that may be used to construct a sample pad (such as glass fiber, woven fibers, screen, non-woven fibers, cellosic fibers or paper), a cellulose sample pad may be beneficial if a large bed volume (e.g., 250 µl/cm$^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose (including pure nitrocellulose and modified nitrocellulose), nitrocellulose direct cast on polyester support, polyvinylidene fluoride, or nylon), and considerations for applying a capture reagent to such membranes have been discussed previously.

3. Conjugate Pad

The conjugate pad (such as conjugate pad 19 in FIG. 3A) serves to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In a particular disclosed embodiment, the detector reagent in conjugate pad 19 is a gold-conjugated antibody.

4. Absorbent Pad

The use of an absorbent pad 18 in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

The disclosure is illustrated by the following non-limiting Examples.

EXAMPLES

Example 1

Materials and Methods

Subjects: From a prospective observational study, 40 subjects were chosen for salivary proteome analysis. In the study group, 10 each had impaired glucose tolerance (IGT), both IGT and impaired fasting glucose (IFG), or (previously diagnosed) diabetes (DM). The diagnosis of DM and pre-diabetes (IFG and IGT) was based on American Diabetes Association criteria. IFG was diagnosed if the fasting plasma glucose level was elevated (between 100 and 125 mg/dl after an overnight fast), and IGT if the 2-hour plasma glucose level was elevated (between 140 and 199 mg/dl) after an oral glucose tolerance test. The control group consisted of 10 clinically healthy humans between 36 and 62 years of age. Exclusion criteria for the control group included pregnancy, alcohol consumption, tobacco products (former or current), chronic medical illness, history of drug treatment or therapy within the previous months, or history of diabetes. Subjects were asked not to eat, smoke, or drink (except water) for an overnight fast prior to collection of saliva samples. Their diets were similar with respect to protein content and uptake of fat and carbohydrates. Socioeconomic status was similar for all groups (based on survey data). The clinical characteristics of healthy controls and study subjects are shown in Table 4. Informed consent was obtained from the subjects following the institutional review board guidelines for human subjects (Nizam's Institute of Medical Sciences, Hyderabad, India).

LC-MS/MS analysis: Portions of each fraction (9 µl) were analyzed by LC-MS/MS using an Agilent 1100 series capillary LC system and an LTQ ion-trap mass spectrometer (Thermo Electron, San Jose, Calif.) with an Ion Max electrospray source (ThermoFinnigan, San Jose, Calif.). Samples were applied at 20 µl/min to a trap cartridge, and then switched onto a 0.5×250-mm Zorbax SB-C18 column (Agilent Technologies, Palo Alto, Calif.) using mobile phase A containing 0.1% formic acid. Survey MS scans were alternated with three data-dependent MS/MS scans using the dynamic exclusion feature of the control software to increase

TABLE 4

Clinical characteristics of controls and subjects with pre-clinical and type-2 diabetes

|  | Controls | IGT | IFG + IGT | DM |
|---|---|---|---|---|
| Age (years) | 46.20 ± 11.32 | 43.8 ± 13.18 | 48.80 ± 8.23 | 49.75 ± 7.89 |
| Duration of DM (years) | NA | NA | NA | 4.00 ± 2.16 |
| Height (cm) | 163.00 ± 13.42 | 167.80 ± 7.53 | 166.40 ± 4.04 | 168.50 ± 6.95 |
| Weight (kg) | 73.66 ± 17.74 | 72.36 ± 8.44 | 71.70 ± 6.51 | 71.18 ± 10.89 |
| BMI (kg/m$^2$) | 27.57 ± 4.47 | 25.81 ± 3.64 | 25.90 ± 1.96 | 25.01 ± 2.76 |
| Waist (cm) | 93.40 ± 13.20 | 92.20 ± 6.83 | 94.80 ± 6.61 | 88.75 ± 4.50 |
| Hip (cm) | 99.40 ± 6.84 | 95.20 ± 6.53 | 96.80 ± 6.02 | 93.25 ± 6.02 |
| Waist-to-hip ratio | 0.94 ± 0.08 | 0.97 ± 0.09 | 0.98 ± 0.02 | 0.95 ± 0.02 |
| Blood pressure, |  |  |  |  |
| systolic (mmHg) | 135.40 ± 29.80 | 135.60 ± 27.25 | 139.40 ± 17.46 | 127.00 ± 16.95 |
| diastolic (mmHg) | 84.00 ± 9.67 | 89.00 ± 11.18 | 89.40 ± 9.61 | 79.25 ± 12.37 |
| Plasma glucose, fasting (mg/dl), | 86.00 ± 8.57 | 93.60 ± 6.69 | 106.40 ± 7.44 | 158.00 ± 69.66 |
| 2 hours after oral glucose (mg/dl) | 113.40 ± 21.03 | 154.80 ± 19.23 | 159.80 ± 16.72 | 248.00 ± 134.71 |
| Serum cholesterol (mg/dl) | 201.80 ± 13.97 | 215.20 ± 42.76 | 153.60 ± 15.99 | 202.75 ± 45.32 |
| Triglycerides (mg/dl) | 116.60 ± 36.69 | 147.80 ± 54.27 | 178.40 ± 94.11 | 232.25 ± 205.61 |
| HDL cholesterol (mg/dl) | 44.60 ± 21.27 | 39.40 ± 6.27 | 32.40 ± 4.10 | 33.50 ± 7.72 |

Data are mean ± SD.
NA: not applicable;
IFG: impaired fasting glucose;
IGT: impaired glucose tolerance;
DM: type-2 diabetes.

Sample collection and processing: Unstimulated saliva (20 ml) from diabetic, pre-diabetic, and control groups was collected. Briefly, at 8 AM (before breakfast), the subjects were asked to rinse their mouths thoroughly with water, then to tilt their heads forward and allow saliva to flow into a sterile container for 5 minutes. These specimens were immediately frozen and stored at −80° C. until analysis. Saliva samples (10 ml) were centrifuged at 10,000×g for 20 min at 4° C. to discard cellular debris and nuclei. The supernatants were transferred to 4-ml Ultrafree 5K membrane concentrators (Millipore, Billerica, Mass., USA) and spun at 7000×g to reduce the volumes to ~1 ml. A total of 5 saliva samples from the control and DM groups were pooled together and subjected to two-dimensional liquid chromatography (2-DLC) and LC-tandem mass spectrometry (LC-MS/MS) analysis as described before (Nagalla et al., *J Proteome Res* 6:1245-1257, 2007) and briefly outlined below.

2-DLC sample processing: Following protein assay, 1-mg portions of samples were reduced, alkylated, digested with trypsin, and the resulting peptides separated with strong cation-exchange (SCX) chromatography. SCX chromatography was performed using a 100×2.1-mm polysulfoethyl A column (The Nest Group, Southborough, Mass.). A total of 80 fractions were collected and desalted using a 96-well Vydac C18 silica spin plate (The Nest Group). The desalted fractions were consolidated into 31 fractions, dried, dissolved in 20 µl of 5% formic acid for LC-MS/MS analysis.

the number of unique peptides analyzed. Mass spectra files were generated using Bioworks Browser software (version 3.1, ThermoFinnigan, San Jose, Calif.) with m/z range of 400-4000 Da, a minimum of 15 ions, and a low TIC threshold of 500. A total of 1,729,998 tandem mass spectra were generated from all LC-MS/MS analyses.

Peptide and protein identification: Tandem mass spectra were searched against a composite protein database containing forward and reversed entries (decoy proteins) of Swiss-Prot (version 52.1) and TrEmbl (version 35.1) databases selected for human subspecies. Splice variants were generated using the varsplice program from the SwissKnife package (version 1.62). Forward and reverse entries of the generated splice variants were also added to the composite protein database. All searches were performed using the X! Tandem (Craig et al., *Bioinformatics* 20:1466-1467, 2004) search engine configured to use 1.8 Da and 0.4 Da as parent and fragment ion mass tolerances, respectively, trypsin enzyme specificity, a fixed carbamidomethyl modification on cysteine residues, and several potential in vivo modifications. Peptide identifications from samples were assembled into proteins using probabilistic protein identification algorithms (Nesvizhskii et al., *Anal Chem* 75:4646-4658, 2003) implemented in Scaffold software (version 1.6, Proteome Software, Portland, Oreg.).

Peptide and protein identifications in all samples were compiled together to generate a comprehensive diabetic salivary proteome. Proteins with one or more unique peptide identifications (p≧0.8) were considered as likely to be present in the sample. Protein entries were further curated to reduce redundancy by removing subset proteins and collapsing degenerate protein identifications into a single entry. All immunoglobulin variants identified in the sample were also collapsed into a single entry. Annotations of identified hypothetical sequences were corrected, if possible, by checking their sequence homology with known proteins in the Swiss-Prot human database (version 52.1) using NCBI BLAST software. A hypothetical annotation was accepted into the final protein list if the corresponding blast search did not turn up any homologous (≧90% sequence homology) known human proteins. Protein identifications with at least three unique peptide identifications in at least one sample were considered to be present in saliva.

Label-free quantification: The total number of tandem mass spectra matched to a protein (spectral counting) is a label-free, sensitive, and semi-quantitative measure for estimating its abundance in complex mixtures (Liu et al., Anal. Chem. 76: 4193-4201, 2004; Old et al., Mol. Cell. Proteomics 4: 1487-1502, 2005). The spectral count difference between two complex samples is used to quantify the relative expression of a protein (Nagalla et al., J. Proteome Res. 6: 1245-1257, 2007). In this study, salivary proteins with at least three unique peptide identifications in at least one sample were considered for label-free quantification. Shared spectral counts of non-degenerate proteins belonging to the same family with significant sequence homology (>50%) were combined into single entry. Shared spectral counts of non-degenerate proteins that did not fit the afore-mentioned criteria were assigned to one of the proteins using Occam's razor approach. Curated proteins were subjected to independent pair-wise comparisons to determine differentially abundant proteins between control and diabetes groups using either a $2 \times 2$ $\chi^2$ or Fisher's exact test. Normalization of spectral counts to account for experimental variability was built into the pair-wise comparison model automated using a SAS program (version 9.1). A protein was considered as significantly differentially abundant between the samples if the comparison had a p-value of ≦0.05 in either the $\chi^2$ or Fisher's exact test. The fold change (FC) in the level of differentially abundant proteins was calculated using the equation described by Old et al. (Old et al., Mol. Cell. Proteomics 4: 1487-1502, 2005).

Western immunoblotting: Fifteen micrograms of saliva protein from each experimental group (CTRL, IGT, IGT+ IFG, and DM) were resolved on 10-20% Tris-Tricine gels and transferred to PVDF membranes. Membranes were blocked with 5% fat-free milk in TBST for 2 hours at room temperature and incubated with primary antibody (alpha-1-antitrypsin, cystatin C, alpha-2-macroglobulin, and transthyretin from Dako North America Inc., Carpinteria, Calif.; and salivary alpha amylase from Sigma, Atlanta, Ga.) for 1 hour. All primary antibodies were diluted 1:4000, except alpha-1-antitrypsin (A1AT), which was diluted 1:5000. After three 10-minute washes with TBST, membranes were incubated with anti-rabbit IgG-HRP secondary antibody (Santa Cruz Biotechnology, Inc., Santa Cruz, Calif.; catalog #SC2004) for 1 hour, washed again in TBST, and then visualized with the SuperSignal West Pico chemiluminescent substrate system (Pierce, Rockford, Ill.). Chemiluminescence was scanned on a LAS-3000 instrument using the LAS-3000 Lite software, and scanned images were visualized and quantified using MultiGauge v.3.1 software (FujiFilm Life Science, Inc, Stamford, Conn.).

ELISAs were performed individually on 5 subjects in each group using a microtiter plate assay. Primary, secondary antibodies, and reference proteins were obtained from Dako North America, Inc. A standard curve was generated by four-parameter curve-fitting using SoftmaxPro V 1.11 software, (Molecular Devices Corporation). The concentrations of the individual samples were estimated from the average values of triplicates in comparison to the standard curve. Concentrations of individual biomarkers are expressed as means +/−SEM. Statistical significance was estimated by Kruskal-Wallis nonparametric ANOVA for 4-group comparison and the Wilcoxon two-sample test for pair-wise comparisons.

Example 2

Human Diabetic Salivary Proteome

A total of 2172 proteins were identified at a single unique-peptide (p≦0.8) threshold. To reduce the false-positive rate, a stringent three-unique-peptide threshold was adapted which resulted in 586 identifications with a false-positive rate of 0.5%. The protein list was further curated by collapsing all the immunoglobulin entries into a single entry, and sample processing artifacts (such as trypsin and keratin) and decoy proteins were removed. The resulting 487 proteins of the salivary proteome and their corresponding spectral count in control and diabetes subject was evaluated. Salivary proteomes from this study and the current literature (Hu et al., *Proteomics* 5:1714-1728, 2005; Hu et al., *Expert Rev Proteomics* 4:531-538, 2007; Vitorino et al., *Proteomics* 4:1109-1115, 2004; Wilmarth et al., *J Proteome Res* 3:1017-1023, 2004) were cross-referenced and marked accordingly in Supplemental Table 1 (Rao et al., *J. Proteome Res.* 8:239-245, 2009, incorporated herein by reference). A total of 315 (67%) proteins found in this study were confirmed by other studies. Thus, 33% of the salivary proteins identified were newly identified.

The type-2 diabetes salivary proteome was functionally annotated using GO annotations from DAVID and BioHarvester informatics resources as shown in FIG. 1. A majority of the salivary proteins have metabolic (42%) and immune response (11%) functions. Proteins with other cellular functions included such as cell organization and biogenesis (11%), cell communication and proliferation (6%), development (5%), and apoptosis (5%).

Example 3

Quantification of Diabetic Salivary Proteome Using Spectral Counts

The spectral counts of the salivary proteins were subjected to label-free quantification to find differentially abundant proteins between the control and diabetes groups. Proteins with a relative differential abundance of ≧2.0 fold and which passed the label-free quantification with a p-value of ≦0.05 were considered as significantly differentially abundant between the two groups. A total of 65 differentially abundant salivary proteins are shown in Table 5 grouped according to their functional annotations. Spectral counts of human salivary proteins with three or more unique peptide identifications were subjected to label-free quantification and those that were significantly differentially abundant (p-value≦0.05) by at least ±2.0-fold are shown in Table 5.

TABLE 5

Proteins differentially present in saliva in subjects with type-2 diabetes and controls

| Function | Swiss-Prot Accession | Description | Fold Change Diabetes vs. Control | P-value |
|---|---|---|---|---|
| Metabolism | P23280 | Carbonic anhydrase 6 | 3.84 | <0.0001 |
|  | P14618 | Pyruvate kinase isozymes M1/M2 | 3.47 | 0.0002 |
|  | P06737 | Glycogen phosphorylase, liver form | 3.32 | 0.0105 |
|  | Q549C7 | Transthyretin | 2.4 | 0.0246 |
|  | P22894 | Neutrophil collagenase | 2.36 | 0.0039 |
|  | P00491 | Purine nucleoside phosphorylase | −2.08 | 0.0032 |
|  | O60235 | Transmembrane protease, serine 11D | −2.13 | 0.012 |
|  | P30838 | Aldehyde dehydrogenase, dimeric NADP-preferring | −2.19 | 0.0034 |
|  | Q13231-3 | Isoform 2, 3 and 4 of Chitotriosidase-1 | −2.2 | 0.0263 |
|  | Q9UBR2 | Cathepsin Z | −2.85 | 0.0361 |
|  | P00558 | Phosphoglycerate kinase 1 | −3.18 | <0.0001 |
|  | O60218 | Aldo-keto reductase family 1 member B10 | −3.32 | 0.0127 |
|  | Q13787 | Apolipoprotein B-100 | −4.13 | <0.0001 |
|  | P00915 | Carbonic anhydrase 1 | −4.36 | <0.0001 |
|  | P00918 | Carbonic anhydrase 2 | −5.54 | 0.0002 |
|  | Q86U62 | Proteasome (prosome, macropain) subunit, beta type, 7 | −6.11 | 0.0184 |
|  | P27824 | Calnexin | −7.74 | 0.0005 |
| Immune response | Q6FHH3 | Uteroglobin | 10.43 | <0.0001 |
|  | Q4VAX6 | Serpin peptidase inhibitor, clade B | 6.05 | 0.0101 |
|  | Q9NP55 | Protein Plunc | 5.48 | <0.0001 |
|  | P13671 | Complement component C6 | 4.75 | 0.036 |
|  | P01009 | Alpha-1-antitrypsin | 3.24 | <0.0001 |
|  | P01034 | Cystatin-C | 2.22 | 0.0007 |
|  | P30740 | Leukocyte elastase inhibitor | 2.03 | 0.011 |
|  | P01040 | Cystatin-A | −2.42 | 0.0042 |
|  | P04083 | Annexin A1 | −3.57 | <0.0001 |
| Development | Q4VB24 | Histone cluster 1, H1e | 6.05 | 0.0101 |
|  | Q09666 | Neuroblast differentiation-associated protein AHNAK | 3.08 | 0.0472 |
|  | Q9NZT1 | Calmodulin-like protein 5 | −2.17 | 0.0151 |
|  | Q01469 | Fatty acid-binding protein, epidermal | −2.55 | <0.0001 |
|  | Q06830 | Peroxiredoxin-1, -2 and -6 | −2.59 | <0.0001 |
|  | Q96RM1 | Small proline-rich protein 2F | −2.85 | 0.0361 |
|  | P31151 | Protein S100-A7 | −2.94 | 0.003 |
|  | Q5TCI8 | Lamin A/C | −3.26 | <0.0001 |
|  | P07355 | Annexin A2 | −4.25 | 0.0014 |
|  | P15924 | Desmoplakin | −5.88 | <0.0001 |
|  | P30043 | Flavin reductase | −6.11 | 0.0003 |
| Extracellular matrix Protein | P07998 | Ribonuclease pancreatic | 3.78 | 0.0015 |
|  | A2RTY6 | Inter-alpha (Globulin) inhibitor H2 | 3.16 | 0.0102 |
|  | P19827 | Inter-alpha-trypsin inhibitor heavy chain H1 | 2.8 | 0.0042 |
|  | P36222 | Chitinase-3-like protein 1 | 2.65 | 0.0173 |
|  | Q14624 | Inter-alpha-trypsin inhibitor heavy chain H4 | 2.59 | 0.006 |
|  | P80303 | Nucleobindin-2 | 2.05 | 0.005 |
|  | Q9UKR3 | Kallikrein-13 | −4.48 | 0.0265 |
|  | O43240 | Kallikrein-10 | −4.99 | 0.0024 |
| Signal transduction | Q7M4Q5 | Basic proline-rich peptide IB-8a | 5.4 | 0.019 |
|  | P39687 | Acidic leucine-rich nuclear phosphoprotein 32 family | 3.32 | 0.0105 |
|  | Q5VY30 | Retinol binding protein 4, plasma | 2.15 | 0.0143 |
|  | P23528 | Cofilin-1 | 2.11 | 0.0464 |
|  | P62258 | 14-3-3 protein epsilon | −2.25 | 0.01 |
|  | P12429 | Annexin A3 | −2.68 | 0.008 |
|  | Q04917 | 14-3-3 protein eta | −2.95 | 0.0438 |
| Cell organization and biogenesis | O15511 | Actin-related protein 2/3 complex subunit 5 | 6.05 | 0.0101 |
|  | P60953-2 | Isoform 2 of P60953 Cell division control protein 42 homolog precursor | 4.75 | 0.036 |
|  | P01023 | Alpha-2-macroglobulin | 2.23 | <0.0001 |
|  | P28676 | Grancalcin | −7.09 | 0.0083 |
| Cell motility | P61160 | Actin-like protein 2 | 3.36 | 0.0476 |
|  | P26038 | Moesin | 2.04 | 0.0006 |

TABLE 5-continued

Proteins differentially present in saliva in subjects with type-2 diabetes and controls

| Function | Swiss-Prot Accession | Description | Fold Change Diabetes vs. Control | P-value |
|---|---|---|---|---|
| | O95274 | Ly6/PLAUR domain-containing protein 3 | −2.3 | 0.0236 |
| | P67936-2 | Isoform 2 of P67936 Tropomyosin alpha-4 chain | −3.75 | 0.0006 |

Spectral counts of human salivary proteins with 3 or more unique peptide identifications were subjected to label-free quantification. Proteins that were significantly differentially abundant (p-value ≦0.05) by at least ±2.0-fold are shown above. Proteins are grouped according to their function. Fold change between the groups was quantified using equation described by Old et al. (*Mol Cell Proteomics* 2005, 4, (10), 1487-502).

Example 4

Validation of Potential Biomarkers Using Immunodetection

Figure 2A:
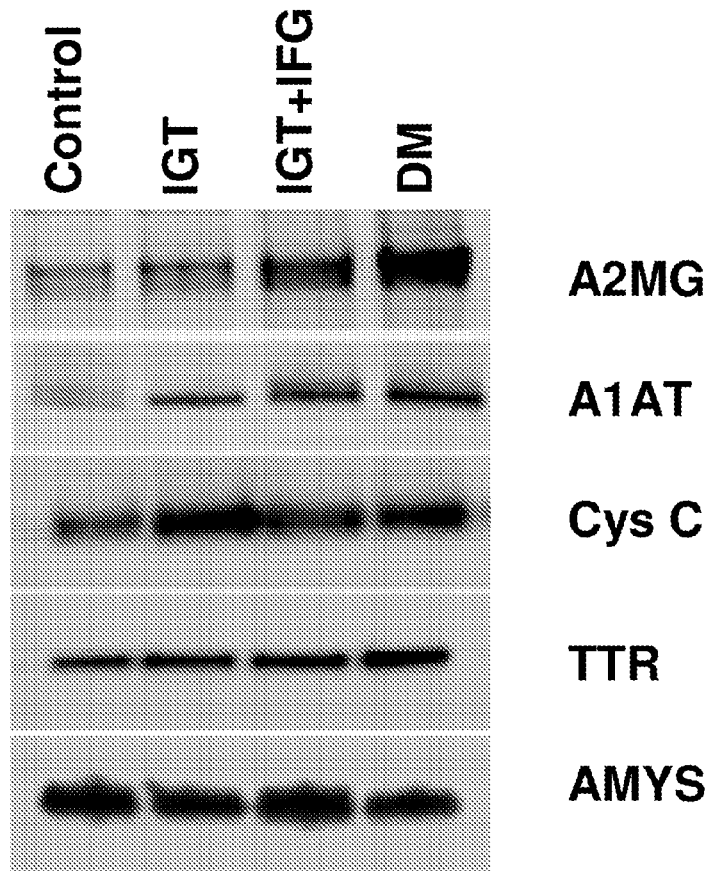
FIG. 2A is a digital image of a Western blot analysis of alpha-2 macroglobulin (A2MG), alpha-1-antitrypsin (A1AT), cystatin C (Cys C), Transthyretin (TTR), and salivary alpha-amylase (AMYS).
Figure 2B:
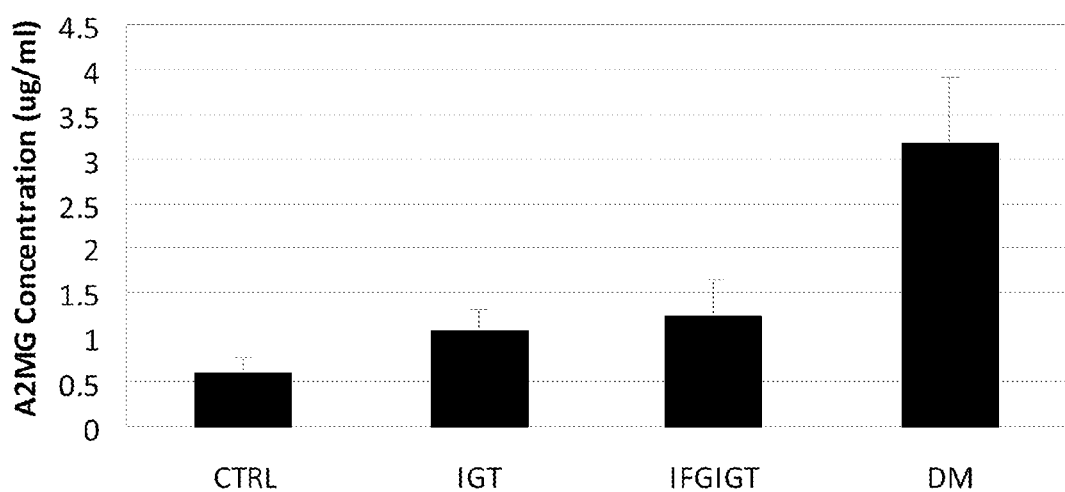
FIG. 2B is a bar graph showing ELISA analysis of saliva A2MG showing mean concentrations in controls (CTRL) and study subjects with impaired glucose tolerance (IGT), IGT and impaired fasting glucose (IFG), and diabetes mellitus (DM). Error bars denote SEM. p=0.0186 for the 4-group comparison via Kruskal-Wallis nonparametric ANOVA. p=0.0137 for pair.

To independently confirm the relative abundance of salivary proteins identified by 2D-LC-MS analysis, immunoquantification was performed using western blotting. To further explore their potential performance in pre-diabetes, samples were tested from IGT and IGT+IFG groups in addition to type-2 diabetes. As shown in FIG. 2, the levels of A1AT, cystatin C (CysC), alpha-2-macroglobulin (A2MG), and transthyretin (TTR) were elevated in type-2 diabetes, which correlated with the results of spectral counting. Scanning densitometry analysis showed the relative levels of A2MG as 1.4, 1.9, and 2.1, A1AT as 1.4, 2.0, and 2.5, and TTH as 1.26, 1.38 and 1.68-fold higher in the IGT, IGT+IFG, and type-2 diabetes groups, respectively, compared to control (1.0). As also shown in FIG. 2, A1AT, A2MG, and TTR showed a relative increase in expression with disease progression. In contrast, the relative levels of CysC were 1.54, 1.28, and 1.29-fold higher in the IGT, IGT+IFG, and type-2 diabetes groups, respectively, compared to control; i.e., highest in the IGT group.

Immunoassay measurements of A2MG on individual subjects correlated with the western blot data and their differential abundance based upon label-free quantification (FIG. 2). There were significant differences in A2MG concentrations in the 4 groups when compared via Kruskal-Wallis nonparametric ANOVA (p=0.0186 for the 4-group comparison). In pair-wise comparisons, the group significantly different from control was the DM group (p=0.0137 via Wilcoxon two-sample test). These data suggest that the differential abundance of specific salivary proteins in DM saliva is potentially presaged by their differential abundance in pre-diabetes.

Diabetes is a major problem worldwide and is a leading cause of morbidity that is attributable to largely preventable metabolic complications. To date, however, no robust marker of diabetes or its vascular complications has been validated for general clinical use. With the emergence of disease-modification drugs in diabetes, there is an increasing need for diagnostic markers to ensure that these therapies are targeted to the correct patient population.

Saliva has multiple advantages as a diagnostic body fluid due to its non-invasive, safe, simple, and cost-effective nature. By using a comprehensive and rigorous proteomic approach comprised of 2-DLC fractionation, LC-MS/MS identification, and spectral counting quantification, 487 proteins were characterized in human whole saliva and 65 were identified that were significantly different in relative abundance between controls and type-2 diabetes patients. The majority of the differently abundant proteins are predicted to have functions in metabolism, followed by the functional categories of development, cell organization and biogenesis, immune function, cell communication and proliferation, and apoptosis.

Among the up-regulated proteins identified in this study are proteins associated with immune function that have been previously reported to be associated with diabetes in other body fluids. The presence of inflammatory factors among this biomarker set is consistent with the proposed role of a chronic sub-clinical inflammatory state in the genesis of the metabolic syndrome and diabetes. The protease inhibitors CysC, leukocyte elastase inhibitor (LEI), and uteroglobin also have individually be associated with diabetes. CysC is a potent inhibitor of lysosomal cysteine proteinases. In serum, it is a known marker for glomerular filtration and has been shown to be significantly elevated in cardiovascular disease and diabetes (Larrson et al., *Int J Cardiol,* 2007). LEI regulates the activity of neutrophil proteases, including polymorphonuclear elastase (PMN-E). In human plasma, PMN-E is a marker for hypertension and micro- and macro-vascular disease in type-2 diabetes (Piwowar et al., *Clin Chem Lab Med* 38:1257-1261, 2000). Human uteroglobin, also called blastokinin, is secreted from Clara cells (nonciliated cells of the surface epithelium of the pulmonary airways). In human urine, it is a known indicator of renal tubular function in diabetes (Hong et al., *J Diabetes Complications* 12:43-60, 1998). Neutrophil collagenase or MMP-8 has been linked to local tissue damage rather than to neutrophil dysfunction in saliva from patients with uncontrolled type-2 diabetes (Collin et al., *J Periodontal Res* 35:259-265, 2000). However, serum MMP-8 levels were reported to be elevated in coronary heart disease independent of known risk factors, including diabetes (Qiang et al., *Nan Fang Yi Ke Da Xue Xue Bao* 27:831-833, 2007). Thus, up-regulated MMP-8 in human saliva in type-2 diabetes could be a non-specific inflammatory marker. TTR, or prealbumin, is a known transport protein for both thyroxine and retinol (vitamin A). Stockholm Diabetes Prevention Program investigators have reported both up- and down-regulation of serum TTR, depending on the particular patient cohort studied (Sundsten et al., *Diabetes Metab Res Rev,* 2007)

It is disclosed herein that A1AT, A2MG and plasma retinol binding protein 4 (RBP4) were elevated in diabetic saliva. These proteins have been implicated in diabetes. A1AT, potentially through its demonstrated anti-apoptotic activity, has also been shown to prevent or reverse diabetes, prevent the development of type-1 diabetes in mice, prolong islet allograft survival in rodents, and reduce beta-cell apoptosis in vitro (Zhang et al., *Diabetes* 56:1316-1323, 2007). Overexpression of A1AT has been seen in the urine of patients with diabetic nephropathy. RBP4 is a novel adipokine of the lipocalin family involved in the development of obesity and insulin resistance (Rao et al., *Diabetes Care* 30:629-637, 2007). Its abundance in human saliva in the present study was consistent with elevated RBP4. A2M variations in diabetes were reported with protease-antiprotease imbalance in children who were at greater risk of developing vascular complications (Lisowska-Myjak et al., *Acta Diabetol* 43:88-92, 2006). A cardiac isoform of A2MG has been shown to be an early marker of cardiac hypertrophy and increased left-ventricular mass in myocardial-infracted diabetic patients (Annapoorani et al., *Atherosclerosis* 186:173-176, 2006), and A2MG in human saliva was reported as a proinflammatory factor (Aurer et al., *Coll Antropol* 29:435-439, 2005). Carbonic anhydrase I (CA-I) was down-regulated in saliva, and was reported to be decreased in erythrocytes (Gambhir et al., *Biochem Genet.* 45:431-439, 2007) and increased in vitreous of type-2 diabetes patients. Apolipoprotein (apo) B-100, is one of the two main forms of apoB in chylomicrons and low-density lipoproteins. Diabetic subjects are known to have elevated apoB-100 as a result of increased production and reduced fractional catabolic rates (Hogue et al., *J Lipid Res* 48:1336-1342, 2007). One of the nine development-related salivary proteins down-regulated in type-2 diabetes was lamin A/C. Mutations in the LMNA gene are characterized by loss of subcutaneous adipose tissue, insulin resistance, dyslipidemia, and type-2 diabetes (Hegele et al., *J Clin Endocrinol Metab* 92:4566-4568, 2007).

The studies disclosed herein established a subset of salivary biomarkers of established type-2 diabetes identified by proteomic profiling. These biomarkers were differentially abundant in the saliva of patients with IGT alone and IGT+IFG as assessed by direct Western immunoblot analysis. The relative increase of some of these markers in association with progression of pre-diabetes to the diabetic state underscores the importance of a systematic analysis of these candidate biomarkers in pre-diabetic saliva, as well as their variability in individual samples, by immunoassays. As recent studies have shown that early and multi-factorial intervention in type-2 diabetes prevents cardiovascular complications and mortality, accurate diagnosis of this condition facilitates early intervention.

Example 5

Additional Biomarkers for Pre-diabetes and Diabetes

Additional salivary glycoprotein markers of pre-diabetes and diabetes were evaluated using an ELISA assay. A cohort of 159 subjects including controls (OGTT<140 mg/dl), pre-diabetes (OGTT 140-199 mg/dl), and type 2 diabetes (OGTT>199 mg/dl) were tested for the presence of alpha 1 acid glycoprotein (A1AG) and lipocalin 2 in saliva samples.

There were significant differences in both A1AG and lipocalin 2 concentrations in between control and pre-diabetes and diabetes groups when compared via one way analysis of variance using Dunnett's post-hoc correction factor for pairwise comparisons versus control (Table 6).

TABLE 6

Protein Concentration in Saliva Samples from Subjects with Pre-diabetes or Diabetes

| | Reactivity (ng/ml) | | |
|---|---|---|---|
| | Control (n = 42) | Pre-diabetes (n = 83) | Diabetes (n = 34) |
| A1AG | | | |
| Geometric Mean (SD) | 1046 (3) | 1718 (3) | 1836 (3) |
| P value[1] | Referent | 0.02 | 0.03 |
| Lipocalin 2 | | | |
| Geometric Mean (SD) | 776 (2) | 1214 (2) | 1278 (3) |
| P value[1] | Referent | 0.01 | 0.02 |

[1]One-way analysis of variance using Dunnett's post-hoc correction factor for pairwise comparisons versus the control Example 6

Exemplary Diagnostic Study

A subject presents with a BMI greater than or equal to about 30 kg/m$^2$ and a family history of diabetes. The subject reports a sedentary lifestyle. A saliva sample is obtained from the subject. An ELISA is performed on the saliva sample, and the amount of at least one protein listed in Table 1, such as 1, 2, 3, 4, 5, 6, 7, 8, 9, 10, 11, 12, 13, 14 or 15 proteins is determined relative to amount of these proteins in a saliva sample from a subject without diabetes. The subject is identified as having at least one such protein altered as compared to a control. The subject is identified with relative levels of one such protein as at least 1.3, 1.4, 1.5, 1.6, 1.7, 1.8, 1.9, 2.0, 2.1, 2.2, 2.3, 2.4 or 2.5-fold higher than the control. For example, the subject is identified with relative levels of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin as 1.3, 1.4, 1.5, 1.6, 1.7, 1.8, 1.9, 2.0, 2.1, 2.2, 2.3, 2.4 or 2.5-fold altered as compared to the level of the protein in the control. Thus, the subject is identified as pre-diabetic. The amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is also determined relative to the amount of these proteins in a saliva sample from a subject known to be diabetic. A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is altered when compared to the amount of these proteins in the saliva sample from the diabetic subject. This confirms that the subject is pre-diabetic, and does not have frank type 2 diabetes. Thus, the method can be used to distinguish pre-diabetes from diabetes.

Example 7

Exemplary Diagnostic Study

A subject presents with FPG of 100 mg/dl and a OGTT of 140 mg/dl. A saliva sample is obtained from the subject. An ELISA is performed on the saliva sample, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is determined relative to amount of these proteins in a saliva sample from a control subject without diabetes. The amount of at least one of the proteins set forth in Table 2 is also determined relative to the amount of this protein in a saliva sample from the control. Hemoglobin A1C is also assessed.

The subject is identified as having all of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin altered as compared to a control. The subject is identified with relative levels of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin as 1.3, 1.4, 1.5, 1.6, 1.7, 1.8, 1.9, 2.0, 2.1, 2.2, 2.3, 2.4 or 2.5-fold higher than the control. The amount of at least one of the protein set forth in Table 2 also differs 2.0, 2.1, 2.2, 2.3, 2.4, 2.5, 3.0 or 3.5-fold from the control.

A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin compared to the amount of these proteins in the saliva sample from the normal subject. Both the glycosylated form and the unglycosylated form of the protein are measured. Thus, the subject is identified as pre-diabetic. The amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is also determined relative to the amount of these proteins in a saliva sample from a subject known to be diabetic. A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is altered from the amount of these proteins in the saliva sample from the diabetic subject. This confirms that the subject is pre-diabetic.

Example 8

Evaluating Progression of Diabetes

A subject presents with FPG of 120 mg/dl and a OGTT of 190 mg/dl. The subject is treated with metformin. After one month of treatment, a saliva sample is obtained from the subject. An ELISA is performed on the saliva sample, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is determined relative to amount of these proteins in a saliva sample from a control subject without diabetes.

A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is determined and is compared to the amount of these proteins in the saliva sample from the control subject. Following treatment, the subject is identified as having an amount of at least one of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin that does not significantly differ from the amount of the protein in the saliva sample from the control.

Thus, the therapy is identified as effective for the treatment of the subject. The subject maintains the therapy for an additional year, and a second saliva sample is obtained from the subject. An ELISA is performed on the saliva sample, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is determined and is compared to amount of these proteins in a saliva sample from a control subject without diabetes.

A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is not increased relative to the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin to compare the amount of these proteins in the saliva sample from the control subject. The subject is identified as having an amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin that does not significantly differ from the amount of the protein in the saliva sample from the control. Thus, the therapy is continued for an additional year.

A third saliva sample is obtained from the subject. An ELISA is performed on the saliva sample, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is determined.

A statistical analysis is performed, and the amount protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is altered relative to the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin in the saliva sample is compared to the amount in the saliva from a control subject. The amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin is also determined relative to the amount of these proteins in a saliva sample from a subject known to be diabetic. A statistical analysis is performed, and the amount of protein plunc, pancreatic ribonuclease, inter-α-trypsin inhibitor heavy chain H1, inter-α-trypsin heavy chain H4, nucleobindin-2, moesin, 14-3-3-epsilon, cystatin A, annexin A3, Protein S100-A7, phosphoglycerate kinase 1, annexin A1, isoform2 of P67936 tropomyosin α-4, kallikrein-10, desmoplakin, flavin reductase, grancalcin, and calnexin does not differ significantly from than the amount of these proteins in the saliva sample from the diabetic subject. This confirms that the therapy is no longer effective in treating the subject. The subject is started on insulin therapy and is instructed to make further lifestyle modifications.

Example 9

Exemplary Lateral Flow Device Diagnostic Tests

This example describes exemplary lateral flow devices for diagnosis of pre-diabetes or diabetes, such as sandwich immunoassay and competitive immunoassay formats.

Sandwich Immunoassay Format

Figure 4:
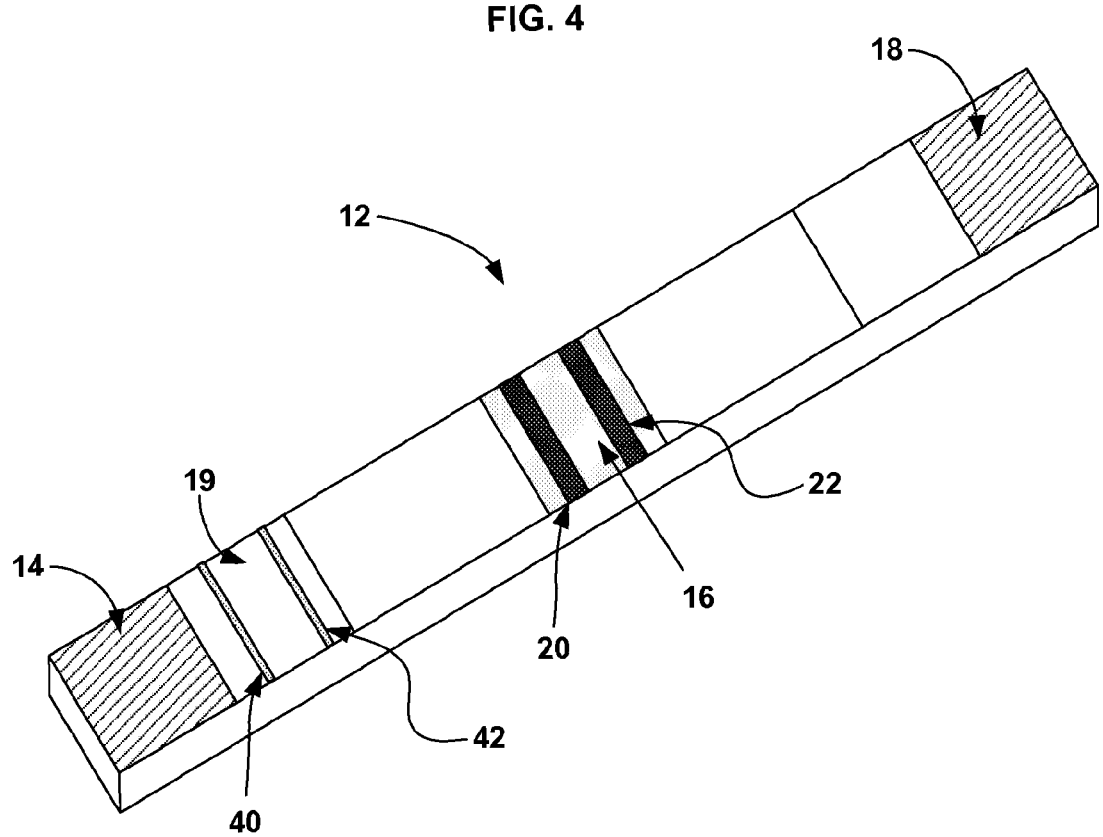
FIG. 4 is a perspective view of a physical embodiment of an exemplary lateral flow test strip for diagnosing pre-diabetes or diabetes utilizing a sandwich immunoassay format.

FIG. 4 schematically illustrates an exemplary lateral flow device for diagnosis of pre-diabetes or diabetes utilizing a sandwich immunoassay format. As in the prior embodiment of FIG. 3A, a labeled first specific binding pair (SBP) member is diffusively bound on the matrix on a conjugate pad 19 at a point upstream of the test result zone 16. The sample is added to a sample application pad 14 on the matrix at a point upstream of the labeling zone and allowed to flow through the labeling zone. The labeled first SBP member located within the conjugate pad is capable of being freely moblizible in the sample. Therefore, if analyte is present in the sample, the labeled first SBP member binds to the analyte and the resulting analyte-labeled first SBP member complex is transported to and through the test result zone. The extent of complex formation between the analyte and the labeled SBP member is directly proportional to the amount of analyte present in the sample. A second SBP member capable of binding to the analyte-first SBP member complex is immobilized on the test result zone. This second SBP member is not capable of binding the labeled first SBP member unless the labeled first SBP member is bound to the analyte. Thus, the amount of labeled SBP member that accumulates on the test result zone is directly proportional to the amount of analyte present in the sample.

In the exemplary device (FIG. 4), the conjugate pad 19 includes a first SBP reagent 40 (such as a first A1AT antibody covalently attached to blue latex particles) and a first test line 20 that includes a second A1AT antibody that recognizes a different epitope of A1AT than the first A1AT antibody. The conjugate pad 19 also includes a second SBP reagent 42 (such as a first A1AG antibody covalently attached to blue latex) and the second test line 22 includes a second A1AG antibody that recognizes a different epitope than the first A1AG antibody.

The test is performed by applying a sample (such as saliva) from a subject to the sample application pad 14. The sample flows through the conjugate pad 19, releasing the first SBP reagent and releasing the second SBP reagent. The displaced first SBP reagent is captured by the first test line 20 if A1AT is bound to the first SBP. The displaced second SBP reagent is captured by the second test line 22 if A1AG is bound to the second SBP. The first and second test line intensity is compared a control (for example, visually or using a reader). If the first or second test line intensity (or both) is greater than the control, then the subject has pre-diabetes or diabetes. If the first or second test line intensity (or both) is less than the control, then the subject is normal.

Competitive Immunoassay Format

Figure 5:
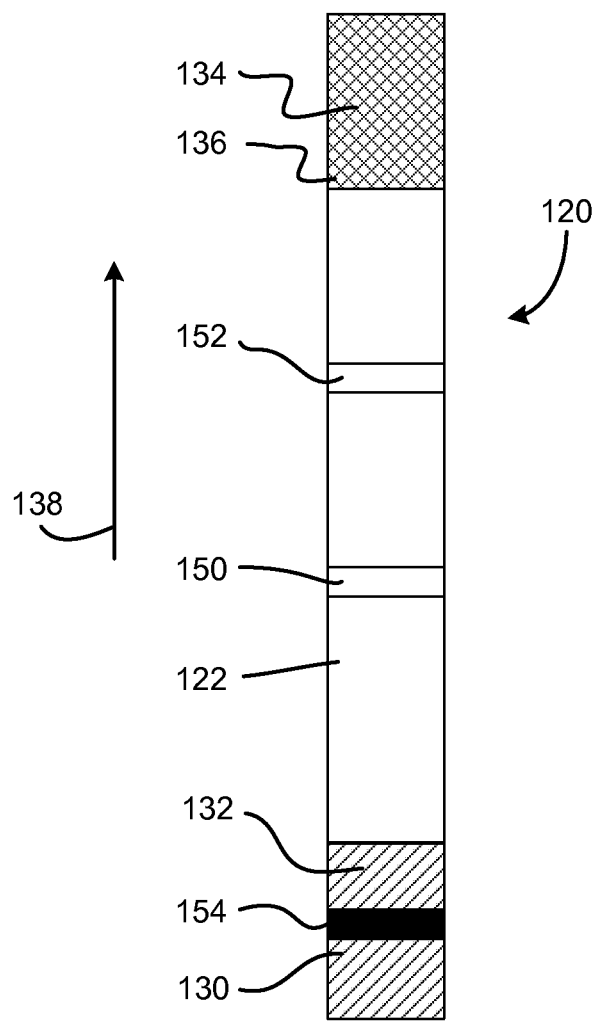
FIG. 5 is a perspective view of a physical embodiment of an exemplary lateral flow test strip for diagnosing pre-diabetes or diabetes utilizing a competitive immunoassay format.

In another embodiment, the lateral flow device for the diagnosis of pre-diabetes or diabetes uses a competitive immunoassay format. FIG. 5 shows strip 120 to include an elongated, narrow, bibulous liquid collection member 122 with a flat proximal edge 124 and a flat distal edge 126. Strip 120 is mounted on a rigid or semi-rigid plastic support 128, and a proximal absorbent sample collection pad 130 is also mounted to the support 128 such that it is contiguous with collection member 122 through portion 132. A distal reservoir pad 134 is attached to a distal end of support 128. Liquid (such as a biological fluid, for example, saliva) placed on collection pad 130 moves by capillary action in a distal direction 138 through collection member 122 into reservoir pad 134.

Capture agents (such as specific binding partners, for example antibodies such as monoclonal antibodies) are aligned in spaced indicator lines 150, 152, each of which extends transversely on the strip, and respectively form the primary and secondary capture zones. A mobilization zone 154 is located on collection member 122 underneath pad 130 and indicator line 150. The mobilization zone 154 contains an analyte (or analyte analog, for example A1AT and/or A1AG) linked to a label, such as a colored latex microsphere (referred to as an A-L-T conjugate). In this embodiment, the fluid sample (such as saliva) is applied to sample pad 130, which mobilizes the A-L-T conjugate in mobilization zone 154. The A-L-T conjugate moves with the liquid sample through pad 130 and contiguous portion 132.

Since the sample is applied to the surface of pad 130, it is designed to encounter less resistance and migrate more quickly through pad 130 than the subjacent larger or heavier A-L-T conjugate (which must be hydrated and mobilized), so that the sample (and any analyte in the sample) therefore the primary capture line 150 before the A-L-T conjugate. If the analyte is present and the A-L-T conjugate reaches the antibodies (such as anti-A1AT and/or anti-A1 AG) in primary capture line 150, the specific binding sites are already occupied by any analyte (for example, A1AT and/or A1AG) from the sample, which reduces the number of binding sites available to bind A-L-T. Hence the A-L-T conjugate continues to migrate by capillary action through the porous material of collection member 122 until it reaches secondary capture line 152, where it is bound by the specific binding partner immobilized therein (for example, streptavidin). The presence of analyte in the sample is detected by a positive signal (such as a color change from the colored latex microsphere) in secondary capture line 152. If a positive signal is present at secondary capture line 152, then the result indicates that subject has pre-diabetes or diabetes. If analyte is not present in the sample (or is present below a pre-selected threshold) then in the absence of competition to A-L-T binds to primary capture line 150 without migrating in substantial amount to secondary capture line 152. The absence of a significant positive signal (such as a color change) at secondary capture line 152 indicates that the subject does not have pre-diabetes or diabetes.

It will be apparent that the precise details of the methods or compositions described may be varied or modified without departing from the spirit of the described invention. We claim all such modifications and variations that fall within the scope and spirit of the claims below.

The invention claimed is:

1. A method for determining if a subject of interest has pre-diabetes or diabetes, comprising
   (a) comparing a proteomic profile of a test sample of saliva from a subject of interest with a proteomic profile of at least one control sample, wherein the proteomic profile of the test sample and the at least one control sample comprise information on the expression of at least one of cystatin C, alpha 2-macroglobulin (A2MG), transthyretin (TTR), plasma retinol binding protein 4 (RBP4) and/or lipocalin 2, and wherein:
      (i) if the at least one control sample is a non-diabetic reference value or a saliva sample from a non-diabetic subject, and the proteomic profile of the test sample does not show an elevated level of cystatin C, alpha 2-macroglobin (A2MG), transthyretin (TTR), plasma retinol binding protein 4 RBP4) and/or lipocalin 2 relative to the proteomic profile of the at least one control sample, the subject is determined not to have pre-diabetes or diabetes, and wherein if the proteomic profile of the test sample shows an elevated level of cystatin C, alpha 2-macroglobin (A2MG), transthyretin (TTR), plasma retinol binding protein 4 (RBP4) and/or lipocalin 2 relative to the proteomic profile of the at least one control-sample, the subject is determined to have prediabetes or diabetes;
      (ii) if the at least one control sample is a diabetic reference value or a saliva sample from a subject with diabetes and the proteomic profile of the test sample does not show a decreased level of cystatin C, alpha 2-macroglobin (A2MG) transthyretin (TTR), plasma retinol binding protein 4 (RBP4) and/or lipocalin 2 relative to the proteomic profile of the at least one control sample, then the subject is determined to have diabetes, and wherein if the proteomic profile of the test sample shows a decreased level of cystatin C, alpha 2-macroglobin (A2MG), transthyretin (TTR), plasma retinol binding protein 4 (RBP4) and/or lipocalin 2 relative to the proteomic profile of the at least one control sample, the subject is determined not to have diabetes; and
      (iii) if the at least one control sample comprises a negative control comprising a non-diabetic reference value or a saliva sample from a non-diabetic subject and a positive control comprising a diabetic reference value or a saliva sample from a subject with diabetes, and the proteomic profile of the test sample shows a level of cystatin C, alpha 2-macroglobin (A2MG), transthyretin (TTR), plasma retinol binding protein 4 (RBP4) and/or lipocalin 2 that is intermediate between the proteomic profiles of the negative control and the positive control, then the subject is determined to have pre-diabetes.

2. The method of claim 1, wherein the proteomic profile of the test sample and at least one control sample further comprise information on the expression of at least one additional protein, wherein the at least one additional protein comprises alpha-1-antitrypsin, alpha 1 acid glycoprotein, uteroglobin, carbonic anhydrase 6 pyruvate kinase isozymes MIIM2, neutrophil collagenase, purine nucleoside phosphorylase, aldehyde dehydrogenase, fatty acid biding protein (epidermal), peroxiredoxin-1 -2, +-6 lamin AIC apolipoprotein B-100, annexin A2, carbonic anhydrase 1, carbonic anhydrase 2,
   protein plunc, pancreatic ribonuclease, inter-a-trypsin inhibitor heavy chain HI, inter-a-trypsin heavy chain H4, nucleobindin-2, moesin, 14-3-3- epsilon, cystatin A, annexin A3, Protein S100-A7, phosphoglycerate kinase 1, annexin Al , isoform2 of P67936 tropomyosin a-4, kallikrein-10, desmoplakin, flavin reductase, grancalcin, and/or calnexin, and wherein:
      (i) if the at least one control sample is a non-diabetic reference value or a saliva sample from a non-diabetic subject, and the proteomic profile of the test sample does not show an elevated level of the at least one additional protein relative to the proteomic profile of the at least one control sample, the subject is determined not to have pre-diabetes or diabetes, and wherein if the proteomic profile of the test sample shows an elevated level of the at least one additional protein relative to the proteomic profile of the at least one control sample, the subject is determined to have prediabetes or diabetes;
      (ii) if the reference sample is a diabetic reference value or a saliva sample from a diabetic subject, and the proteomic profile of the test sample does not show a decreased level of the at least one additional protein relative to the proteomic profile of the at least one control sample, the subject is determined to have pre-diabetes or diabetes, and wherein if the proteomic profile of the test sample shows a decreased level of the at least one additional protein relative to the proteomic profile of the at least one control sample, the subject is determined not to have pre-diabetes or diabetes; and
      (iii) if the at least one control sample comprises a negative control comprising a non-diabetic reference value or a saliva sample from a non-diabetic subject, and a positive control comprising a diabetic reference value or a saliva sample from a subject with diabetes, and the proteomic profile of the test sample shows a level of the at least one additional protein that is intermediate between the proteomic profiles of the negative control and the positive control, then the subject is determined to have pre-diabetes.

3. The method of claim 1, wherein an increased level of cystatin C, alpha 2-macroglobin (A2MG), transthyretin (TTR), plasma retinol binding protein 4 (RBP4) and/or lipocalin 2 comprises at least a 1.2-fold increase relative to the proteomic profile of the at least one control sample; and wherein a decreased level of alpha 2-macroglobin (A2MG), transthyretin (TTR), plasma retinol binding protein 4 (RBP4) and/or lipocalin 2 comprises at least a 1.2-fold decrease relative to the proteomic profile of the at least one sample.

4. The method of claim 1, wherein the proteomic profile further comprises information on the expression of one or more of proteasome subunit, aldo-keto reductase family 1 member B 10, cathepsin Z, chitotriosidase isoform 2, 3, +4, transmembrane protease, serine 1 ID, transthyretin, glycogen phosphorylase, heterogeneous nuclear RNPs A21B 1, leukocyte elastase inhibitor, small proline-rich protein 2F, calmodulin-like protein 5, neuroblast differentiation AHNAK, histone cluster 1, Hle, kallikrein-13, chitinase-3-like protein 1, inter-alpha (Globulin) inhibitor H2, 14-3-3 protein eta, cofilin-1, retinol binding protein 4, plasma, basic proline-rich peptide IB-8a, isoform 2 of P60953 cdc 42 homolog, actin-related protein 213 complex subunit 5, ly61PLAUR domain-containing protein 3, actin-like protein 2, Rearranged VKA17V gene segment, brain acid soluble protein 1, golgi phosphoprotein 2, protein FAM49B (LI), and acidic leucine-rich nuclear phosphoprotein 32.

5. The method of claim 2, wherein the proteomic profile comprises information on the expression of five or more of protein plunc, pancreatic ribonuclease, inter-a-trypsin inhibitor heavy chain HI, inter-a-trypsin heavy chain H4, nucleobindin-2, moesin, 14-3-3-epsilon, cystatin A, annexin A3, Protein S100-A7, phosphoglycerate kinase 1, annexin Al, isoform2 of P67936 tropomyosin a-4, kallikrein-10, desmoplakin, flavin reductase, grancalcin, and calnexin.

6. The method of claim 2, wherein the proteomic profile comprises information on the expression of ten or more of protein plunc, pancreatic ribonuclease, inter-a-trypsin inhibitor heavy chain HI, inter-a-trypsin heavy chain 5 H4, nucleobindin-2, moesin, 14-3-3-epsilon, cystatin A, annexin A3, Protein S100-A7, phosphoglycerate kinase 1, annexin Al, isoform2 of P67936 tropomyosin a-4, kallikrein-10, desmoplakin, flavin reductase, grancalcin, and calnexin.

7. The method of claim 2, wherein the proteomic profile comprises information on the expression of fifteen or more of protein plunc, pancreatic ribonuclease, inter-a-trypsin inhibitor heavy chain HI, inter-a-trypsin heavy chain H4, nucleobindin-2, moesin, 14-3-3-epsilon, cystatin A, annexin A3, Protein S100-A7, phosphoglycerate kinase 1, annexin Al, isoform2 of P67936 tropomyosin a-4, kallikrein-10, desmoplakin, flavin reductase, grancalcin, and calnexin.

8. The method of claim 2, wherein the proteomic profile comprises all of protein plunc, pancreatic ribonuclease, inter-a-trypsin inhibitor heavy chain HI inter-a-trypsin heavy chain H4, nucleobindin-2, moesin, 14-3-3-epsilon, cystatin A, annexin A3, Protein S100-A7, phosphoglycerate kinase 1, annexin Al, isoform2 of P67936 tropomyosin a-4, kallikrein-10, desmoplakin, flavin reductase, grancalcin, and calnexin.

9. The method of claim 2, wherein the proteomic profile further comprises information on the expression of alpha-1-antitrypsin, alpha 2-macroglobulin, cystatin C, plasma retinol binding protein 4 (RBP4), and transthyretin.

10. The method of claim 1, wherein the diabetes is type 2 diabetes.

11. The method of claim 1, wherein the diabetes is type 1 diabetes.

12. The method of claim 1, further comprising determining a level of hemoglobin A1C for the subject, wherein an elevated level of hemoglobin A1C relative to a non-diabetic A1C control value confirms a diagnosis of pre-diabetes or diabetes.

13. The method of claim 1, wherein the subject is obese.

14. The method of claim 1, wherein the proteomic profile is determined using a lateral flow device.

15. A method for monitoring the efficacy of an anti-diabetes therapy in a subject comprising:
obtaining a first saliva sample from the subject at a first time point;
administering the anti-diabetes therapy to the subject;
obtaining a second saliva sample from the subject at a second time point;
determining a proteomic profile for each of the first and second saliva samples, wherein the proteomic profiles of the first and second saliva samples comprise information on the expression of at least one of cystatin C, alpha 2-macroglobulin (A2MG), transthyretin (TTR), plasma retinol binding protein 4 (RBP4) and lipocalin 2, and wherein:
  (i) if the proteomic profile of the second saliva sample shows a decrease in a level of cystatin C, alpha 2-macroglobin (A2MG), transthyretin (TTR), plasma retinol binding protein 4 (RBP4) and/or lipocalin 2 relative to the proteomic profile of the first saliva sample, the anti-diabetes therapy is determined to be effective; and
  (ii) if the proteomic profile of the second saliva sample does not show a decrease in a level of cystatin C, alpha 2-macroglobin (A2MG), transthyretin (TTR), plasma retinol binding protein 4 (RBP4) and/or lipocalin 2 relative to the proteomic profile of the first saliva sample, the anti-diabetes therapy is determined to be ineffective.

16. The method of claim 15, wherein the proteomic profiles of the first and second saliva samples further comprise information on the expression of at least one additional protein, wherein the at least one additional protein comprises alpha-1-antitrypsin, alpha 1 acid glycoprotein, uteroglobin, carbonic anhydrase 6, pyruvate kinase isozymes MIIM2, neutrophil collagenase, purine nucleoside phosphorylase, aldehyde dehydrogenase, fatty acid biding protein (epidermal), peroxiredoxin-1, -2, +-6, lamin AIC, apolipoprotein B-100, annexin A2, carbonic anhydrase 1, carbonic anhydrase 2, protein plunc, pancreatic ribonuclease, inter-a-trypsin inhibitor heavy chain HI, inter-a-trypsin heavy chain H4, nucleobindin-2, moesin, 14-3-3- epsilon, cystatin A, annexin A3, Protein S100-A7, phosphoglycerate kinase 1, annexin Al, isoform2 of P67936 tropomyosin a-4, kallikrein-10, desmoplakin, flavin reductase, grancalcin, and/or calnexin, and wherein:
  (i) if the proteomic profile of the second saliva sample shows a decrease in a level of the at least one additional protein relative to the proteomic profile of the first saliva sample, the anti-diabetes therapy is determined to be effective; and
  (ii) if the proteomic profile of the second saliva sample does not show a decrease in a level of the at least one additional protein relative to the proteomic profile of the first saliva sample, the anti-diabetes therapy is determined to be ineffective.

* * * * *